US006906006B1

(12) United States Patent
Fischer et al.

(10) Patent No.: US 6,906,006 B1
(45) Date of Patent: Jun. 14, 2005

(54) N-ARLY-SUBSTITUTED NITROGEN-CONTAINING HETEROCYCLES, PROCESSES AND NOVEL INTERMEDIATES FOR THEIR PREPARATION, AND THEIR USE AS HERBICIDES AND PLANT GROWTH REGULATORS

(75) Inventors: Reiner Fischer, Monheim (DE); Uta Jensen-Korte, Dusseldorf (DE); Franz Kunisch, Odenthal (DE); Albrecht Marhold, Leverkusen (DE); Pieter Ooms, Krefeld (DE); Otto Schallner, Monheim (DE); Hans-Joachim Santel, Leawood, KS (US); Robert-Rudolf Schmidt, Bergisch Gladbach (DE); Birgit Krauskopf, Odenthal (DE); Robert-Harry Strang, Dusseldorf (DE)

(73) Assignee: Bayer Aktiengesellschaft, Leverkkusen (DE)

( * ) Notice: Subject to any disclaimer, the term of this patent is extended or adjusted under 35 U.S.C. 154(b) by 0 days.

(21) Appl. No.: 08/470,563

(22) Filed: Jun. 6, 1995

Related U.S. Application Data

(60) Continuation-in-part of application No. 08/148,094, filed on Nov. 5, 1993, now abandoned, which is a continuation-in-part of application No. 07/918,895, filed on Jul. 20, 1992, now Pat. No. 5,554,580, which is a continuation-in-part of application No. 07/618,335, filed on Nov. 26, 1990, now abandoned, which is a division of application No. 07/435, 898, filed on Nov. 13, 1989, now Pat. No. 5,006,148.

(30) Foreign Application Priority Data

Nov. 23, 1988 (DE) .......................................... 38 39 480
Nov. 12, 1992 (DE) .......................................... 42 38 125

(51) Int. Cl.$^7$ ...................... A01N 43/653; C07D 249/12
(52) U.S. Cl. ....................... 504/273; 504/193; 504/199; 548/110; 548/112; 548/263.2; 548/263.8
(58) Field of Search ................................ 548/110, 112, 548/263.2, 263.8; 504/193, 199, 273

(56) References Cited

U.S. PATENT DOCUMENTS

| | | | |
|---|---|---|---|
| 4,059,434 | A | 11/1977 | Wolf |
| 4,108,628 | A | 8/1978 | Wolf |
| 4,124,373 | A | 11/1978 | Wolf |
| 4,124,374 | A | 11/1978 | Wolf |
| 4,608,080 | A | 8/1986 | Haga et al. |
| 4,624,699 | A | 11/1986 | Nagano et al. |
| 4,670,043 | A | 6/1987 | Nagano et al. |
| 4,695,312 | A | 9/1987 | Hayase et al. |
| 4,702,763 | A | 10/1987 | Maravetz |
| 4,705,557 | A | 11/1987 | Maravetz |
| 4,746,354 | A | 5/1988 | Gehring et al. |
| 4,752,325 | A | 6/1988 | Haga et al. |
| 4,758,673 | A | 7/1988 | Gehring et al. |
| 4,818,275 | A | 4/1989 | Theodoridis |
| 4,826,867 | A | 5/1989 | Jensen-Korte et al. |
| 4,846,875 | A | 7/1989 | Chang |
| 4,943,583 | A | 7/1990 | Luthy |
| 5,006,148 | A | 4/1991 | Fischer et al. |

FOREIGN PATENT DOCUMENTS

| | | |
|---|---|---|
| EP | 0138527 | 4/1985 |
| EP | 347382 | 12/1989 |
| EP | 0370332 | 5/1990 |
| EP | 0422469 | 4/1991 |
| EP | 0431373 | 6/1991 |
| EP | 0441004 | 8/1991 |
| JP | 233061 | 11/1985 |
| JP | 252465 | 12/1985 |
| JP | 291573 | 12/1986 |
| JP | 9987 | 1/1989 |
| WO | WO9103470 | 3/1991 |

OTHER PUBLICATIONS

Chemical Abstracts, vol. 105, No. 25, Dec. 22, 1986, Columbus, Ohio, USA Yanagi Mikio et al. "Preparation of (nitrophenyl) pyrazoles as herbicides" p. 791, para. 1, Zusammenfassung–No. 226 556j & Japan; Kokai Tokyo Koho JP 61 165 373 (86 165 373).

*Chemical Abstracts*, vol. 102, No. 23, Jun. 10, 1985, 102:204066k, p. 609; "Mono (cyclopentadienyl) titanium (IV) derivatives . . . ", Pandey et al.

*Primary Examiner*—Patricia L. Morris
(74) *Attorney, Agent, or Firm*—Norris McLaughlin & Marcus

(57) ABSTRACT

Substituted triazolinone compounds of the formula:

(Ia)

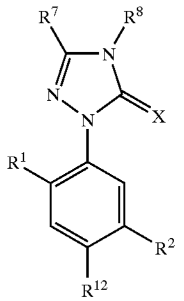

wherein the variables $R^1$, $R^2$, $R^7$, $R^8$, $R^{12}$ and X are as defined in the specification are useful as herbicides, plant growth regulators, insecticides and acaricides. Processes for the preparation of these compounds, and intermediates useful in such preparation are also disclosed.

19 Claims, No Drawings

N-ARLY-SUBSTITUTED NITROGEN-CONTAINING HETEROCYCLES, PROCESSES AND NOVEL INTERMEDIATES FOR THEIR PREPARATION, AND THEIR USE AS HERBICIDES AND PLANT GROWTH REGULATORS

This application is an continuation-in-part of U.S. Ser. No. 08/148,094, filed on Nov. 5, 1993, now abandoned; and also a continuation-in-part of U.S. Ser. No. 07/918,895, filed on Jul. 20, 1992, now U.S. Pat. No. 5,554,580, which is, in turn, a continuation of U.S. Ser. No. 07/618,335, filed on Nov. 26, 1990, now abandoned, which is, in turn, a division of U.S. Ser. No. 07/435,898, filed on Nov. 13, 1989, now U.S. Pat. No. 5,006,148.

The invention relates to novel N-aryl-substituted nitrogen-containing heterocycles, several processes and novel intermediates for their preparation, and their use as herbicides and plant growth regulators. The triazolinone compounds further have a utility as an insecticide or as an ascaricide (cf patent application Ser. No. 08/148,094) disclosure herein incorporated by reference.

It is known that certain N-aryl-substituted nitrogen-containing heterocycles, such as, for example, the compound 1-(2-chloro-4-trifluoromethylphenyl)-5-methyl-4-nitropyrazole, possess herbicidal properties (cf., for example, European Patent 200,872).

Likewise has been disclosed that certain substituted triazolinones such as, for example, the compound 3,4-dimethyl-1-(3-fluoro-4-cyano-phenyl)-1,2,4-triazolin-5-one or the compound 3-methyl-4-propargyl-1-(2,5-difluoro-4-cyano-phenyl)-1,2,4-triazolin-5-one have herbicidal properties (cf., for example, U.S. Pat. No. DE 3,839,480).

However, the herbicidal activity of these previously known compounds against problem weeds, as well as their tolerance by important crop plants, are not entirely satisfactory in all fields of application.

Nothing has been known to date about a plant growth-regulating effect of the previously known compounds.

Novel N-aryl-substituted nitrogen-containing heterocycles of the general formula (I)

(I)

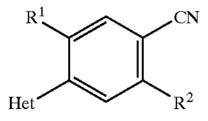

in which

Het represents a heterocycle of the formula

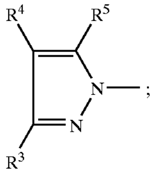 ; 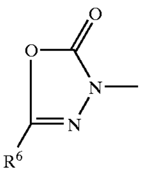 or 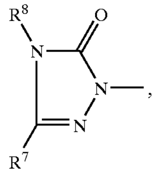 , $R^1$ represents hydrogen or halogen and $R^2$ represents halogen or a radical —X—$R^9$, where $R^3$ represents hydrogen, alkyl or halogenoalkyl and $R^4$ represents hydrogen, halogen, alkyl or halogenoalkyl, or $R^3$ and $R^4$ together represent double-linked alkanediyl, $R^5$ represents hydrogen, halogen, alkyl or halogenoalkyl, $R^6$ represents hydrogen, alkyl, alkoxyalkyl, halogenoalkyl, alkenyl, halogenoalkenyl, alkinyl, halogenoalkinyl, or represents optionally substituted cycloalkyl, $R^7$ represents hydrogen, alkyl, alkoxyalkyl, halogenoalkyl, alkenyl, halogenoalkenyl, alkinyl, halogenoalkinyl, or represents optionally substituted cycloalkyl and $R^8$ represents hydrogen, alkyl, halogenoalkyl, alkenyl, halogenoalkenyl, alkinyl or halogenoalkinyl, or $R^7$ and $R^8$ together represent double-linked alkanediyl, $R^9$ represents in each case optionally substituted alkyl, alkenyl, alkinyl or cycloalkyl and X represents oxygen or sulphur, have been found.

Additionally, new substituted triazolinones of the general formula (Ia)

(Ia)

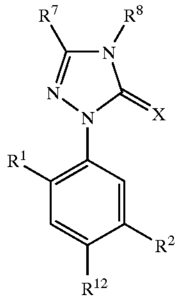

in which $R^1$ represents hydrogen or halogen, $R^2$ represents nitro, cyano, halogen, heterocyclylalkoxy, a radical of the formula $R^{13}$, —O—$R^{13}$, —S—$R^{13}$, —S(O)—$R^{13}$, —$SO_2$—O—$R^{13}$, —$SO_2$—O —$R^{13}$, —O—$SO_2$—$R^{13}$, —C(O) O—$R^{13}$, —$NR^{13}R^{14}$, —$SO_2$—$NR^{13}R^{14}$, —C(O)—NR—$R^{14}$, —NH—P(O)($OR^{13}$)($R^{14}$) or —NH—P(O)($OR^{13}$)($OR_{14}$)or a radical of the formula

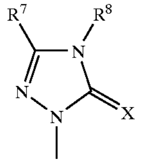

and

X represents oxygen or sulphur, where $R^7$ represents halogenalkyl, $R^8$ represents hydrogen, amino, cyano, alkyl, alkenyl, alkinyl, halogenoalkyl, halogenoalkenyl, halogenoalkinyl, alkoxyalkyl, alkylideneimino, or in each case optionally substituted cycloalkyl or cycloalkylalkyl, $R^{13}$ and $R^{14}$ independtly of one another in each case represent hydrogen or in each case straight-chain or branched, optionally substituted alkyl, alkenyl, alkinyl, cycloalkyl, cycloalkylalkyl, arylalkyl or aryl, $R^{12}$ represents cyano or nitro, have now been found.

Where appropriate, the compounds of the formula (I) or (Ia) can exist in the form of geometric and/or optical isomers or isomer mixtures of various compositions, depending on the nature of the substituents. The invention claims the pure isomers and the isomer mixtures.

Furthermore, it has been found that the novel N-aryl-substituted nitrogen-containing heterocycles of the general formula (I)

(I)

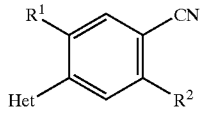

in which

Het represents a heterocycle of the formula

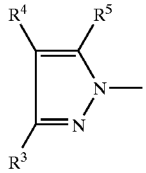 ; 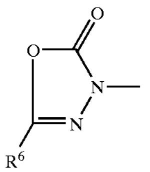 or 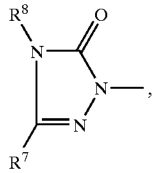 , $R^1$ represents hydrogen or halogen and $R^2$ represents halogen or a radical —X—$R^9$, where $R^3$ represents hydrogen, alkyl or halogenoalkyl and $R^4$ represents hydrogen, halogen, alkyl or halogenoalkyl, or $R^3$ and $R^4$ together represent double-linked alkanediyl, $R^5$ represents hydrogen, halogen, alkyl or halogenoalkyl, $R^6$ represents hydrogen, alkyl, alkoxyalkyl, halogenoalkyl, alkenyl, halogenoalkenyl, alkinyl, halogenoalkinyl, or represents optionally substituted cycloalkyl, $R^7$ represents hydrogen, alkyl, alkoxyalkyl, halogenoalkyl, alkenyl, halogenoalkenyl, alkinyl, halogenoalkinyl, or represents optionally substituted cycloalkyl and $R^8$ represents hydrogen, alkyl, halogenoalkyl, alkenyl, halogenoalkenyl, alkinyl or halogenoalkinyl, or $R^7$ and $R^8$ together represent double-linked alkanediyl, $R^9$ represents in each case optionally substituted alkyl, alkenyl, alkinyl or cycloalkyl and X represents oxygen or sulphur, are obtained by one of the processes described below:

(a) N-aryl-substituted nitrogen-containing heterocycles of the formula (Ia')

(Ia')

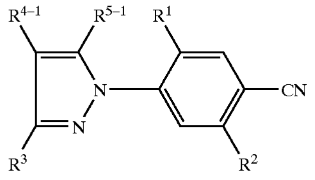

in which $R^{4-1}$ represents hydrogen, alkyl or halogenoalkyl or together with $R^3$ represents a double-linked alkanediyl radical, $R^{5-1}$ represents hydrogen, alkyl or halogenoalkyl and $R^1$, $R^2$ and $R^3$ have the abovementioned meaning, are obtained when 4-cyanophenylhydrazines of the formula (II)

(II)

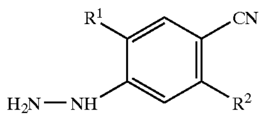

in which $R^1$ and $R^2$ have the abovementioned meaning, are reacted with 1,3-diketones of the formula (III)

(III)

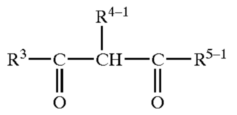

in which $R^3$, $R^{4-1}$ and $R^{5-1}$ have the abovementioned meaning, or with derivatives of these diketones, such as, for example, enol ethers, enol esters, ketals, enol ether ketals, enamines or β-halogenovinyl ketones, if appropriate in the presence of a diluent and if appropriate in the presence of a reaction auxiliary;

(b) N-aryl-substituted nitrogen-containing heterocycles of the formula (Ib')

(Ib')

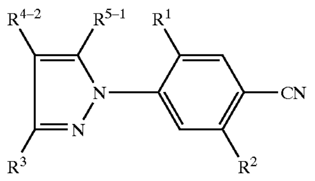

in which $R^{4-2}$ represents halogen, $R^{5-1}$ represents hydrogen, alkyl or halogenoalkyl and $R^1$, $R^2$ and $R^3$ have the abovementioned meaning, are obtained when N-aryl-substituted nitrogen-containing heterocycles of the formula (Ij')

(Ij')

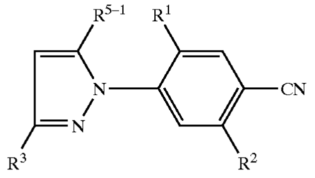

in which $R^1$, $R^2$, $R^3$ and $R^{5-1}$ have the abovementioned meaning, are reacted with a halogenating agent, if appropriate in the presence of a diluent;

(c) N-aryl-substituted nitrogen-containing heterocycles of the formula (Ic')

(Ic')

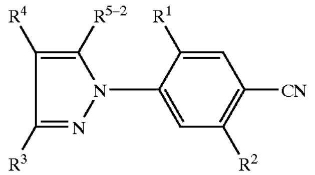

in which $R^{5-1}$ represents halogen and $R^1$, $R^2$, $R^3$ and $R^4$ have the abovementioned meaning, are obtained when N-aryl-pyrazolinones of the formula (IV)

(IV)

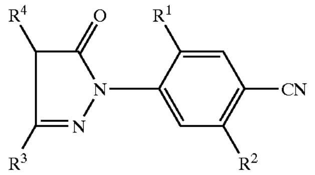

in which $R^1$, $R^2$, $R^3$ and $R^4$ have the abovementioned meaning, are reacted with a halogenating agent, if appropriate in the presence of a diluent and if appropriate in the presence of a reaction auxiliary;

(d) N-aryl-substituted nitrogen-containing heterocycles of the formula (Id')

(Id')

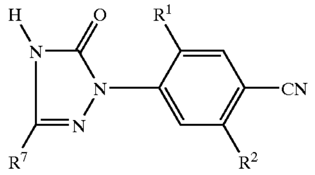

in which $R^1$, $R^2$ and $R^7$ have the abovementioned meaning, are obtained when 4-cyanophenylhydrazines of the formula (II)

(II)

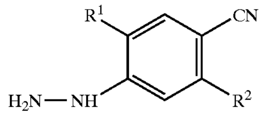

in which $R^1$ and $R^2$ have the abovementioned meaning, are reacted with iminocarboxylic acid esters of the formula (V)

(V)

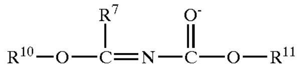

in which $R^{10}$ and $R^{12}$ independently of one another each represent alkyl and $R^7$ has the abovementioned meaning, if appropriate in the presence of a diluent;

(e) N-aryl-substituted nitrogen-containing heterocycles of the formula (Ie')

(Ie')

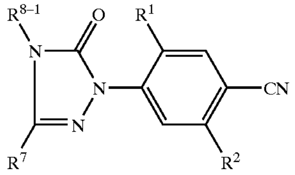

in which $R^{8-1}$ represents alkyl, halogenoalkyl, alkenyl, halo genoalkenyl, alkinyl or halogenoalkinyl and $R^1$, $R^2$ and $R^7$ have the abovementioned meaning, are obtained when N-aryl-substituted nitrogen-con (Id')

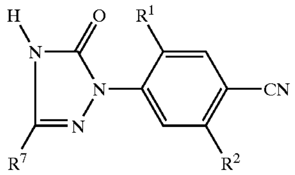

in which $R^1$, $R^2$ and $R^7$ have the abovementioned meaning, are reacted with alkylating agents of the formula (VI)

$$R^{8-1'}-E1 \quad \text{(VI)}$$

in which $R^{8-1}$ has the abovementioned meaning and $E^1$ represents an electron-withdrawing leaving group, if appropriate in the presence of a diluent and if appropriate in the presence of a reaction auxiliary;

(f) N-aryl-substituted nitrogen-containing heterocycles of the formula (If')

(If')

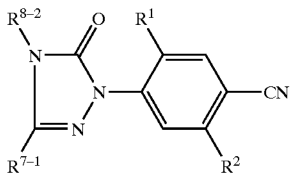

in which $R^{7-1}$ and $R^{8-2}$ together represent a double-linked alkanediyl radical are obtained when amidrazones of the formula (VII)

(VII)

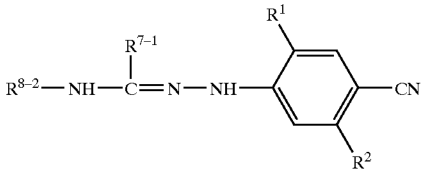

in which $R^{7-1}$ and $R^{8-2}$ have the abovementioned meaning, are reacted with phosgene, if appropriate in the presence of a diluent and if appropriate in the presence of a reaction auxiliary;

(g) N-aryl-substituted nitrogen-containing heterocycles of the formula (Ig)

(Ig')

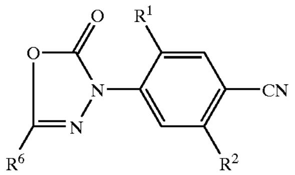

in which $R^1$, $R^2$ and $R^8$ have the abovementioned meaning, are obtained when phenylhydrazides of the formula (VIII)

(VIII)

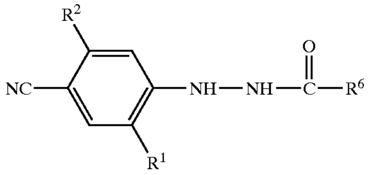

in which $R^1R^2$ and $R^6$ have the abovementioned meaning, are reacted with phosgene, if appropriate in the presence of a diluent and if appropriate in the presence of a reaction auxiliary;

(h) N-aryl-substituted nitrogen-containing heterocycles of the formula (Ih')

(Ih')

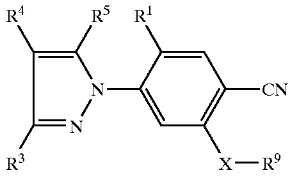

in which $R^1$, $R^3$, $R^4$, $R^5$, $R^9$ and X have the abovementioned meaning, are alternatively also obtained when (α) N-aryl-substituted nitrogen-containing hetero cycles of the formula (Ik')

(Ik')

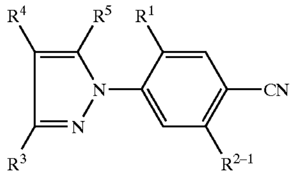

in which $R^{2-1}$ represents halogen and $R^1$, $R^3$, $R^4$ and $R^5$ have the abovementioned meaning, are reacted with alcohols or thiols of the formula (IX)

$R^9$—XH (IX)

in which $R^9$ and X have the abovementioned meaning, if appropriate in the presence of a diluent and if appropriate in the presence, of a reaction auxiliary, or when (β) (thio)phenol derivatives of the formula (X)

(X)

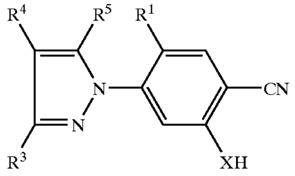

in which $R^1$, $R^3$, $R^4$, $R^5$ and X have the abovementioned meaning, are reacted with alkylating or acylating agents of the formula (XI)

$R^9$—$E^2$ (XI)

in which $R^9$ has the abovementioned meaning and $E^2$ represents an electron-withdrawing leaving group, if appropriate in the presence of a diluent and if appropriate in the presence of a reaction auxiliary;

(i) n-aryl-substituted nitrogen-containing heterocycles of the formula (Ii')

(Ii')

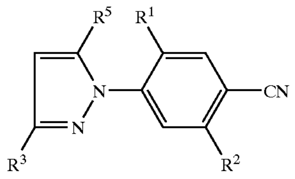

in which $R^1$, $R^2$, $R^3$ and $R^5$ have the abovementioned meaning, are alternatively also obtained when 1-arylpyrazolyl-4-carboxylic acid esters of the formula (XII)

(XII)

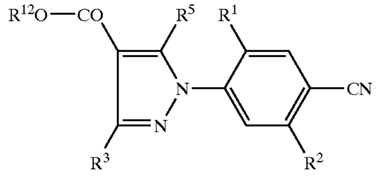

in which $R^{12}$ represents alkyl and $R^1$, $R^2$, $R^3$ and $R^5$ have the abovementioned meaning, are hydrolyzed in the presence of an acid or basic catalyst and, if appropriate, in the presence of a diluent, and the product is subsequently thermally decarboxylated.

Finally, it has been found that the novel N-aryl-substituted nitrogen-containing heterocycles of the general formula (I) possess herbicidal and plant growth-regulating properties.

Furthermore, it has been found that the new substituted triazolinones of the general formula (Ia)

(Ia)

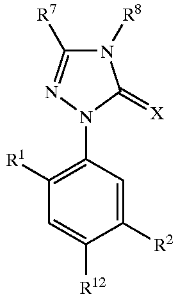

in which $R^1$, $R^2$, $R^7$, $R^8$, and $R^{12}$ are defined above are obtained when $R^4$ represents cyano or nitro, a") 1H-triazolinones of the Formula (XX)

(XX)

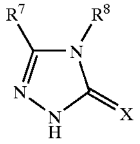

in which $R^7$, $R^8$ and X have the abovementioned meanings, are reacted with halogenobenzene derivatives of the formula (XXI)

(XXI)

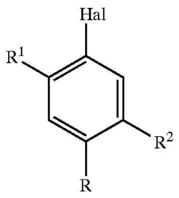

in which $R^1$, $R^2$, and $R^{12}$ have the abovementioned meanings and Hal represents halogen, if appropriate in the presence of a diluent and if appropriate in the presence of a reaction auxiliary, or when b") substituted triazolinones of the formula (Ia")

(Ia")

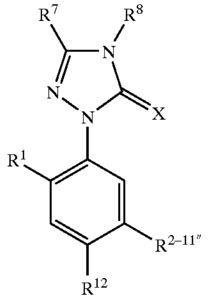

in which $R^1$, $R^7$, $R^8$, $R^{12}$ and X have the abovementioned meanings and $R^{2\text{-}1"}$ represents halogen, are reacted with nucleophiles of the formula (XXII)

$R^{6\text{-}1"}$—Z—H (XXII)

in which

Z represents oxygen or sulphur and $R^{6\text{-}1"}$ represents in each case straight-chain or branched, optionally substituted alkyl, alkenyl, alkinyl, cycloalkyl or aryl, and furthermore, in the event that Z represents oxygen, $R^{6\text{-}1"}$ also represents heterocyclyl, if appropriate in the presence of a diluent and if appropriate in the presence of a reaction auxiliary, or when c") substituted tirazolinones of the formula (Ib")

(Ib")

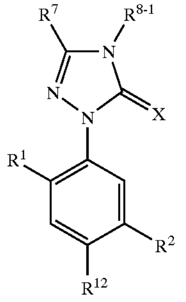

in which $R^1$, $R^2$, $R^7$, $R^{12}$ and X have the abovementioned meanings and $R^{8\text{-}1}$ represents amino, are reacted with sodium nitrite in the presence of an acid and, if appropriate, in the presence of a diluent, or when d") substituted triazolinones of the formula (Ic")

(Ic")

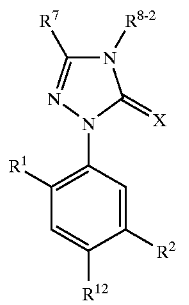

in which $R^1$, $R^2$, $R^7$, $R^{12}$ and X have the abovementioned meanings and $R^{8-2}$ represent hydrogen, are reacted with alkylating agents of the formula (XXIII)

$R^{2-3"}$—E (XXIII)

in which $R^{2-3"}$ represents alkyl, alkenyl, alkinyl, halogenoalkyl, halogenoalkenyl, halogenoalkinyl, alkoxyalkyl or optionally substituted cycloalkyl and E represents an electron-attracting leaving group, if appropriate in the presence of a diluent and if appropriate in the presence of a reaction auxiliary.

Finally, it has been found that the new substituted triazolinones of the general formula (Ia) have herbicidal, insecticidal and acaricidal properties.

Surprisingly, the substituted triazolinones of the general formula (Ia) according to the invention have a considerably better herbicidal activity against problem weeds and unexpectedly, at the same time, also a considerably better acaricidal activity compared with the substituted triazolinones known from the prior art such as, for example, the compound 3,4-dimethyl-1-(3-fluoro-4-cyano-phenyl)-1,2,4-triazolin-5-one or the compound 3-methyl-4-propargyl-1-(2,5-difluoro-4-cyano-phenyl)-1,2,4,triazolin-5-one, which are similar compounds chemically and from the point of view of their action.

Surprisingly, the N-aryl-substituted nitrogen-containing heterocycles of the general formula (I) according to the invention show a markedly better herbicidal activity towards important problem weeds when compared with the N-aryl-substituted nitrogen-containing heterocycles known from the prior art, such as, for example, the compound 1-(2-chloro-4-trifluoromethylphenyl)-5-methyl-4-nitropyrazole, which are chemically similar compounds of a similar type of action, while having a comparatively good or better selectivity towards crop plants.

Moreover, the compounds of the formula (I) according to the invention unexpectedly show an additional, plant growth-regulating effect.

Formula (I) provides a general definition of the N-aryl-substituted nitrogen-containing heterocycles according to the invention. Preferred compounds of the formula (I) are those in which Het represents a heterocycle of the formula

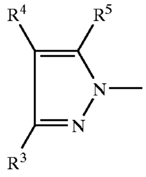 ; 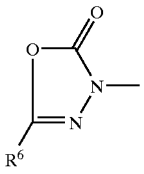 or 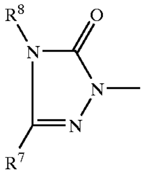 , $R^1$ represents hydrogen, fluorine, chlorine or bromine and $R^2$ represents fluorine, chlorine or bromine, or represents a radical —X—$R^9$, where $R^3$ represents hydrogen, represents straight-chain or branched alkyl having 1 to 6 carbon atoms or represents straight-chain or branched halogenoalkyl having 1 to 4 carbon atoms and 1 to 9 identical or different halogen atoms and $R^4$ represents hydrogen, fluorine, chlorine, bromine, iodine, represents straight-chain or branched alkyl having 1 to 6 carbon atoms or represents straight-chain or branched halogenoalkyl having 1 to 4 carbon atoms and 1 to 9 identical or different halogen atoms, or $R^3$ and $R^4$ together represent a double-linked alkanediyl radical having 2 to 6 carbon atoms, $R^5$ represents hydrogen, fluorine, chlorine, bromine, iodine, represents straight-chain or branched alkyl having 1 to 6 carbon atoms or represents straight-chain or branched halogenoalkyl having. 1 to 4 carbon atoms and 1 to 9 identical or different halogen atoms, $R^6$ represents hydrogen, represents in each case straight-chain or branched alkyl having 1 to 6 carbon atoms, alkenyl having 3 to 6 carbon atoms, alkinyl having 3 to 6 carbon atoms, halogenoalkyl having 1 to 4 carbon atoms and 1 to 9 identical or different halogen atoms, halogenoalkenyl having 3 to 6 carbon atoms and 1 to 5 identical or different halogen atoms, halogenoalkinyl having 3 to 6 carbon atoms and 1 to 5 identical or different halogen atoms or alkoxyalkyl having in each case 1 to 4 carbon atoms in the individual straight-chain or branched alkyl moieties or represents cycloalkyl which has 3 to 7 carbon atoms and which is optionally monosubstituted or polysubstituted by identical or different substituents, suitable substituents being: halogen, and in each case straight-chain or branched alkyl or alkoxy, each having 1 to 4 carbon atoms, $R^7$ represents hydrogen, represents in each case straight-chain or branched alkyl having 1 to 6 carbon atoms, alkenyl having 3 to 6 carbon atoms, alkinyl having 3 to 6 carbon atoms, halogenoalkyl having 1 to 4 carbon atoms and 1-to 9 identical or different halogen atoms, halogenoalkenyl having 3 to 6 carbon atoms and 1 to 5 identical or different halogen atoms, halogenoalkinyl having 3 to 6 carbon atoms and 1 to 5 identical or different halogen atoms or alkoxyalkyl having in each case 1 to 4 carbon atoms in the individual straight-chain or branched alkyl moieties or represents cycloalkyl which has 3 to 7 carbon atoms and which is optionally monosubstituted or polysubstituted by identical or different substituents, suitable substituents being: halogen, and in each case straight-chain or branched alkyl or alkoxy, having in each case 1 to 4 carbon atoms, and $R^8$ represents hydrogen or represents in each case straight-chain or branched alkyl having 1 to 6 carbon atoms, alkenyl having 3 to 6 carbon atoms, alkinyl having 3 to 6 carbon atoms, halogenoalkyl having 1 to 4 carbon atoms and 1 to 9 identical or different halogen atoms, halogenoalkenyl having 3 to 6 carbon atoms and 1 to 5 identical or different halogen atoms or halogenoalkinyl having 3 to 6 carbon atoms and 1 to 5 identical or different halogen atoms, or $R^7$ and $R^8$ together represent a double-linked alkanediyl radical having 2 to 6 carbon atoms, $R^9$ represents in each case straight-chain or branched alkyl having 1 to 8 carbon atoms, alkenyl having 2 to 8 carbon atoms, alkinyl having 3 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 3 to 8 carbon atoms and 1 to 13 identical or different halogen atoms, represents cyanoalkyl, alkoxyalkyl, alkylthioalkyl, halogenoalkoxyalkyl, alkoxyalkoxyalkyl, (bis-alkoxy)alkyl, (bis-alkylthio) alkyl, alkylcarbonylalkyl, alkoxycarbonylalkyl or alkoxyalkoxycarbonylalkyl, each having 1 to 8 carbon atoms in the individual alkyl moieties and if appropriate 1 to 9 identical or different halogen atoms, represents cycloalkyl, cycloalkyloxycarbonylalkyl or cycloalkylalkyl, each of which has 3 to 7 carbon atoms in the cycloalkyl moiety and if appropriate 1 to 4 carbon atoms in the straight-chain or branched alkyl moiety-and each of which is optionally monosubstituted or polysubstituted by identical or different substituents, suitable substituents in each case being: halogen and in each case straight-chain or branched alkyl or alkoxy, each having 1 to 4 carbon atoms, $R^9$ furthermore represents oxetanylalkyl, tetrahydrofuranylalkyl, tetrahydrofuranylalkyloxycarbonylalkyl or tetrahydropyranylalkyl, each of which has 1 to 3 carbon atoms in the respective alkyl moieties and each of which is optionally substituted by alkyl having 1 to 4 carbon atoms or. $R^9$ represents aralkyl which has 6 to 10 carbon atoms in the aryl moiety and 1 to 4 carbon atoms in the straight-chain or branched alkyl moiety and which is optionally monosubstituted or polysubstituted by identical or different substituents, suitable aryl substituents being: halogen, cyano, nitro, in each case straight-chain or branched alkyl, alkoxy, alkylthio or alkoxycarbonyl, each having 1 to 4 carbon atoms, or in each case straight-chain or branched halogenoalkyl, halogenoalkoxy or halogenoalkylthio, each having 1 to 4 carbon atoms and 1 to 9 identical or different halogen atoms, and X represents oxygen or sulphur.

Particularly preferred compounds of the formula (I) are those in which

Het represents a heterocycle of the formula

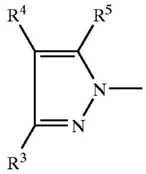
;
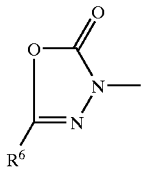
or
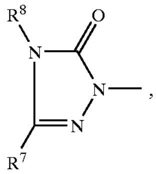
, $R^1$ represents hydrogen, fluorine or chlorine and $R^2$ represents fluorine, chlorine or represents a radical —X—$R^9$, where $R^3$ represents hydrogen, methyl, ethyl, n- or i-propyl, n-, i-, s- or t-butyl, represents fluoromethyl, difluoromethyl, trifluoromethyl, chloromethyl, dichloromethyl, trichloromethyl, difluorochloromethyl or dichlorofluoromethyl and $R^4$ represents hydrogen, fluorine, chlorine, bromine, represents methyl, ethyl, n- or i-propyl, n-, i-, s- or t-butyl, represents fluoromethyl, difluoromethyl, trifluoromethyl, chloromethyl, dichloromethyl, trichloromethyl, difluorochloromethyl or dichlorofluoromethyl, or $R^3$ and $R^4$ together represent a 1,3-propanediyl radical, a 1,4-butanediyl radical or a 1,5-pentanediyl radical, $R^5$ represents hydrogen, fluorine, chlorine, bromine, represents methyl, ethyl, n- or i-propyl, n-, i-, s- or t-butyl, represents fluoromethyl, difluoromethyl, trifluoromethyl, chloromethyl, dichloromethyl, trichloromethyl, difluorochloromethyl or dichlorofluoromethyl, $R^6$ represents hydrogen, represents methyl, ethyl, n- or i-propyl, n-, i-, s- or t-butyl, represents methyl, ethyl or t-butyl, each of which is monosubstituted, disubstituted or trisubstituted by fluorine and/or chlorine, represents allyl, represents n- or i-butenyl, represents chloroallyl, represents dichloroallyl, represents propargyl, represents chloropropargyl, represents methoxymethyl or represents cyclopropyl, cyclopentyl or cyclohexyl, each of which is optionally monosubstituted to pentasubstituted by identical or different substituents from the series comprising fluorine, chlorine, methyl and/or methoxy, $R^7$ represents hydrogen, represents methyl, ethyl, n- or i-propyl, n-, i-, s- or t-butyl, represents methyl, ethyl or t-butyl, each of which is optionally monosubstituted, disubstituted or trisubstituted by fluorine and/or chlorine, represents allyl, represents n- or i-butenyl, represents chloroallyl, represents dichloroallyl, represents propargyl, represents chloropropargyl, represents methoxymethyl or represents cyclopropyl, cyclopentyl or cyclohexyl, each of which is optionally monosubstituted to pentasubstituted by identical or different substituents from the series comprising fluorine, chlorine, methyl and/or methoxy and $R^8$ represents hydrogen, represents methyl, ethyl, n- or i-propyl, n-, i-, s- or t-butyl, represents methyl, ethyl or t-butyl, each of which is optionally monosubstituted, disubstituted or trisubstituted by fluorine and/or chlorine, represents allyl, represents n- or i-butenyl, represents chloroallyl, represents dichloroallyl, represents propargyl or represents chloropropargyl, or $R^7$ and $R^8$ together represent a 1,3-propanediyl radical, a 1,4-butanediyl radical or a 1,5-pentanediyl radical, $R^9$ represents methyl, ethyl, n- or i-propyl, n-, i-, s- or t-butyl, represents allyl, propargyl, represents in each case straight-chain or branched pentyl, hexyl, butenyl, pentenyl, hexenyl, butinyl, pentinyl or hexinyl, moreover represents in each case straight-chain or branched halogenoalkyl having 1 to 4 carbon atoms, halogenoalkinyl or halogenoalkenyl having in each case 3 to 5 carbon atoms and in each case 1 to 8 identical or different halogen atoms, in particular fluorine, chlorine or bromine, represents in each case straight-chain or branched cyanoalkyl, alkoxyalkyl, alkylthioalkyl, halogenoalkoxyalkyl, alkoxyalkoxyalkyl, alkylcarbonylalkyl, alkoxycarbonylalkyl or alkoxyalkoxycarbonylalkyl, each having 1 to 5 carbon atoms in the individual alkyl moieties, moreover represents cyclopropylmethyl, cyclopentylmethyl, cyclohexylmethyl, cyclopropyloxycarbonylmethyl, cyclopentyloxycarbonylmethyl, cyclohexyloxycarbonylmethyl, cyclopropyl, cyclopentyl or cyclohexyl, each of which is optionally monosubstituted to trisubstituted by identical or different substituents from the series comprising methyl, methoxy, fluorine or chlorine, represents oxetanylmethyl, oxetanylethyl, tetrahydrofuranylmethyl, tetrahydrofuranylethyl, tetrahydrofuranylmethyloxycarbonylmethyl, tetrahydropyranylmethyl or tetrahydropyranylethyl, each of which is optionally substituted by methyl or ethyl, or represents benzyl or phenylethyl, each of which is optionally monosubstituted to trisubstituted by identical or different substitutents, suitable substituents in each case being: fluorine, chlorine, bromine, cyano, nitro, methyl, ethyl, n- or i-propyl, n-, i-, s- or t-butyl, methoxy, ethoxy, n- or i-propoxy, methylthio, ethylthio, methoxycarbonyl, ethoxycarbonyl, trifluoromethyl, trifluoromethoxy or trifluoromethylthio and X represents oxygen or sulphur.

Very particularly preferred compounds of the formula (I) are those in which

Het represents a heterocycle of the formula

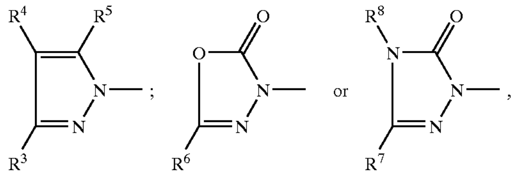

$R^1$ represents hydrogen or fluorine and $R^2$ represents fluorine or represents a radical —X—$R^9$, where $R^3$ represents hydrogen, methyl, ethyl, n- or i-propyl, n-, i-, s- or t-butyl, represents fluoromethyl, difluoromethyl or trifluoromethyl and $R^4$ represents hydrogen, chlorine, bromine, methyl or trifluoromethyl, or $R^3$ and $R^4$ together represent a 1,3-propanediyl radical or represent a 1,4-butanediyl radical, $R^5$ represents hydrogen, chlorine, bromine, methyl, ethyl, t-butyl or trifluoromethyl, $R^6$ represents methyl, ethyl, n- or i-propyl, n-, i-, s- or t-butyl, represents trifluoromethyl, represents fluoro-1,1-dimethylethyl or represents cyclopropyl which is optionally monosubstituted to pentasubstituted by identical or different substituents from the series comprising fluorine, chlorine or methyl, $R^7$ represents methyl and $R^8$ represents hydrogen, methyl, ethyl, allyl, propargyl, fluoromethyl, difluoromethyl or trifluoromethyl, or $R^7$ and $R^8$ together represent a 1,3-propanediyl radical or represent a 1,4-butanediyl radical, $R^9$ represents methyl, ethyl, n- or i-propyl, n-, i-, s- or t-butyl, represents allyl, propargyl, represents in each case straight-chain or branched pentyl, hexyl, butenyl, pentenyl, hexenyl, butinyl, pentinyl or hexinyl, moreover represents in each case straight-chain or branched halogenoalkyl having 1 to 4 carbon atoms or halogenoalkenyl having 3 to 5 carbon atoms and in each case 1 to 5 identical or different halogen atoms, in particular fluorine, chlorine or bromine, represents in each case straight-chain or branched cyanoalkyl, alkoxyalkyl, alkoxyalkoxyalkyl or alkoxycarbonylalkyl having in each case 1 to 5 carbon atoms in the individual alkyl moieties, moreover represents cyclopropylmethyl, cyclopentylmethyl, cyclohexylmethyl, cyclopropyloxycarbonylmethyl, cyclopentyloxycarbonylmethyl, cyclohexyloxycarbonylmethyl, cyclopropyl, cyclopentyl, cyclohexyl, each of which is optionally monosubstituted to trisubstituted by identical or different substituents from the series comprising methyl, methoxy, fluorine or chlorine, represents oxetanylmethyl, oxetanylethyl, tetrahydrofuranylmethyl, tetrahydrofuranylmethyloxycarbonylmethyl or tetrahydropyranylmethyl, each of which is optionally substituted by methyl or ethyl, or represents benzyl or phenylethyl, each of which is optionally monosubstituted to trisubstituted by identical or different substituents, suitable substituents in each case being; fluorine, chlorine, bromine, cyano, nitro, methyl, ethyl, n- or i-propyl, n-, i-, s- or t-butyl, methoxy, ethoxy, n- or i-propoxy, methylthio, ethylthio, methoxycarbonyl, ethoxycarbonyl, trifluoromethyl, trifluoromethoxy or trifluoromethylthio, and X represents oxygen or sulphur.

Formula (Ia) provides a general definition of the substituted triazolinones according to the invention. Preferred compounds of the formula (Ia) are those in which $R^7$ represents straight-chain or branched halogenoalkyl having 1 to 6 carbon atoms and 1 to 13 identical or different halogen atoms, in particular fluorine, chlorine, bromine or iodine, $R^8$ represents hydrogen, amino, cyano, straight-chain or branched alkyl having 1 to 8 carbon atoms, in each case straight-chain or branched alkenyl or alkinyl, each of which has 2 to 6 carbon atoms, straight-chain or branched halogenoalkyl having 1 to 6 carbon atoms and 1 to 13 identical or different halogen atoms, in particular fluorine, chlorine, bromine or iodine, in each case straight-chain or branched halogenoalkenyl or halogenoalkinyl, each of which has 2 to 6 carbon atoms and 1 to 11 identical or different halogen atoms, in particular fluorine, chlorine, bromine or iodine, straight-chain or branched alkoxyalkyl having 1 to 4 carbon atoms in each of the individual alkyl moieties, straight-chain or branched alkylideneimino having 1 to 8 carbon atoms, or cycloalkyl or cycloalkylalkyl, each of which has 3 to 8 carbon atoms in the cycloalkyl moiety and, if appropriate, 1 to 4 carbon atoms in the straight-chain or branched alkyl moiety, and each of which is optionally monosubstituted or polysubstituted in the cycloalkyl moiety by identical or different halogen substituents, in particular fluorine, chlorine, bromine and/or iodine, $R^1$ represents hydrogen, fluorine, chlorine, bromine or iodine, $R^2$ represents nitro, cyano, fluorine, chlorine, bromine, iodine or heterocyclyl —$C_1$–$C_4$-alkoxy, the heterocyclyl radical being represented by a three- to seven-membered, optionally benzo-fused, saturated or unsaturated heterocycle having 1 to 3 identical or different hetero atoms, in particular nitrogen, oxygen and/or sulphur, or a radical of the formula $R^{12}$, —O—$R^{13}$, —S—$R^{13}$, —S(O)—$R^{13}$, —$SO_2$—$R^{13}$, —$SO_2$—O—$R^{13}$, —O-$SO_2$—$R^{13}$, —C(O)—O—$R^{13}$, —$NR^{13}R^{14}$, —$SO_2$—$NR^{13}R^{14}$, —C(O)—$NR^{13}R^{14}$, —NH—P(O)($OR^{13}$)($R^{14}$) or —NH—P(O)($OR^{13}$)($OR^{14}$) or a radical of the formula

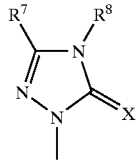

and

X represents oxygen or sulphur, where $R^{13}$ and $R^{14}$ independently of one another in each case represent hydrogen or straight-chain or branched alkyl which has 1 to 8 carbon atoms and which is optionally monosubstituted or polysubstituted by identical or different substituents, suitable substituents being: halogen, in particular fluorine, chlorine, bromine and/or iodine, cyano, carboxyl, carbamoyl, in each case straight-chain or branched alkoxy, alkoxy—alkoxy, alkylthio, alkylsulphinyl, alkylsulphonyl, alkoxycarbonyl, alkoxycarbonylalkyl, N-alkylaminocarbonyl, cycloalkylaminocarbonyl, N,N-dialkylaminocarbonyl, trialkylsilyl or alkylsulphonylaminocarbonyl, each of which has 1 to 8 carbon atoms in the individual alkyl moieties, or heterocyclyl, the heterocyclyl being represented by a five- to seven-membered, optionally benzo-fused, saturated or unsaturated heterocycle having 1 to 3 identical or different hetero atoms, in particular nitrogen, oxygen and/or sulphur;

$R^{13}$ and $R^{14}$ furthermore represent alkenyl or alkinyl, each of which has 2 to 8 carbon atoms and each of which is optionally monosubstituted or polysubstituted by identical or different halogen substituents, in particular fluorine, chlorine, bromine and/or iodine;

$R^{13}$ and $R^{14}$ furthermore represent cycloalkyl which has 3 to 7 carbon atoms and which is optionally monosubstituted or polysubstituted by identical or different halogen substituents, in particular fluorine, chlorine, bromine and/or iodine, and/or by straight-chain or branched alkyl having 1 to 4 carbon atoms, or represent $C_3$-cycloalkyl-$C_1$–$C_3$-alkyl, or $R^{13}$ and $R^{14}$ represent arylalkyl or aryl, each of which has 6 to 10 carbon atoms in the aryl moiety and, if appropriate, 1 to 4 carbon atoms in the straight-chain or branched alkyl moiety, and each of which is optionally monosubstituted or polysubstituted in the aryl moiety by identical or different substituents, suitable aryl substituents in each case being:

halogen, cyano, nitro, in each case straight-chain or branched alkyl, alkoxy, alkylthio, alkylsulphinyl or alkylsulphonyl, each of which has 1 to 6 carbon atoms, in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched alkoxycarbonyl or alkoximinoalkyl, each of which has 1 to 6 carbon atoms in the individual alkyl moieties, and phenyl which is optionally monosubstituted or polysubstituted by identical or different halogen substituents and/or by straight-chain or branched alkyl or alkoxy, each of which has 1 to 6 carbon atoms, and/or by straight-chain or branched halogenoalkyl or halogenoalkoxy, each of which has 1 to 6 carbon atoms and 1 to 13 identical or different halogen atoms.

Particularly preferred compounds of the formula (Ia) are those in which $R^7$ represents straight-chain or branched halogenoalkyl having 1 to 4 carbon atoms and 1 to 9 identical or different halogen atoms, in particular fluorine, chlorine or bromine, $R^8$ represents hydrogen, amino, cyano, straight-chain or branched alkyl having 1 to 6 carbon atoms, in each case straight-chain or branched alkenyl or alkinyl, each of which has 2 to 4 carbon atoms, straight-chain or branched halogenoalkyl having 1 to 4 carbon atoms and 1 to 9 identical or different halogen atoms, in particular fluorine, chlorine or bromine, in each case straight-chain or branched halogenoalkenyl or halogenoalkinyl, each of which has 2 to 4 carbon atoms and 1 to 7 identical or different halogen atoms, in particular fluorine, chlorine or bromine, straight-chain or branched alkoxyalkyl having 1 to 3 carbon atoms in each of the individual alkyl moieties, straight-chain or branched alkylideneimino having 1 to 6 carbon atoms, or cycloalkyl or cycloalkylalkyl, each of which has 3 to 7 carbon atoms in the cycloalkyl moiety and, if appropriate, 1 to 3 carbon atoms in the straight-chain or branched alkyl moiety, and each of which is optionally monosubstituted to tetrasubstituted in the cycloalkyl moiety by identical or different halogen substituents, in particular fluorine, chlorine and/or bromine, $R^1$ represents hydrogen, fluorine, chlorine or bromine, $R^{12}$ represents cyano or nitro, $R^2$ represents nitro, cyano, fluorine, chlorine, bromine or heterocyclyl —$C_1$–$C_3$-alkoxy, the heterocyclyl radical being represented by a four- or six-membered, saturated or unsaturated heterocycle having 1 to 3 identical or different hetero atoms, in particular nitrogen, oxygen and/or sulphur, or a radical of the formula $R^6$, —O—$R^6$, —S—$R^6$, —S(O)—$R^6$, —$SO_2$—$R^6$, —$SO_2$—O—$R^6$, —O—$SO_2$—$R^6$, —C(O)—O—$R^6$, —$NR^6R^7$, —$SO_2$—$NR^6R^7$, —C(O)—$NR^6R^7$, —NH—P(O)($OR^6$)($R^7$) or —NH—P(O)($OR^6$)($OR^7$) or a radical of the formula

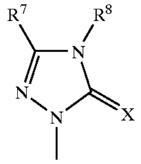

and

X represents oxygen or sulphur, where $R^{13}$ and $R^{14}$ independently of one another in each case represent hydrogen or straight-chain or branched alkyl which has 1 to 6 carbon atoms and which is optionally monosubstituted, suitable substituents being:

cyano, carboxyl, carbamoyl, in each case straight-chain or branched alkoxy, alkoxyalkoxy, alkylthio, alkylsulphinyl, alkylsulphonyl, alkoxycarbonyl, alkoxycarbonylalkyl, N-alkylaminocarbonyl, N,N-dialkylaminocarbonyl, trialkylsilyl or alkylsulphonylaminocarbonyl, each of which has 1 to 6 carbon atoms in the individual alkyl moieties, or heterocyclyl, the heterocyclyl radical being represented by a five- or six-membered, saturated or unsaturated heterocycle having 1 to 3 identical or different hetero atoms, in particular nitrogen, oxygen and/or sulphur;

$R^{13}$ and $R^{14}$ furthermore represent straight-chain or branched halogenoalkyl having 1 to 4 carbon atoms and 1 to 9 identical or different halogen atoms, in particular fluorine, chlorine or bromine and being optionally further substituted $C_{1-2}$ alkoxycarbonyl, $C_{1-6}$ cycloalkylaminocarbonyl or cyano, $R^{13}$ and $R^{14}$ furthermore represent alkenyl or alkinyl, each of which has 2 to 6 carbon atoms and each of which is optionally monosubstituted to trisubstituted by identical or different halogen substituents, in particular fluorine, chlorine or bromine;

$R^{13}$ and $R^{14}$ furthermore represent cycloalkyl which has 3 to 6 carbon atoms and which is optionally monosubstituted to tetrasubstituted by identical or different halogen substituents, in particular fluorine, chlorine or bromine, and/or by straight-chain or branched alkyl having 1 to 3 carbon atoms, or represent $C_{3-6}$-cycloalkyl-$C_1$–$C_2$-alkyl, or represent phenylalkyl or phenyl, the first-mentioned has 1 to 3 carbon atoms in the straight-chain or branched alkyl moiety and each of which is optionally monosubstituted to trisubstituted in the phenyl moiety by identical or different substituents, suitable phenyl substituents in each case being:

halogen, cyano, nitro, in each case straight-chain or branched alkyl, alkoxy, alkylthio, alkylsulphinyl or alkylsulphonyl, each of which has 1 to 4 carbon atoms, in each case straight-chain or branched halogenoalkyl, halogenoalkoxy, halogenoalkylthio, halogenoalkylsulphinyl or halogenoalkylsulphonyl, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different halogen substituents and/or by straight-chain or branched alkyl or alkoxy, each of which has 1 to 4 carbon atoms, and/or by straight-chain or branched halogenoalkyl or halogenoalkoxy, each of which has 1 to 4 carbon atoms and 1 to 9 identical or different halogen atoms.

Very particularly preferred compounds of the formula (Ia) are those in which $R^7$ represents halogenoalkyl having 1 or 2 carbon atoms and 1 to 5 identical or different halogen atoms, in particular fluorine or chlorine, $R^8$ represents hydrogen, amino, cyano, straight-chain or branched alkyl having 1 to 4 carbon atoms, in each case straight-chain or branched alkenyl or alkinyl, each of which has 2 to 3 carbon atoms, halogenoalkyl having 1 or 2 carbon atoms and 1 to 5 identical or different halogen atoms, in particular fluorine, chlorine or bromine, in each case straight-chain or branched halogenoalkenyl or halogenoalkinyl, each of which has 2 to 3 carbon atoms and 1 to 3 identical or different halogen atoms, in particular fluorine or chlorine, straight-chain or branched alkoxyalkyl having 1 or 2 carbon atoms in each of the individual alkyl moieties, straight-chain or branched alkylideneimino having 1 to 6 carbon atoms, or cyclopropyl, cyclopropylmethyl, cyclohexyl or cyclohexylmethyl, each of which is optionally monosubstituted or disubstituted in the cycloalkyl moiety by identical or different halogen substituents, in particular fluorine or chlorine, $R^1$ represents hydrogen, fluorine or chlorine, $R^2$ represents nitro, cyano, fluorine, chlorine, bromine or heterocyclylmethoxy, the heterocyclyl radical being represented by a five- or six-membered, saturated or unsaturated heterocycle having 1 to 3 identical or different hetero atoms, in particular nitrogen, oxygen and/or sulphur, or represents a radical of the formula $R^{13}$, —O—$R^{13}$, —S—$R^{13}$, —S(O)—$R^{13}$, —$SO_2$—$R^{13}$, —$SO_2$—O—$R^{13}$, —O—$SO_2$—$R^{13}$, —C(O)—O—$R^{13}$, —$NR^{13}R^{14}$, —SO—$NR^{13}R^{14}$, —C(O)—NR $R^{14}$, —NH—P(O)($OR^{13}$)($R^{14}$) or —NH—P(O)($OR^{13}$)($OR^{14}$) or a radical of the formula

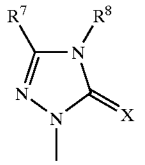

$R^{12}$ represents cyano or nitro, and

X represents oxygen or sulphur, where $R^{13}$ and $R^{14}$ independently of one another in each case represent hydrogen or optionally monosubstituted straight-chain or branched alkyl having 1 to 4 carbon atoms, suitable substituents being:

cyano, carboxyl, carbamoyl, in each case straight-chain or branched alkoxy, alkoxyalkoxy, alkylthio, alkylsulphinyl, alkylsulphonyl, alkoxycarbonyl, alkylcarbonylalkyl, N-alkylaminocarbonyl, N,N-dialkylaminbcarbonyl, trialkylsilyl or alkylsulphonylaminocarbonyl, each of which has 1 to 4 carbon atoms in the individual alkyl moieties, or heterocyclyl, the heterocyclyl radical being represented by a five- or six-membered saturated or unsaturated heterocycle having 1 to 3 identical or different hetero atoms, in particular nitrogen, oxygen and/or sulphur;

$R^{13}$ and $R^{14}$ furthermore represent halogenoalkyl having 1 or 2 carbon atoms and 1 to 5 identical or different halogen atoms, in particular fluorine or chlorine and being optionally further substituted by methoxycarbonyl, ethoxycarbonyl, cyano or cyclopropylaminocarbonyl;

$R^{13}$ and $R^{14}$ furthermore represent alkenyl or alkinyl, each of which has 2 to 5 carbon atoms and each of which is optionally monosubstituted by halogen, in particular fluorine or chlorine;

$R^{13}$ and $R^{14}$ furthermore represent cyclopropyl or cyclohexyl, each of which is optionally monosubstituted or disubstituted by identical or different substituents from the series comprising fluorine, chlorine, methyl and/or ethyl, or represent cyclopropylmethyl, cyclopentylmethyl or cyclohexylmethyl, or $R^{13}$ and $R^{14}$ represent phenylalkyl or phenyl, the first-mentioned has 1 or 2 carbon atoms in the alkyl moiety and each of which is optionally monosubstituted or disubstituted in the phenyl moiety by identical or different substituents, suitable phenyl substituents in each case being:

fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, methylsulphonyl, trifluoromethyl, difluoromethyl, trifluoromethoxy, difluoromethoxy, trifluoromethylthio, trfluoromethylsulphinyl, trifluoromethylsulphonyl, methoxycarbonyl, ethoxycarbonyl, methoximinomethyl, methoximinoethyl, ethoximinomethyl, ethoximinoethyl, or phenyl which is optionally monosubstituted to disubstituted by identical or different substituents from the series comprising fluorine, chlorine, bromine, methyl, ethyl, methoxy, ethoxy, trifluoromethyl and/or trifluoromethoxy.

The following N-aryl-substituted nitrogen-containing heterocycles of the general formula (I) may be mentioned individually in addition to the compounds mentioned in the Preparation Examples:

(I)

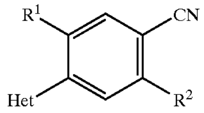

| Het | $R^1$ | $R^2$ |
|---|---|---|
| 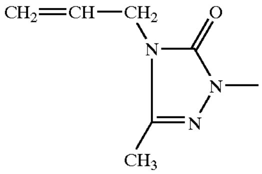 | F | 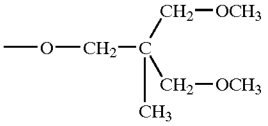 |
| 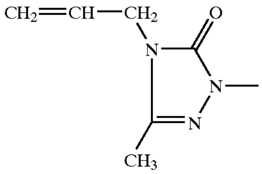 | F | 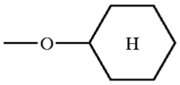 |
| 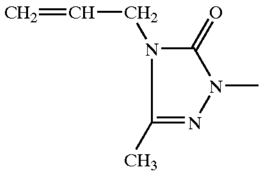 | F | 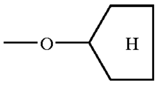 |
| 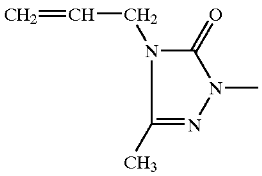 | F | 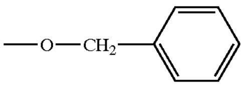 |
| 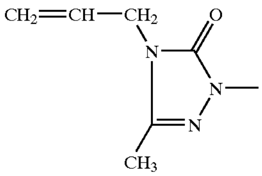 | F | $—O—CH_2—CN$ |
| 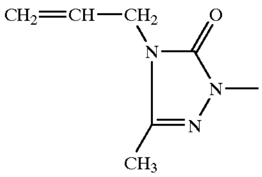 | F | $—O—CH_2—COOC_2H_5$ |

-continued
(I)
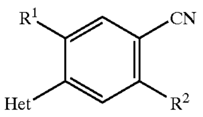
| Het | $R^1$ | $R^2$ |
| --- | --- | --- |
| 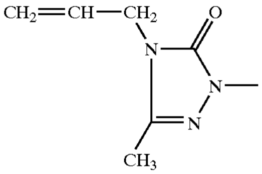 | F | 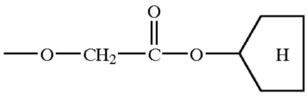 |
| 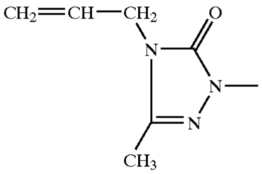 | F | 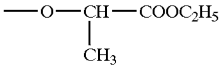 |
| 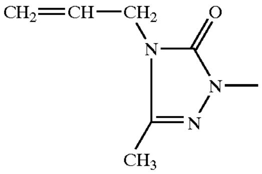 | F | 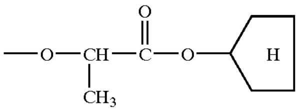 |
| 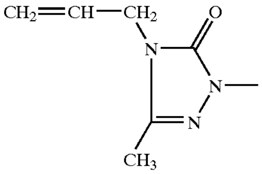 | F | 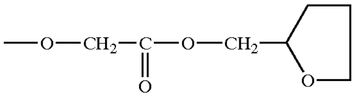 |
| 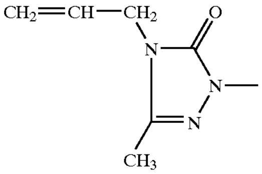 | F | 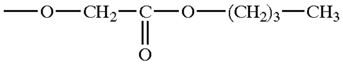 |
| 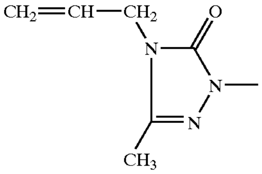 | F | 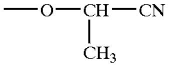 |
| 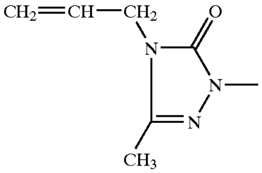 | F | $—O—CH_2—CH_2—O—CH_3$ |

-continued
(I)
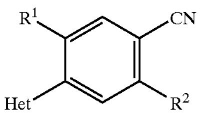
| Het | $R^1$ | $R^2$ |
|---|---|---|
| 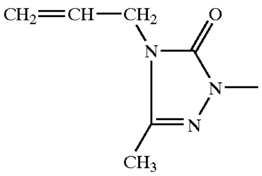 | F | 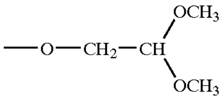 |
| 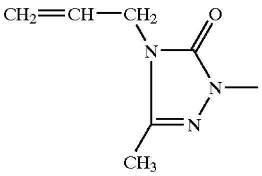 | F | 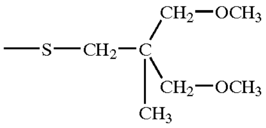 |
| 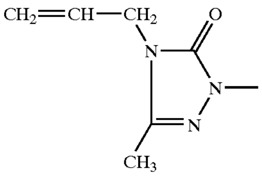 | F | 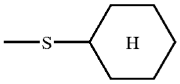 |
| 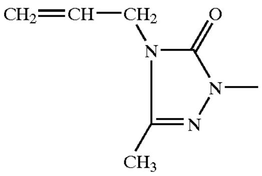 | F | 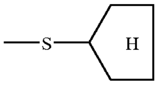 |
| 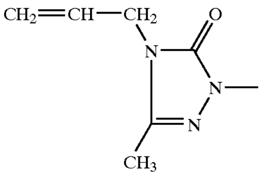 | F | 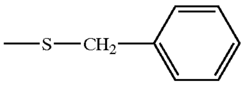 |
| 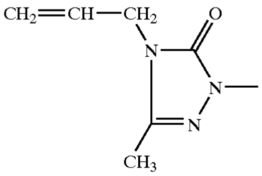 | F | $-S-CH_2-CN$ |
| 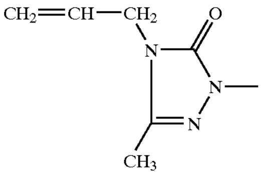 | F | $-S-CH_2-COOC_2H_5$ |

-continued
(I)
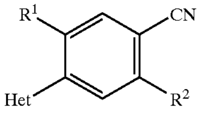
| Het | $R^1$ | $R^2$ |
| --- | --- | --- |
| 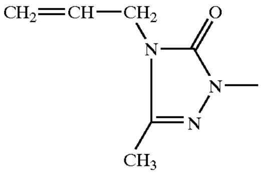 | F | 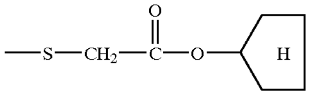 |
| 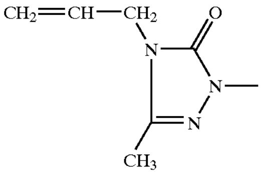 | F | 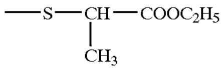 |
| 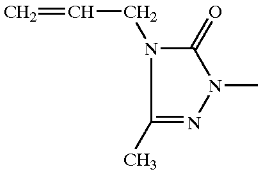 | F | 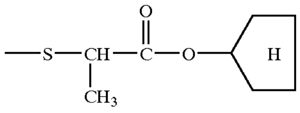 |
| 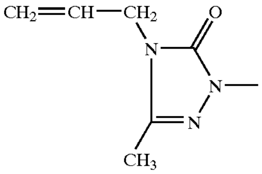 | F | 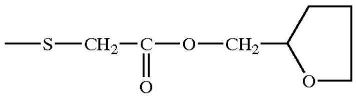 |
| 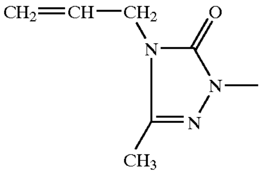 | F | 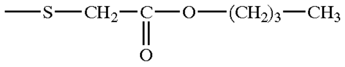 |
| 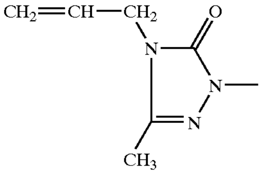 | F | 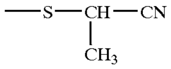 |
| 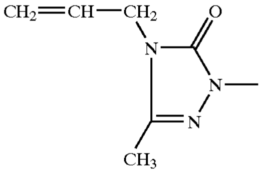 | F | $-S-CH_2-CH_2-O-CH_3$ |

-continued
(I)
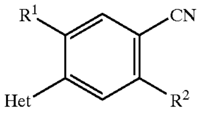
| Het | $R^1$ | $R^2$ |
|---|---|---|
| 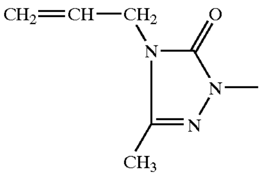 | F | 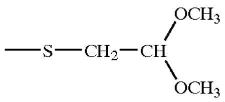 |
| 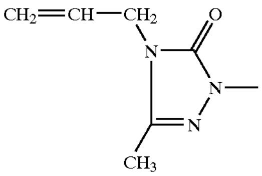 | F | $—OCH_3$ |
| 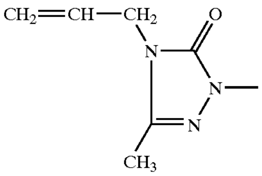 | F | $—OC_2H_5$ |
| 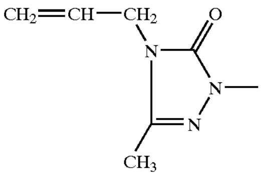 | F | $—O—CH(CH_3)_2$ |
| 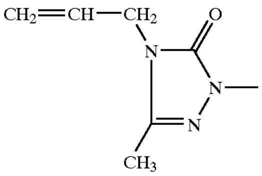 | F | $—O—CH_2—CH{=}CH_2$ |
| 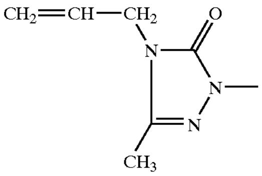 | F | $—O—CH_2—CH{=}CH—CH_3$ |
| 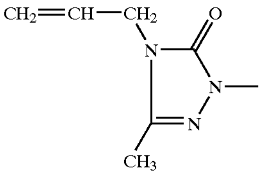 | F | $—O—CH_2—CH{=}CH—Cl$ |

-continued
(I)
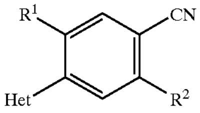
| Het | $R^1$ | $R^2$ |
|---|---|---|
| 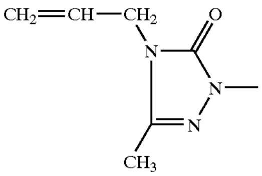 | F | 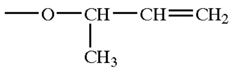 |
| 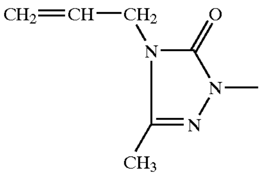 | F | $—O—CH_2—C≡CH$ |
| 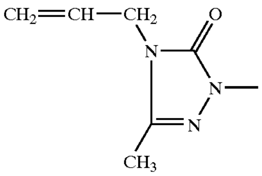 | F | 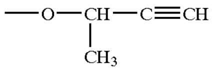 |
| 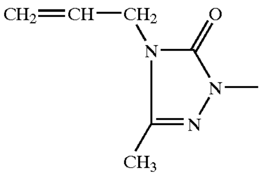 | F | 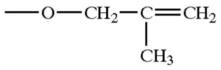 |
| 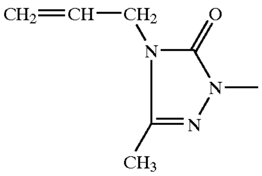 | F | $—O—CH_2—CH_2—OC_2H_5$ |
| 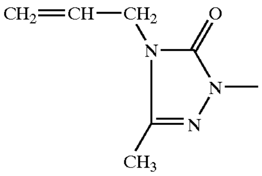 | F | 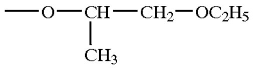 |
| 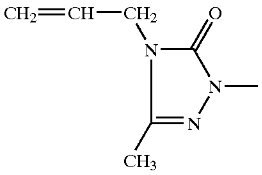 | F | 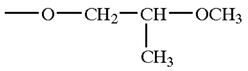 |

-continued
(I)
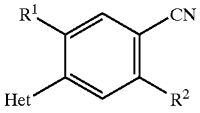
| Het | $R^1$ | $R^2$ |
|---|---|---|
| 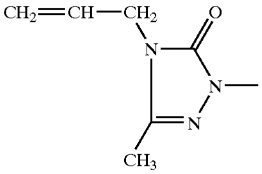 | F | 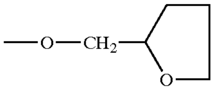 |
| 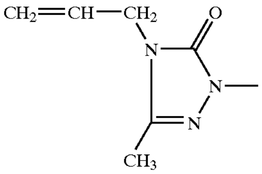 | F | 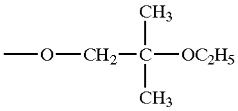 |
| 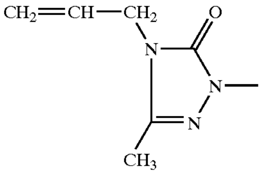 | F | $—O—CH_2—CH_2—O—CH_2—CH_2—OCH_3$ |
| 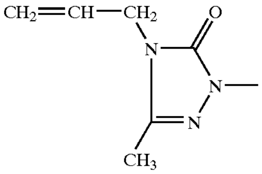 | F | $—O—CH_2—CH_2—O—CH_2—CH_2—OC_2H_5$ |
| 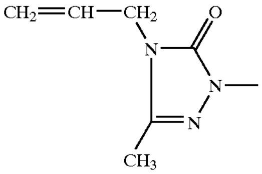 | F | 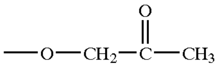 |
| 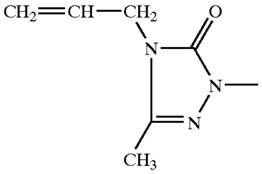 | F | 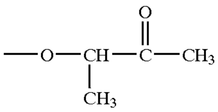 |
| 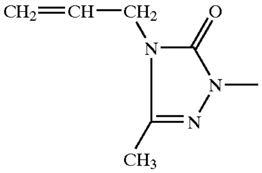 | F | $—SCH_3$ |

-continued
(I)
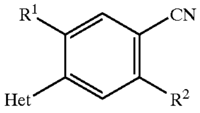
| Het | $R^1$ | $R^2$ |
| --- | --- | --- |
| 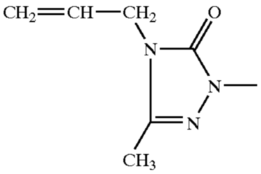 | F | $-SC_2H_5$ |
| 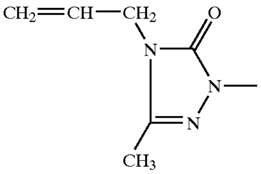 | F | $-S-CH(CH_3)_2$ |
| 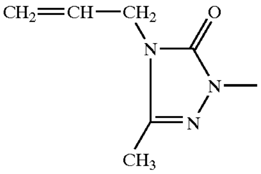 | F | $-S-CH_2-CH=CH_2$ |
| 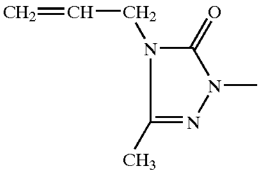 | F | $-S-CH_2-CH=CH-Cl$ |
| 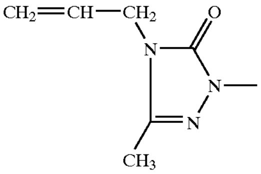 | F | $-S-CH_2-CH=CH-CH_3$ |
| 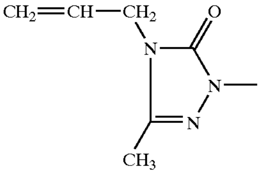 | F | 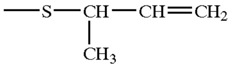 |
| 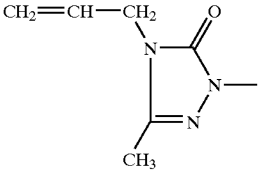 | F | $-S-CH_2-C\equiv CH$ |

-continued
(I)
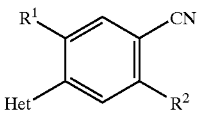
| Het | $R^1$ | $R^2$ |
|---|---|---|
| 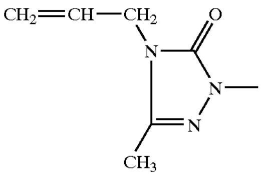 | F | 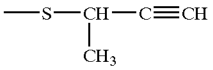 |
| 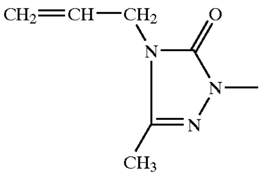 | F | 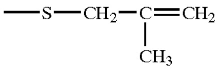 |
| 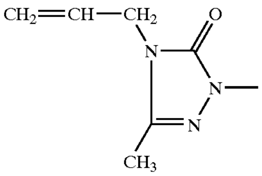 | F | $-S-CH_2-CH_2-OC_2H_5$ |
| 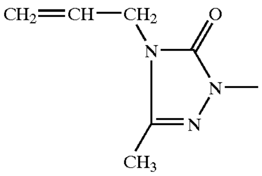 | F | 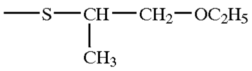 |
| 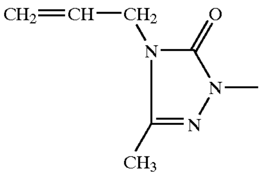 | F | 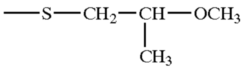 |
| 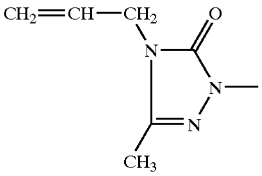 | F | 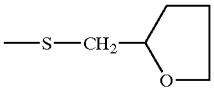 |
| 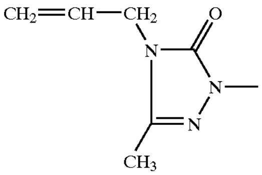 | F | 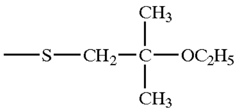 |

-continued
(I)
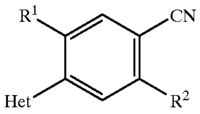
| Het | $R^1$ | $R^2$ |
| --- | --- | --- |
| 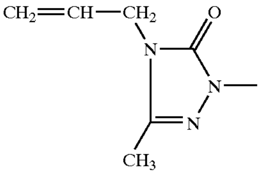 | F | $—S—CH_2—CH_2—O—CH_2—CH_2—OCH_3$ |
| 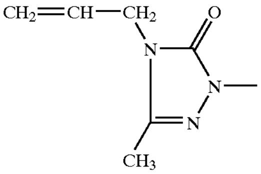 | F | $—S—CH_2—CH_2—O—CH_2—CH_2—OC_2H_5$ |
| 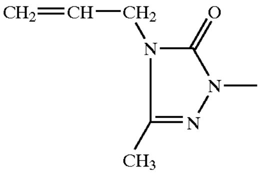 | F | 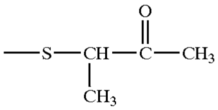 |
| 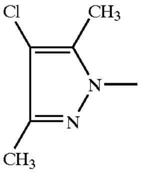 | F | 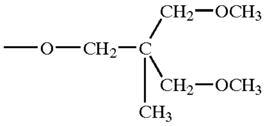 |
| 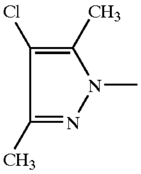 | F | 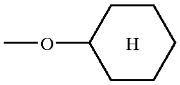 |
| 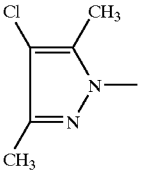 | F | 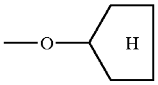 |
| 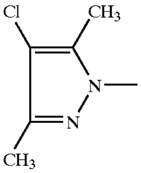 | F | 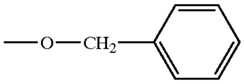 |

-continued
(I)
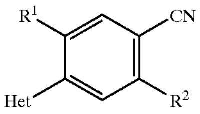
| Het | $R^1$ | $R^2$ |
|---|---|---|
| 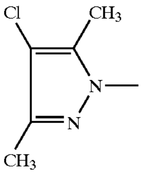 | F | $—O—CH_2—CN$ |
| 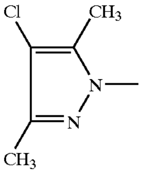 | F | $—O—CH_2—COOC_2H_5$ |
| 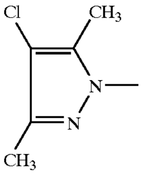 | F | 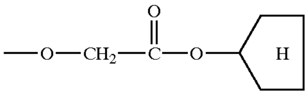 |
| 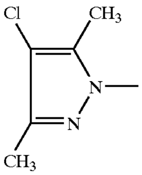 | F | 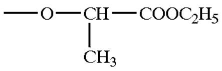 |
| 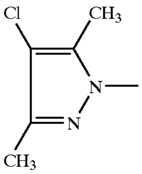 | F | 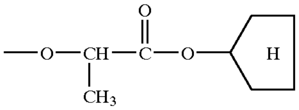 |
| 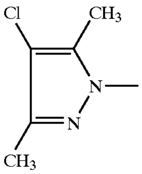 | F | 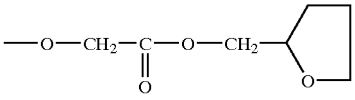 |
| 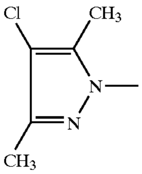 | F | 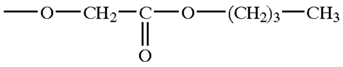 |

-continued
(I)
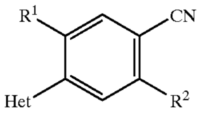
| Het | $R^1$ | $R^2$ |
| --- | --- | --- |
| 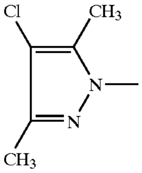 | F | 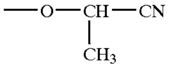 |
| 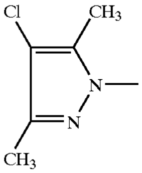 | F | —O—$CH_2$—$CH_2$—O—$CH_3$ |
| 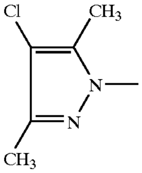 | F | 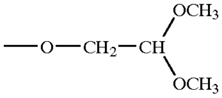 |
| 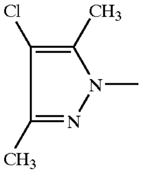 | F | 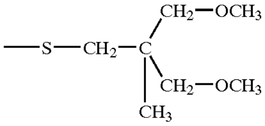 |
| 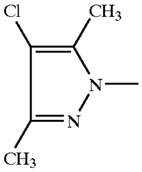 | F | 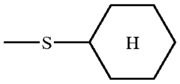 |
| 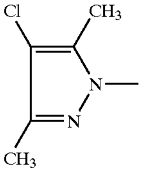 | F | 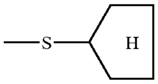 |
| 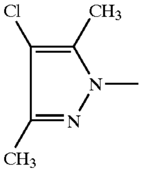 | F | 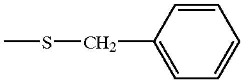 |

-continued
| | | |
|---|---|---|
| 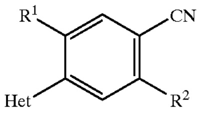 | | (I) |
| Het | $R^1$ | $R^2$ |
| 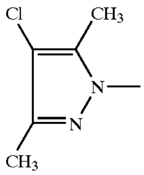 | F | $—S—CH_2—CN$ |
| 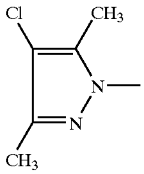 | F | $—S—CH_2—COOC_2H_5$ |
| 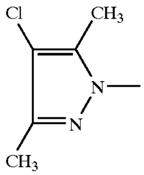 | F | 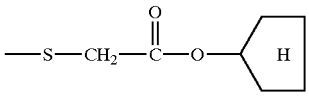 |
| 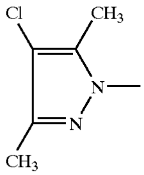 | F | 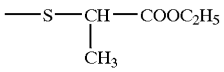 |
| 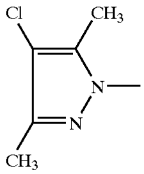 | F | 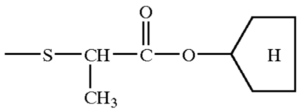 |
| 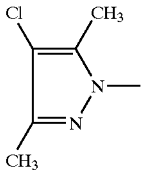 | F | 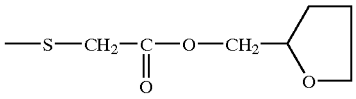 |
| 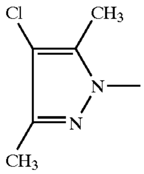 | F | 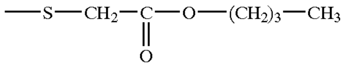 |

-continued
(I)
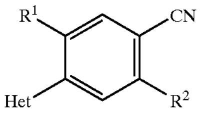
| Het | $R^1$ | $R^2$ |
|---|---|---|
| 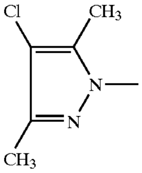 | F | 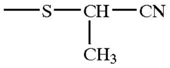 |
| 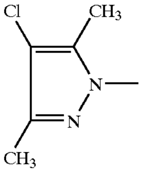 | F | $-S-CH_2-CH_2-O-CH_3$ |
| 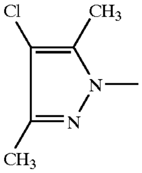 | F | 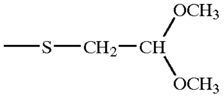 |
| 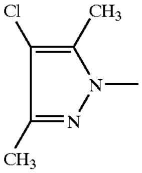 | F | $-OCH_3$ |
| 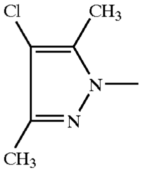 | F | $-OC_2H_5$ |
| 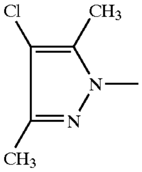 | F | $-O-CH(CH_3)_2$ |
| 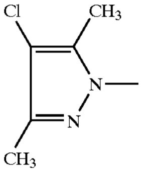 | F | $-O-CH_2-CH=CH_2$ |

-continued
(I)
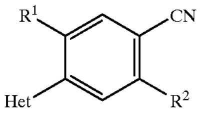
| Het | $R^1$ | $R^2$ |
| --- | --- | --- |
| 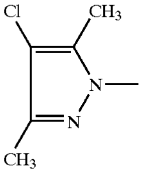 | F | $—O—CH_2—CH{=}CH—CH_3$ |
| 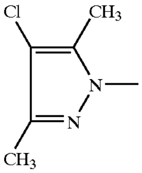 | F | $—O—CH_2—CH{=}CH—Cl$ |
| 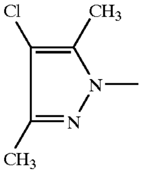 | F | 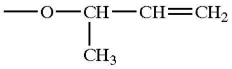 |
| 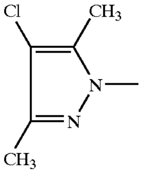 | F | $—O—CH_2—C{\equiv}CH$ |
| 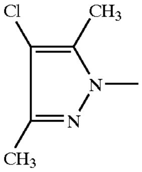 | F | 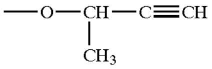 |
| 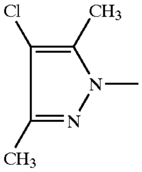 | F | 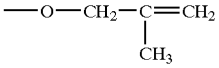 |
| 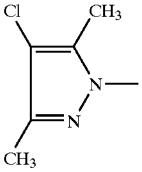 | F | $—O—CH_2—CH_2—OC_2H_5$ |

-continued
(I)
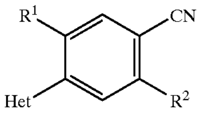
| Het | $R^1$ | $R^2$ |
| --- | --- | --- |
| 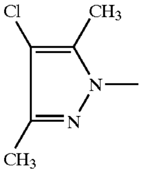 | F | 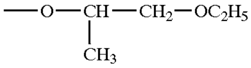 |
| 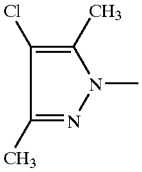 | F | 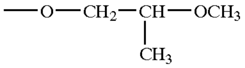 |
| 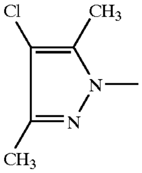 | F | 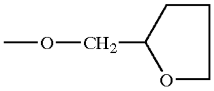 |
| 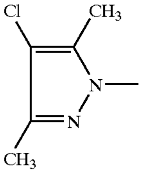 | F | 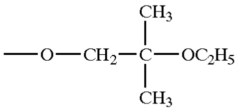 |
| 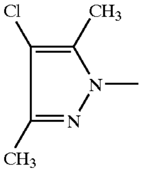 | F | $—O—CH_2—CH_2—O—CH_2—CH_2—OCH_3$ |
| 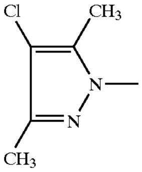 | F | $—O—CH_2—CH_2—O—CH_2—CH_2—OC_2H_5$ |
| 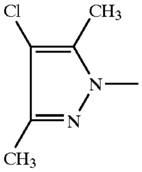 | F | 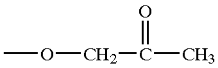 |

-continued
(I)
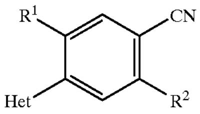
| Het | $R^1$ | $R^2$ |
|---|---|---|
| 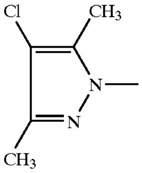 | F | 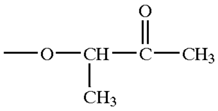 |
| 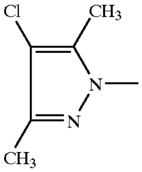 | F | $—SCH_3$ |
| 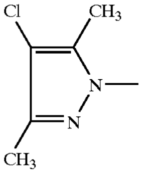 | F | $—SC_2H_5$ |
| 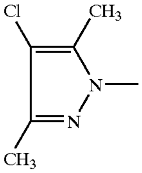 | F | $—S—CH(CH_3)_2$ |
| 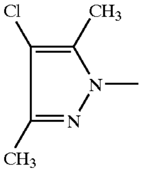 | F | $—S—CH_2—CH{=}CH_2$ |
| 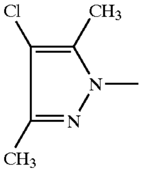 | F | $—S—CH_2—CH{=}CH—Cl$ |
| 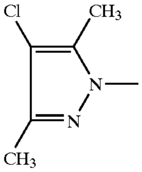 | F | $—S—CH_2—CH{=}CH—CH_3$ |

-continued
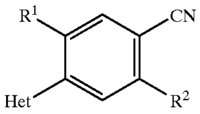
(I)
| Het | $R^1$ | $R^2$ |
|---|---|---|
| 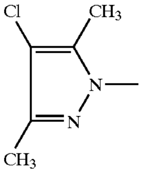 | F | 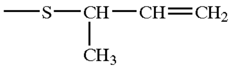 |
| 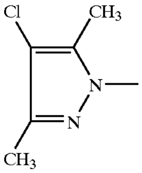 | F | $—S—CH_2—C≡CH$ |
| 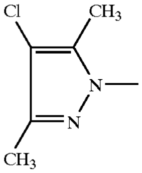 | F | 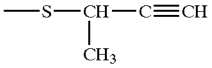 |
| 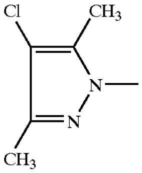 | F | 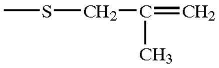 |
| 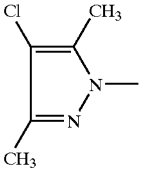 | F | $—S—CH_2—CH_2—OC_2H_5$ |
| 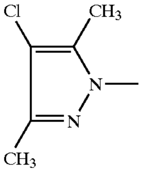 | F | 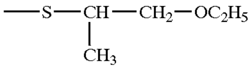 |
| 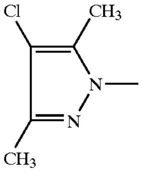 | F | 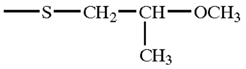 |

-continued
(I)
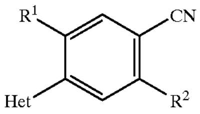
| Het | $R^1$ | $R^2$ |
|---|---|---|
| 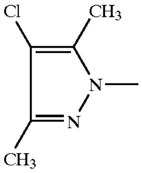 | F | 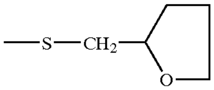 |
| 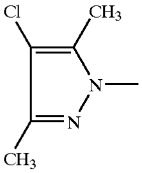 | F | 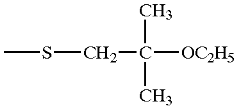 |
| 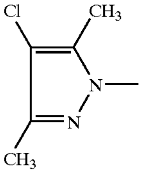 | F | $-S-CH_2-CH_2-O-CH_2-CH_2-OCH_3$ |
| 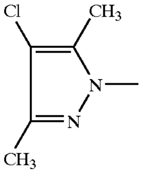 | F | $-S-CH_2-CH_2-O-CH_2-CH_2-OC_2H_5$ |
| 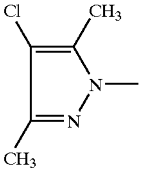 | F | 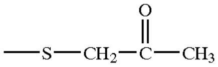 |
| 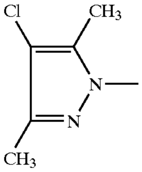 | F | 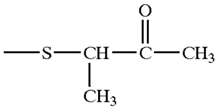 |
| 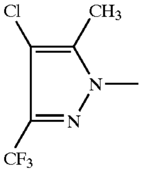 | F | 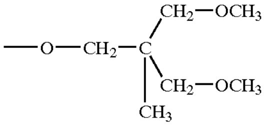 |

-continued
(I)
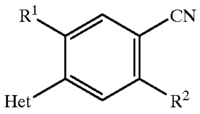
| Het | $R^1$ | $R^2$ |
|---|---|---|
| 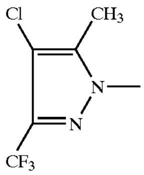 | F | 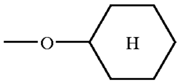 |
| 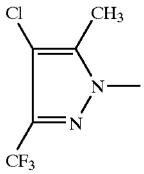 | F | 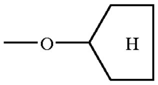 |
| 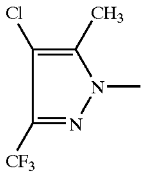 | F | 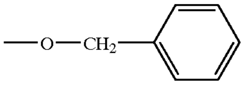 |
| 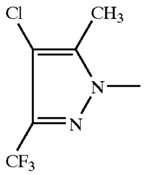 | F | $—O—CH_2—CN$ |
| 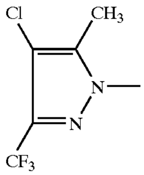 | F | $—O—CH_2—COOC_2H_5$ |
| 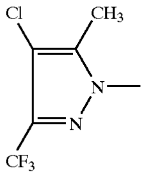 | F | 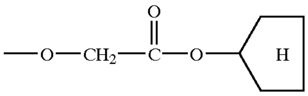 |
| 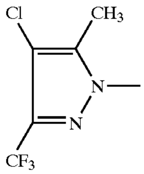 | F | 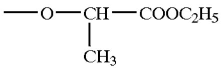 |

-continued
(I)
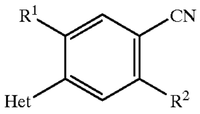
| Het | $R^1$ | $R^2$ |
|---|---|---|
| 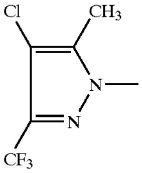 | F | 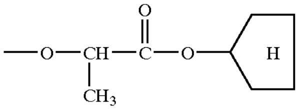 |
| 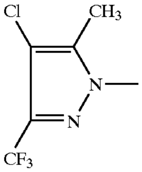 | F | 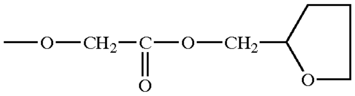 |
| 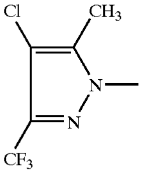 | F | 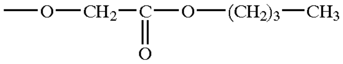 |
| 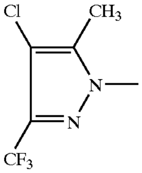 | F | 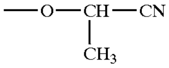 |
| 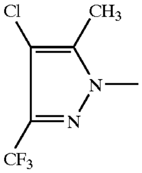 | F | $—O—CH_2—CH_2—O—CH_3$ |
| 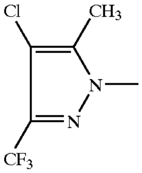 | F | 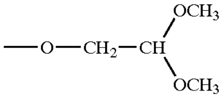 |
| 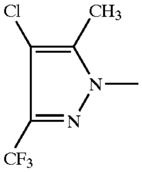 | F | 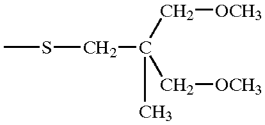 |

-continued
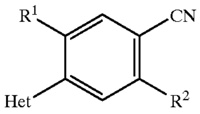
(I)
| Het | $R^1$ | $R^2$ |
|---|---|---|
| 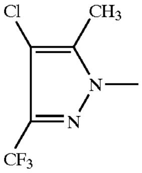 | F | 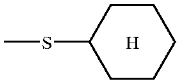 |
| 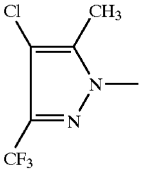 | F | 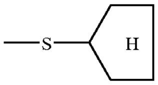 |
| 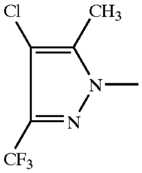 | F | 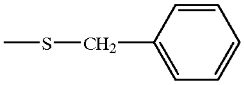 |
| 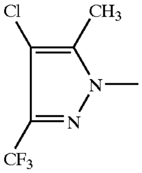 | F | $-S-CH_2-CN$ |
| 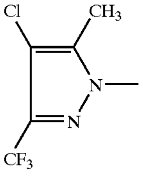 | F | $-S-CH_2-COOC_2H_5$ |
| 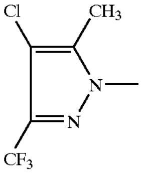 | F | 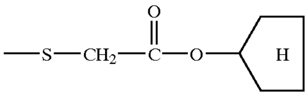 |
| 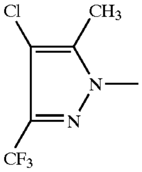 | F | 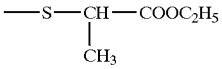 |

-continued
(I)
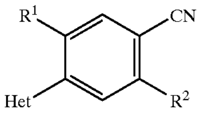
| Het | $R^1$ | $R^2$ |
| --- | --- | --- |
| 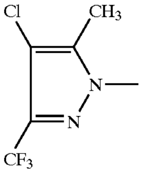 | F | 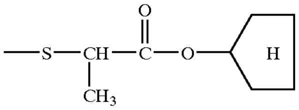 |
| 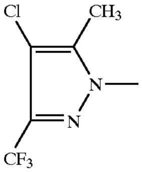 | F | 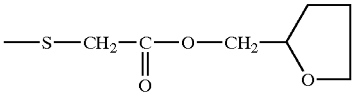 |
| 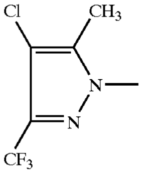 | F | 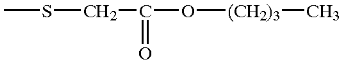 |
| 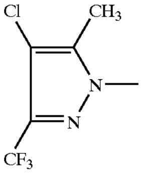 | F | 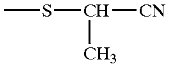 |
| 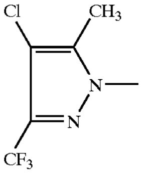 | F | $—S—CH_2—CH_2—O—CH_3$ |
| 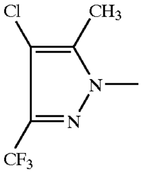 | F | 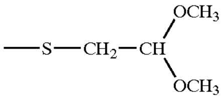 |
| 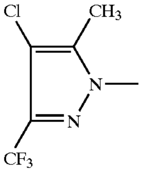 | F | $—OCH_3$ |

-continued
(I)
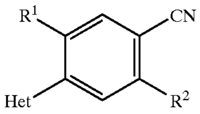
| Het | $R^1$ | $R^2$ |
|---|---|---|
| 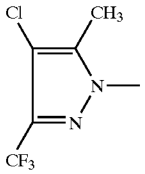 | F | $-OC_2H_5$ |
| 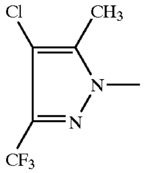 | F | $-O-CH(CH_3)_2$ |
| 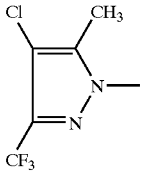 | F | $-O-CH_2-CH=CH_2$ |
| 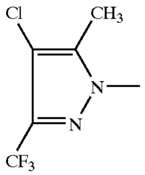 | F | $-O-CH_2-CH=CH-CH_3$ |
| 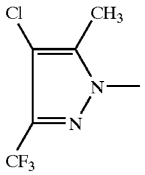 | F | $-O-CH_2-CH=CH-Cl$ |
| 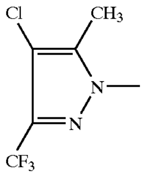 | F | 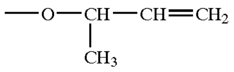 |
| 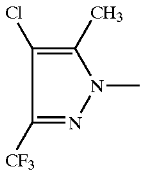 | F | $-O-CH_2-C\equiv CH$ |

-continued
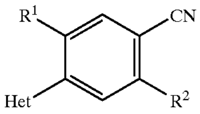
(I)
| Het | $R^1$ | $R^2$ |
|---|---|---|
| 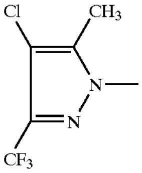 | F | 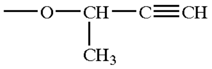 |
| 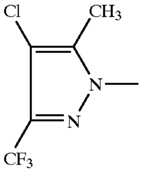 | F | 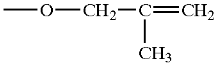 |
| 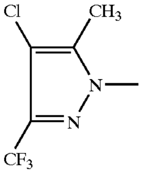 | F | $—O—CH_2—CH_2—OC_2H_5$ |
| 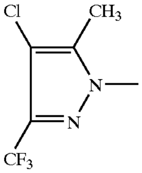 | F | 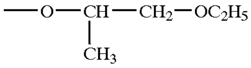 |
| 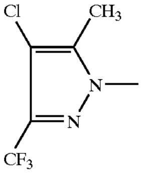 | F | 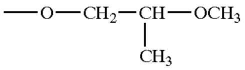 |
| 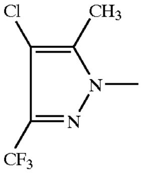 | F | 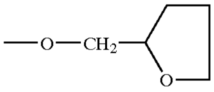 |
| 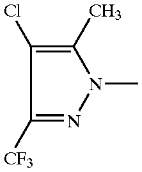 | F | 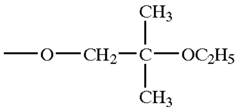 |

-continued
(I)
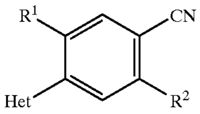
| Het | $R^1$ | $R^2$ |
|---|---|---|
| 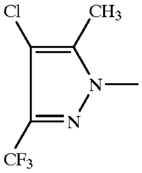 | F | $—O—CH_2—CH_2—O—CH_2—CH_2—OCH_3$ |
| 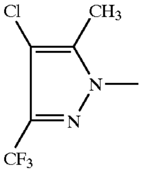 | F | $—O—CH_2—CH_2—O—CH_2—CH_2—OC_2H_5$ |
| 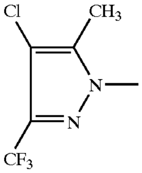 | F | 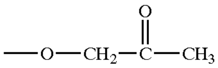 |
| 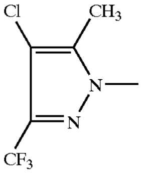 | F | 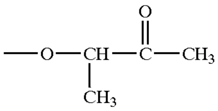 |
| 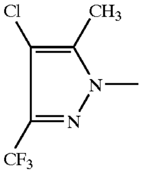 | F | $—SCH_3$ |
| 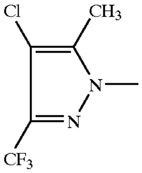 | F | $—SC_2H_5$ |
| 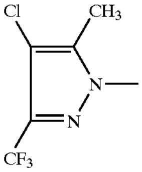 | F | $—S—CH(CH_3)_2$ |

-continued
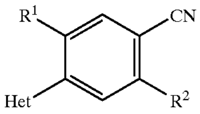
(I)
| Het | $R^1$ | $R^2$ |
| --- | --- | --- |
| 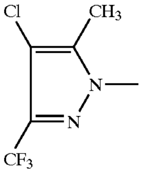 | F | $-S-CH_2-CH=CH_2$ |
| 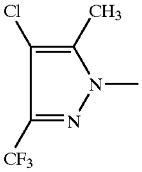 | F | $-S-CH_2-CH=CH-Cl$ |
| 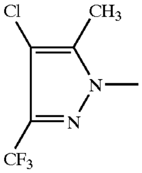 | F | $-S-CH_2-CH=CH-CH_3$ |
| 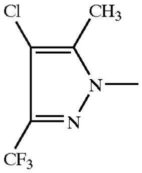 | F | 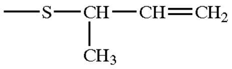 |
| 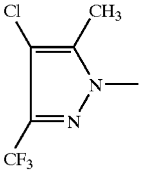 | F | $-S-CH_2-C\equiv CH$ |
| 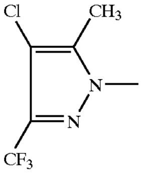 | F | 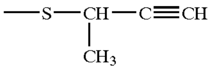 |
| 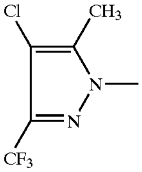 | F | 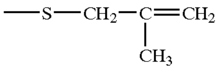 |

-continued
(I)
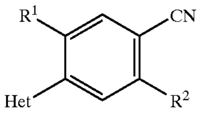
| Het | $R^1$ | $R^2$ |
|---|---|---|
| 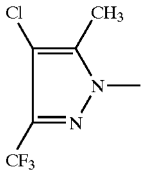 | F | $-S-CH_2-CH_2-OC_2H_5$ |
| 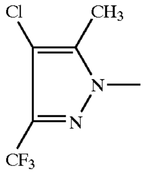 | F | 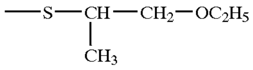 |
| 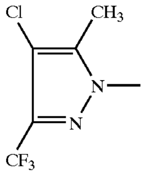 | F | 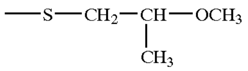 |
| 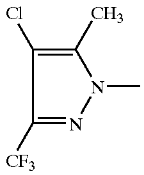 | F | 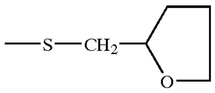 |
| 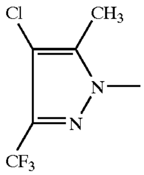 | F | 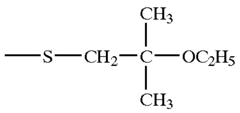 |
| 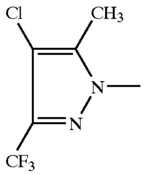 | F | $-S-CH_2-CH_2-O-CH_2-CH_2-OCH_3$ |
| 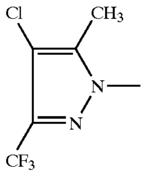 | F | $-S-CH_2-CH_2-O-CH_2-CH_2-OC_2H_5$ |

-continued
(I)
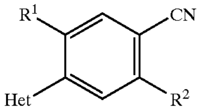
| Het | $R^1$ | $R^2$ |
|---|---|---|
| 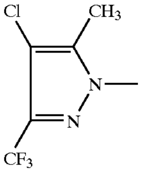 | F | 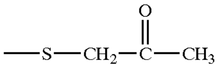 |
| 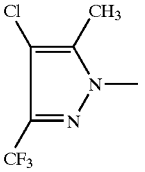 | F | 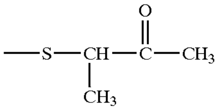 |
| 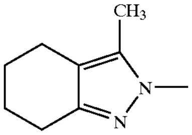 | F | 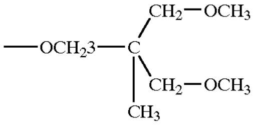 |
| 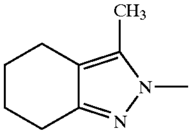 | F | 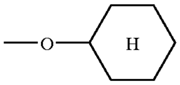 |
| 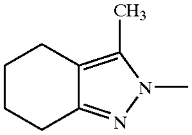 | F | 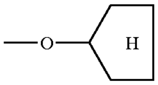 |
| 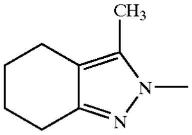 | F | 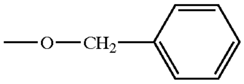 |
| 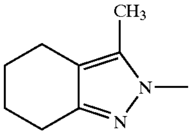 | F | $—O—CH_2—CN$ |
| 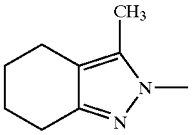 | F | $—O—CH_2—COOC_2H_5$ |
| 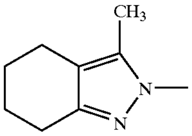 | F | 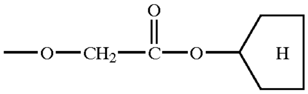 |

-continued
(I)
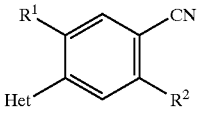
| Het | $R^1$ | $R^2$ |
|---|---|---|
| 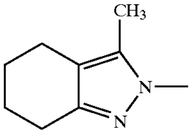 | F | 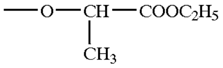 |
| 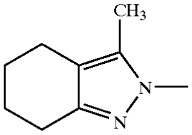 | F | 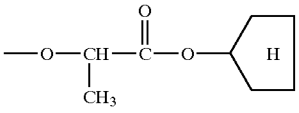 |
| 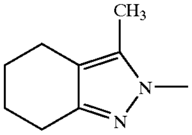 | F | 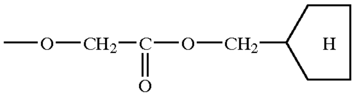 |
| 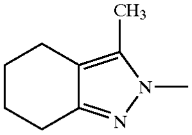 | F | 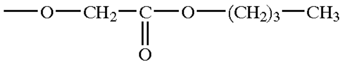 |
| 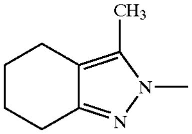 | F | 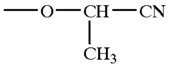 |
| 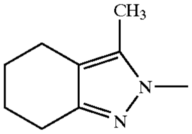 | F | $—O—CH_2—CH_2—O—CH_3$ |
| 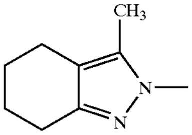 | F | 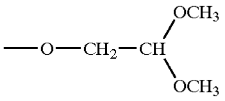 |
| 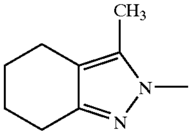 | F | 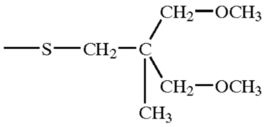 |
| 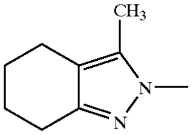 | F | 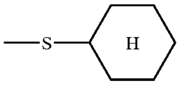 |

-continued
(I)
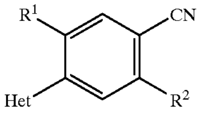
| Het | $R^1$ | $R^2$ |
|---|---|---|
| 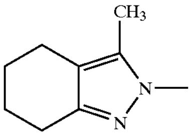 | F | 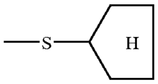 |
| 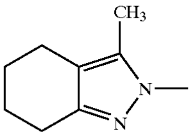 | F | 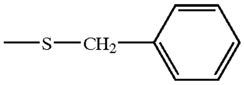 |
| 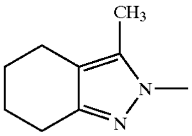 | F | $—S—CH_2—CN$ |
| 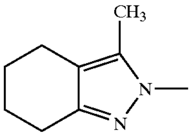 | F | $—S—CH_2—COOC_2H_5$ |
| 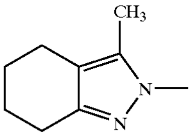 | F | 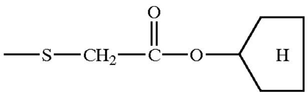 |
| 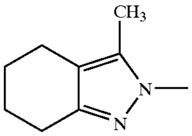 | F | 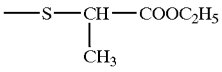 |
| 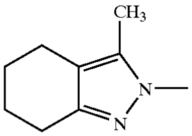 | F | 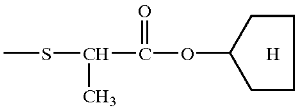 |
| 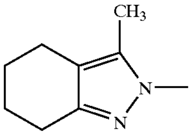 | F | 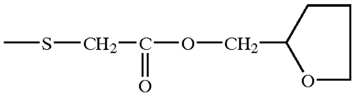 |
| 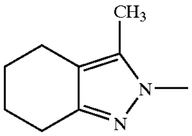 | F | 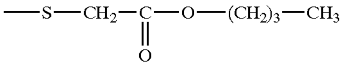 |

-continued
(I)
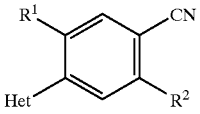
| Het | $R^1$ | $R^2$ |
|---|---|---|
| 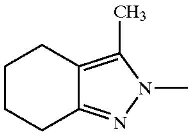 | F | 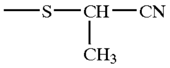 |
| 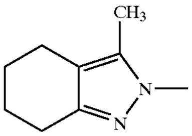 | F | $—S—CH_2—CH_2—O—CH_3$ |
| 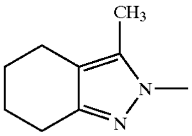 | F | 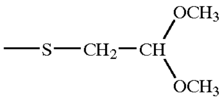 |
| 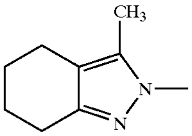 | F | $—OCH_3$ |
| 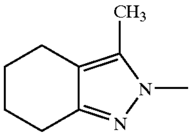 | F | $—OC_2H_5$ |
| 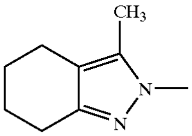 | F | $—O—CH(CH_3)_2$ |
| 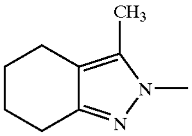 | F | $—O—CH_2—CH≡CH_2$ |
| 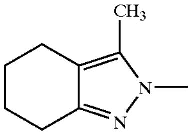 | F | $—O—CH_2—CH=CH—CH_3$ |
| 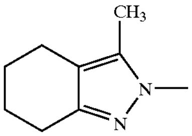 | F | $—O—CH_2—CH=CH—Cl$ |

-continued
(I)
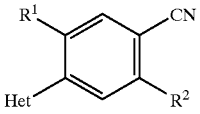
| Het | $R^1$ | $R^2$ |
|---|---|---|
| 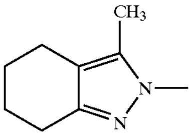 | F | 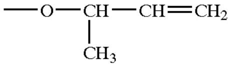 |
| 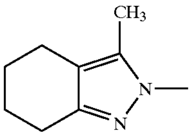 | F | $—O—CH_2—C{\equiv}CH$ |
| 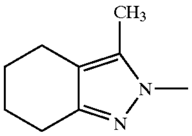 | F | 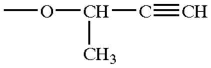 |
| 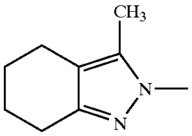 | F | 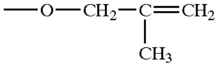 |
| 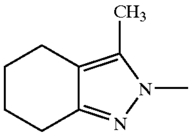 | F | $—O—CH_2—CH_2—OC_2H_5$ |
| 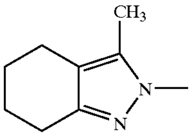 | F | 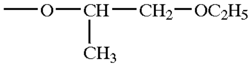 |
| 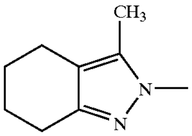 | F | 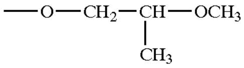 |
| 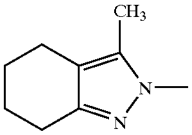 | F | 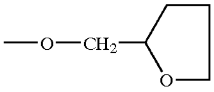 |
| 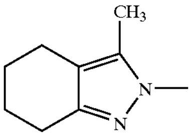 | F | 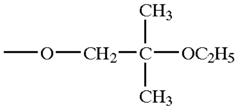 |

-continued
(I)
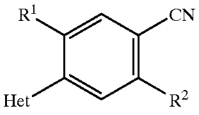
| Het | $R^1$ | $R^2$ |
|---|---|---|
| 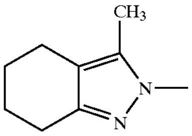 | F | $-O-CH_2-CH_2-O-CH_2-CH_2-OCH_3$ |
| 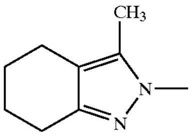 | F | $-OCH_2-CH_2-O-CH_2-CH_2-OC_2H_5$ |
| 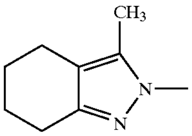 | F | 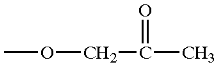 |
| 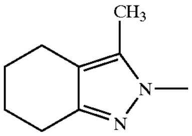 | F | 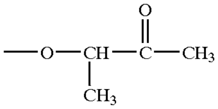 |
| 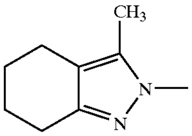 | F | $-SCH_3$ |
| 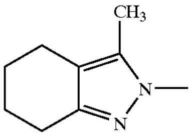 | F | $-SC_2H_5$ |
| 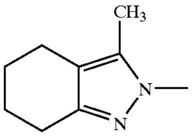 | F | $-S-CH(CH_3)_2$ |
| 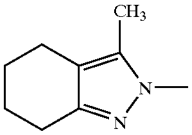 | F | $-S-CH_2-CH=CH_2$ |
| 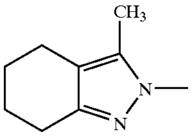 | F | $-S-CH_2-CH=CH-Cl$ |

-continued
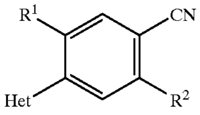
(I)
| Het | $R^1$ | $R^2$ |
| --- | --- | --- |
| 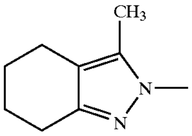 | F | $—S—CH_2—CH{=}CH—CH_3$ |
| 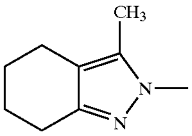 | F | 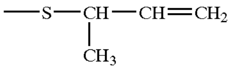 |
| 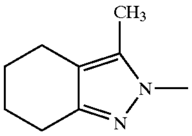 | F | $—S—CH_2—C{\equiv}CH$ |
| 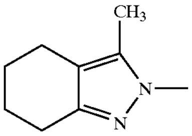 | F | 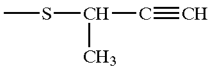 |
| 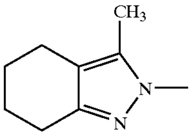 | F | 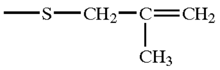 |
| 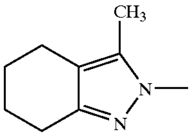 | F | $—S—CH_2—CH_2—OC_2H_5$ |
| 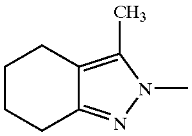 | F | 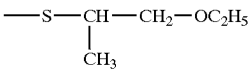 |
| 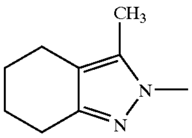 | F | 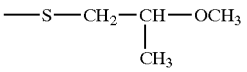 |
| 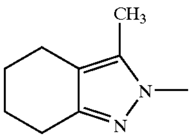 | F | 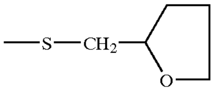 |

-continued
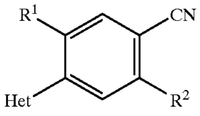
(I)
| Het | $R^1$ | $R^2$ |
|---|---|---|
| 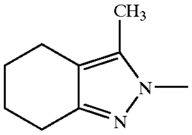 | F | 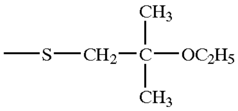 |
| 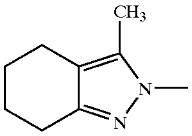 | F | $—S—CH_2—CH_2—O—CH_2—CH_2—OCH_3$ |
| 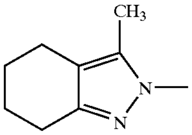 | F | $—S—CH_2—CH_2—O—CH_2—CH_2—OC_2H_5$ |
| 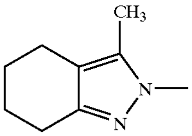 | F | 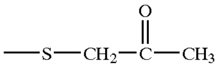 |
| 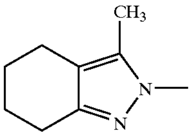 | F | 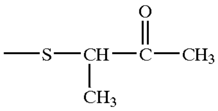 |
| 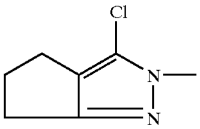 | F | 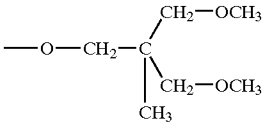 |
| 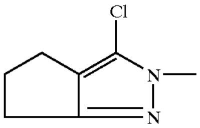 | F | 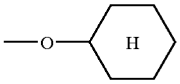 |
| 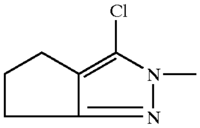 | F | 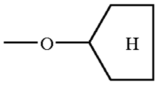 |
| 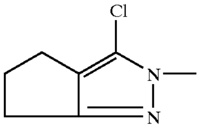 | F | 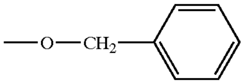 |

-continued
(I)
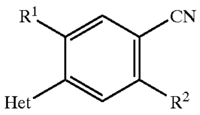
| Het | $R^1$ | $R^2$ |
|---|---|---|
| 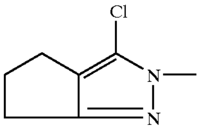 | F | $—O—CH_2—CN$ |
| 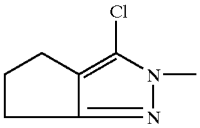 | F | $—O—CH_2—COOCH_3$ |
| 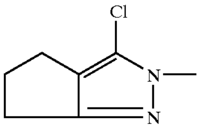 | F | $—O—CH_2—COOC_2H_5$ |
| 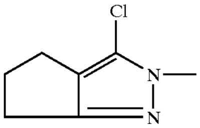 | F | 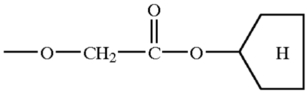 |
| 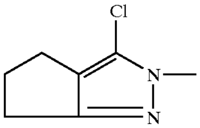 | F | 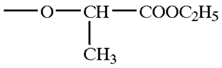 |
| 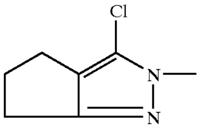 | F | 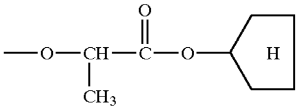 |
| 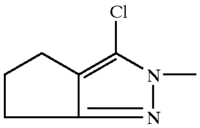 | F | 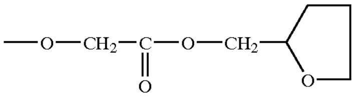 |
| 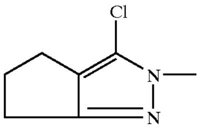 | F | 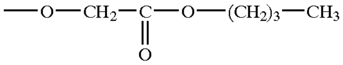 |
| 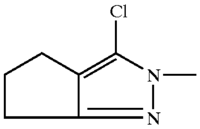 | F | 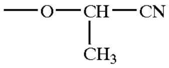 |

-continued
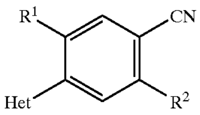
(I)
| Het | $R^1$ | $R^2$ |
|---|---|---|
| 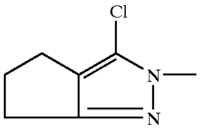 | F | $-O-CH_2-CH_2-O-CH_3$ |
| 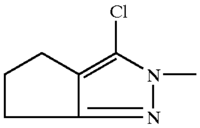 | F | 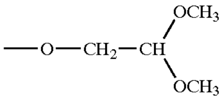 |
| 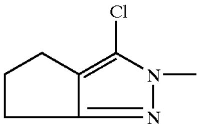 | F | 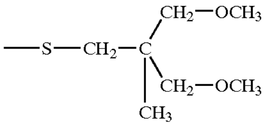 |
| 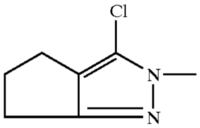 | F | 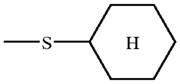 |
| 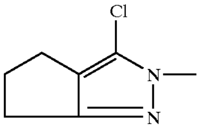 | F | 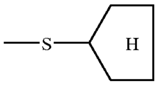 |
| 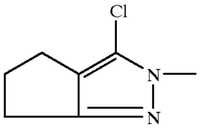 | F | 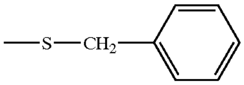 |
| 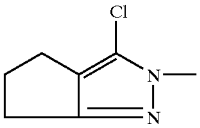 | F | $-S-CH_2-CN$ |
| 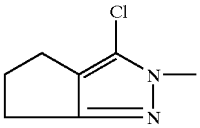 | F | $-S-CH_2-COOC_2H_5$ |
| 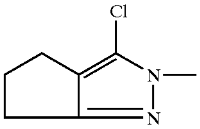 | F | 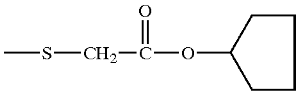 |

-continued
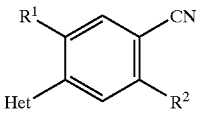
(I)
| Het | $R^1$ | $R^2$ |
| --- | --- | --- |
| 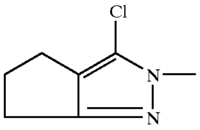 | F | 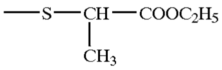 |
| 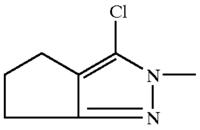 | F | 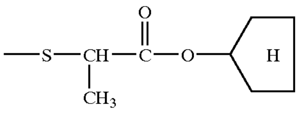 |
| 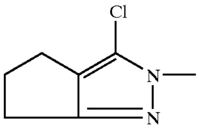 | F | 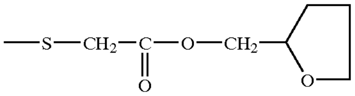 |
| 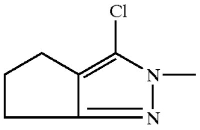 | F | 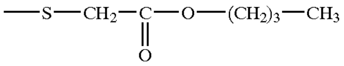 |
| 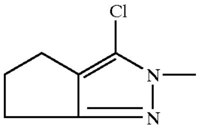 | F | 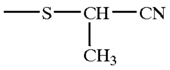 |
| 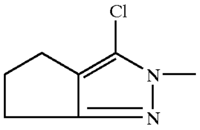 | F | $-S-CH_2-CH_2-O-CH_3$ |
| 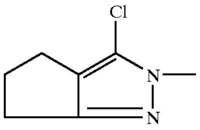 | F | 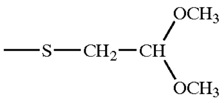 |
| 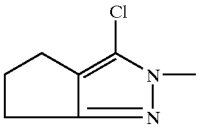 | F | $-OCH_3$ |
| 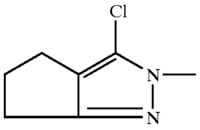 | F | $-OC_2H_5$ |

-continued
(I)
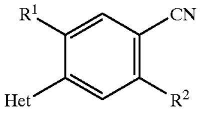
| Het | $R^1$ | $R^2$ |
|---|---|---|
| 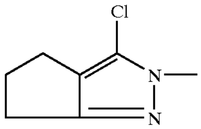 | F | $—OCH(CH_3)_2$ |
| 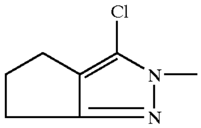 | F | $—O—CH_2—CH{=}CH_2$ |
| 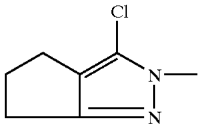 | F | $—O—CH_2—CH{=}CH—CH_3$ |
| 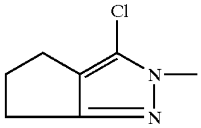 | F | $—O—CH_2—CH{=}CH—Cl$ |
| 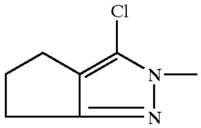 | F | 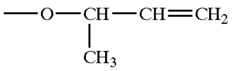 |
| 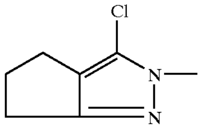 | F | $—O—CH_2—C{\equiv}CH$ |
| 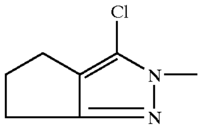 | F | 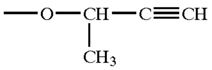 |
| 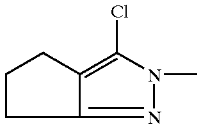 | F | 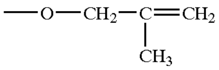 |
| 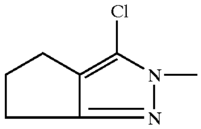 | F | $—OCH_2—CH_2—OC_2H_5$ |

-continued
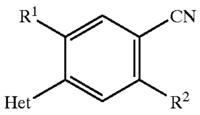
(I)
| Het | $R^1$ | $R^2$ |
|---|---|---|
| 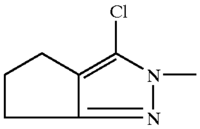 | F | 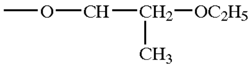 |
| 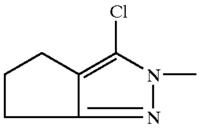 | F | 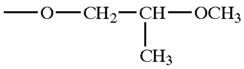 |
| 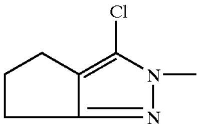 | F | 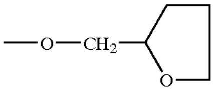 |
| 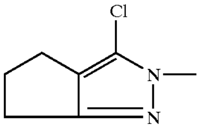 | F | 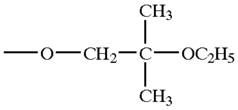 |
| 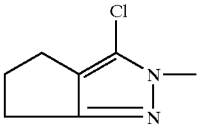 | F | $—O—CH_2—CH_2—O—CH_2—CH_2—OCH_3$ |
| 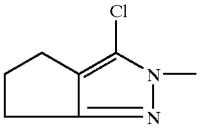 | F | $—O—CH_2—CH_2—O—CH_2—CH_2—OC_2H_5$ |
| 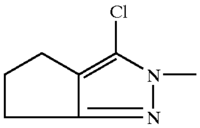 | F | 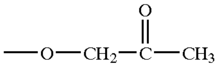 |
| 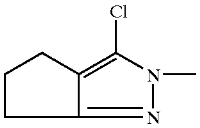 | F | 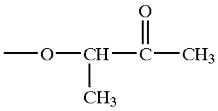 |
| 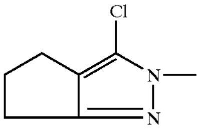 | F | $—SCH_3$ |

-continued
(I)
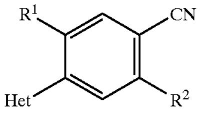
| Het | $R^1$ | $R^2$ |
| --- | --- | --- |
| 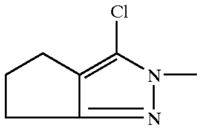 | F | $—SC_2H_5$ |
| 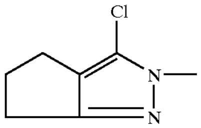 | F | $—S—CH(CH_3)_2$ |
| 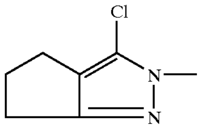 | F | $—S—CH_2—CH═CH_2$ |
| 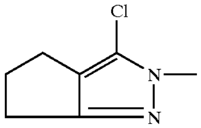 | F | $—S—CH_2—CH═CH—Cl$ |
| 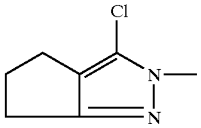 | F | $—S—CH_2—CH═CH—CH_3$ |
| 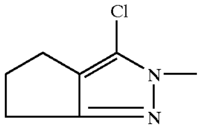 | F | 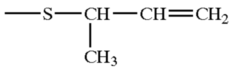 |
| 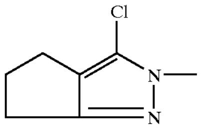 | F | $—S—CH_2—C≡CH$ |
| 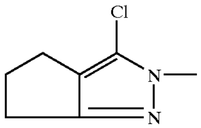 | F | 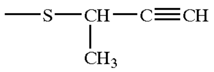 |
| 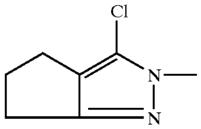 | F | 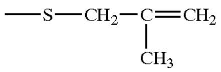 |

-continued
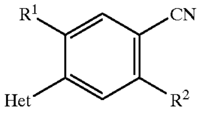
(I)
| Het | $R^1$ | $R^2$ |
|---|---|---|
| 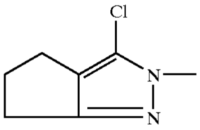 | F | $—S—CH_2—CH_2—OC_2H_5$ |
| 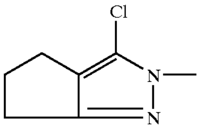 | F | 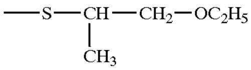 |
| 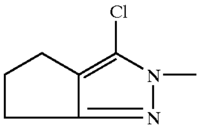 | F | 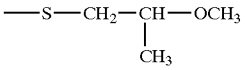 |
| 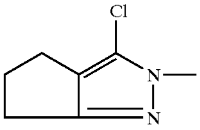 | F | 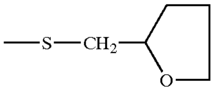 |
| 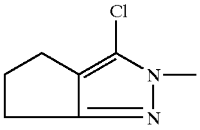 | F | 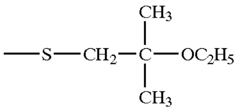 |
| 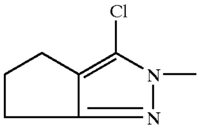 | F | $—S—CH_2—CH_2—O—CH_2—CH_2—OCH_3$ |
| 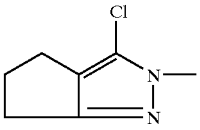 | F | $—S—CH_2—CH_2—O—CH_2—CH_2—OC_2H_5$ |
| 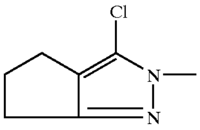 | F | 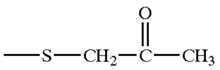 |
| 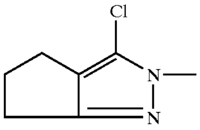 | F | 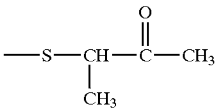 |

-continued
| | | |
|---|---|---|
| | 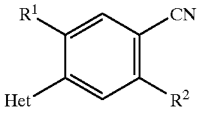 | (I) |
| Het | $R^1$ | $R^2$ |
| 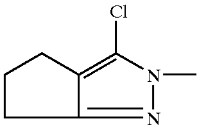 | H | 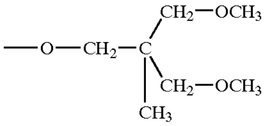 |
| 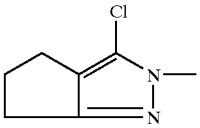 | H | 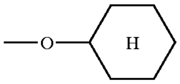 |
| 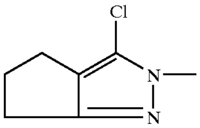 | H | 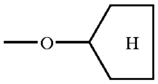 |
| 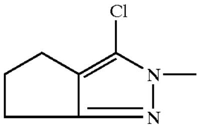 | H | 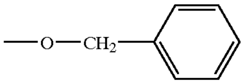 |
| 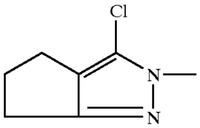 | H | $—O—CH_2—CN$ |
| 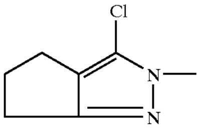 | H | $—O—CH_2—COOC_2H_5$ |
| 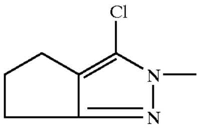 | H | 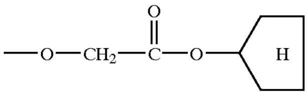 |
| 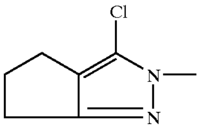 | H | 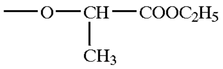 |
| 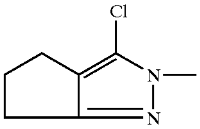 | H | 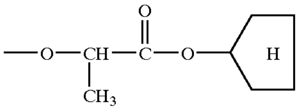 |

-continued
(I)
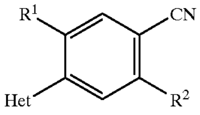
| Het | $R^1$ | $R^2$ |
|---|---|---|
| 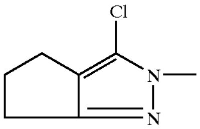 | H | 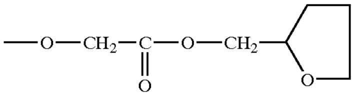 |
| 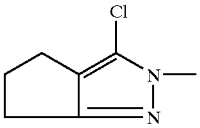 | H | 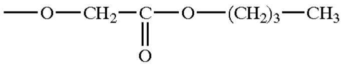 |
| 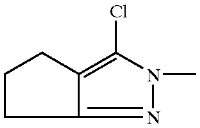 | H | 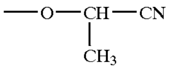 |
| 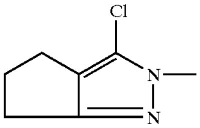 | H | $—O—CH_2—CH_2—O—CH_3$ |
| 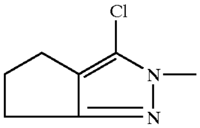 | H | 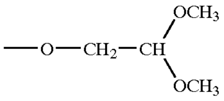 |
| 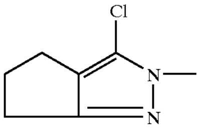 | H | 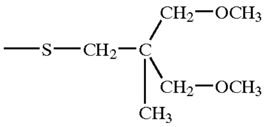 |
| 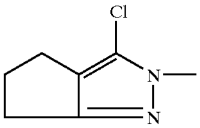 | H | 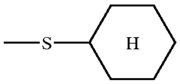 |
| 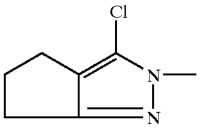 | H | 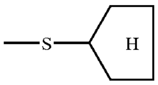 |
| 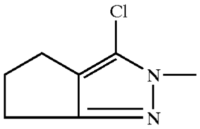 | H | 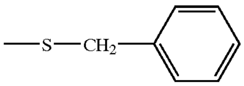 |

-continued
(I)
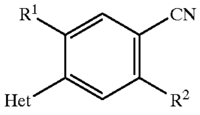
| Het | $R^1$ | $R^2$ |
|---|---|---|
| 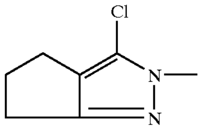 | H | $—S—CH_2—CN$ |
| 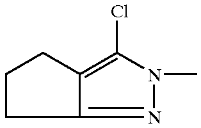 | H | $—S—CH_2—COOC_2H_5$ |
| 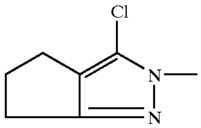 | H | 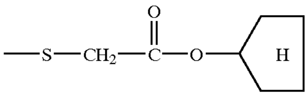 |
| 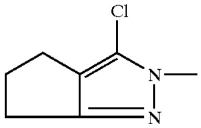 | H | 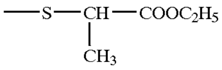 |
| 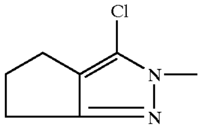 | H | 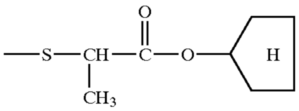 |
| 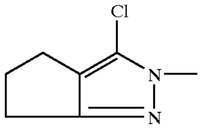 | H | 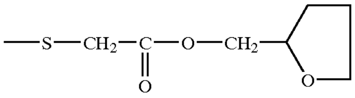 |
| 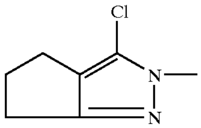 | H | 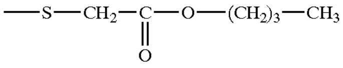 |
| 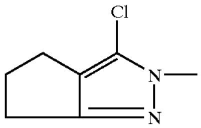 | H | 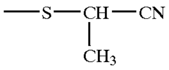 |
| 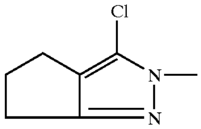 | H | $—S—CH_2—CH_2—O—CH_3$ |

-continued
(I)
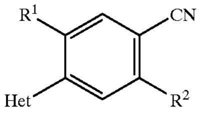
| Het | $R^1$ | $R^2$ |
|---|---|---|
| 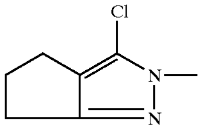 | H | 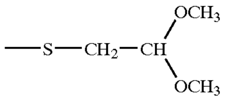 |
| 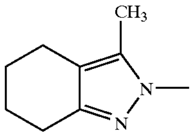 | H | $—OCH_3$ |
| 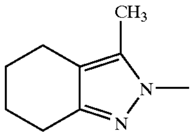 | H | $—OC_2H_5$ |
| 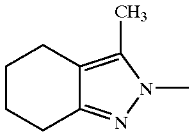 | H | $—O—CH(CH_3)_2$ |
| 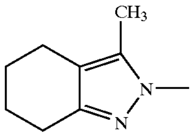 | H | $—O—CH_2—CH{=}CH_2$ |
| 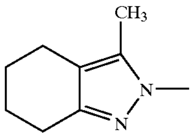 | H | $—O—CH_2—CH{=}CH—CH_3$ |
| 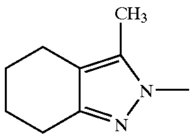 | H | $—O—CH_2—CH{=}CH—Cl$ |
| 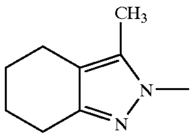 | H | 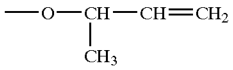 |
| 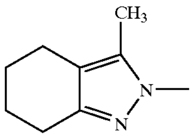 | H | $—O—CH_2—C{\equiv}CH$ |

-continued
(I)
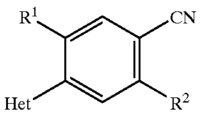
| Het | $R^1$ | $R^2$ |
|---|---|---|
| 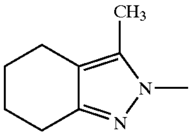 | H | 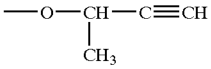 |
| 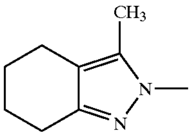 | H | 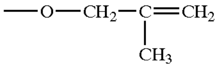 |
| 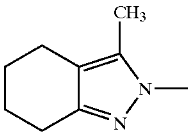 | H | $—O—CH_2—CH_2—OC_2H_5$ |
| 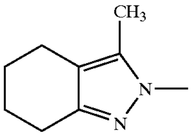 | H | 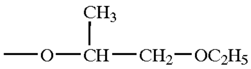 |
| 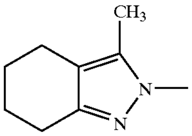 | H | 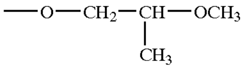 |
| 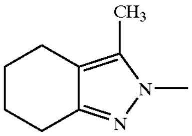 | H | 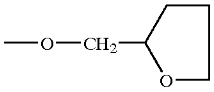 |
| 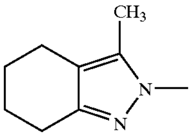 | H | 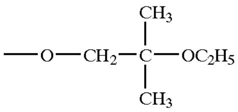 |
| 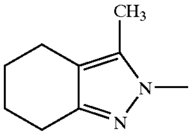 | H | $—O—CH_2—CH_2—O—CH_2—CH_2—OCH_3$ |
| 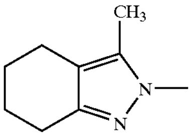 | H | $—O—CH_2—CH_2—O—CH_2—CH_2—OC_2H_5$ |

-continued
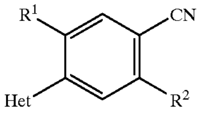
(I)
| Het | $R^1$ | $R^2$ |
|---|---|---|
| 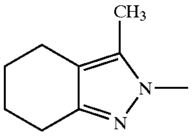 | H | 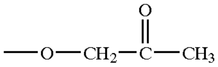 |
| 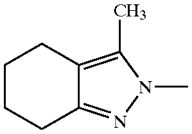 | H | 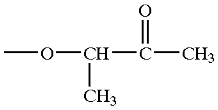 |
| 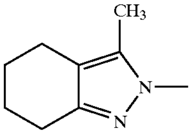 | H | $—SCH_3$ |
| 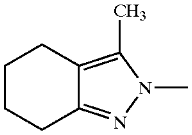 | H | $—SC_2H_5$ |
| 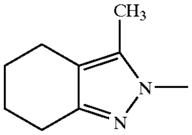 | H | $—S—CH(CH_3)_2$ |
| 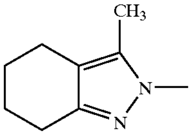 | H | $—S—CH_2—CH{=}CH_2$ |
| 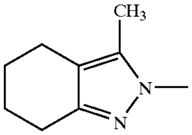 | H | $—S—CH_2—CH{=}CH—Cl$ |
| 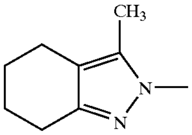 | H | $—S—CH_2—CH{=}CH—CH_3$ |
| 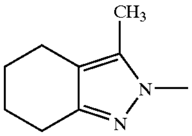 | H | 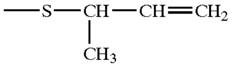 |

-continued
(I)
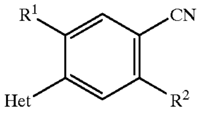
| Het | $R^1$ | $R^2$ |
| --- | --- | --- |
| 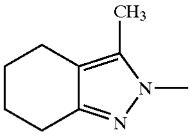 | H | $—S—CH_2—C≡CH$ |
| 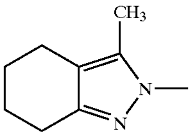 | H | 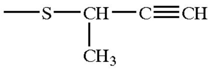 |
| 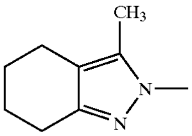 | H | 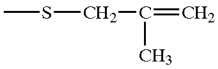 |
| 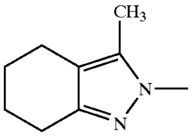 | H | $—S—CH_2—CH_2—OC_2H_5$ |
| 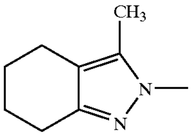 | H | 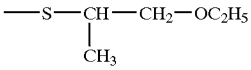 |
| 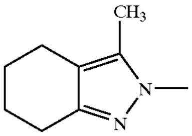 | H | 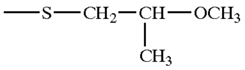 |
| 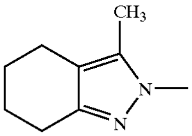 | H | 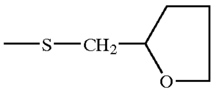 |
| 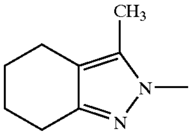 | H | 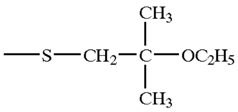 |
| 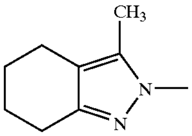 | H | $—S—CH_2—CH_2—O—CH_2—CH_2—OCH_3$ |

-continued
(I)
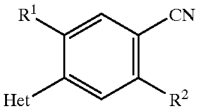
| Het | $R^1$ | $R^2$ |
|---|---|---|
| 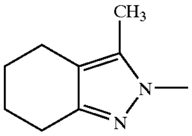 | H | $—S—CH_2—CH_2—O—CH_2—CH_2—OC_2H_5$ |
| 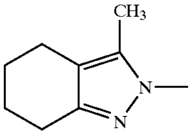 | H | 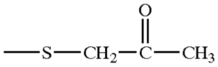 |
| 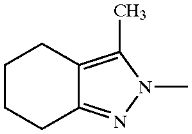 | H | 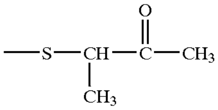 |
| 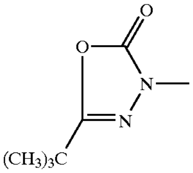 | F | 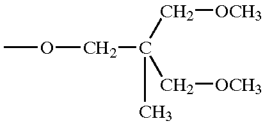 |
| 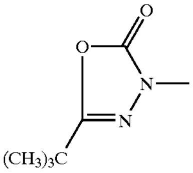 | F | 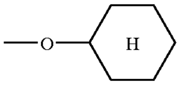 |
| 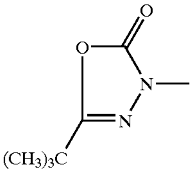 | F | 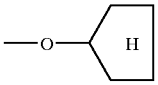 |
| 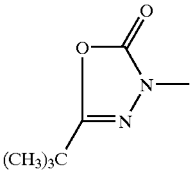 | F | 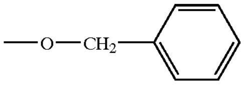 |
| 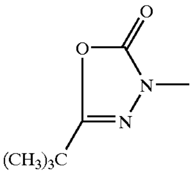 | F | $—O—CH_2—CN$ |

-continued
(I)
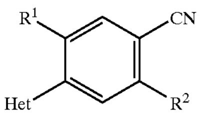
| Het | $R^1$ | $R^2$ |
|---|---|---|
| 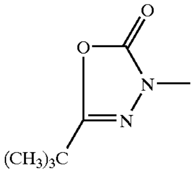 | F | $-O-CH_2-COOC_2H_5$ |
| 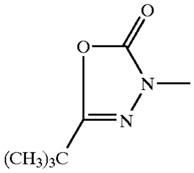 | F | 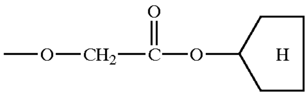 |
| 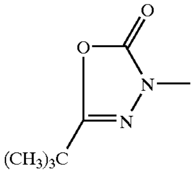 | F | 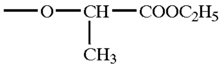 |
| 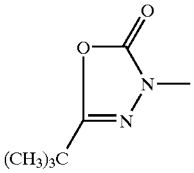 | F | 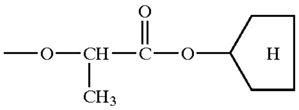 |
| 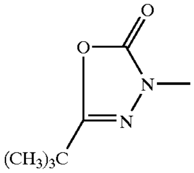 | F | 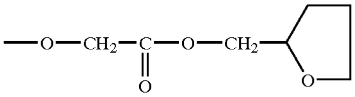 |
| 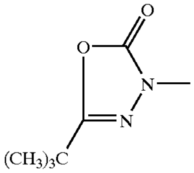 | F | 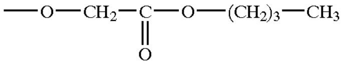 |
| 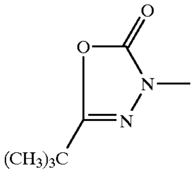 | F | 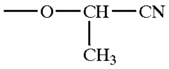 |

-continued
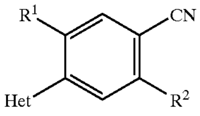
(I)
| Het | $R^1$ | $R^2$ |
|---|---|---|
| 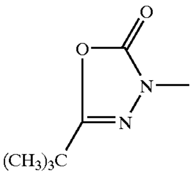 | F | $—O—CH_2—CH_2—O—CH_3$ |
| 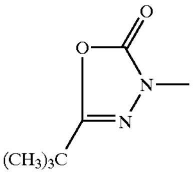 | F | 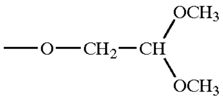 |
| 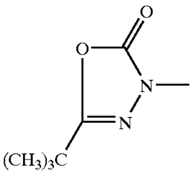 | F | 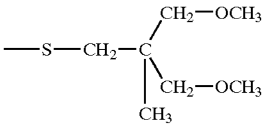 |
| 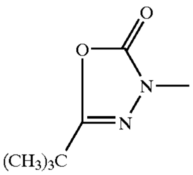 | F | 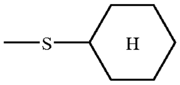 |
| 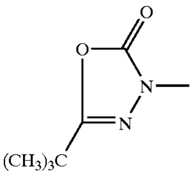 | F | 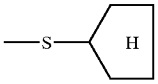 |
| 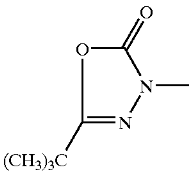 | F | 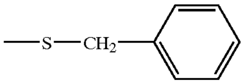 |
| 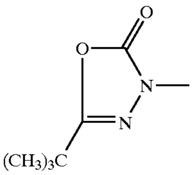 | F | $—S—CH_2—CN$ |

-continued
(I)
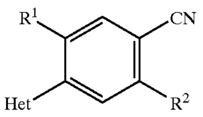
| Het | $R^1$ | $R^2$ |
|---|---|---|
| 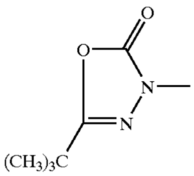 | F | $-S-CH_2-COOC_2H_5$ |
| 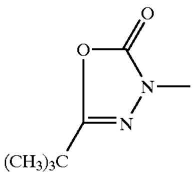 | F | 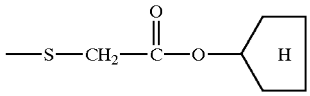 |
| 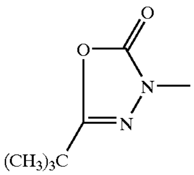 | F | 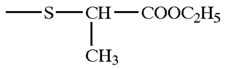 |
| 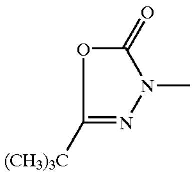 | F | 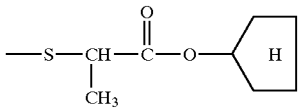 |
| 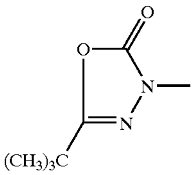 | F | 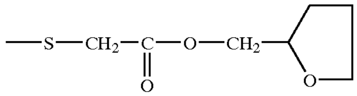 |
| 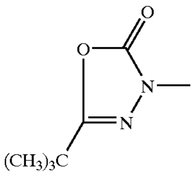 | F | 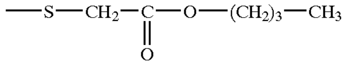 |
| 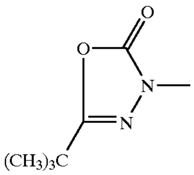 | F | 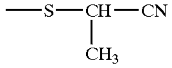 |

-continued
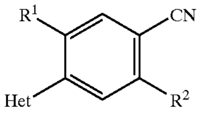
(I)
| Het | $R^1$ | $R^2$ |
|---|---|---|
| 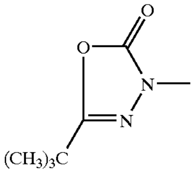 | F | $-S-CH_2-CH_2-O-CH_3$ |
| 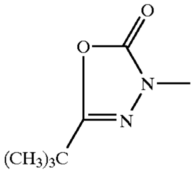 | F | 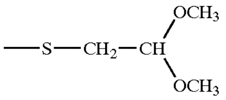 |
| 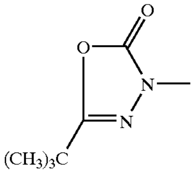 | F | $-OCH_3$ |
| 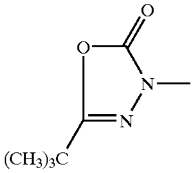 | F | $-OC_2H_5$ |
| 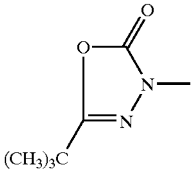 | F | $-O-CH(CH_3)_2$ |
| 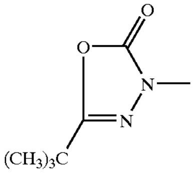 | F | $-O-CH_2-CH=CH_2$ |
| 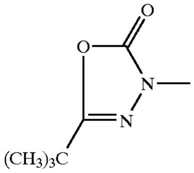 | F | $-O-CH_2-CH=CH-CH_3$ |

-continued
(I)
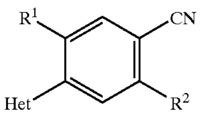
| Het | $R^1$ | $R^2$ |
| --- | --- | --- |
| 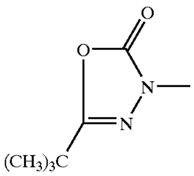 | F | $-O-CH_2-CH=CH-Cl$ |
| 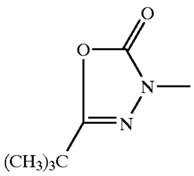 | F | 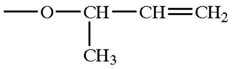 |
| 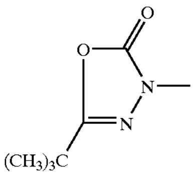 | F | $-O-CH_2-C\equiv CH$ |
| 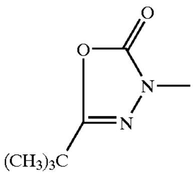 | F | 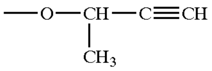 |
| 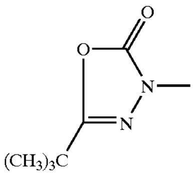 | F | 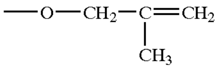 |
| 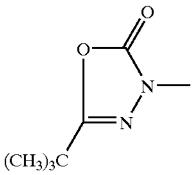 | F | $-O-CH_2-CH_2-OC_2H_5$ |
| 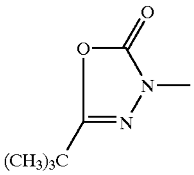 | F | 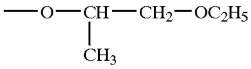 |

-continued
(I)
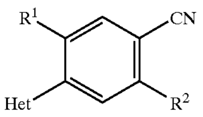
| Het | $R^1$ | $R^2$ |
| --- | --- | --- |
| 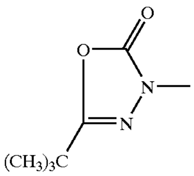 | F | 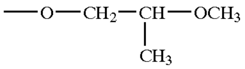 |
| 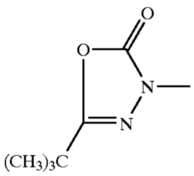 | F | 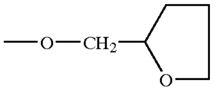 |
| 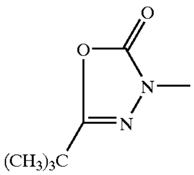 | F | 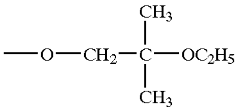 |
| 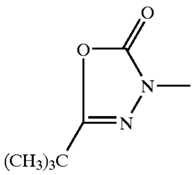 | F | $—O—CH_2—CH_2—O—CH_2—CH_2—OCH_3$ |
| 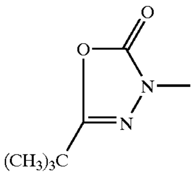 | F | $—O—CH_2—CH_2—O—CH_2—CH_2—OC_2H_5$ |
| 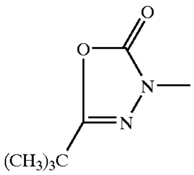 | F | 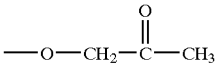 |
| 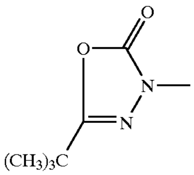 | F | 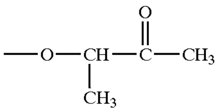 |

-continued
(I)
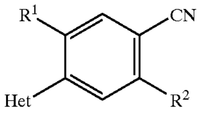
| Het | $R^1$ | $R^2$ |
|---|---|---|
| 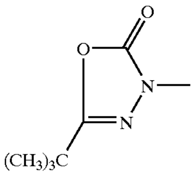 | F | $—SCH_3$ |
| 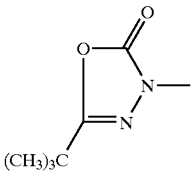 | F | $—SC_2H_5$ |
| 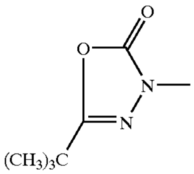 | F | $—S—CH(CH_3)_2$ |
| 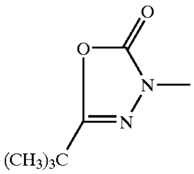 | F | $—S—CH_2—CH{=}CH_2$ |
| 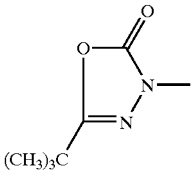 | F | $—S—CH_2—CH{=}CH—Cl$ |
| 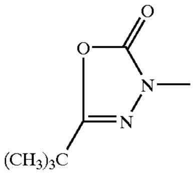 | F | $—S—CH_2—CH{=}CH—CH_3$ |
| 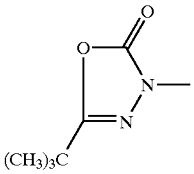 | F | 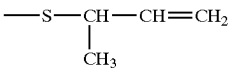 |

-continued
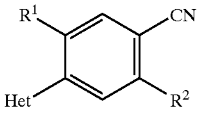
(I)
| Het | $R^1$ | $R^2$ |
|---|---|---|
| 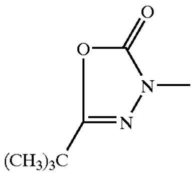 | F | $—S—CH_2—C≡CH$ |
| 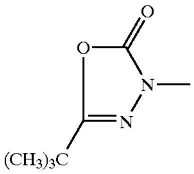 | F | 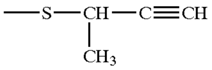 |
| 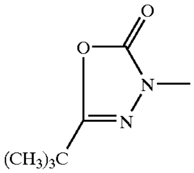 | F | 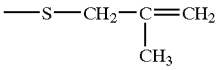 |
| 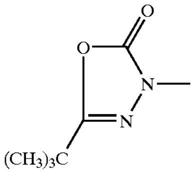 | F | $—S—CH_2—CH_2—OC_2H_5$ |
| 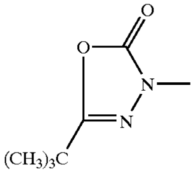 | F | 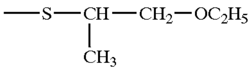 |
| 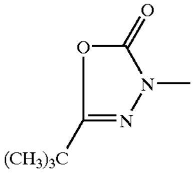 | F | 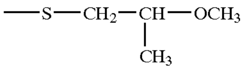 |
| 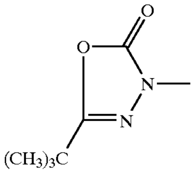 | F | 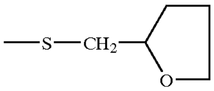 |

-continued
(I)
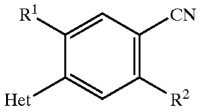
| Het | $R^1$ | $R^2$ |
| --- | --- | --- |
| 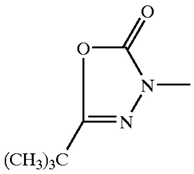 | F | 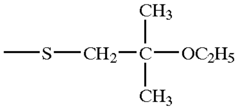 |
| 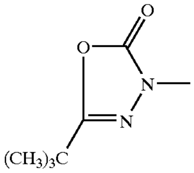 | F | $—S—CH_2—CH_2—O—CH_2—CH_2—OCH_3$ |
| 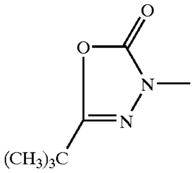 | F | $—S—CH_2—CH_2—O—CH_2—CH_2—OC_2H_5$ |
| 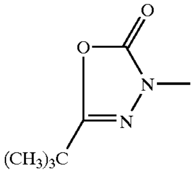 | F | 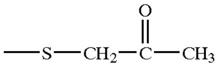 |
| 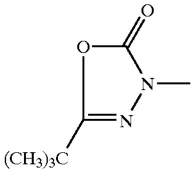 | F | 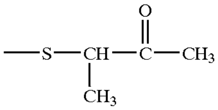 |
| 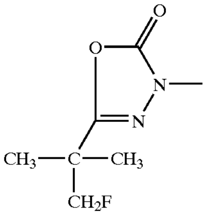 | F | 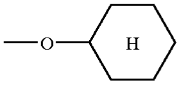 |
| 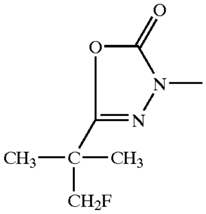 | F | 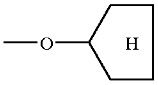 |

-continued
(I)
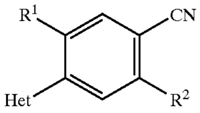
| Het | R¹ | R² |
|---|---|---|
| 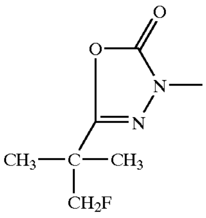 | F | 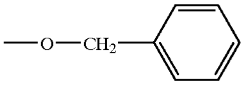 |
| 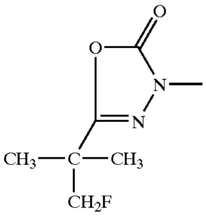 | F | $—O—CH_2—CN$ |
| 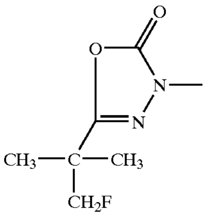 | F | $—O—CH_2—COOC_2H_5$ |
| 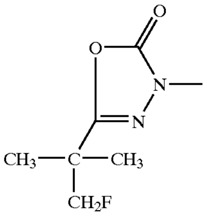 | F | 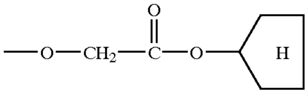 |
| 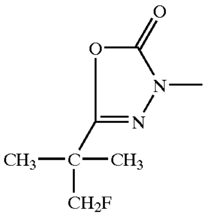 | F | 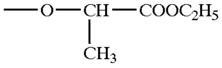 |
| 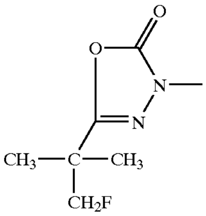 | F | 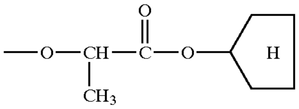 |

-continued
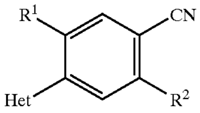
(I)
| Het | $R^1$ | $R^2$ |
| --- | --- | --- |
| 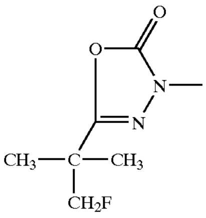 | F | 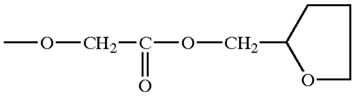 |
| 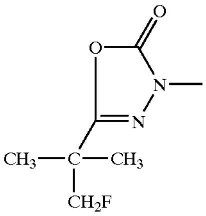 | F | 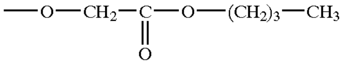 |
| 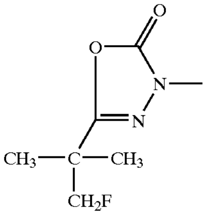 | F | 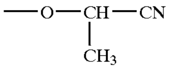 |
| 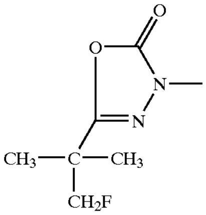 | F | $—O—CH_2—CH_2—O—CH_3$ |
| 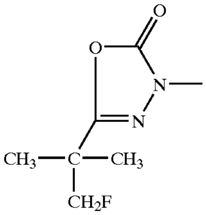 | F | 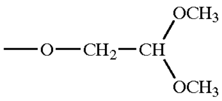 |
| 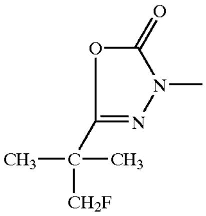 | F | 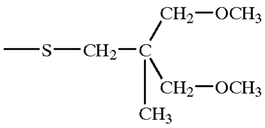 |

-continued
(I)
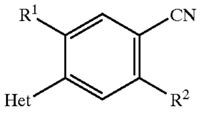
| Het | $R^1$ | $R^2$ |
|---|---|---|
| 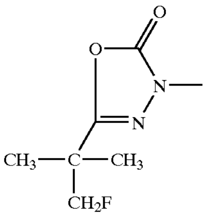 | F | 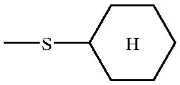 |
| 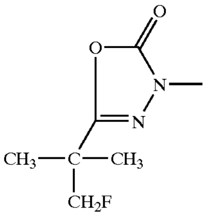 | F | 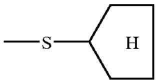 |
| 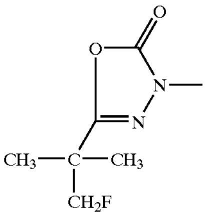 | F | 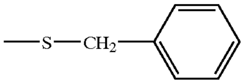 |
| 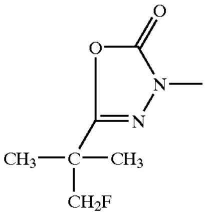 | F | $—S—CH_2—CN$ |
| 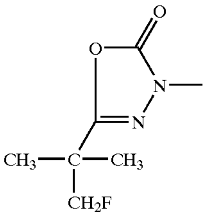 | F | $—S—CH_2—COOC_2H_5$ |
| 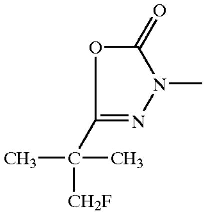 | F | 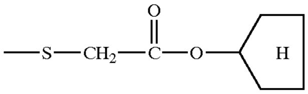 |

-continued
(I)
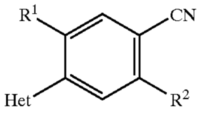
| Het | $R^1$ | $R^2$ |
| --- | --- | --- |
| 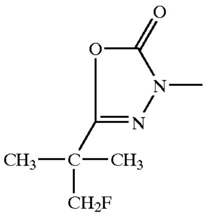 | F | 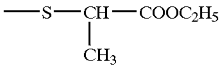 |
| 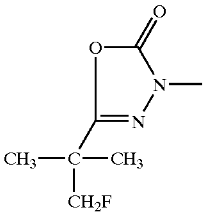 | F | 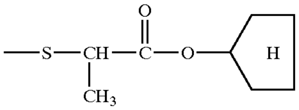 |
| 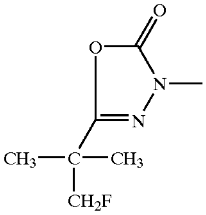 | F | 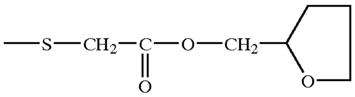 |
| 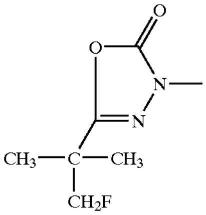 | F | 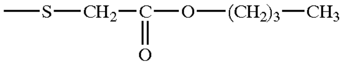 |
| 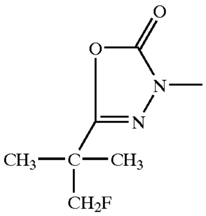 | F | 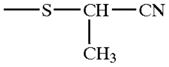 |
| 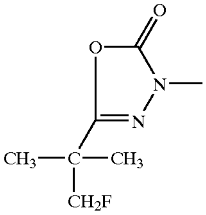 | F | $—S—CH_2—CH_2—OCH_3$ |

-continued
(I)
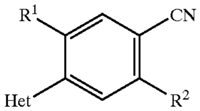
| Het | $R^1$ | $R^2$ |
|---|---|---|
| 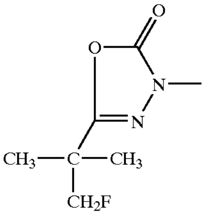 | F | 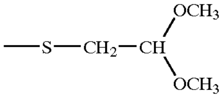 |
| 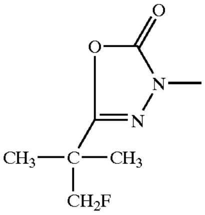 | H | $—O—CH_2—CH_2—O—CH_2—CH_2—OCH_3$ |
| 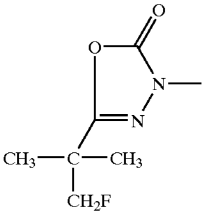 | H | $—O—CH_2—CH_2—O—CH_2—CH_2—OC_2H_5$ |
| 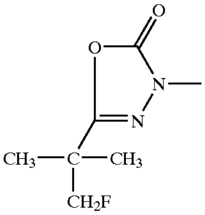 | H | 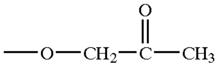 |
| 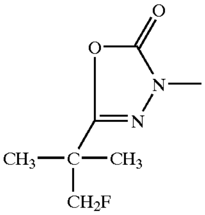 | H | 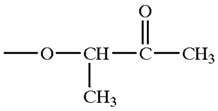 |
| 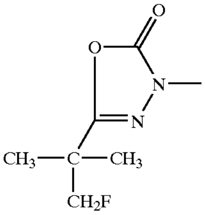 | H | $—SCH_3$ |

-continued
(I)
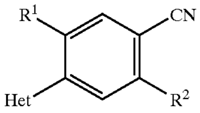
| Het | $R^1$ | $R^2$ |
|---|---|---|
| 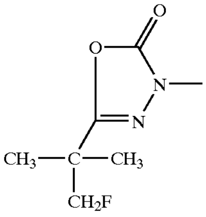 | H | $—SC_2H_5$ |
| 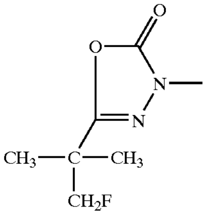 | H | $—S—CH(CH_3)_2$ |
| 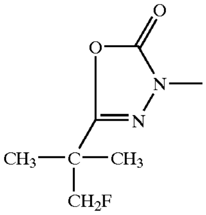 | H | $—S—CH_2—CH{=}CH_2$ |
| 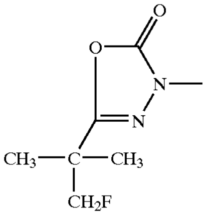 | H | $—S—CH_2—CH{=}CH—Cl$ |
| 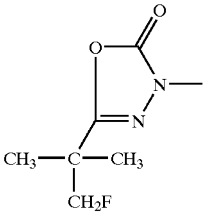 | H | $—S—CH_2—CH{=}CH—CH_3$ |
| 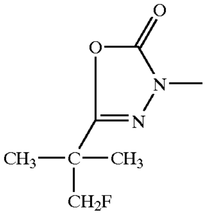 | H | 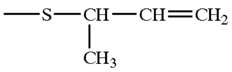 |

-continued
(I)
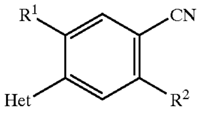
| Het | $R^1$ | $R^2$ |
|---|---|---|
| 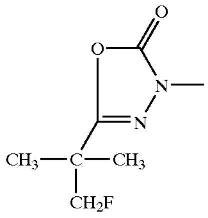 | H | $—S—CH_2—C≡CH$ |
| 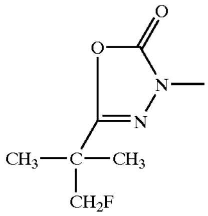 | H | 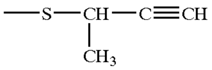 |
| 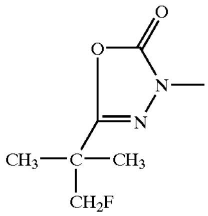 | H | 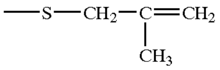 |
| 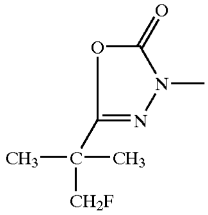 | H | $—S—CH_2—CH_2—OC_2H_5$ |
| 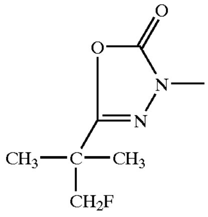 | H | 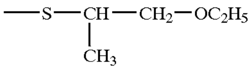 |
| 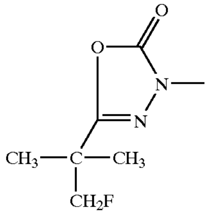 | H | 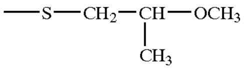 |

-continued
(I)
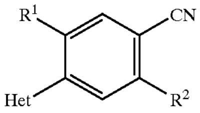
| Het | $R^1$ | $R^2$ |
|---|---|---|
| 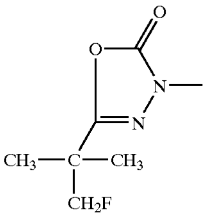 | H | 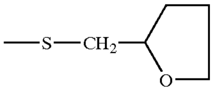 |
| 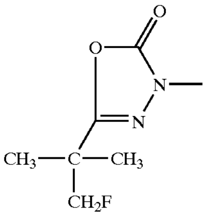 | H | 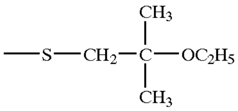 |
| 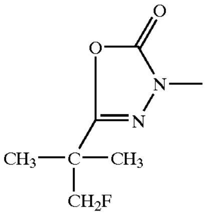 | H | $—S—CH_2—CH_2—O—CH_2—CH_2—OCH_3$ |
| 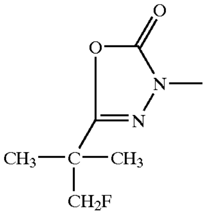 | H | $—S—CH_2—CH_2—O—CH_2—CH_2—OC_2H_5$ |
| 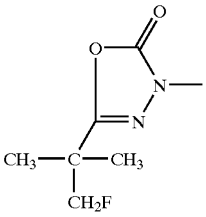 | H | 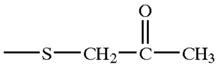 |
| 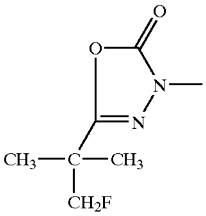 | H | 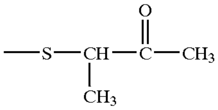 |

-continued
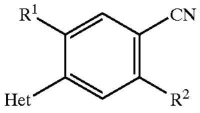
(I)
| Het | $R^1$ | $R^2$ |
|---|---|---|
| 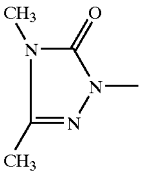 | F | 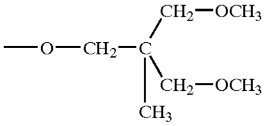 |
| 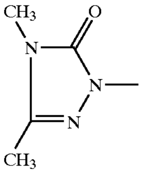 | F | 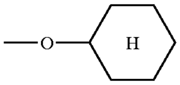 |
| 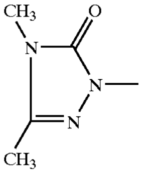 | F | 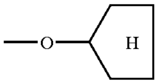 |
| 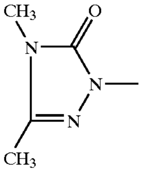 | F | 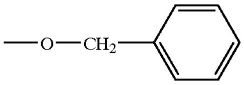 |
| 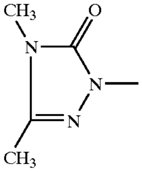 | F | $—O—CH_2—CN$ |
| 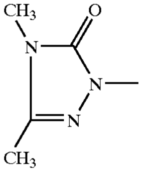 | F | $—O—CH_2—COOC_2H_5$ |
| 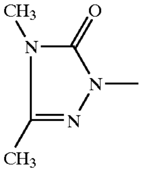 | F | 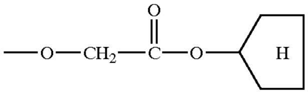 |

-continued
(I)
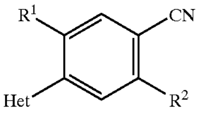
| Het | $R^1$ | $R^2$ |
|---|---|---|
| 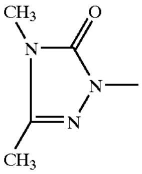 | F | 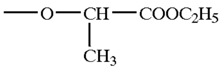 |
| 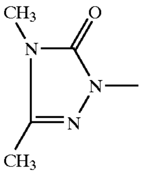 | F | 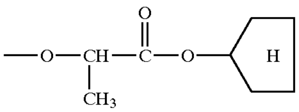 |
| 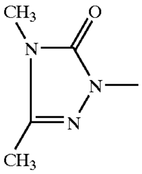 | F | 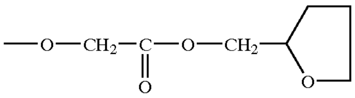 |
| 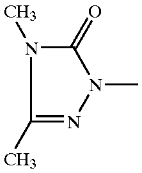 | F | 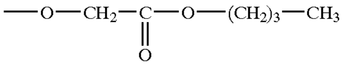 |
| 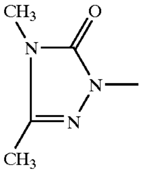 | F | 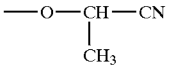 |
| 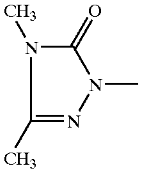 | F | $-O-CH_2-CH_2-O-CH_3$ |
| 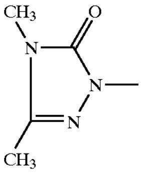 | F | 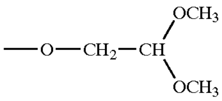 |

-continued
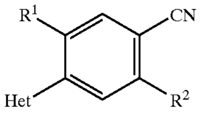
(I)
| Het | $R^1$ | $R^2$ |
| --- | --- | --- |
| 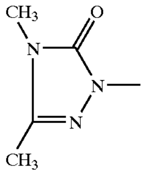 | F | 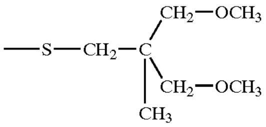 |
| 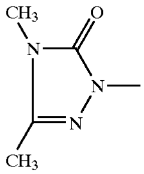 | F | 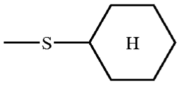 |
| 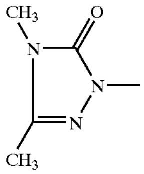 | F | 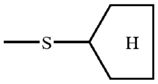 |
| 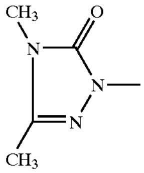 | F | 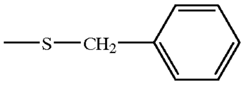 |
| 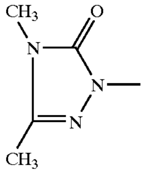 | F | $-S-CH_2-CN$ |
| 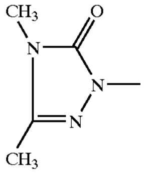 | F | $-S-CH_2-COOC_2H_5$ |
| 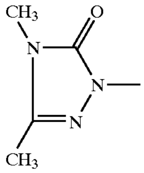 | F | 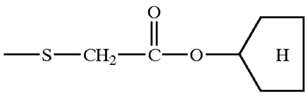 |

-continued
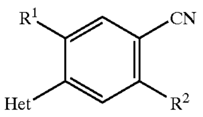
(I)
| Het | $R^1$ | $R^2$ |
|---|---|---|
| 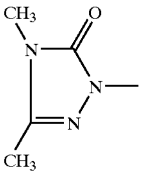 | F | 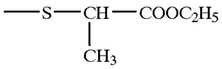 |
| 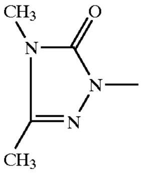 | F | 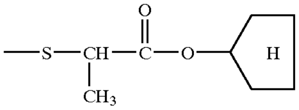 |
| 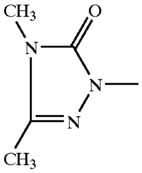 | F | 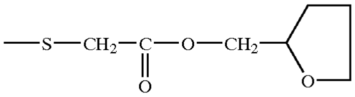 |
| 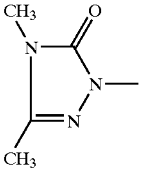 | F | 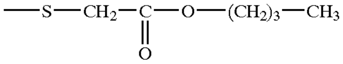 |
| 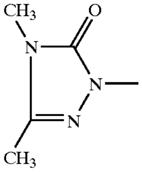 | F | 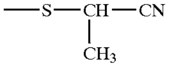 |
| 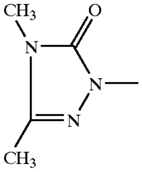 | F | $—S—CH_2—CH_2—O—CH_3$ |
| 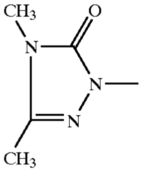 | F | 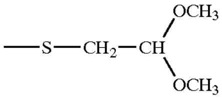 |

-continued
(I)
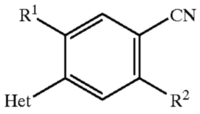
| Het | $R^1$ | $R^2$ |
| --- | --- | --- |
| 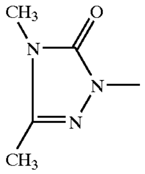 | F | $—OCH_3$ |
| 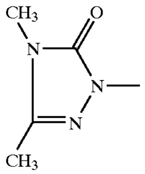 | F | $—OC_2H_5$ |
| 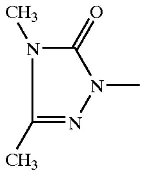 | F | $—O—CH(CH_3)_2$ |
| 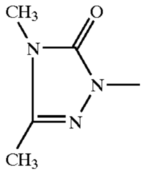 | F | $—O—CH_2—CH{=}CH_2$ |
| 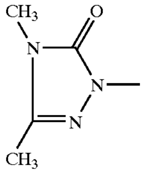 | F | $—O—CH_2—CH{=}CH—CH_3$ |
| 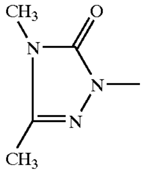 | F | $—O—CH_2—CH{=}CH—Cl$ |
| 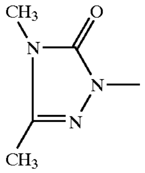 | F | 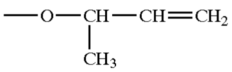 |

-continued
(I)
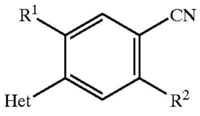
| Het | $R^1$ | $R^2$ |
|---|---|---|
| 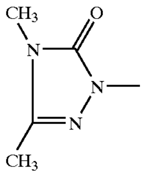 | F | $-O-CH_2-C\equiv CH$ |
| 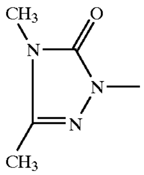 | F | 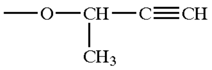 |
| 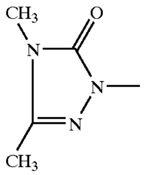 | F | 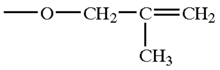 |
| 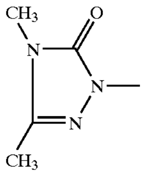 | F | $-O-CH_2-CH_2-OC_2H_5$ |
| 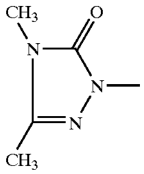 | F | 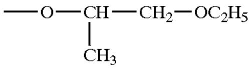 |
| 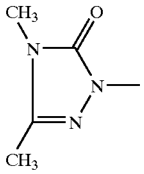 | F | 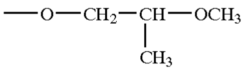 |
| 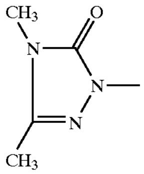 | F | 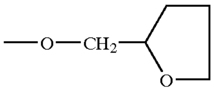 |

-continued
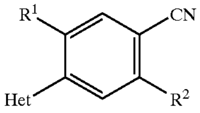
(I)
| Het | $R^1$ | $R^2$ |
|---|---|---|
| 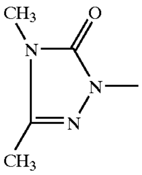 | F | 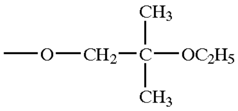 |
| 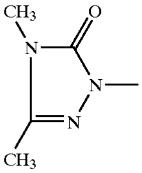 | F | $—O—CH_2—CH_2—O—CH_2—CH_2—OCH_3$ |
| 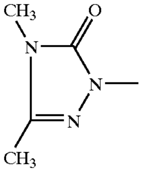 | F | $—O—CH_2—CH_2—O—CH_2—CH_2—OC_2H_5$ |
| 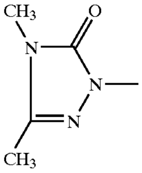 | F | 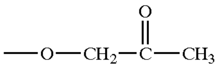 |
| 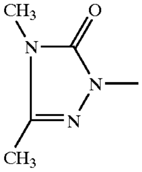 | F | 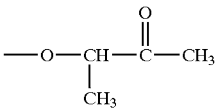 |
| 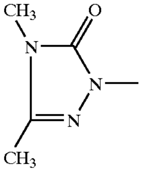 | F | $—SCH_3$ |
| 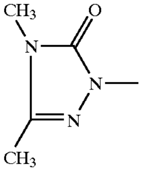 | F | $—SC_2H_5$ |

-continued
(I)
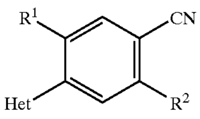
| Het | $R^1$ | $R^2$ |
|---|---|---|
| 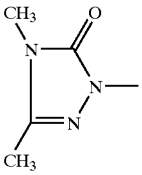 | F | $-S-CH(CH_3)_2$ |
| 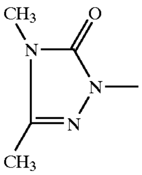 | F | $-S-CH_2-CH{=}CH_2$ |
| 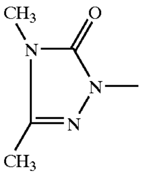 | F | $-S-CH_2-CH{=}CH-Cl$ |
| 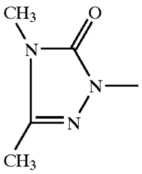 | F | $-S-CH_2-CH{=}CH-CH_3$ |
| 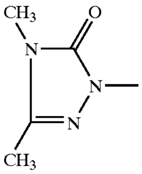 | F | 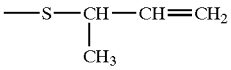 |
| 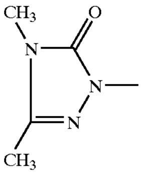 | F | $-S-CH_2-C{\equiv}CH$ |
| 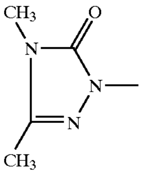 | F | 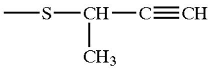 |

-continued
(I)
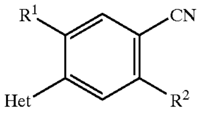
| Het | $R^1$ | $R^2$ |
|---|---|---|
| 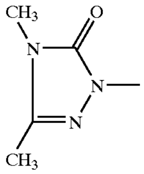 | F | 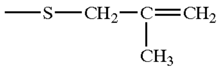 |
| 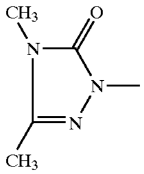 | F | $—S—CH_2—CH_2—OC_2H_5$ |
| 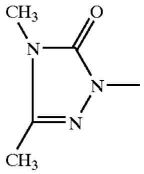 | F | 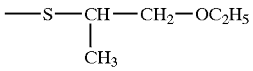 |
| 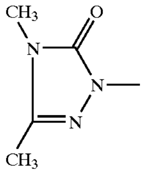 | F | 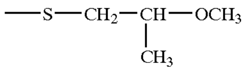 |
| 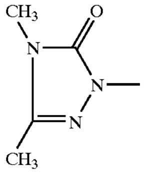 | F | 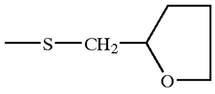 |
| 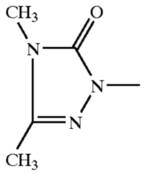 | F | 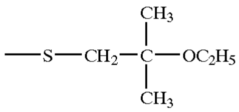 |
| 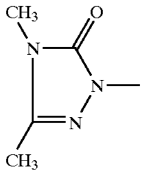 | F | $—S—CH_2—CH_2—O—CH_2—CH_2—OCH_3$ |

-continued
(I)
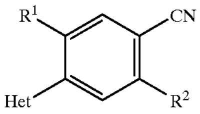
| Het | $R^1$ | $R^2$ |
|---|---|---|
| 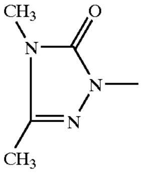 | F | $—S—CH_2—CH_2—O—CH_2—CH_2—OC_2H_5$ |
| 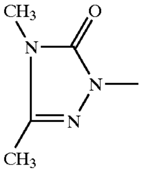 | F | 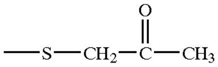 |
| 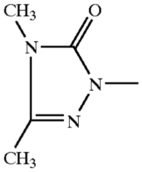 | F | 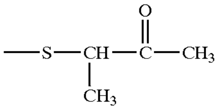 |
| 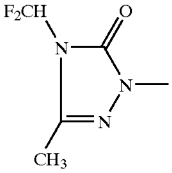 | F | 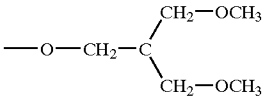 |
| 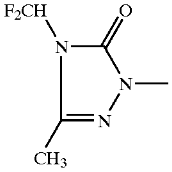 | F | 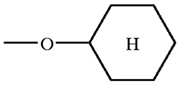 |
| 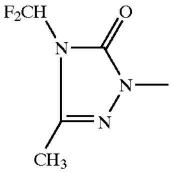 | F | 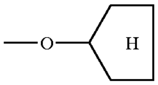 |
| 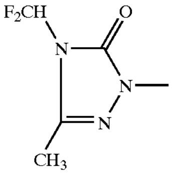 | F | 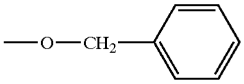 |

-continued
(I)
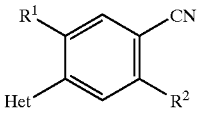
| Het | $R^1$ | $R^2$ |
| --- | --- | --- |
| 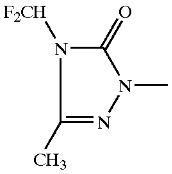 | F | $-O-CH_2-CN$ |
| 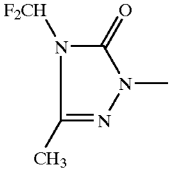 | F | $-O-CH_2-COOC_2H_5$ |
| 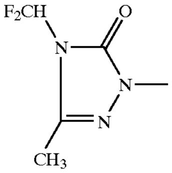 | F | 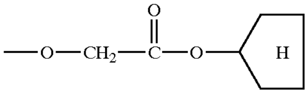 |
| 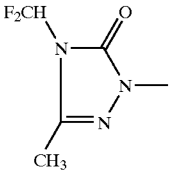 | F | 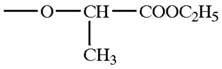 |
| 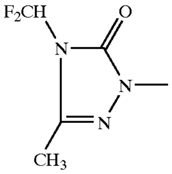 | F | 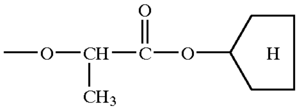 |
| 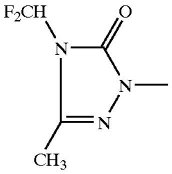 | F | 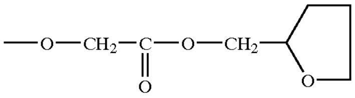 |
| 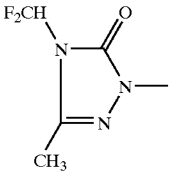 | F | 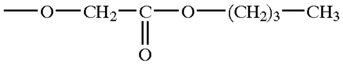 |

-continued
(I)
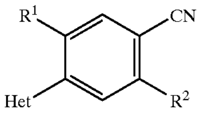
| Het | $R^1$ | $R^2$ |
|---|---|---|
| 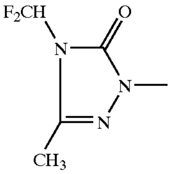 | F | 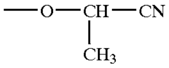 |
| 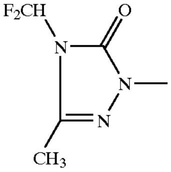 | F | $—O—CH_2—CH_2—O—CH_3$ |
| 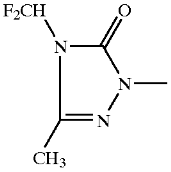 | F | 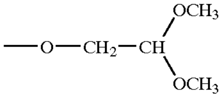 |
| 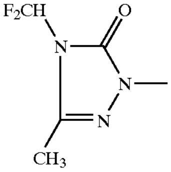 | H | 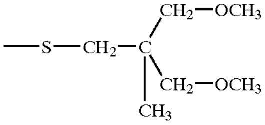 |
| 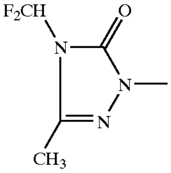 | H | 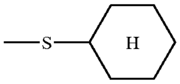 |
| 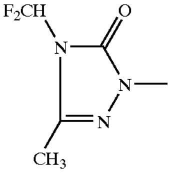 | H | 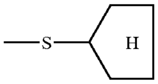 |
| 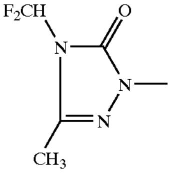 | H | 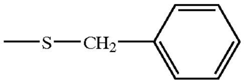 |

-continued
(I)
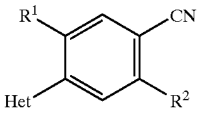
| Het | $R^1$ | $R^2$ |
|---|---|---|
| 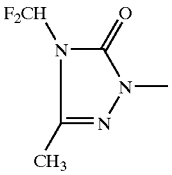 | H | $—S—CH_2—CN$ |
| 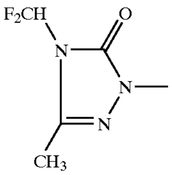 | H | $—S—CH_2—COOC_2H_5$ |
| 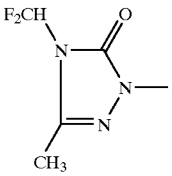 | H | 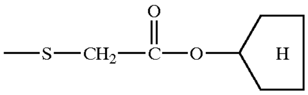 |
| 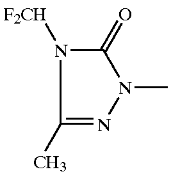 | H | 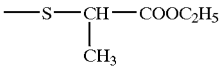 |
| 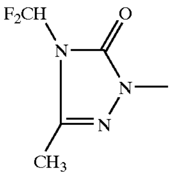 | H | 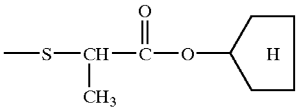 |
| 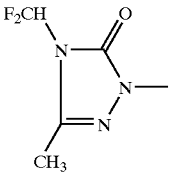 | H | 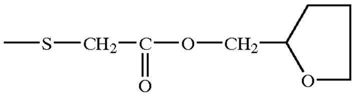 |
| 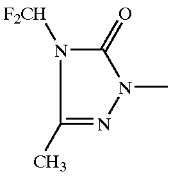 | H | 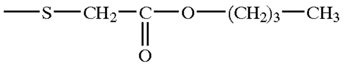 |

-continued
(I)
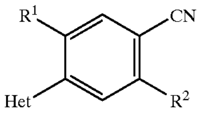
| Het | $R^1$ | $R^2$ |
|---|---|---|
| 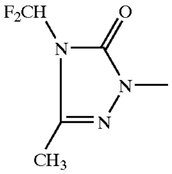 | H | 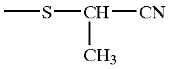 |
| 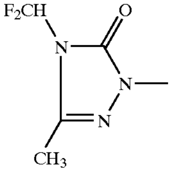 | H | $-S-CH_2-CH_2-O-CH_3$ |
| 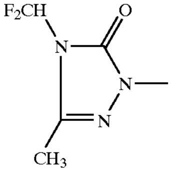 | H | 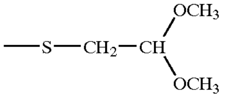 |
| 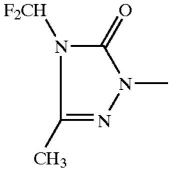 | F | $-OCH_3$ |
| 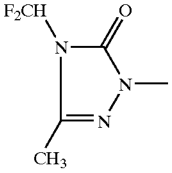 | F | $-OC_2H_5$ |
| 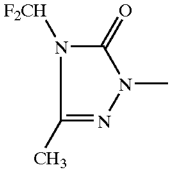 | F | $-O-CH(CH_3)_2$ |
| 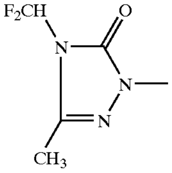 | F | $-O-CH_2-CH\equiv CH_2$ |

-continued
(I)
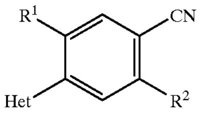
| Het | $R^1$ | $R^2$ |
|---|---|---|
| 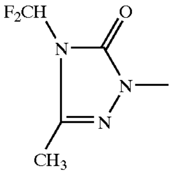 | F | $—O—CH_2—CH{=}CH—CH_3$ |
| 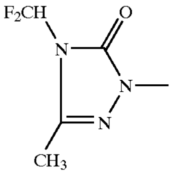 | F | $—O—CH_2—CH{=}CH—Cl$ |
| 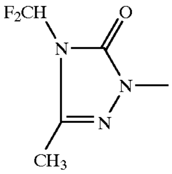 | F | 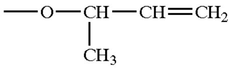 |
| 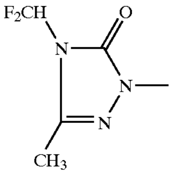 | F | $—O—CH_2—C{\equiv}CH$ |
| 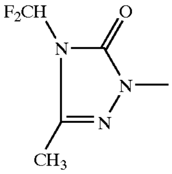 | F | 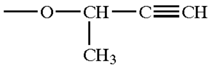 |
| 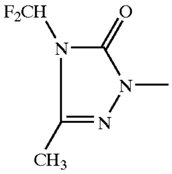 | F | 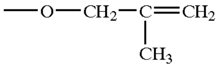 |
| 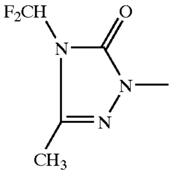 | F | $—O—CH_2—CH_2—OC_2H_5$ |

-continued
(I)
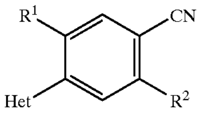
| Het | $R^1$ | $R^2$ |
|---|---|---|
| 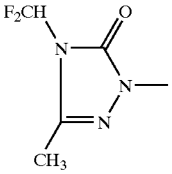 | F | 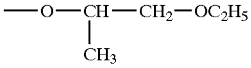 |
| 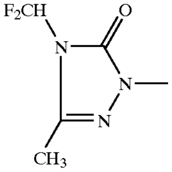 | F | 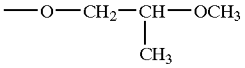 |
| 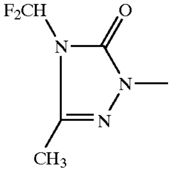 | F | 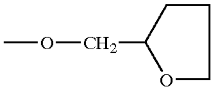 |
| 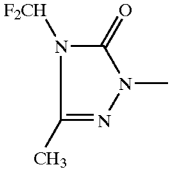 | F | 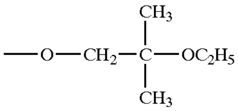 |
| 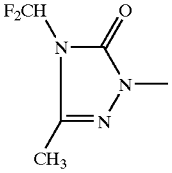 | F | $—O—CH_2—CH_2—O—CH_2—CH_2—OCH_3$ |
| 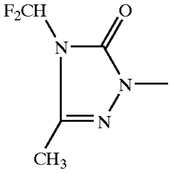 | F | $—O—CH_2—CH_2—O—CH_2—CH_2—OC_2H_5$ |
| 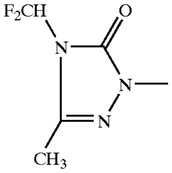 | F | 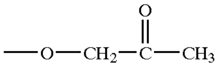 |

-continued
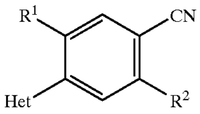
(I)
| Het | $R^1$ | $R^2$ |
|---|---|---|
| 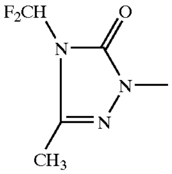 | F | 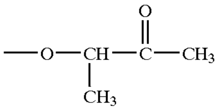 |
| 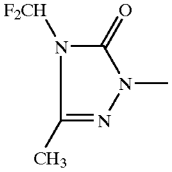 | H | $—SCH_3$ |
| 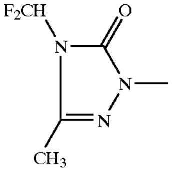 | H | $—SC_2H_5$ |
| 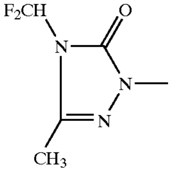 | H | $—S—CH(CH_3)_2$ |
| 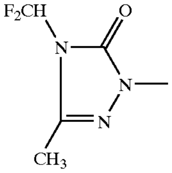 | H | $—S—CH_2—CH{=}CH_2$ |
| 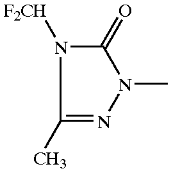 | H | $—S—CH_2—CH{=}CH—Cl$ |
| 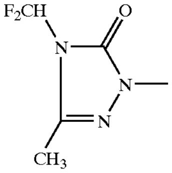 | H | $—S—CH_2—CH{=}CH—CH_3$ |

-continued
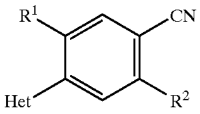
(I)
| Het | $R^1$ | $R^2$ |
| --- | --- | --- |
| 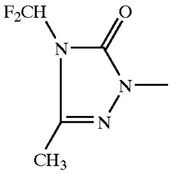 | H | 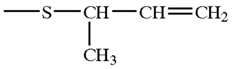 |
| 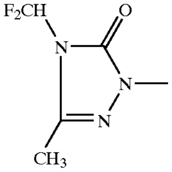 | H | $—S—CH_2—C{\equiv}CH$ |
| 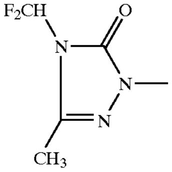 | H | 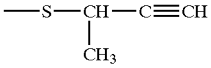 |
| 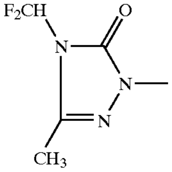 | H | 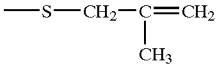 |
| 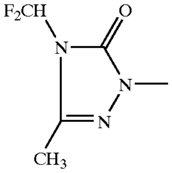 | H | $—S—CH_2—CH_2—OC_2H_5$ |
| 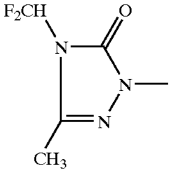 | H | $—S—CH—CH_2—OC_2H_5$ |
| 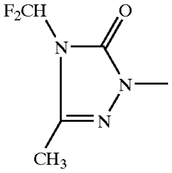 | H | 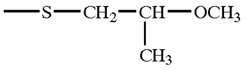 |

-continued
(I)
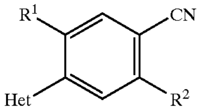
| Het | $R^1$ | $R^2$ |
| --- | --- | --- |
| 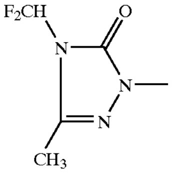 | H | 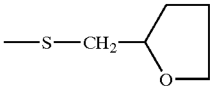 |
| 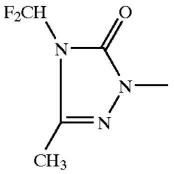 | H | 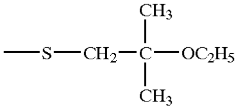 |
| 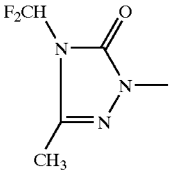 | H | $-S-CH_2-CH_2-O-CH_2-CH_2-OCH_3$ |
| 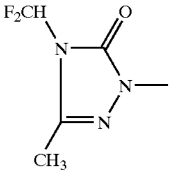 | H | $-S-CH_2-CH_2-O-CH_2-CH_2-OC_2H_5$ |
| 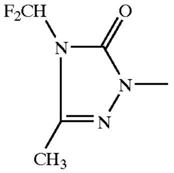 | H | 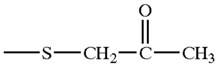 |
| 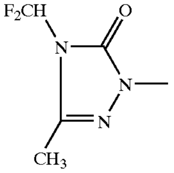 | H | 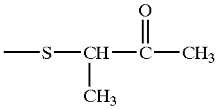 |
| 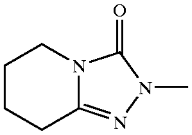 | F | 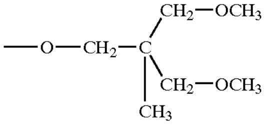 |
| 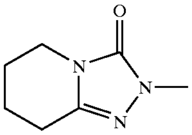 | F | 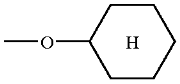 |

-continued
(I)
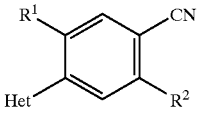
| Het | $R^1$ | $R^2$ |
|---|---|---|
| 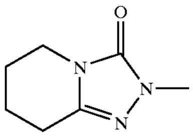 | F | 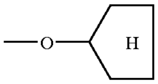 |
| 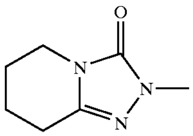 | F | 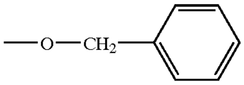 |
| 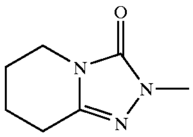 | F | $—O—CH_2—CN$ |
| 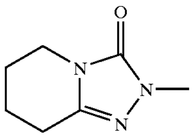 | F | $—O—CH_2—COOC_2H_5$ |
| 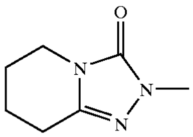 | F | 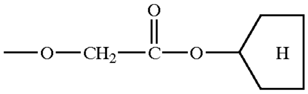 |
| 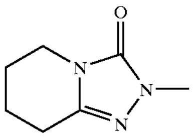 | F | 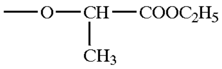 |
| 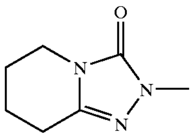 | F | 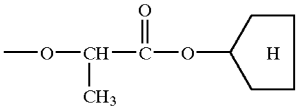 |
| 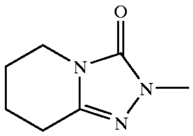 | F | 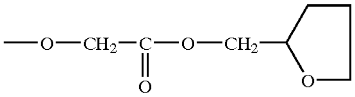 |
| 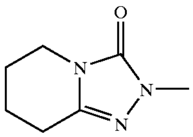 | F | 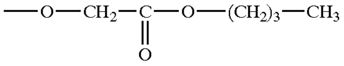 |

-continued
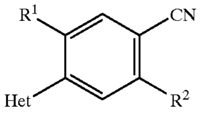
(I)
| Het | $R^1$ | $R^2$ |
|---|---|---|
| 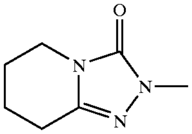 | F | 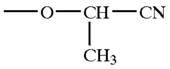 |
| 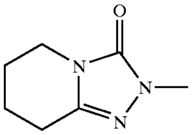 | F | $—O—CH_2—CH_2—O—CH_3$ |
| 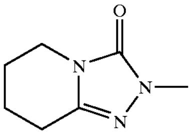 | F | 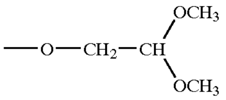 |
| 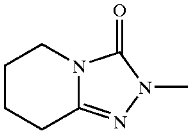 | F | 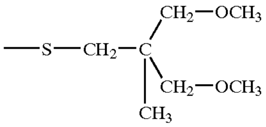 |
| 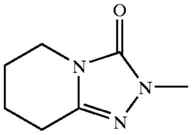 | F | 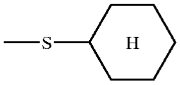 |
| 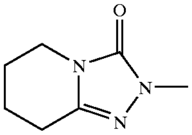 | F | 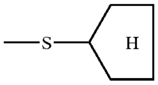 |
| 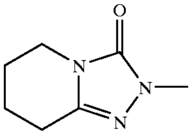 | F | 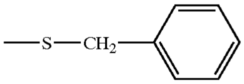 |
| 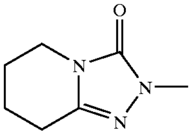 | F | $—S—CH_2—CN$ |
| 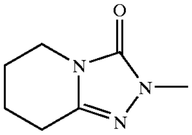 | F | $—S—CH_2—COOC_2H_5$ |

-continued
(I)
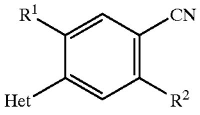
| Het | $R^1$ | $R^2$ |
|---|---|---|
| 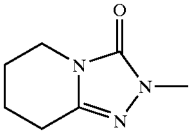 | F | 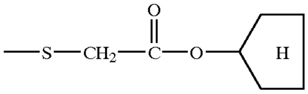 |
| 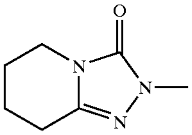 | F | 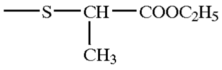 |
| 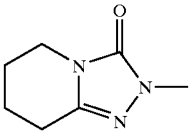 | F | 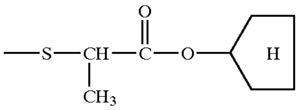 |
| 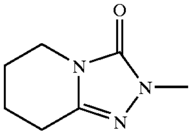 | F | 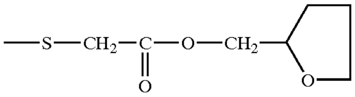 |
| 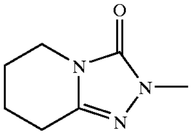 | F | 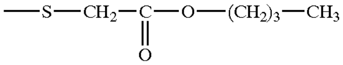 |
| 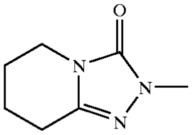 | F | 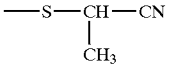 |
| 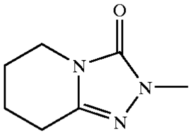 | F | $-S-CH_2-CH_2-O-CH_3$ |
| 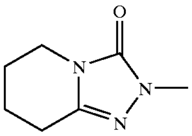 | F | 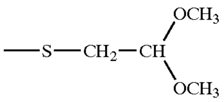 |
| 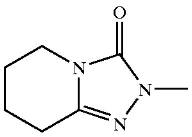 | F | $-OCH_3$ |

-continued
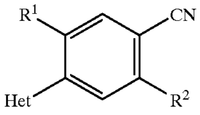
(I)
| Het | $R^1$ | $R^2$ |
|---|---|---|
| 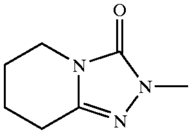 | F | $-OC_2H_5$ |
| 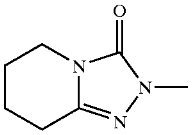 | F | $-O-CH(CH_3)_2$ |
| 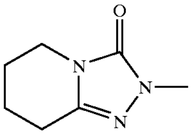 | F | $-O-CH_2-CH=CH_2$ |
| 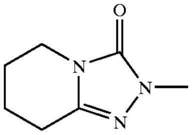 | F | $-O-CH_2-CH=CH-CH_3$ |
| 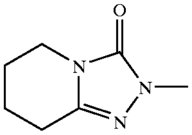 | F | $-O-CH_2-CH=CH-Cl$ |
| 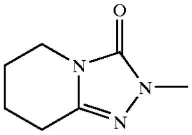 | F | 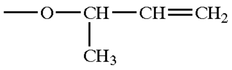 |
| 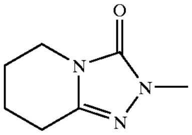 | F | $-O-CH_2-C\equiv CH$ |
| 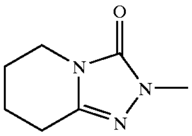 | F | 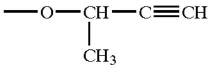 |
| 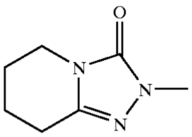 | F | 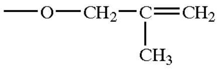 |

-continued
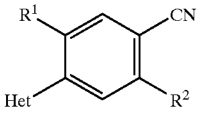
(I)
| Het | $R^1$ | $R^2$ |
|---|---|---|
| 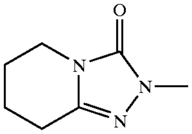 | F | $—O—CH_2—CH_2—OC_2H_5$ |
| 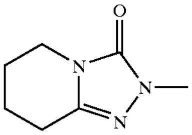 | F | 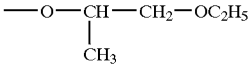 |
| 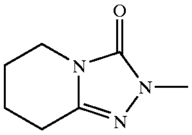 | F | 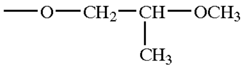 |
| 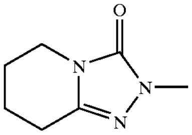 | F | 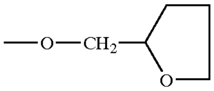 |
| 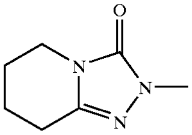 | F | 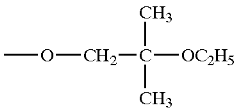 |
| 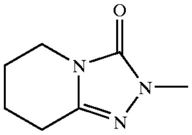 | F | $—O—CH_2—CH_2—O—CH_2—CH_2—OCH_3$ |
| 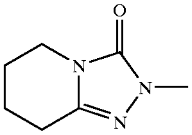 | F | $—O—CH_2—CH_2—O—CH_2—CH_2—OC_2H_5$ |
| 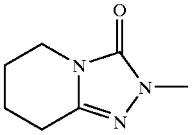 | F | 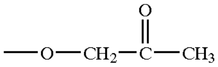 |
| 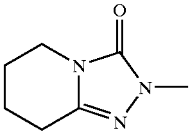 | F | 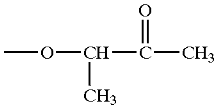 |

-continued
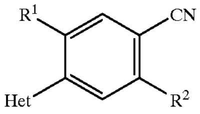
(I)
| Het | $R^1$ | $R^2$ |
|---|---|---|
| 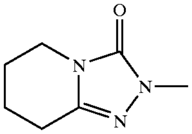 | F | $—SCH_3$ |
| 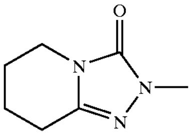 | F | $—SC_2H_5$ |
| 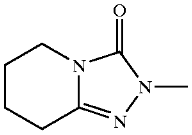 | F | $—S—CH(CH_3)_2$ |
| 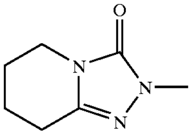 | F | $—S—CH_2—CH{=}CH_2$ |
| 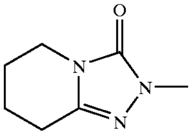 | F | $—S—CH_2—CH{=}CH—Cl$ |
| 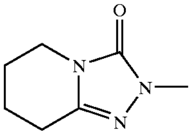 | F | $—S—CH_2—CH{=}CH—CH_3$ |
| 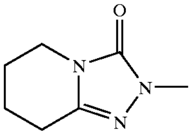 | F | 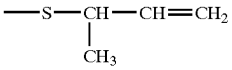 |
| 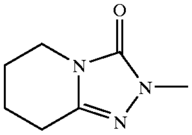 | F | $—S—CH_2—C{\equiv}CH$ |
| 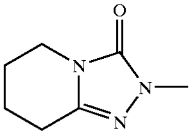 | F | 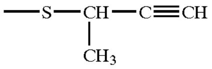 |

-continued
(I)
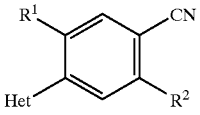
| Het | $R^1$ | $R^2$ |
|---|---|---|
| 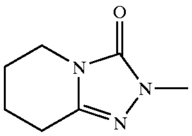 | F | 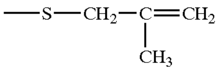 |
| 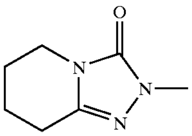 | F | $—S—CH_2—CH_2—OC_2H_5$ |
| 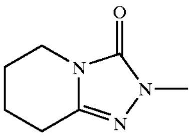 | F | 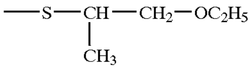 |
| 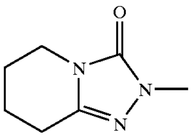 | F | 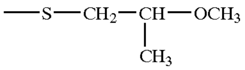 |
| 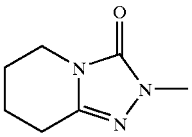 | F | 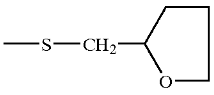 |
| 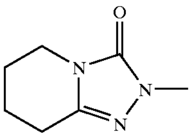 | F | 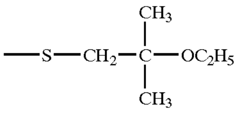 |
| 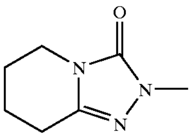 | F | $—S—CH_2—CH_2—O—CH_2—CH_2—OCH_3$ |
| 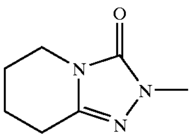 | F | $—S—CH_2—CH_2—O—CH_2—CH_2—OC_2H_5$ |
| 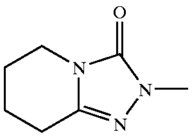 | F | 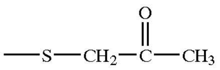 |

-continued
(I)
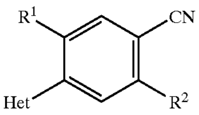
| Het | $R^1$ | $R^2$ |
| --- | --- | --- |
| 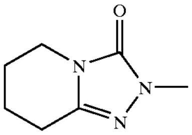 | F | 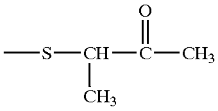 |
| 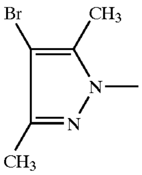 | H | 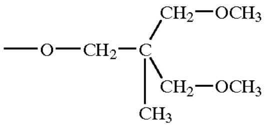 |
| 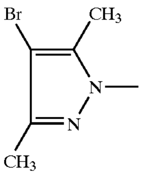 | H | 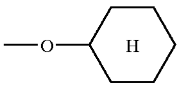 |
| 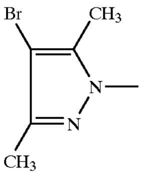 | H | 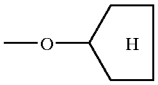 |
| 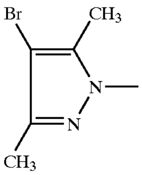 | H | 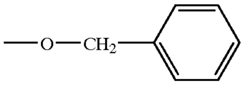 |
| 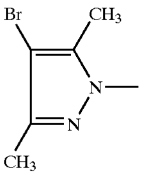 | H | $-O-CH_2-CN$ |
| 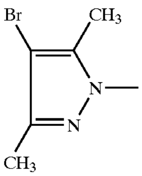 | H | $-O-CH_2-COOC_2H_5$ |

-continued
(I)
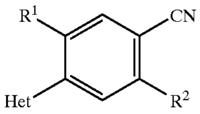
| Het | $R^1$ | $R^2$ |
| --- | --- | --- |
| 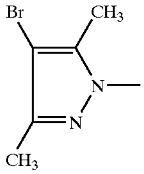 | H | 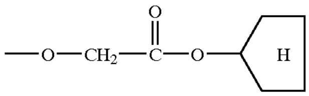 |
| 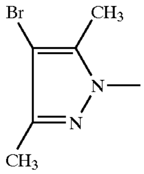 | H | 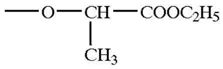 |
| 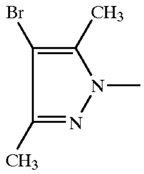 | H | 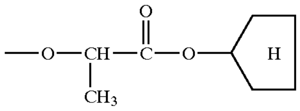 |
| 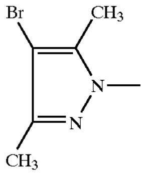 | H | 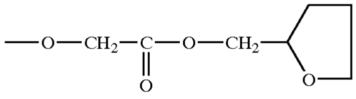 |
| 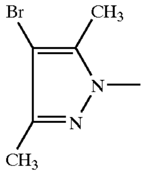 | H | 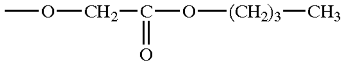 |
| 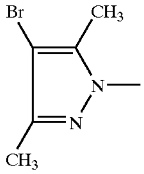 | H | 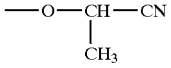 |
| 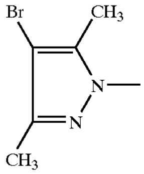 | H | $—O—CH_2—CH_2—O—CH_3$ |

-continued
(I)
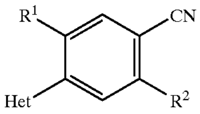
| Het | R¹ | R² |
|---|---|---|
| 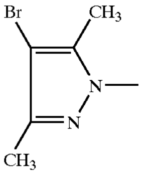 | H | 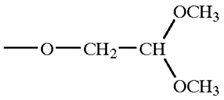 |
| 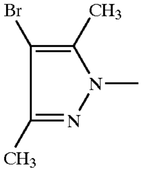 | H | 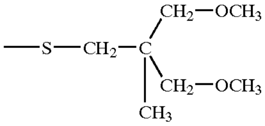 |
| 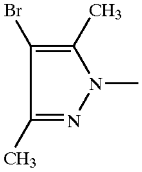 | H | 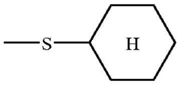 |
| 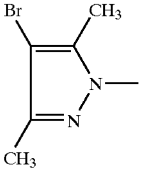 | H | 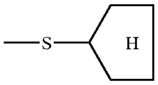 |
| 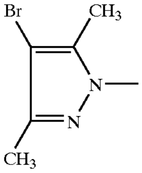 | H | 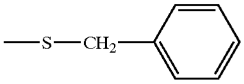 |
| 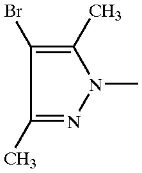 | H | $-S-CH_2-CN$ |
| 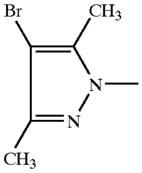 | H | $-S-CH_2-COOC_2H_5$ |

-continued
(I)
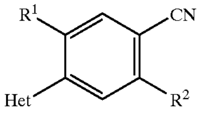
| Het | $R^1$ | $R^2$ |
|---|---|---|
| 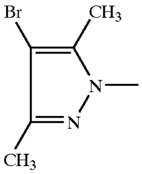 | H | 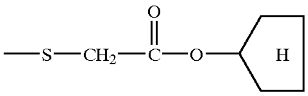 |
| 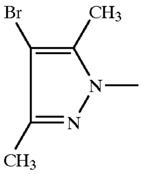 | H | 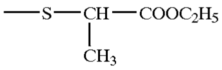 |
| 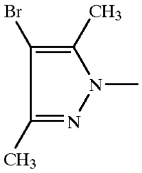 | H | 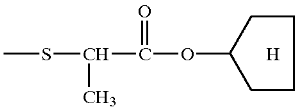 |
| 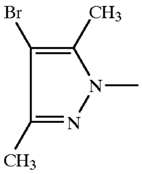 | H | 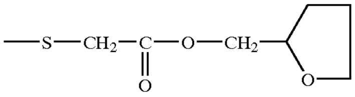 |
| 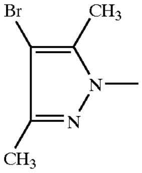 | H | 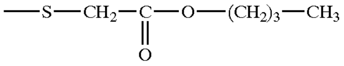 |
| 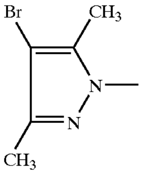 | H | 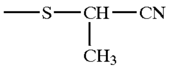 |
| 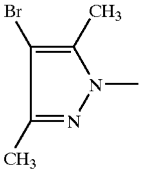 | H | $—S—CH_2—CH_2—O—CH_3$ |

-continued
(I)
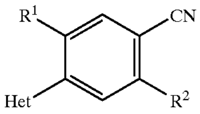
| Het | $R^1$ | $R^2$ |
|---|---|---|
| 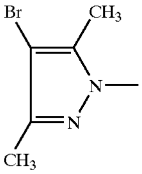 | H | 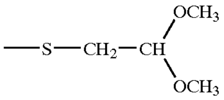 |
| 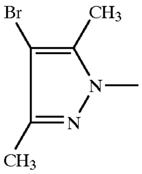 | F | $-OCH_3$ |
| 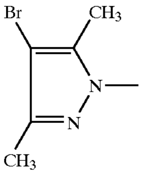 | F | $-OC_2H_5$ |
| 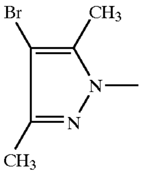 | F | $-O-CH(CH_3)_2$ |
| 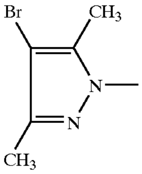 | F | $-O-CH_2-CH=CH_2$ |
| 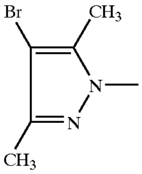 | F | $-O-CH_2-CH=CH-CH_3$ |
| 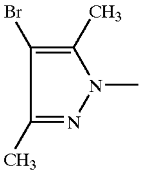 | F | $-O-CH_2-CH=CH-Cl$ |

-continued
(I)
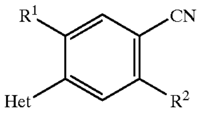
| Het | $R^1$ | $R^2$ |
|---|---|---|
| 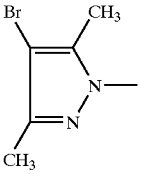 | F | 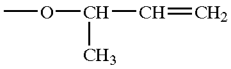 |
| 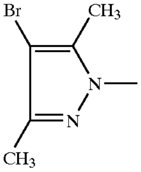 | F | $—O—CH_2—C{\equiv}CH$ |
| 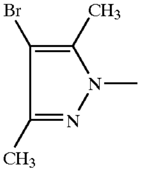 | F | 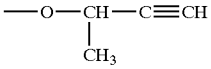 |
| 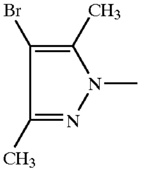 | F | 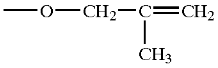 |
| 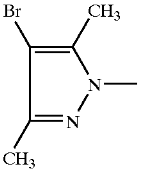 | F | $—O—CH_2—CH_2—OC_2H_5$ |
| 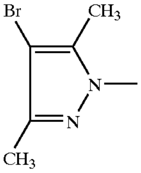 | F | 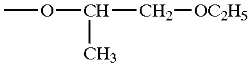 |
| 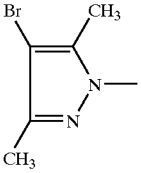 | F | 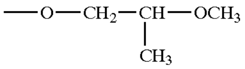 |

-continued
(I)
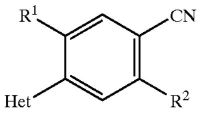
| Het | $R^1$ | $R^2$ |
|---|---|---|
| 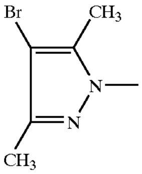 | F | 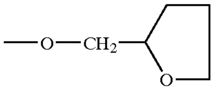 |
| 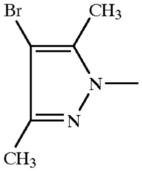 | F | 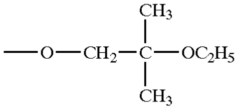 |
| 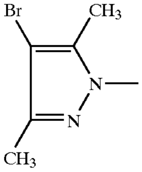 | F | $—O—CH_2—CH_2—O—CH_2—CH_2—OCH_3$ |
| 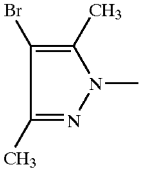 | F | $—O—CH_2—CH_2—O—CH_2—CH_2—OC_2H_5$ |
| 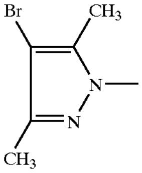 | F | 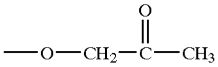 |
| 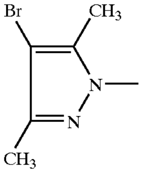 | F | 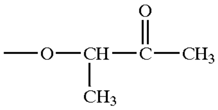 |
| 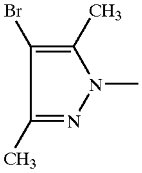 | F | $—SCH_3$ |

-continued
(I)
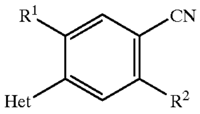
| Het | $R^1$ | $R^2$ |
|---|---|---|
| 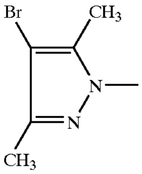 | F | $-SC_2H_5$ |
| 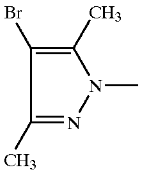 | F | $-S-CH(CH_3)_2$ |
| 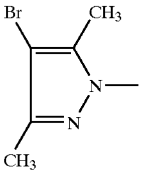 | F | $-S-CH_2-CH=CH_2$ |
| 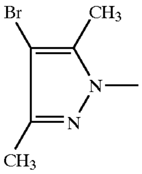 | F | $-S-CH_2-CH=CH-Cl$ |
| 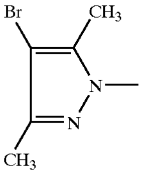 | F | $-S-CH_2-CH=CH-CH_3$ |
| 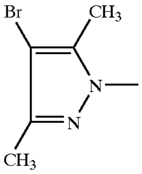 | F | 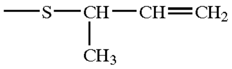 |
| 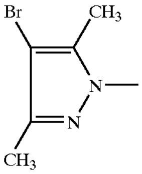 | F | $-S-CH_2-C\equiv CH$ |

-continued
(I)
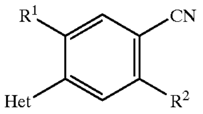
| Het | $R^1$ | $R^2$ |
|---|---|---|
| 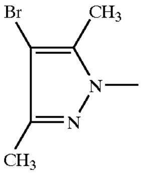 | F | 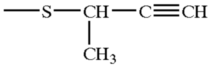 |
| 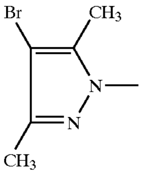 | F | 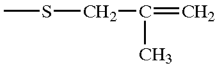 |
| 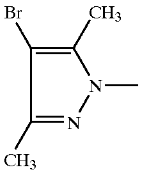 | F | $—S—CH_2—CH_2—OC_2H_5$ |
| 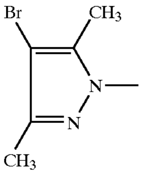 | F | $—S—CH—CH_2—OC_2H_5$ |
| 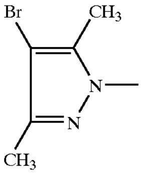 | F | 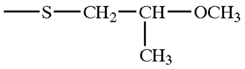 |
| 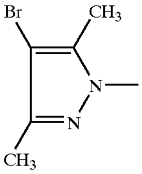 | F | 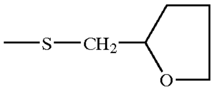 |
| 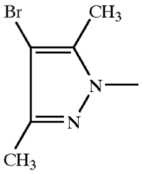 | F | 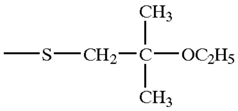 |

-continued
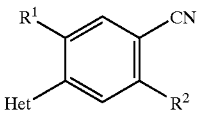
(I)
| Het | $R^1$ | $R^2$ |
|---|---|---|
| 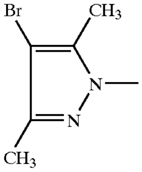 | F | $-S-CH_2-CH_2-O-CH_2-CH_2-OCH_3$ |
| 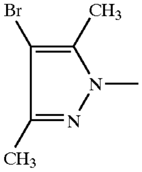 | F | $-S-CH_2-CH_2-O-CH_2-CH_2-OC_2H_5$ |
| 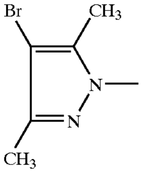 | F | 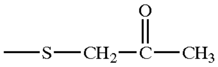 |
| 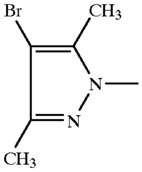 | F | 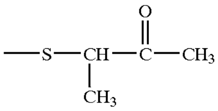 |
| 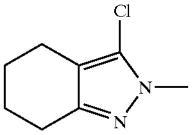 | H | 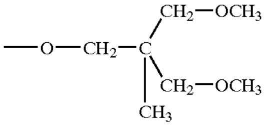 |
| 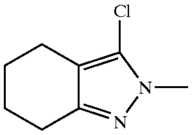 | H | 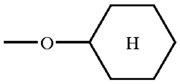 |
| 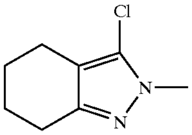 | H | 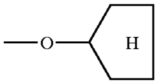 |
| 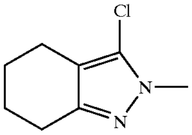 | H | 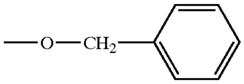 |

-continued
(I)
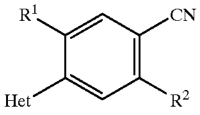
| Het | $R^1$ | $R^2$ |
|---|---|---|
| 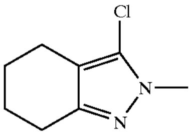 | H | $—O—CH_2—CN$ |
| 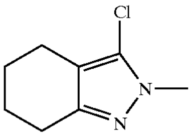 | H | $—O—CH_2—COOC_2H_5$ |
| 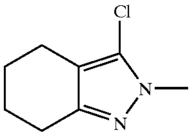 | H | 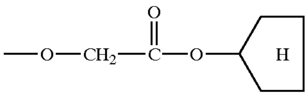 |
| 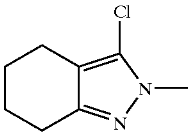 | H | 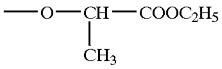 |
| 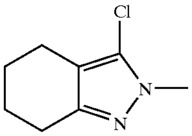 | H | 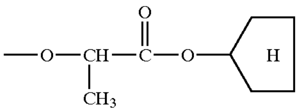 |
| 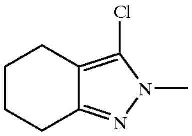 | H | 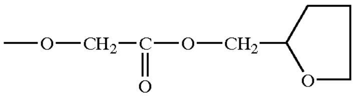 |
| 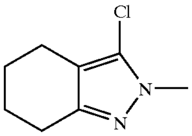 | H | 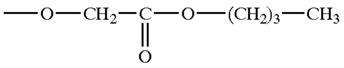 |
| 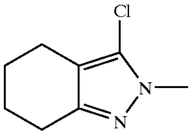 | H | 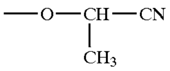 |
| 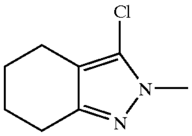 | H | $—O—CH_2—CH_2—O—CH_3$ |

-continued
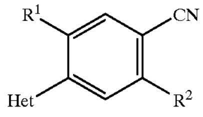
(I)
| Het | R¹ | R² |
| --- | --- | --- |
| 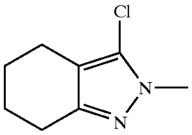 | H | 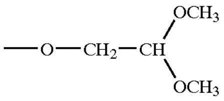 |
| 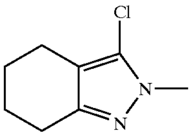 | H | 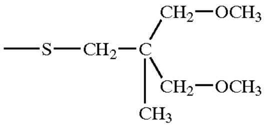 |
| 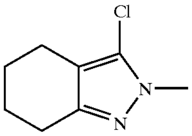 | H | 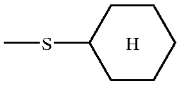 |
| 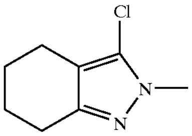 | H | 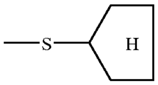 |
| 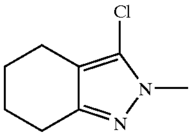 | H | 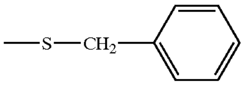 |
| 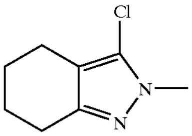 | H | $—S—CH_2—CN$ |
| 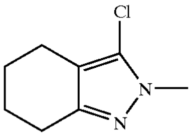 | H | $—S—CH_2—COOC_2H_5$ |
| 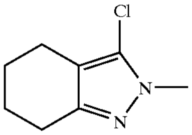 | H | 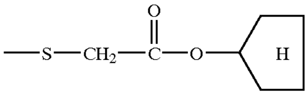 |
| 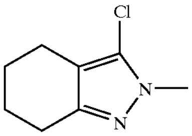 | H | 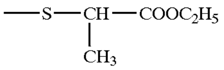 |

-continued
(I)
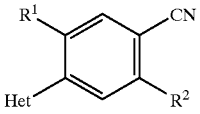
| Het | $R^1$ | $R^2$ |
|---|---|---|
| 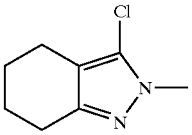 | H | 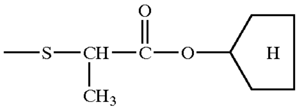 |
| 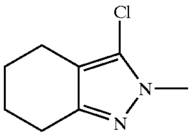 | H | 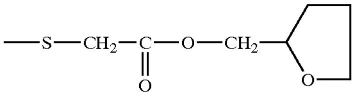 |
| 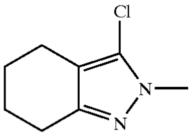 | H | 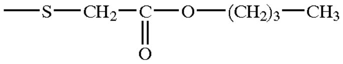 |
| 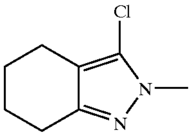 | H | 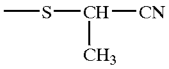 |
| 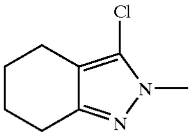 | H | $-S-CH_2-CH_2-O-CH_3$ |
| 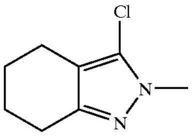 | H | 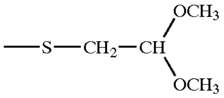 |
| 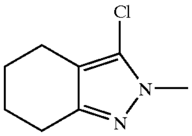 | H | $-OCH_3$ |
| 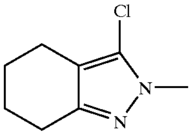 | H | $-OC_2H_5$ |
| 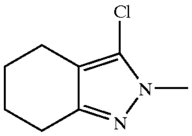 | H | $-O-CH(CH_3)_2$ |

-continued
(I)
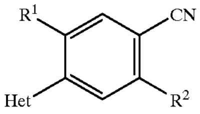
| Het | $R^1$ | $R^2$ |
|---|---|---|
| 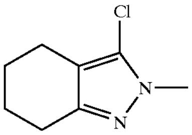 | H | $—O—CH_2—CH{=}CH_2$ |
| 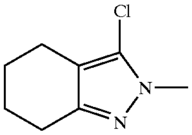 | H | $—O—CH_2—CH{=}CH—CH_3$ |
| 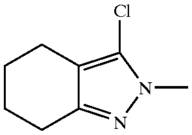 | H | $—O—CH_2—CH{=}CH—Cl$ |
| 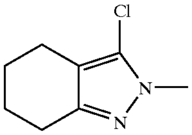 | H | 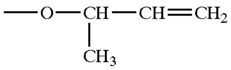 |
| 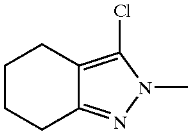 | H | $—O—CH_2—C{\equiv}CH$ |
| 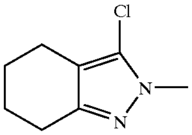 | H | 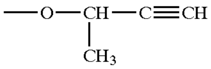 |
| 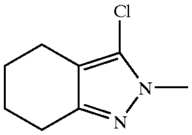 | H | 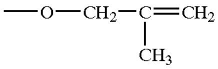 |
| 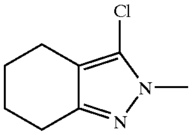 | H | $—O—CH_2—CH_2—OC_2H_5$ |
| 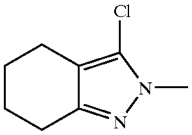 | H | 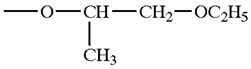 |

-continued
(I)
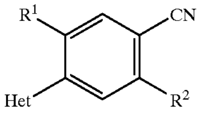
| Het | $R^1$ | $R^2$ |
|---|---|---|
| 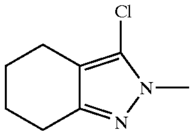 | H | 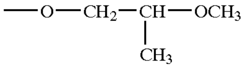 |
| 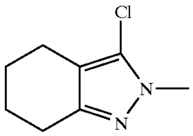 | H | 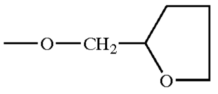 |
| 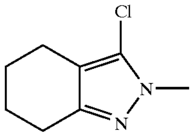 | H | 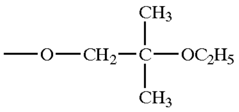 |
| 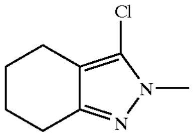 | H | $-O-CH_2-CH_2-O-CH_2-CH_2-OCH_3$ |
| 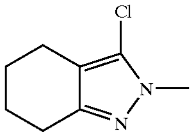 | H | $-O-CH_2-CH_2-O-CH_2-CH_2-OC_2H_5$ |
| 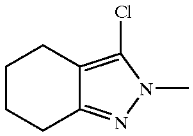 | H | 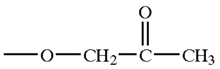 |
| 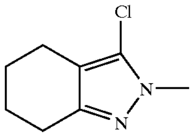 | H | 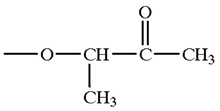 |
| 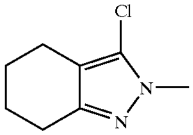 | H | $-SCH_3$ |
| 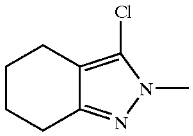 | H | $-SC_2H_5$ |

-continued
(I)
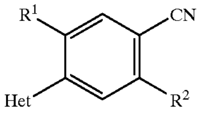
| Het | $R^1$ | $R^2$ |
|---|---|---|
| 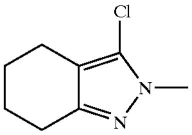 | H | $-S-CH(CH_3)_2$ |
| 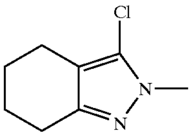 | H | $-S-CH_2-CH=CH_2$ |
| 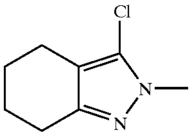 | H | $-S-CH_2-CH=CH-Cl$ |
| 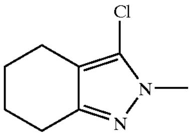 | H | $-S-CH_2-CH=CH-CH_3$ |
| 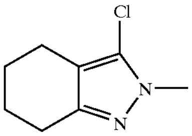 | H | $-S-CH(CH_3)-CH=CH_2$ |
| 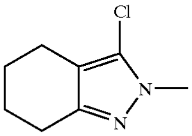 | H | $-S-CH_2-C\equiv CH$ |
| 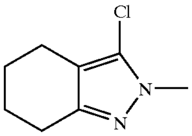 | H | $-S-CH(CH_3)-C\equiv CH$ |
| 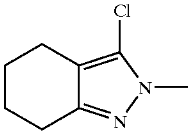 | H | $-S-CH_2-C(CH_3)=CH_2$ |
| 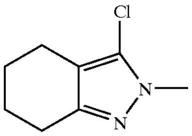 | H | $-S-CH_2-CH_2-OC_2H_5$ |

-continued
(I)
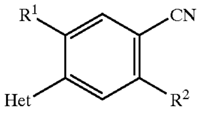
| Het | $R^1$ | $R^2$ |
|---|---|---|
| 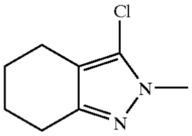 | H | 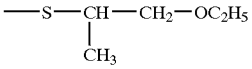 |
| 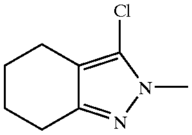 | H | 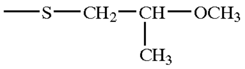 |
| 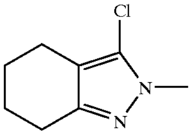 | H | 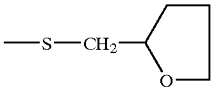 |
| 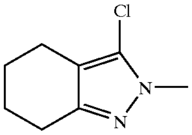 | H | 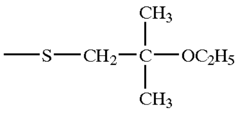 |
| 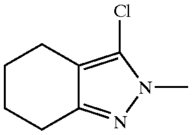 | H | $—S—CH_2—CH_2—O—CH_2—CH_2—OCH_3$ |
| 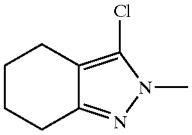 | H | $—S—CH_2—CH_2—O—CH_2—CH_2—OC_2H_5$ |
| 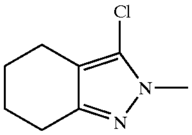 | H | 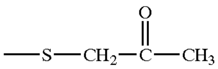 |
| 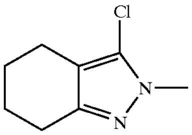 | H | 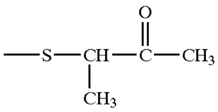 |
| 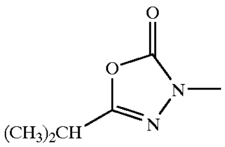 | F | 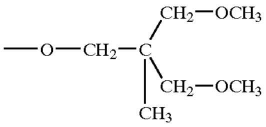 |

-continued
(I)
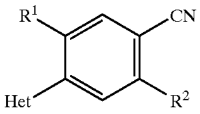
| Het | R¹ | R² |
| --- | --- | --- |
| 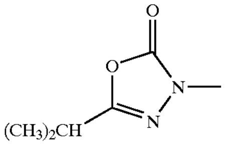 | F | 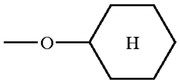 |
| 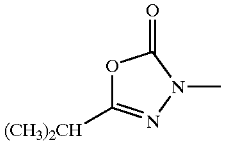 | F | 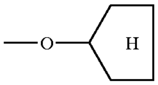 |
| 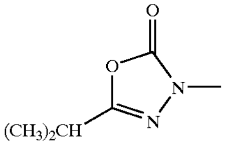 | F | 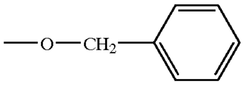 |
| 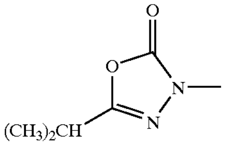 | F | $—O—CH_2—CN$ |
| 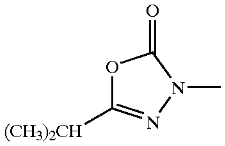 | F | $—O—CH_2—COOC_2H_5$ |
| 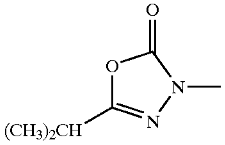 | F | 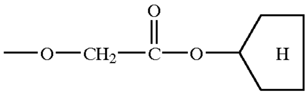 |
| 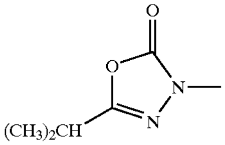 | F | 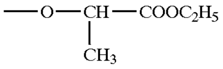 |
| 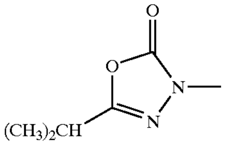 | F | 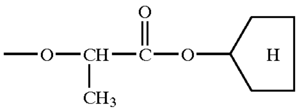 |

-continued
(I)
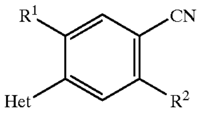
| Het | $R^1$ | $R^2$ |
| --- | --- | --- |
| 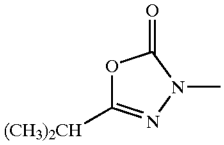 | F | 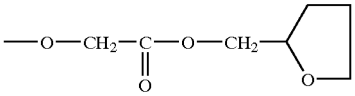 |
| 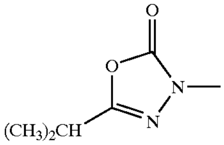 | F | 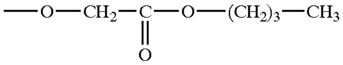 |
| 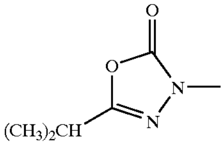 | F | 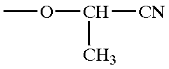 |
| 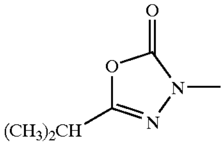 | F | $—O—CH_2—CH_2—O—CH_3$ |
| 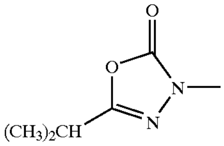 | F | 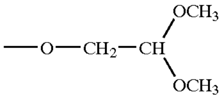 |
| 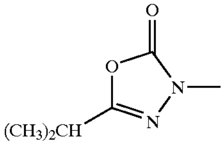 | F | 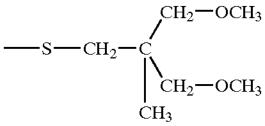 |
| 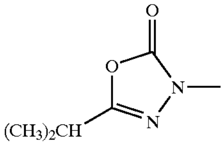 | F | 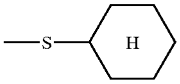 |
| 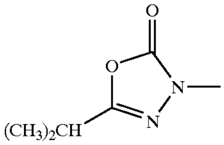 | F | 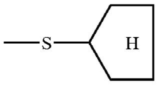 |

-continued
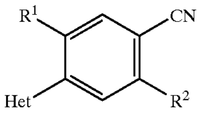
(I)
| Het | $R^1$ | $R^2$ |
|---|---|---|
| 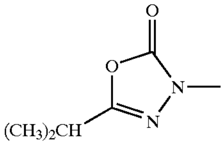 | F | 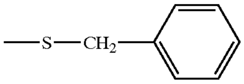 |
| 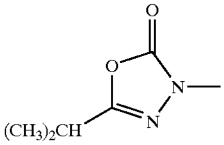 | F | $-S-CH_2-CN$ |
| 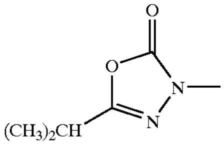 | F | $-S-CH_2-COOC_2H_5$ |
| 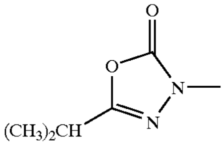 | F | 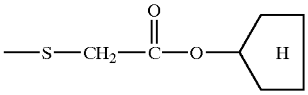 |
| 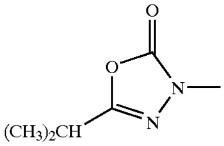 | F | 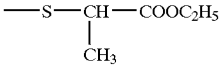 |
| 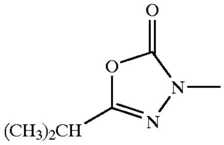 | F | 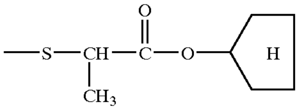 |
| 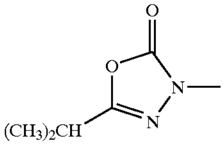 | F | 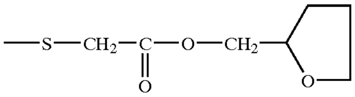 |
| 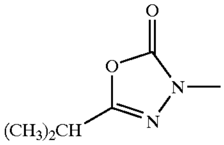 | F | 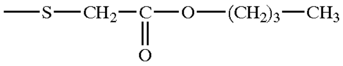 |

-continued
(I)
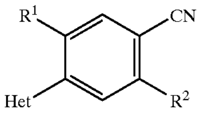
| Het | $R^1$ | $R^2$ |
|---|---|---|
| 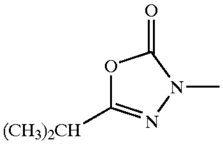 | F | 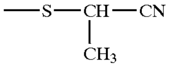 |
| 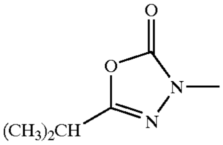 | F | $-S-CH_2-CH_2-O-CH_3$ |
| 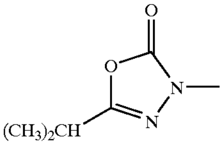 | F | 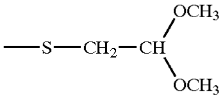 |
| 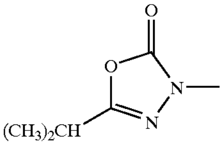 | F | $-OCH_3$ |
| 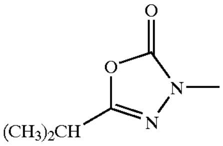 | F | $-OC_2H_5$ |
| 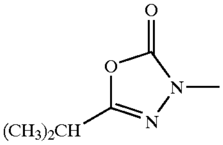 | F | $-O-CH(CH_3)_2$ |
| 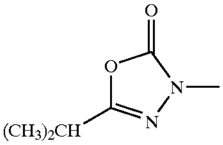 | F | $-O-CH_2-CH{=}CH_2$ |
| 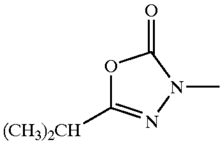 | F | $-O-CH_2-CH{=}CH-CH_3$ |

-continued
(I)
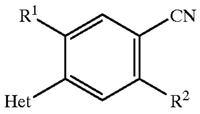
| Het | $R^1$ | $R^2$ |
|---|---|---|
| 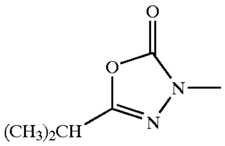 | F | $-O-CH_2-CH=CH-Cl$ |
| 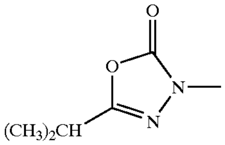 | F | 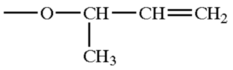 |
| 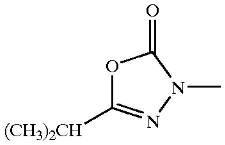 | F | $-O-CH_2-C\equiv CH$ |
| 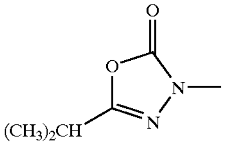 | F | 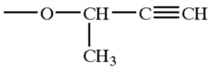 |
| 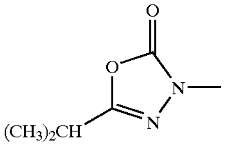 | F | 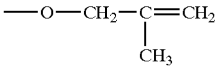 |
| 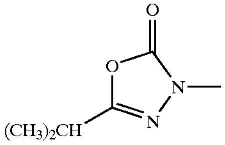 | F | $-O-CH_2-CH_2-OC_2H_5$ |
| 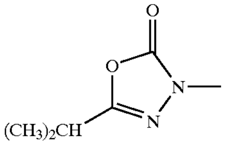 | F | 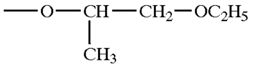 |
| 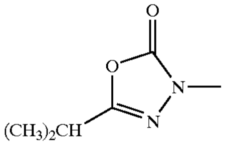 | F | 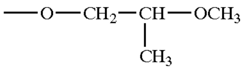 |

-continued
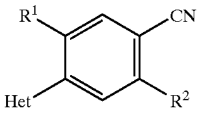
(I)
| Het | $R^1$ | $R^2$ |
|---|---|---|
| 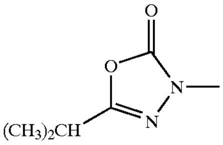 | F | 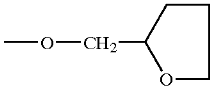 |
| 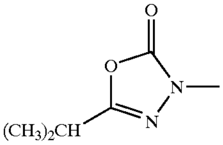 | F | 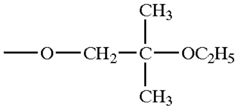 |
| 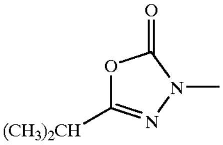 | F | $—O—CH_2—CH_2—O—CH_2—CH_2—OCH_3$ |
| 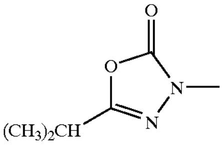 | F | $—O—CH_2—CH_2—O—CH_2—CH_2—OC_2H_5$ |
| 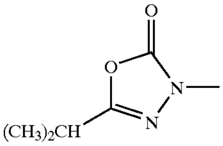 | F | 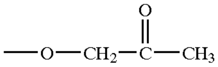 |
| 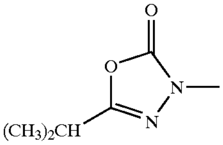 | F | 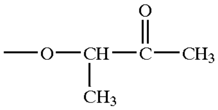 |
| 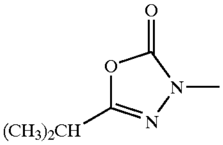 | H | $—SCH_3$ |
| 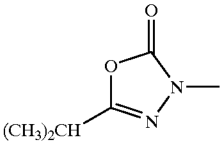 | H | $—SC_2H_5$ |

-continued
(I)
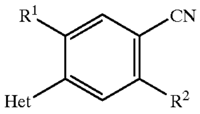
| Het | $R^1$ | $R^2$ |
|---|---|---|
| 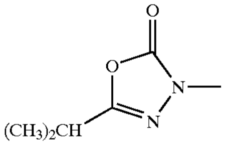 | H | $—S—CH(CH_3)_2$ |
| 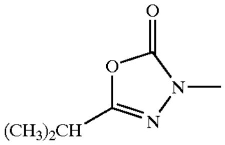 | H | $—S—CH_2—CH{=}CH_2$ |
| 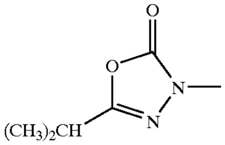 | H | $—S—CH_2—CH{=}CH—Cl$ |
| 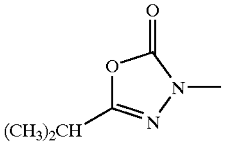 | H | $—S—CH_2—CH{=}CH—CH_3$ |
| 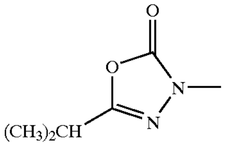 | H | 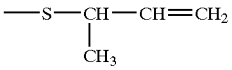 |
| 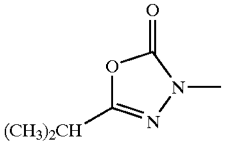 | H | $—S—CH_2—C{\equiv}CH$ |
| 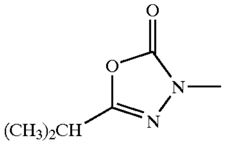 | H | 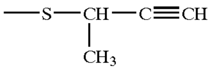 |
| 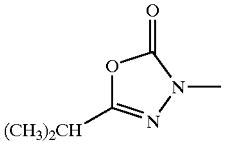 | H | 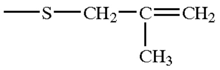 |

-continued
(I)
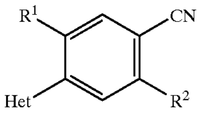
| Het | $R^1$ | $R^2$ |
| --- | --- | --- |
| 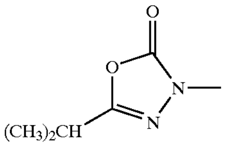 | H | $—S—CH_2—CH_2—OC_2H_5$ |
| 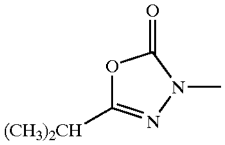 | H | 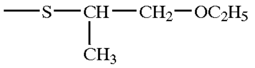 |
| 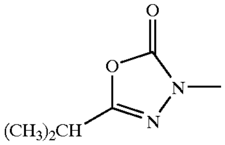 | H | 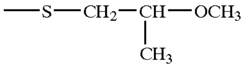 |
| 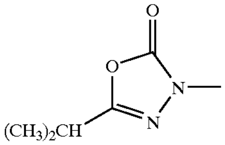 | H | 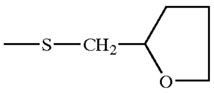 |
| 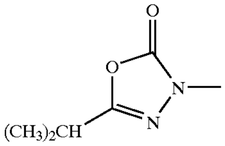 | H | 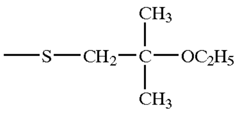 |
| 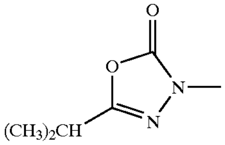 | H | $—S—CH_2—CH_2—O—CH_2—CH_2—OCH_3$ |
| 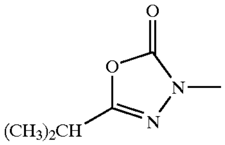 | H | $—S—CH_2—CH_2—O—CH_2—CH_2—OC_2H_5$ |
| 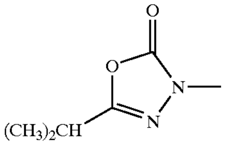 | H | 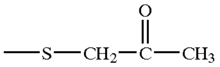 |

-continued
(I)
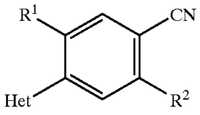
| Het | $R^1$ | $R^2$ |
| --- | --- | --- |
| 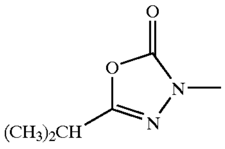 | H | 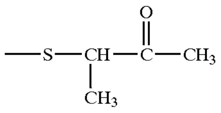 |
| 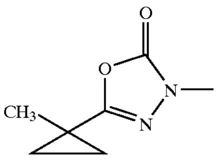 | F | 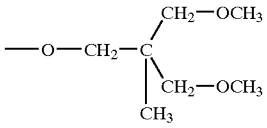 |
| 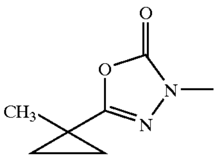 | F | 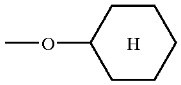 |
| 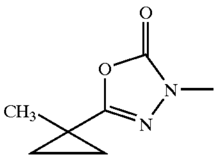 | F | 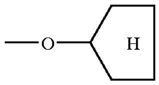 |
| 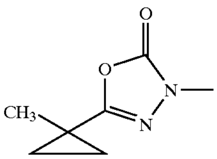 | F | 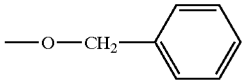 |
| 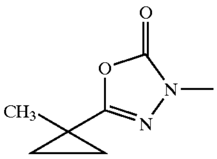 | F | $-O-CH_2-CN$ |
| 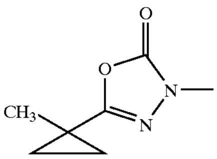 | F | $-O-CH_2-COOC_2H_5$ |
| 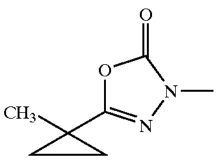 | F | 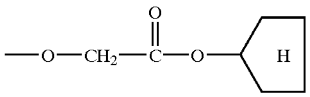 |

-continued
(I)
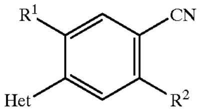
| Het | $R^1$ | $R^2$ |
|---|---|---|
| 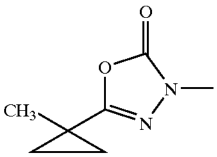 | F | 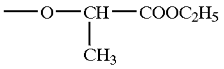 |
| 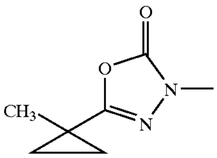 | F | 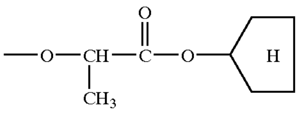 |
| 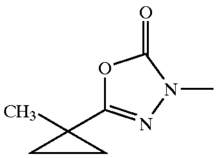 | F | 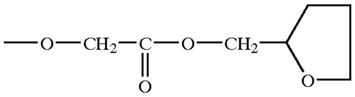 |
| 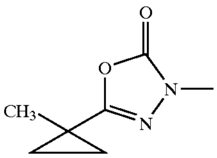 | F | 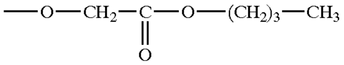 |
| 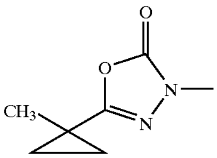 | F | 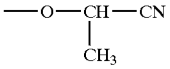 |
| 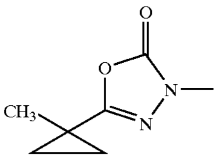 | F | $-O-CH_2-CH_2-O-CH_3$ |
| 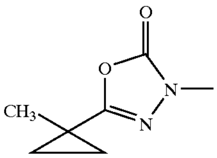 | F | 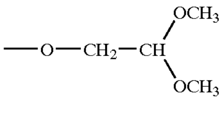 |
| 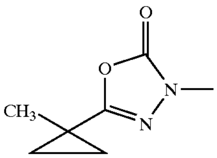 | H | 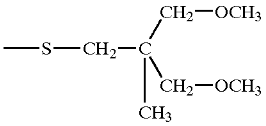 |

-continued
(I)
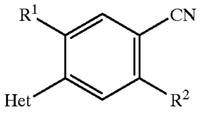
| Het | $R^1$ | $R^2$ |
|---|---|---|
| 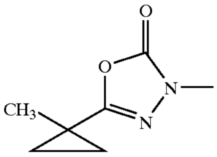 | H | 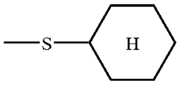 |
| 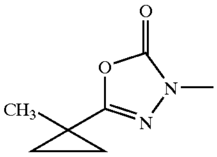 | H | 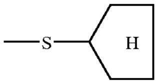 |
| 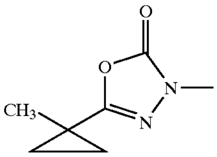 | H | 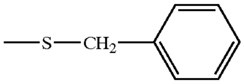 |
| 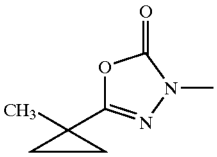 | H | $-S-CH_2-CN$ |
| 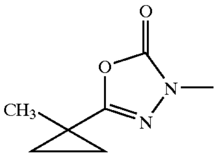 | H | $-S-CH_2-COOC_2H_5$ |
| 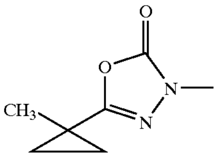 | H | 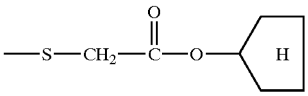 |
| 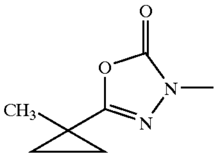 | H | 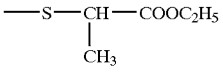 |
| 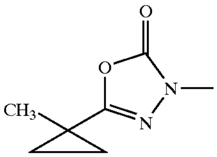 | H | 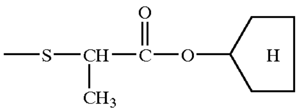 |

-continued
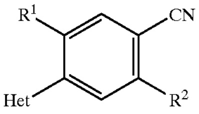
(I)
| Het | $R^1$ | $R^2$ |
|---|---|---|
| 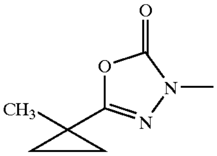 | H | 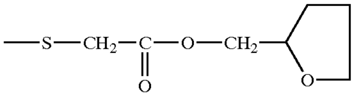 |
| 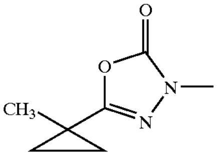 | H | 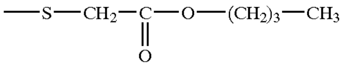 |
| 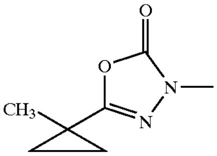 | H | 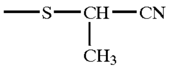 |
| 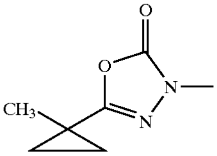 | H | $—S—CH_2—CH_2—O—CH_3$ |
| 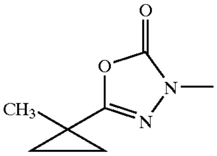 | H | 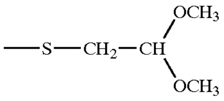 |
| 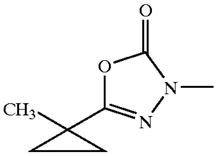 | F | $—OCH_3$ |
| 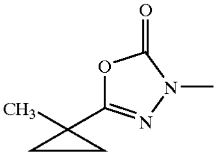 | F | $—OC_2H_5$ |
| 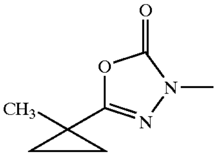 | F | $—O—CH(CH_3)_2$ |

-continued
(I)
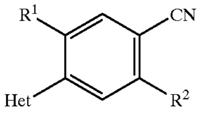
| Het | $R^1$ | $R^2$ |
|---|---|---|
| 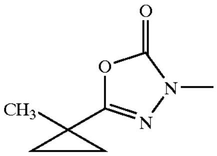 | F | 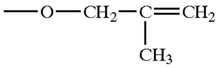 |
| 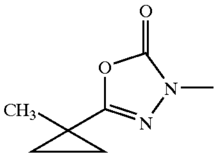 | F | $-O-CH_2-CH_2-OC_2H_5$ |
| 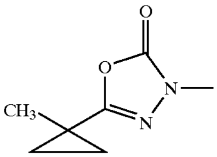 | F | 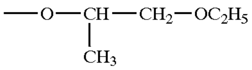 |
| 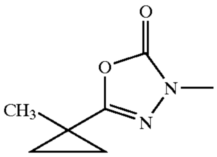 | F | 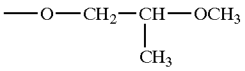 |
| 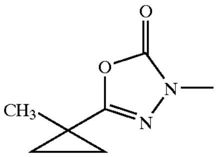 | F | 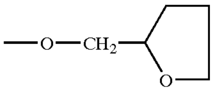 |
| 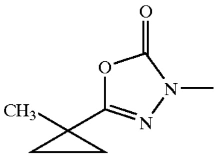 | F | 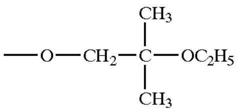 |
| 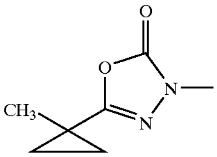 | F | $-O-CH_2-CH_2-O-CH_2-CH_2-OCH_3$ |
| 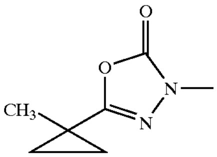 | F | $-O-CH_2-CH_2-O-CH_2-CH_2-OC_2H_5$ |

-continued
(I)
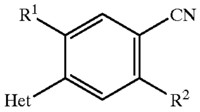
| Het | $R^1$ | $R^2$ |
|---|---|---|
| 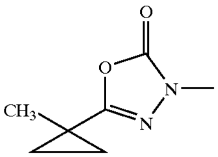 | F | 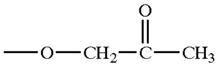 |
| 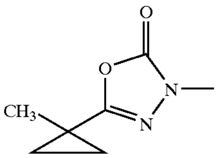 | F | 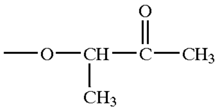 |
| 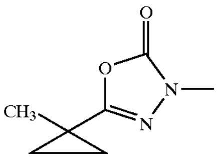 | F | $—SCH_3$ |
| 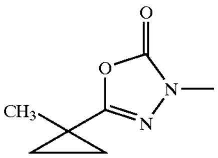 | F | $—SC_2H_5$ |
| 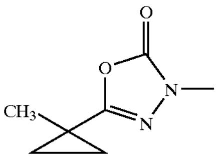 | F | $—S—CH(CH_3)_2$ |
| 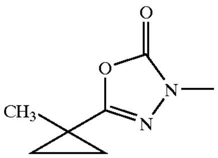 | F | $—S—CH_2—CH{=}CH_2$ |
| 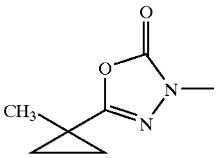 | F | $—S—CH_2—CH{=}CH—Cl$ |
| 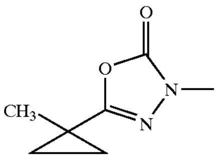 | F | $—S—CH_2—CH{=}CH—CH_3$ |

-continued
(I)
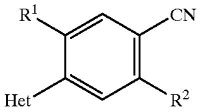
| Het | $R^1$ | $R^2$ |
|---|---|---|
| 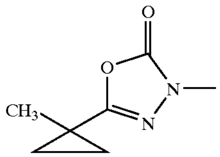 | F | 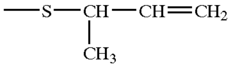 |
| 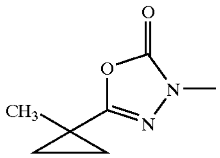 | F | $-S-CH_2-C\equiv CH$ |
| 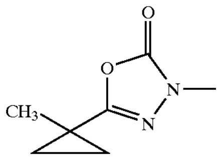 | F | 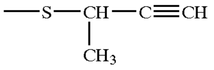 |
| 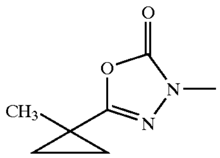 | F | 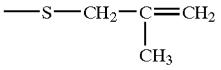 |
| 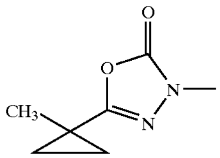 | F | $-S-CH_2-CH_2-OC_2H_5$ |
| 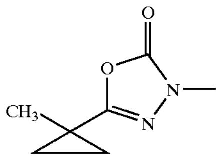 | F | 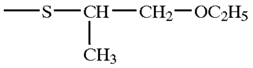 |
| 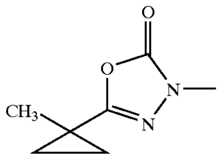 | F | 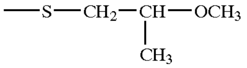 |
| 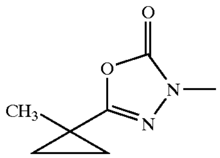 | F | 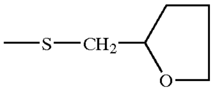 |

-continued
(I)
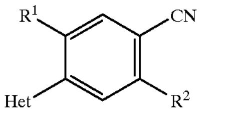
| Het | $R^1$ | $R^2$ |
|---|---|---|
| 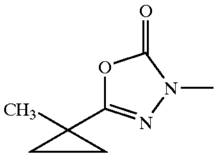 | F | 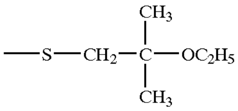 |
| 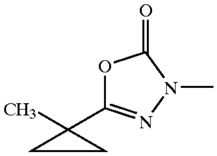 | F | $—S—CH_2—CH_2—O—CH_2—CH_2—OCH_3$ |
| 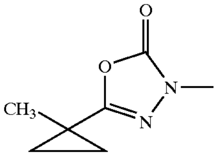 | F | $—S—CH_2—CH_2—O—CH_2—CH_2—OC_2H_5$ |
| 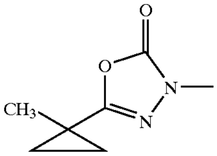 | F | 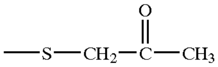 |
| 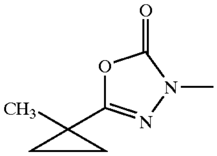 | F | 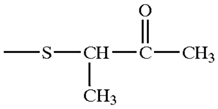 |
| 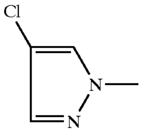 | F | 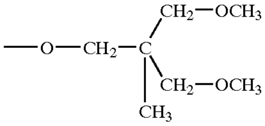 |
| 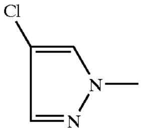 | F | 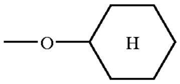 |
| 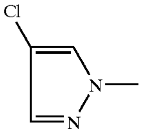 | F | 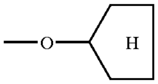 |

-continued
(I)
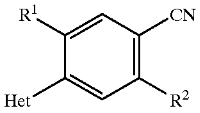
| Het | $R^1$ | $R^2$ |
|---|---|---|
| 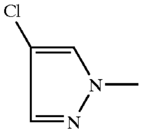 | F | 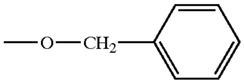 |
| 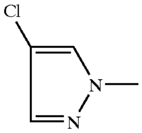 | F | $—O—CH_2—CN$ |
| 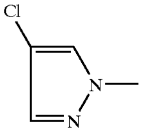 | F | $—O—CH_2—COOC_2H_5$ |
| 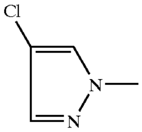 | F | 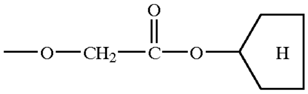 |
| 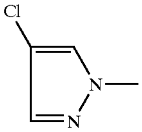 | F | 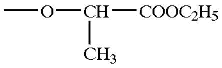 |
| 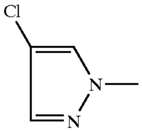 | F | 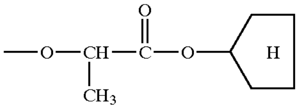 |
| 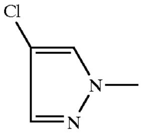 | F | 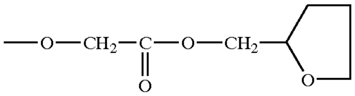 |
| 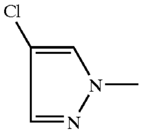 | F | 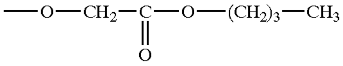 |
| 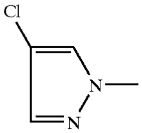 | F | 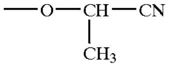 |

-continued
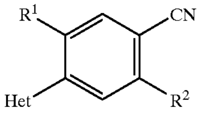
(I)
| Het | $R^1$ | $R^2$ |
|---|---|---|
| 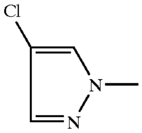 | F | $—O—CH_2—CH_2—O—CH_3$ |
| 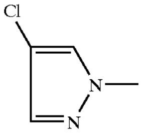 | F | 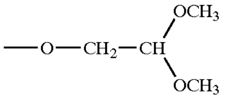 |
| 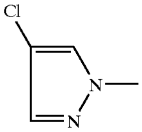 | F | 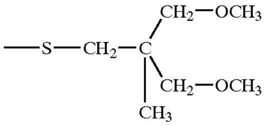 |
| 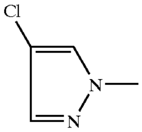 | F | 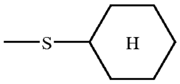 |
| 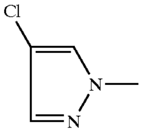 | F | 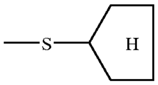 |
| 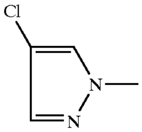 | F | 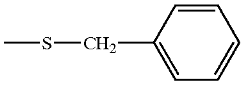 |
| 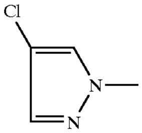 | F | $—S—CH_2—CN$ |
| 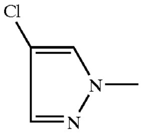 | F | $—S—CH_2—COOC_2H_5$ |
| 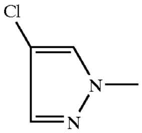 | F | 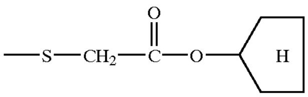 |

-continued
(I)
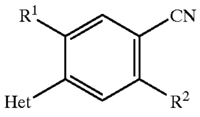
| Het | $R^1$ | $R^2$ |
|---|---|---|
| 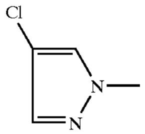 | F | 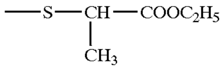 |
| 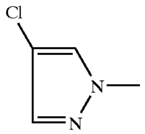 | F | 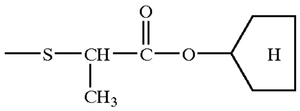 |
| 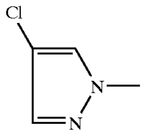 | F | 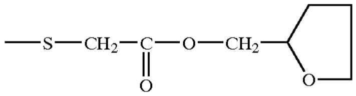 |
| 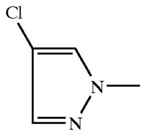 | F | 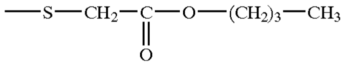 |
| 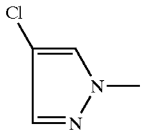 | F | 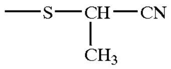 |
| 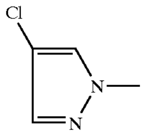 | F | $—S—CH_2—CH_2—O—CH_3$ |
| 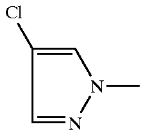 | F | 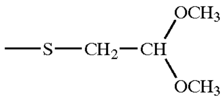 |
| 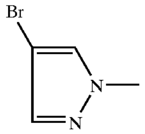 | F | $—OCH_3$ |
| 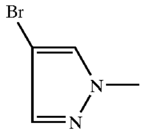 | F | $—OC_2H_5$ |

-continued
(I)
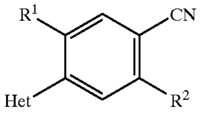
| Het | $R^1$ | $R^2$ |
|---|---|---|
| 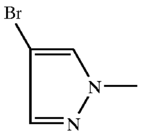 | F | $—O—CH(CH_3)_2$ |
| 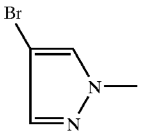 | F | $—O—CH_2—CH═CH_2$ |
| 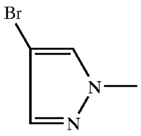 | F | $—O—CH_2—CH═CH—CH_3$ |
| 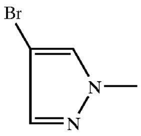 | F | $—O—CH_2—CH═CH—Cl$ |
| 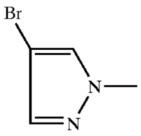 | F | 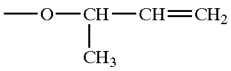 |
| 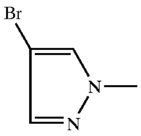 | F | $—O—CH_2—C≡CH$ |
| 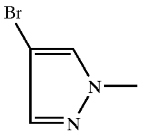 | F | 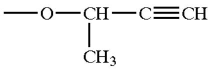 |
| 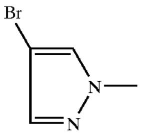 | F | 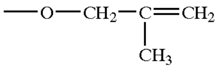 |
| 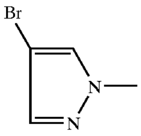 | F | $—O—CH_2—CH_2—OC_2H_5$ |

-continued
(I)
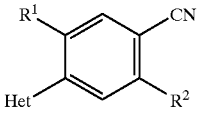
| Het | $R^1$ | $R^2$ |
|---|---|---|
| 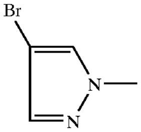 | F | 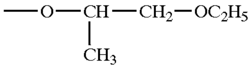 |
| 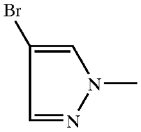 | F | 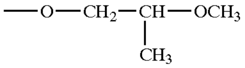 |
| 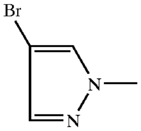 | F | 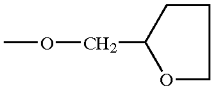 |
| 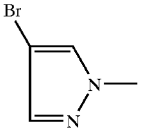 | F | 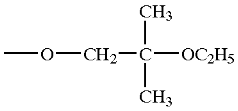 |
| 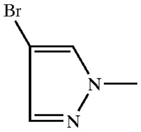 | F | $-O-CH_2-CH_2-O-CH_2-CH_2-OCH_3$ |
| 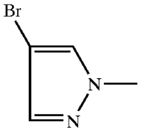 | F | $-O-CH_2-CH_2-O-CH_2-CH_2-OC_2H_5$ |
| 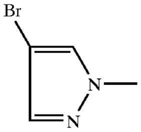 | F | 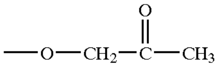 |
| 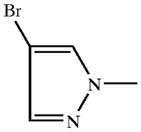 | F | 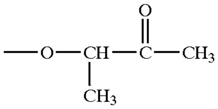 |
| 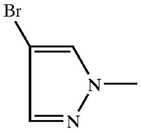 | F | $-SCH_3$ |

-continued
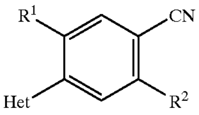
(I)
| Het | $R^1$ | $R^2$ |
|---|---|---|
| 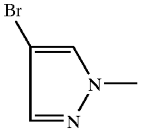 | F | $—SC_2H_5$ |
| 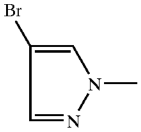 | F | $—S—CH(CH_3)_2$ |
| 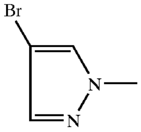 | F | $—S—CH_2—CH{=}CH_2$ |
| 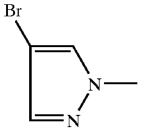 | F | $—S—CH_2—CH{=}CH—Cl$ |
| 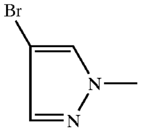 | F | $—S—CH_2—CH{=}CH—CH_3$ |
| 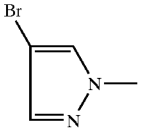 | F | 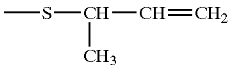 |
| 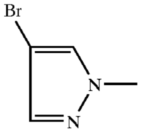 | F | $—S—CH_2—C{\equiv}CH$ |
| 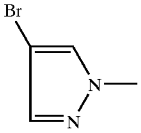 | F | 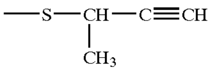 |
| 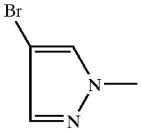 | F | 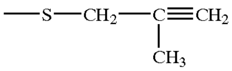 |

-continued
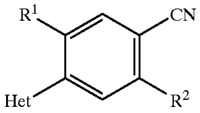
(I)
| Het | $R^1$ | $R^2$ |
| --- | --- | --- |
| 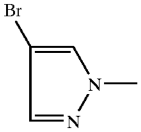 | F | $—S—CH_2—CH_2—OC_2H_5$ |
| 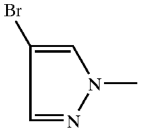 | F | 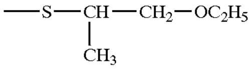 |
| 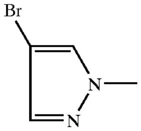 | F | 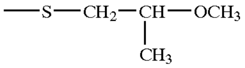 |
| 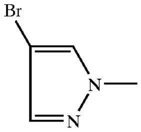 | F | 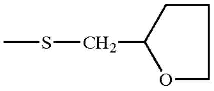 |
| 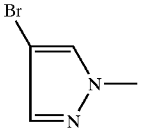 | F | 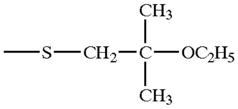 |
| 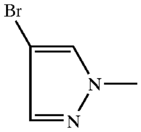 | F | $—S—CH_2—CH_2—O—CH_2—CH_2—OCH_3$ |
| 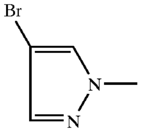 | F | $—S—CH_2—CH_2—O—CH_2—CH_2—OC_2H_5$ |
| 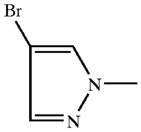 | F | 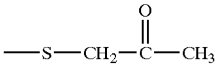 |
| 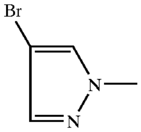 | F | 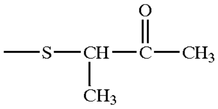 |

-continued
(I)
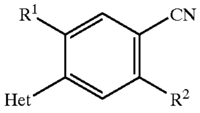
| Het | $R^1$ | $R^2$ |
| --- | --- | --- |
| 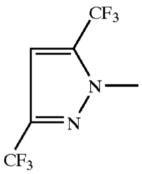 | F | 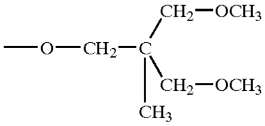 |
| 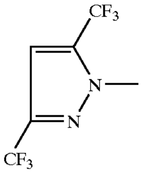 | F | 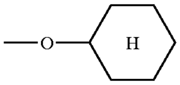 |
| 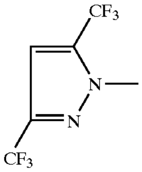 | F | 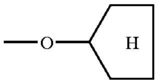 |
| 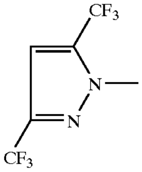 | F | 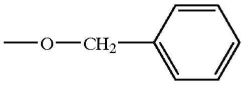 |
| 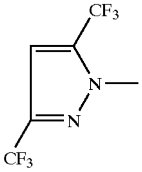 | F | $-O-CH_2-CN$ |
| 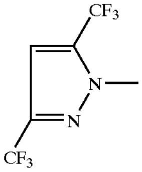 | F | $-O-CH_2-COOC_2H_5$ |
| 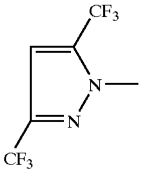 | F | 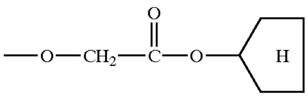 |

-continued
(I)
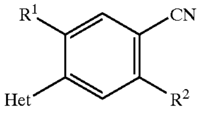
| Het | $R^1$ | $R^2$ |
|---|---|---|
| 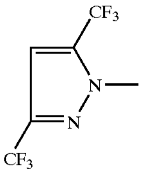 | F | 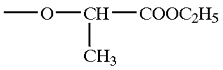 |
| 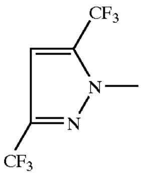 | F | 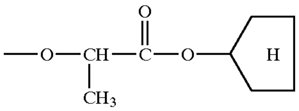 |
| 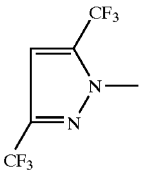 | F | 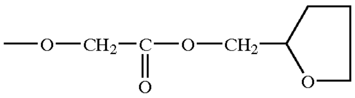 |
| 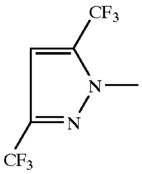 | F | 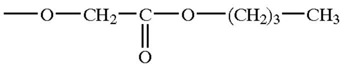 |
| 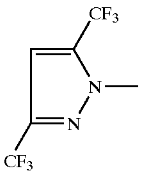 | F | 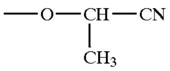 |
| 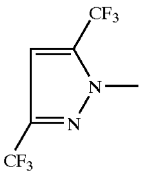 | F | $-O-CH_2-CH_2-O-CH_3$ |
| 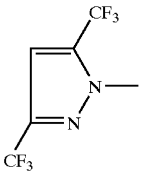 | F | 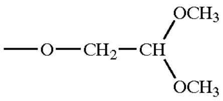 |

-continued
(I)
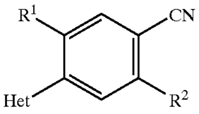
| Het | $R^1$ | $R^2$ |
|---|---|---|
| 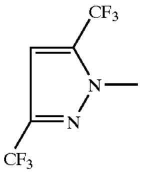 | F | 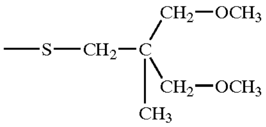 |
| 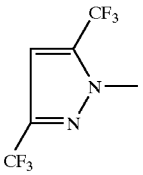 | F | 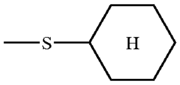 |
| 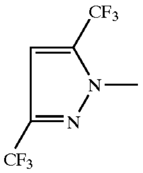 | F | 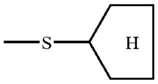 |
| 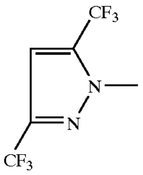 | F | 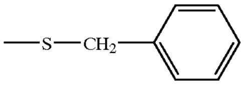 |
| 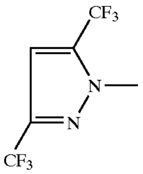 | F | $—S—CH_2—CN$ |
| 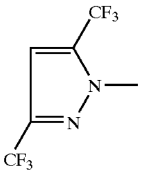 | F | $—S—CH_2—COOC_2H_5$ |
| 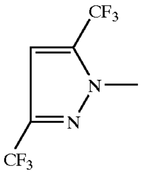 | F | 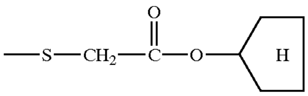 |

-continued
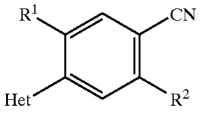
(I)
| Het | $R^1$ | $R^2$ |
|---|---|---|
| 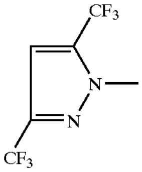 | F | 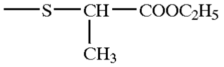 |
| 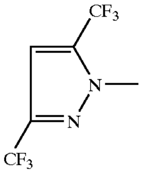 | F | 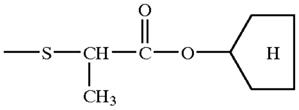 |
| 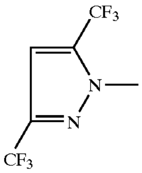 | F | 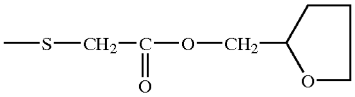 |
| 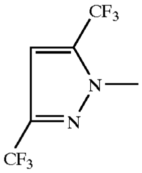 | F | 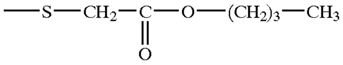 |
| 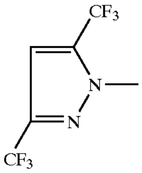 | F | 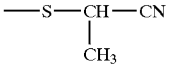 |
| 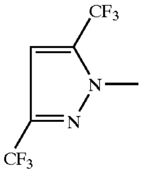 | F | $-S-CH_2-CH_2-O-CH_3$ |
| 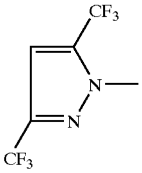 | F | 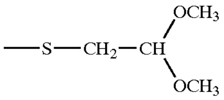 |

-continued
(I)
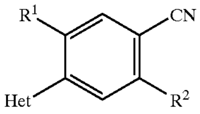
| Het | $R^1$ | $R^2$ |
|---|---|---|
| 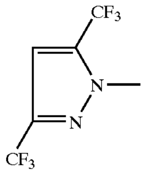 | H | $—OCH_3$ |
| 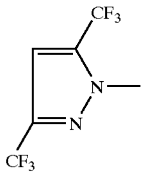 | H | $—OC_2H_5$ |
| 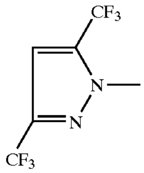 | H | $—O—CH(CH_3)_2$ |
| 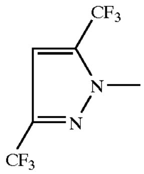 | H | $—O—CH_2—CH{=}CH_2$ |
| 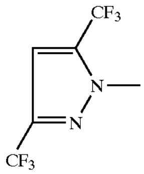 | H | $—O—CH_2—CH{=}CH—CH_3$ |
| 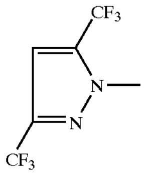 | H | $—O—CH_2—CH—Cl$ |
| 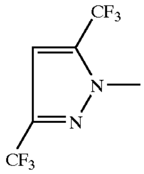 | H | 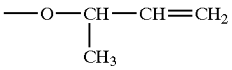 |

-continued
(I)
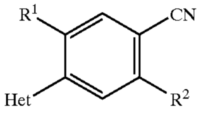
| Het | $R^1$ | $R^2$ |
| --- | --- | --- |
| 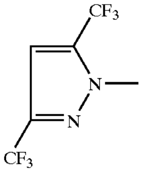 | H | $—O—CH_2—C{\equiv}CH$ |
| 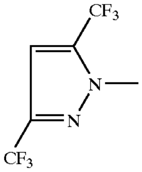 | H | 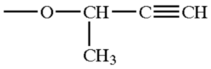 |
| 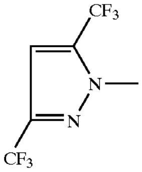 | H | 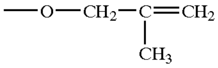 |
| 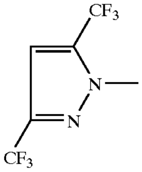 | H | $—O—CH_2—CH_2—OC_2H_5$ |
| 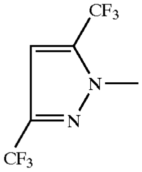 | H | 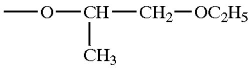 |
| 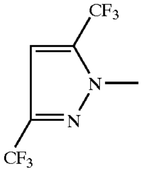 | H | 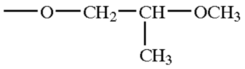 |
| 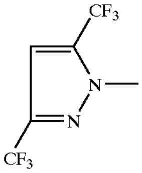 | H | 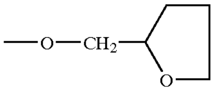 |

-continued
(I)
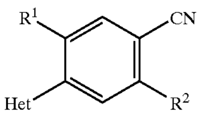
| Het | $R^1$ | $R^2$ |
|---|---|---|
| 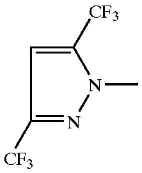 | H | 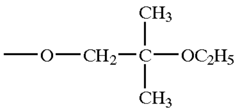 |
| 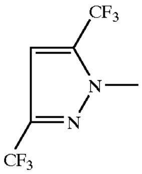 | H | $—O—CH_2—CH_2—O—CH_2—CH_2—OCH_3$ |
| 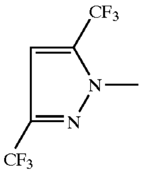 | H | $—O—CH_2—CH_2—O—CH_2—CH_2—OC_2H_5$ |
| 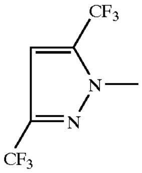 | H | 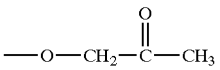 |
| 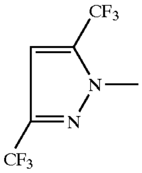 | H | 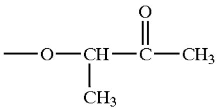 |
| 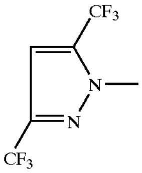 | H | $—SCH_3$ |
| 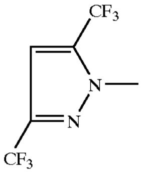 | H | $—SC_2H_5$ |

-continued
(I)
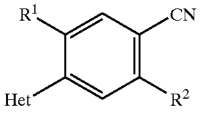
| Het | $R^1$ | $R^2$ |
|---|---|---|
| 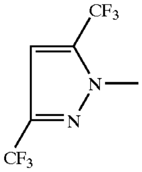 | H | $—S—CH(CH_3)_2$ |
| 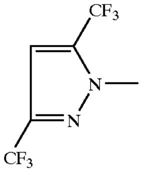 | H | $—S—CH_2—CH{=}CH_2$ |
| 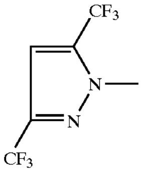 | H | $—S—CH_2—CH{=}CH—Cl$ |
| 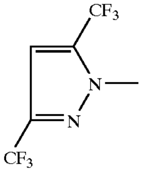 | H | $—S—CH_2—CH{=}CH—CH_3$ |
| 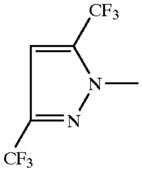 | H | 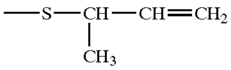 |
| 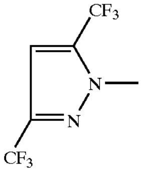 | H | $—S—CH_2—C{\equiv}CH$ |
| 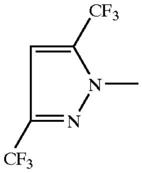 | H | 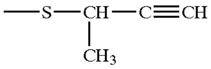 |

-continued
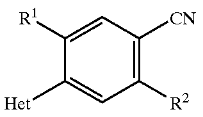
(I)
| Het | $R^1$ | $R^2$ |
|---|---|---|
| 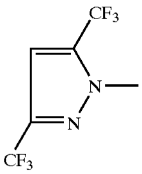 | H | 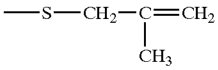 |
| 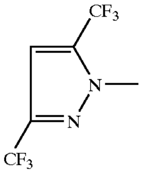 | H | $—S—CH_2—CH_2—OC_2H_5$ |
| 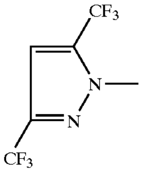 | H | 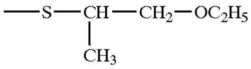 |
| 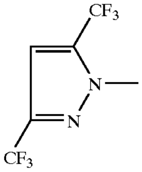 | H | 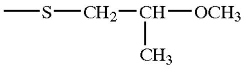 |
| 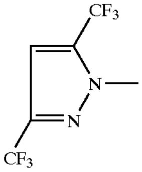 | H | 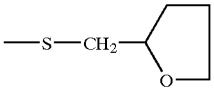 |
| 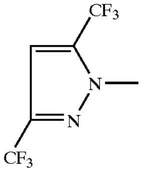 | H | 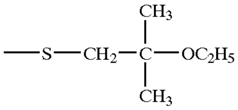 |
| 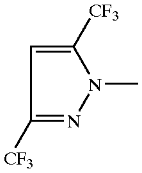 | H | $—S—CH_2—CH_2—O—CH_2—CH_2—OCH_3$ |

-continued
(I)
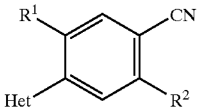
| Het | $R^1$ | $R^2$ |
|---|---|---|
| 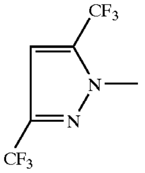 | H | $—S—CH_2—O—CH_2—CH_2—OC_2H_5$ |
| 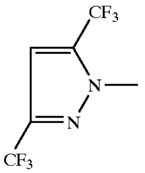 | H | 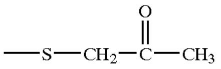 |
| 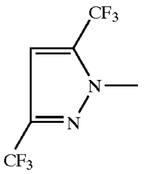 | H | 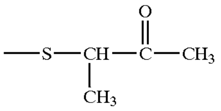 |
| 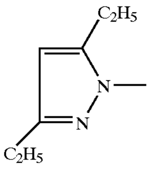 | F | 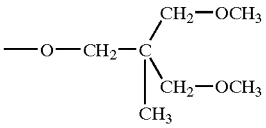 |
| 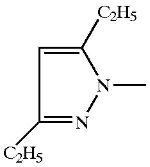 | F | 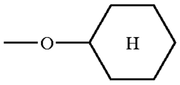 |
| 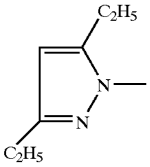 | F | 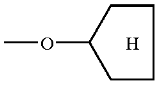 |
| 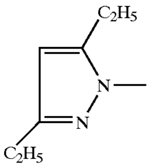 | F | 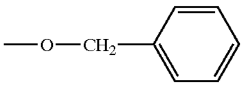 |

-continued
(I)
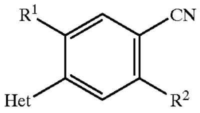
| Het | $R^1$ | $R^2$ |
|---|---|---|
| 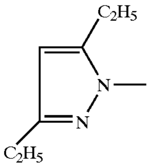 | F | $-O-CH_2-CN$ |
| 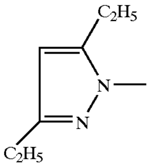 | F | $-O-CH_2-COOC_2H_5$ |
| 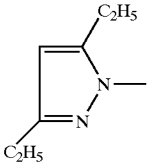 | F | 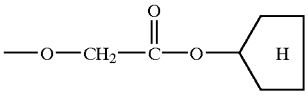 |
| 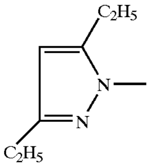 | F | 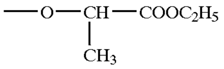 |
| 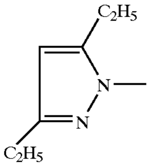 | F | 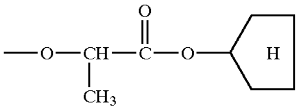 |
| 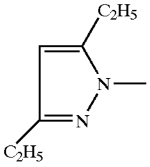 | F | 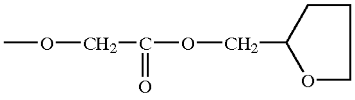 |
| 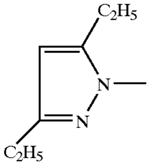 | F | 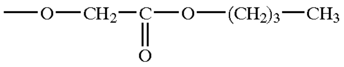 |

-continued
(I)
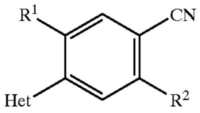
| Het | $R^1$ | $R^2$ |
|---|---|---|
| 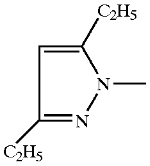 | F | 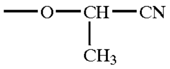 |
| 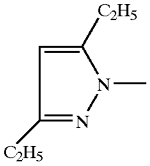 | F | $—O—CH_2—CH_2—O—CH_3$ |
| 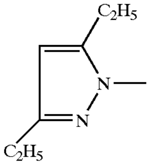 | F | 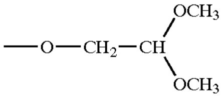 |
| 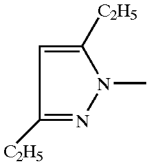 | H | 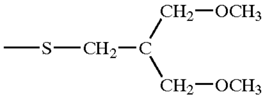 |
| 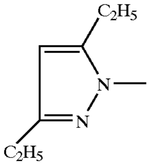 | H | 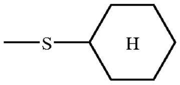 |
| 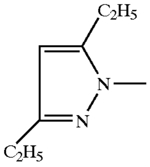 | H | 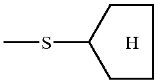 |
| 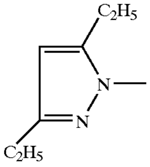 | H | 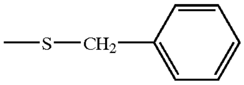 |

-continued
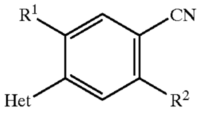
(I)
| Het | $R^1$ | $R^2$ |
|---|---|---|
| 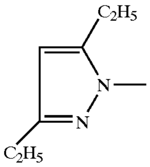 | H | $—S—CH_2—CN$ |
| 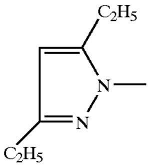 | H | $—S—CH_2—COOC_2H_5$ |
| 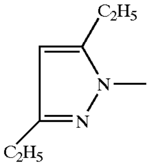 | H | 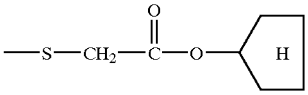 |
| 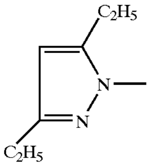 | H | 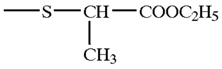 |
| 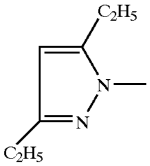 | H | 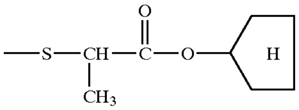 |
| 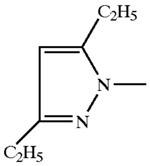 | H | 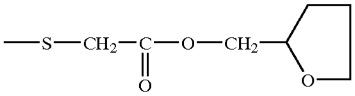 |
| 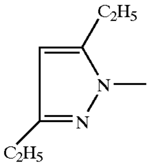 | H | 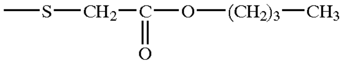 |

-continued
(I)
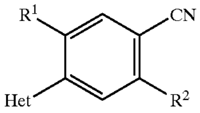
| Het | $R^1$ | $R^2$ |
|---|---|---|
| 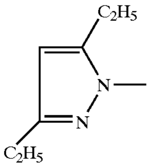 | H | 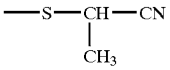 |
| 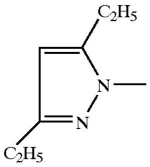 | H | $-S-CH_2-CH_2-O-CH_3$ |
| 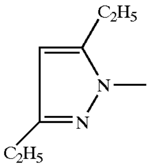 | H | 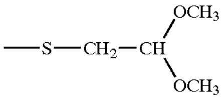 |
| 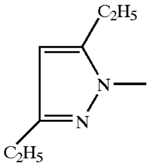 | F | $-OCH_3$ |
| 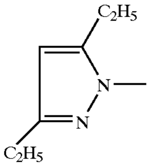 | F | $-OC_2H_5$ |
| 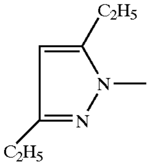 | F | $-O-CH(CH_3)_2$ |
| 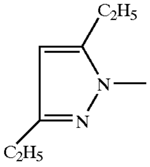 | F | $-O-CH_2-CH=CH_2$ |

-continued
(I)
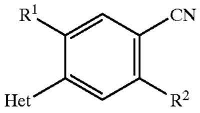
| Het | $R^1$ | $R^2$ |
|---|---|---|
| 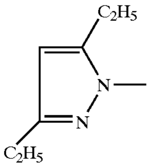 | F | $-O-CH_2-CH=CH-CH_3$ |
| 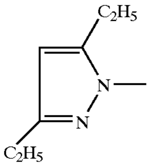 | F | $-O-CH_2-CH=CH-Cl$ |
| 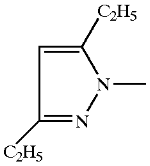 | F | 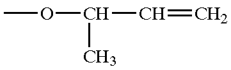 |
| 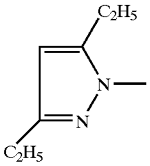 | F | $-O-CH_2-C\equiv CH$ |
| 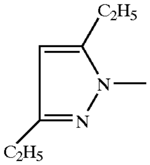 | F | 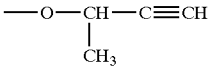 |
| 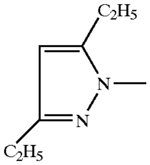 | F | 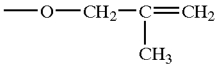 |
| 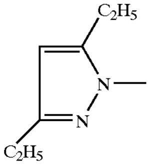 | F | $-O-CH_2-CH_2-OC_2H_5$ |

-continued
(I)
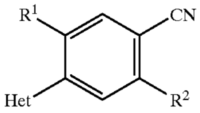
| Het | $R^1$ | $R^2$ |
|---|---|---|
| 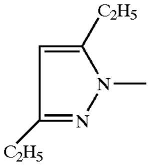 | F | 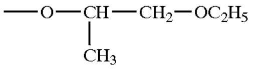 |
| 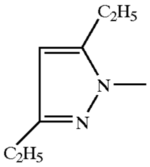 | F | 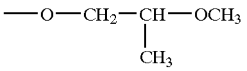 |
| 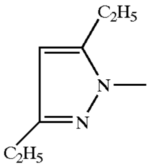 | F | 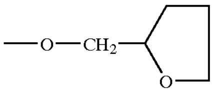 |
| 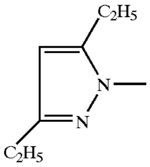 | F | 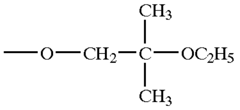 |
| 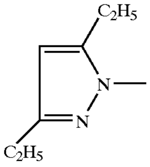 | F | $—O—CH_2—CH_2—OCH_2—CH_2—OCH_3$ |
| 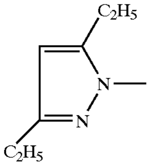 | F | $—O—CH_2—CH_2—O—CH_2—CH_2—OC_2H_5$ |
| 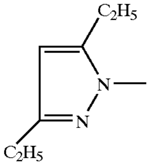 | F | 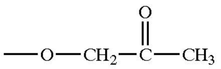 |

-continued
(I)
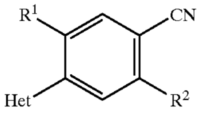
| Het | $R^1$ | $R^2$ |
| --- | --- | --- |
| 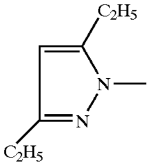 | F | 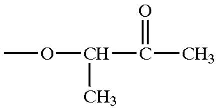 |
| 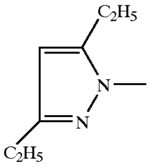 | H | $—SCH_3$ |
| 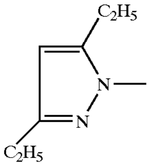 | H | $—SC_2H_5$ |
| 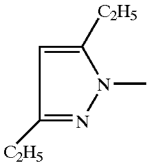 | H | $—S—CH(CH_3)_2$ |
| 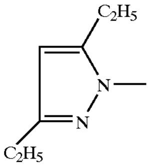 | H | $—S—CH_2—CH═CH_2$ |
| 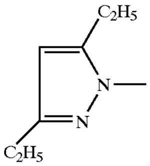 | H | $—S—CH_2—CH═CH—Cl$ |
| 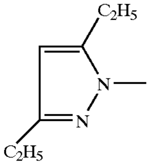 | H | $—S—CH_2—CH═CH—CH_3$ |

-continued
(I)
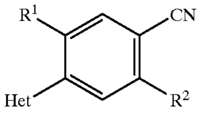
| Het | $R^1$ | $R^2$ |
|---|---|---|
| 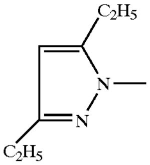 | H | 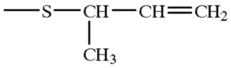 |
| 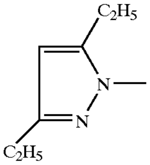 | H | $-S-CH_2-C\equiv CH$ |
| 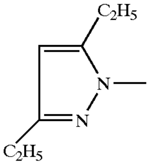 | H | 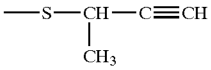 |
| 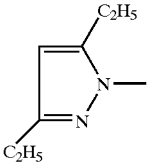 | H | 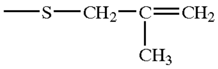 |
| 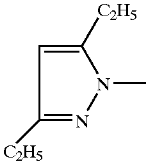 | H | $-S-CH_2-CH_2-OC_2H_5$ |
| 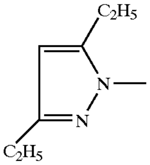 | H | 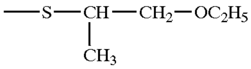 |
| 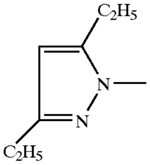 | H | 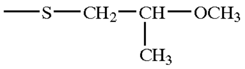 |

-continued
(I)
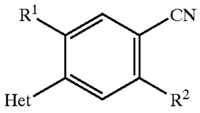
| Het | $R^1$ | $R^2$ |
| --- | --- | --- |
| 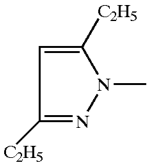 | H | 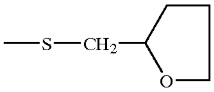 |
| 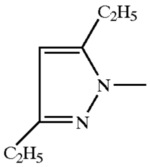 | H | 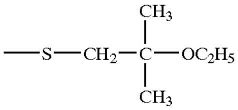 |
| 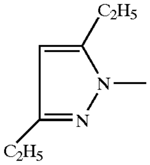 | H | $-S-CH_2-CH_2-O-CH_2-CH_2-OCH_3$ |
| 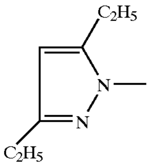 | H | $-S-CH_2-CH_2-O-CH_2-CH_2-OC_2H_5$ |
| 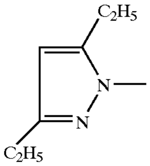 | H | 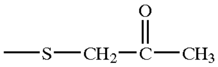 |
| 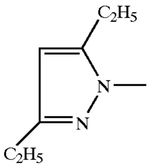 | H | 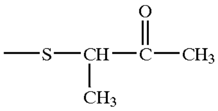 |
| 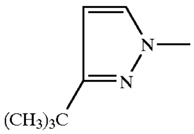 | F | 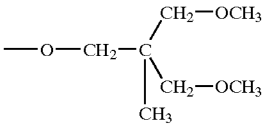 |
| 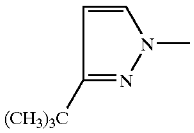 | F | 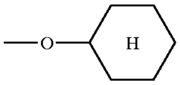 |

-continued
(I)
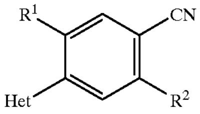
| Het | $R^1$ | $R^2$ |
|---|---|---|
| 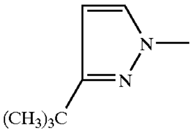 | F | 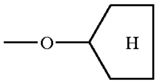 |
| 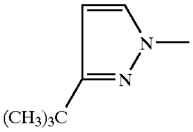 | F | 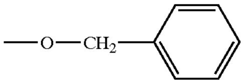 |
| 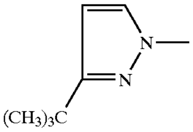 | F | $—O—CH_2—CN$ |
| 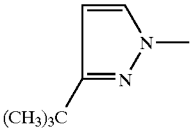 | F | $—O—CH_2—COOC_2H_5$ |
| 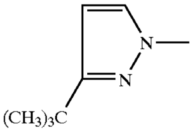 | F | 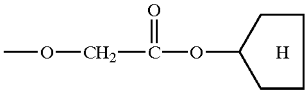 |
| 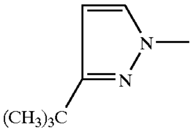 | F | 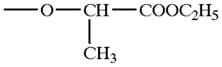 |
| 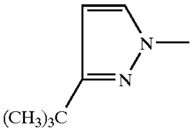 | F | 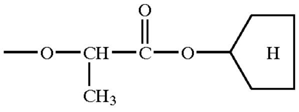 |
| 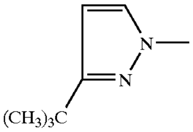 | F | 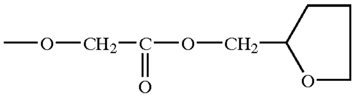 |
| 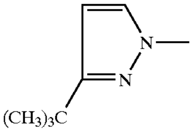 | F | 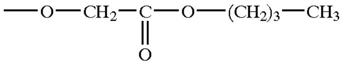 |

-continued
(I)
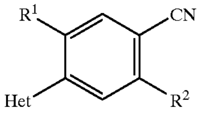
| Het | $R^1$ | $R^2$ |
|---|---|---|
| 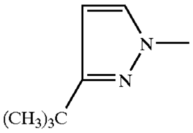 | F | 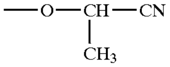 |
| 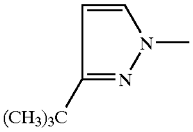 | F | $—O—CH_2—CH_2—O—CH_3$ |
| 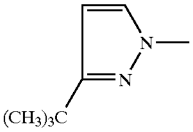 | F | 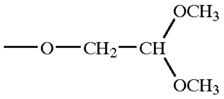 |
| 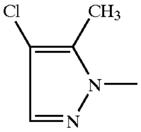 | F | $—OCH_3$ |
| 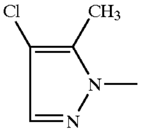 | F | $—OC_2H_5$ |
| 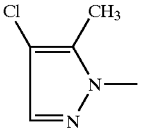 | F | $—O—CH(CH_3)_2$ |
| 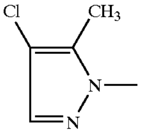 | F | $—O—CH_2—CH{=}CH_2$ |
| 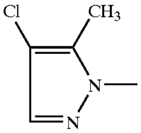 | F | $—O—CH_2—CH{=}CH—CH_3$ |
| 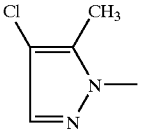 | F | $—O—CH_2—CH{=}CH—Cl$ |

-continued
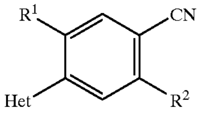
(I)
| Het | $R^1$ | $R^2$ |
|---|---|---|
| 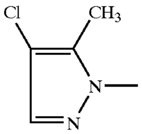 | F | 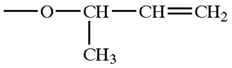 |
| 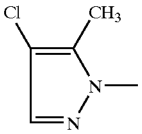 | F | $-O-CH_2-C\equiv CH$ |
| 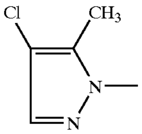 | F | 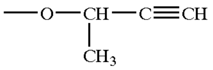 |
| 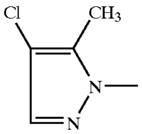 | F | 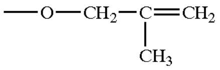 |
| 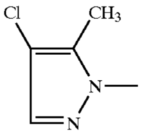 | F | $-O-CH_2-CH_2-OC_2H_5$ |
| 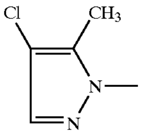 | F | 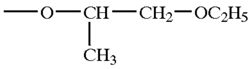 |
| 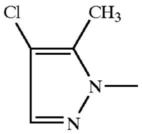 | F | 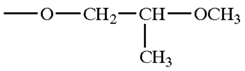 |
| 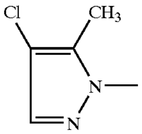 | F | 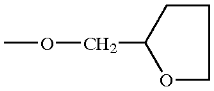 |
| 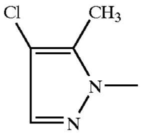 | F | 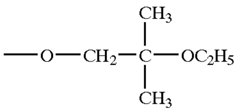 |

-continued
(I)
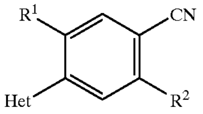
| Het | $R^1$ | $R^2$ |
|---|---|---|
| 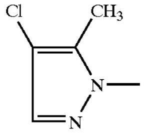 | F | $—O—CH_2—CH_2—O—CH_2—CH_2—OCH_3$ |
| 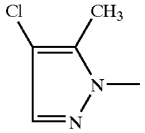 | F | $—O—CH_2—CH_2—O—CH_2—CH_2—OC_2H_5$ |
| 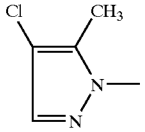 | F | 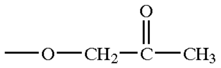 |
| 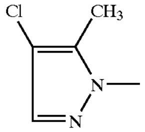 | F | 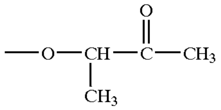 |
| 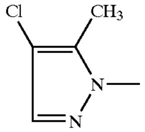 | F | $—SCH_3$ |
| 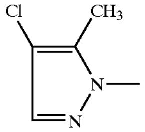 | F | $—SC_2H_5$ |
| 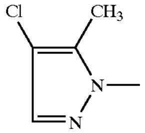 | F | $—S—CH(CH_3)_2$ |
| 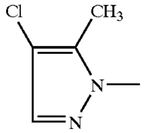 | F | $—S—CH_2—CH{=}CH_2$ |
| 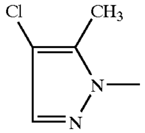 | F | $—S—CH_2—CH{=}CH—Cl$ |

-continued
(I)
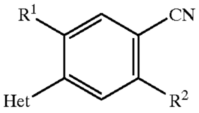
| Het | $R^1$ | $R^2$ |
| --- | --- | --- |
| 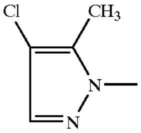 | F | $—S—CH_2—CH{=}CH—CH_3$ |
| 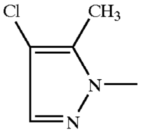 | F | 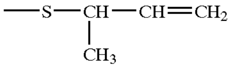 |
| 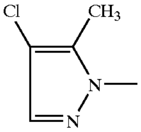 | F | $—S—CH_2—C{\equiv}CH$ |
| 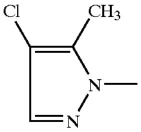 | F | 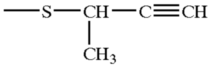 |
| 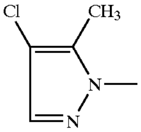 | F | 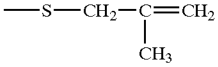 |
| 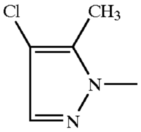 | F | $—S—CH_2—CH_2—OC_2H_5$ |
| 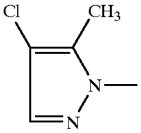 | F | 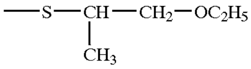 |
| 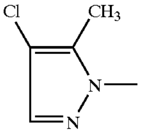 | F | 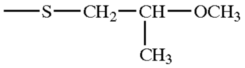 |
| 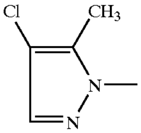 | F | 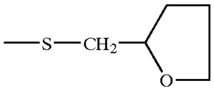 |

-continued
(I)
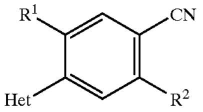
| Het | $R^1$ | $R^2$ |
|---|---|---|
| 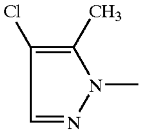 | F | 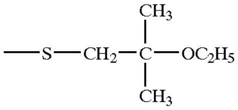 |
| 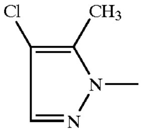 | F | $—S—CH_2—CH_2—O—CH_2—CH_2—OCH_3$ |
| 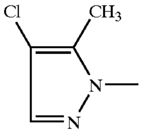 | F | $—S—CH_2—CH_2—O—CH_2—CH_2—OC_2H_5$ |
| 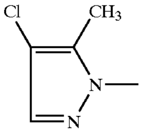 | F | 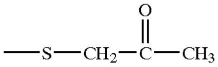 |
| 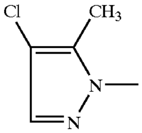 | F | 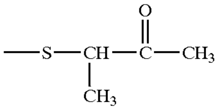 |
| 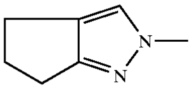 | F | 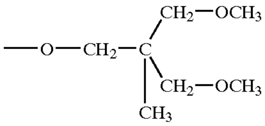 |
| 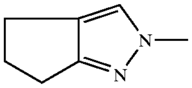 | F | 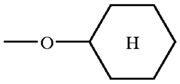 |
| 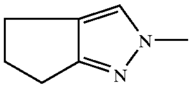 | F | 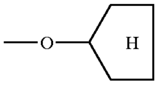 |
| 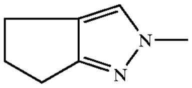 | F | 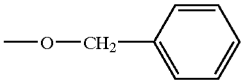 |
| 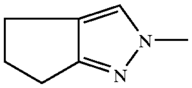 | F | $—O—CH_2—CN$ |
| 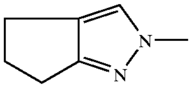 | F | $—O—CH_2—COOC_2H_5$ |

-continued
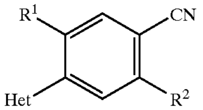
(I)
| Het | $R^1$ | $R^2$ |
| --- | --- | --- |
| 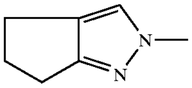 | F | 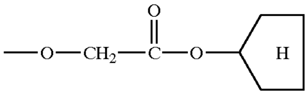 |
| 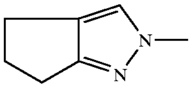 | F | 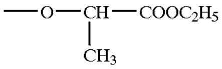 |
| 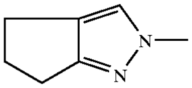 | F | 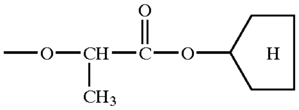 |
| 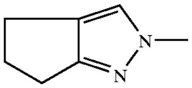 | F | 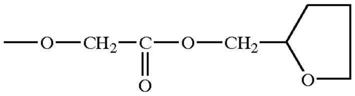 |
| 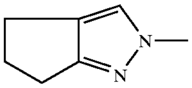 | F | 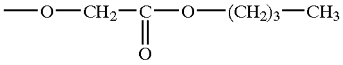 |
| 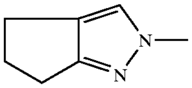 | F | 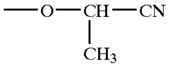 |
| 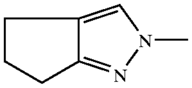 | F | $—O—CH_2—CH_2—O—CH_3$ |
| 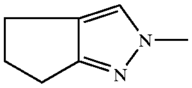 | F | 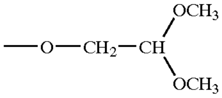 |
| 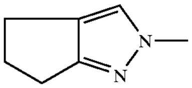 | F | 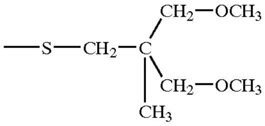 |
| 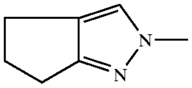 | F | 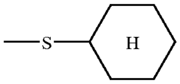 |
| 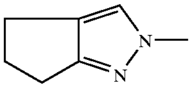 | F | 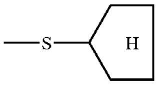 |
| 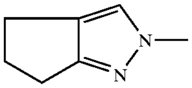 | F | 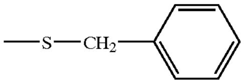 |
| 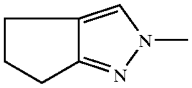 | F | $—S—CH_2—CN$ |

-continued
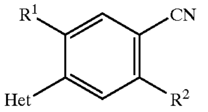
(I)
| Het | $R^1$ | $R^2$ |
|---|---|---|
| 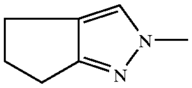 | F | $—S—CH_2—COOC_2H_5$ |
| 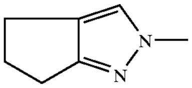 | F | 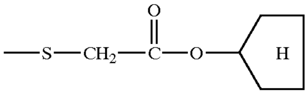 |
| 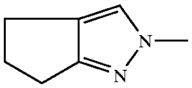 | F | 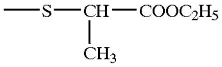 |
| 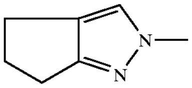 | F | 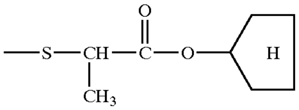 |
| 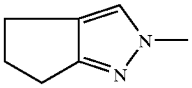 | F | 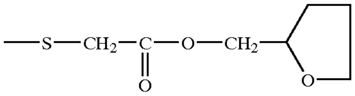 |
| 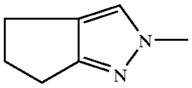 | F | 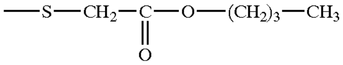 |
| 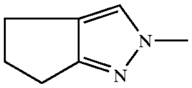 | F | 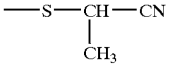 |
| 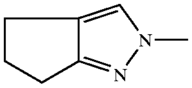 | F | $—S—CH_2—CH_2—O—CH_3$ |
| 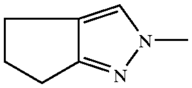 | F | 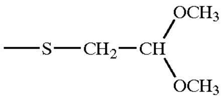 |
| 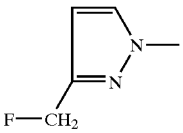 | F | $—OCH_3$ |
| 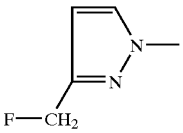 | F | $—OC_2H_5$ |
| 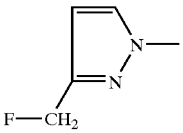 | F | $—O—CH(CH_3)_2$ |

-continued
(I)
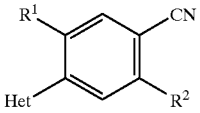
| Het | $R^1$ | $R^2$ |
|---|---|---|
| 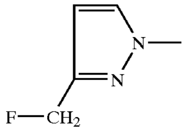 | F | $—O—CH_2—CH{=}CH_2$ |
| 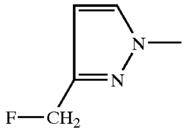 | F | $—O—CH_2—CH{=}CH—CH_3$ |
| 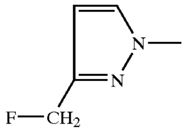 | F | $—O—CH_2—CH{=}CH—Cl$ |
| 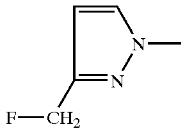 | F | 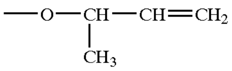 |
| 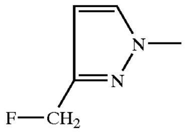 | F | $—O—CH_2—C{\equiv}CH$ |
| 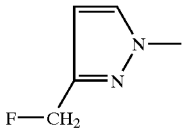 | F | 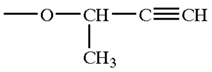 |
| 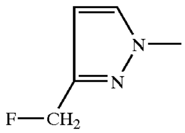 | F | 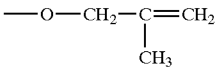 |
| 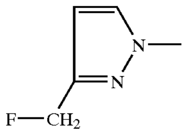 | F | $—O—CH_2—CH_2—OC_2H_5$ |
| 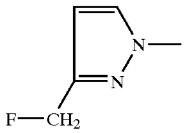 | F | 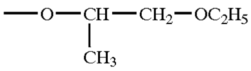 |

-continued
(I)
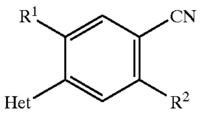
| Het | $R^1$ | $R^2$ |
|---|---|---|
| 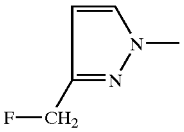 | F | 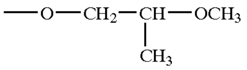 |
| 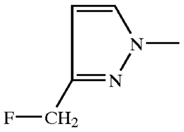 | F | 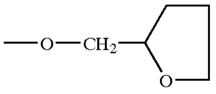 |
| 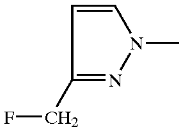 | F | 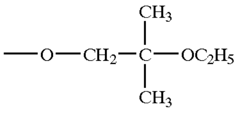 |
| 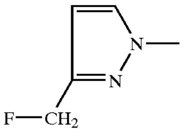 | F | $—O—CH_2—CH_2—O—CH_2—CH_2—OCH_3$ |
| 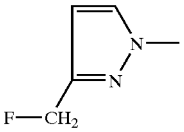 | F | $—O—CH_2—CH_2—O—CH_2—CH_2—OC_2H_5$ |
| 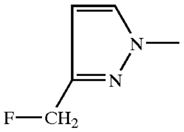 | F | 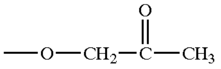 |
| 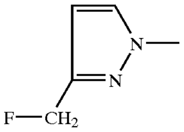 | F | 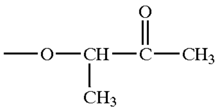 |
| 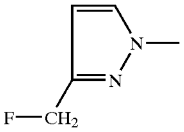 | F | $—SCH_3$ |
| 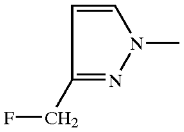 | F | $—SC_2H_5$ |

-continued
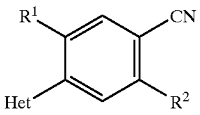
(I)
| Het | $R^1$ | $R^2$ |
|---|---|---|
| 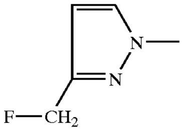 | F | $—S—CH(CH_3)_2$ |
| 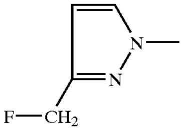 | F | $—S—CH_2—CH{=}CH_2$ |
| 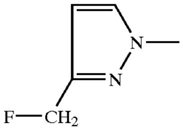 | F | $—S—CH_2—CH{=}CH—Cl$ |
| 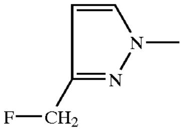 | F | $—S—CH_2—CH{=}CH—CH_3$ |
| 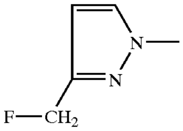 | F | 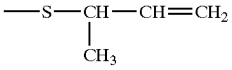 |
| 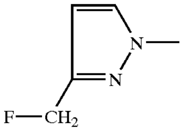 | F | $—S—CH_2—C{\equiv}CH$ |
| 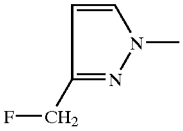 | F | 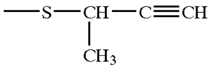 |
| 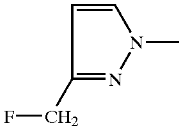 | F | 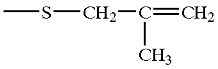 |
| 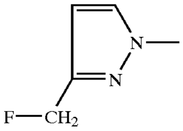 | F | $—S—CH_2—CH_2—OC_2H_5$ |

-continued
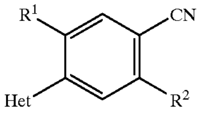
(I)
| Het | $R^1$ | $R^2$ |
|---|---|---|
| 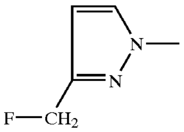 | F | 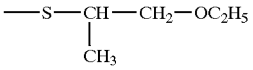 |
| 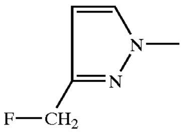 | F | 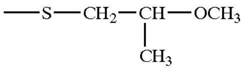 |
| 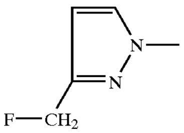 | F | 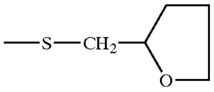 |
| 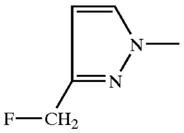 | F | 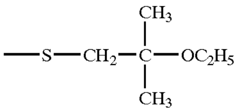 |
| 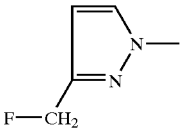 | F | $—S—CH_2—CH_2—O—CH_2—CH_2—OCH_3$ |
| 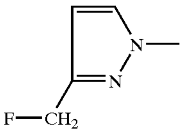 | F | $—S—CH_2—CH_2—O—CH_2—CH_2—OC_2H_5$ |
| 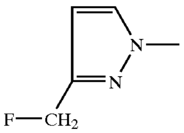 | F | 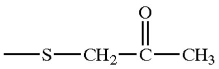 |
| 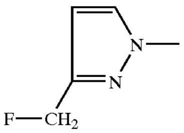 | F | 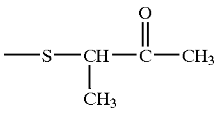 |
| 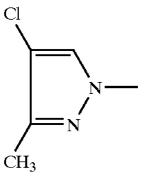 | F | 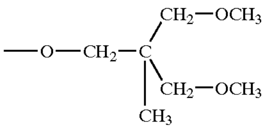 |

-continued
(I)
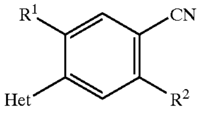
| Het | $R^1$ | $R^2$ |
|---|---|---|
| 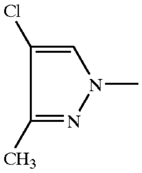 | F | 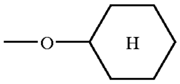 |
| 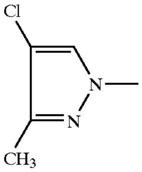 | F | 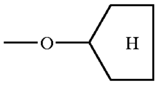 |
| 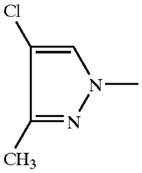 | F | 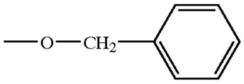 |
| 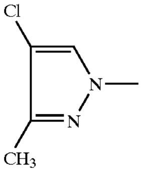 | F | $—O—CH_2—CN$ |
| 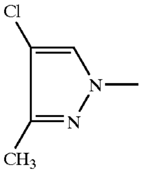 | F | $—O—CH_2—COOC_2H_5$ |
| 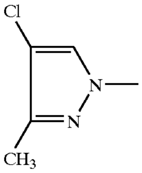 | F | 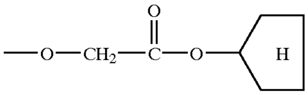 |
| 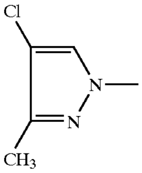 | F | 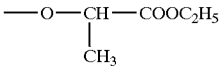 |

-continued
(I)
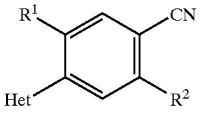
| Het | $R^1$ | $R^2$ |
|---|---|---|
| 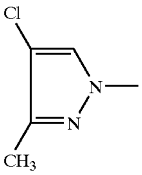 | F | 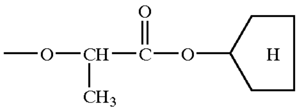 |
| 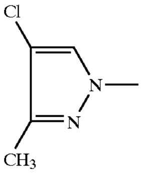 | F | 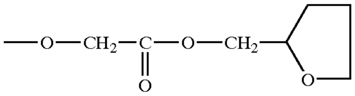 |
| 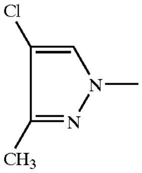 | F | 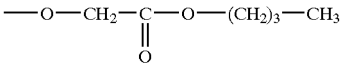 |
| 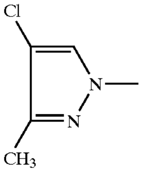 | F | 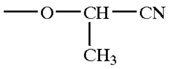 |
| 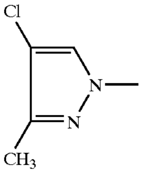 | F | $—O—CH_2—CH_2—O—CH_3$ |
| 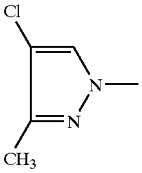 | F | 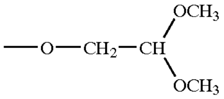 |
| 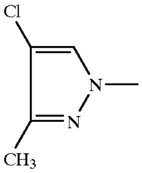 | F | 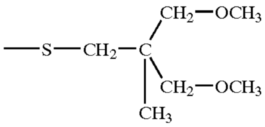 |

-continued
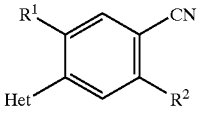
(I)
| Het | $R^1$ | $R^2$ |
|---|---|---|
| 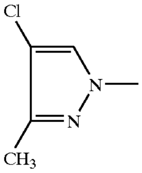 | F | 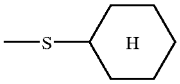 |
| 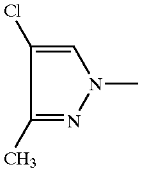 | F | 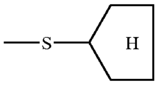 |
| 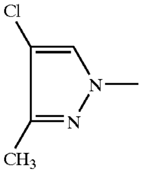 | F | 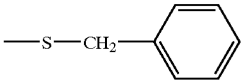 |
| 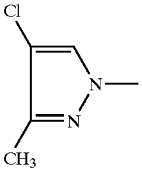 | F | $—S—CH_2—CN$ |
| 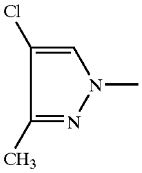 | F | $—S—CH_2—COOC_2H_5$ |
| 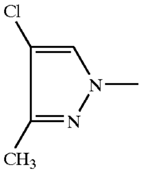 | F | 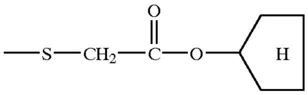 |
| 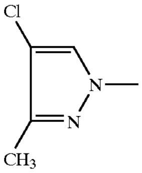 | F | 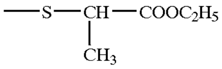 |

-continued
(I)
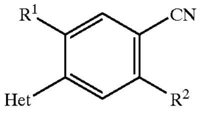
| Het | $R^1$ | $R^2$ |
|---|---|---|
| 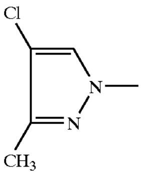 | F | 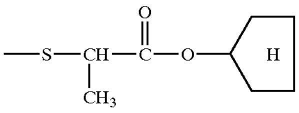 |
| 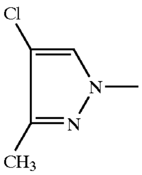 | F | 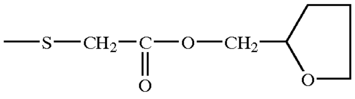 |
| 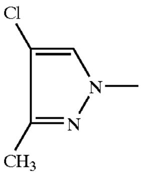 | F | 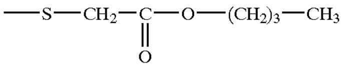 |
| 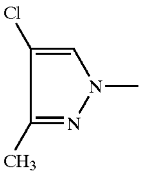 | F | 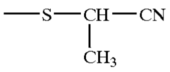 |
| 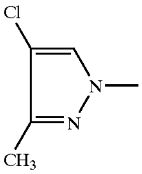 | F | $-S-CH_2-CH_2-O-CH_3$ |
| 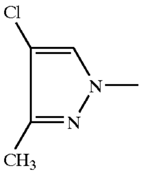 | F | 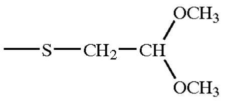 |
| 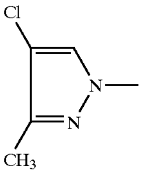 | F | $-OCH_3$ |

-continued
(I)
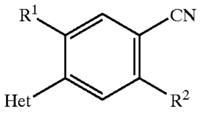
| Het | $R^1$ | $R^2$ |
|---|---|---|
| 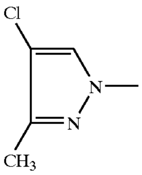 | F | $—OC_2H_5$ |
| 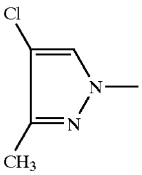 | F | $—O—CH(CH_3)_2$ |
| 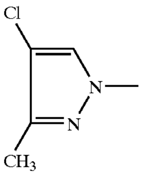 | F | $—O—CH_2—CH{=}CH_2$ |
| 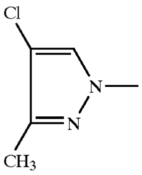 | F | $—O—CH_2—CH{=}CH—CH_3$ |
| 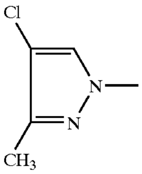 | F | $—O—CH_2—CH{=}CH—Cl$ |
| 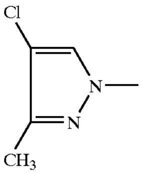 | F | 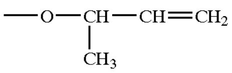 |
| 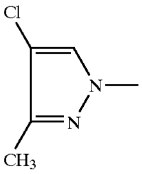 | F | $—O—CH_2—C{\equiv}CH$ |

-continued
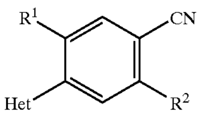
(I)
| Het | $R^1$ | $R^2$ |
|---|---|---|
| 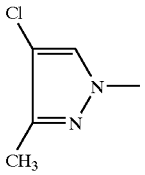 | F | 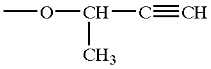 |
| 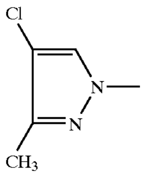 | F | 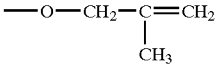 |
| 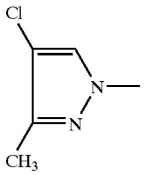 | F | $—O—CH_2—CH_2—OC_2H_5$ |
| 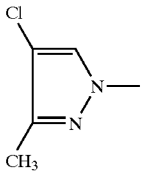 | F | 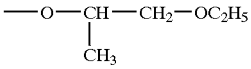 |
| 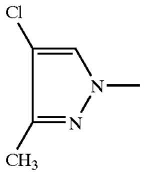 | F | 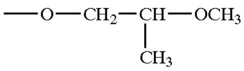 |
| 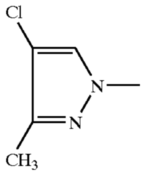 | F | 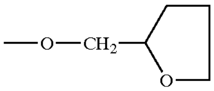 |
| 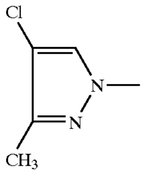 | F | 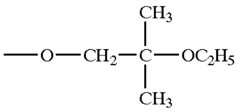 |

-continued
(I)
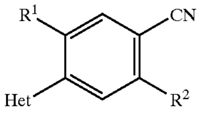
| Het | $R^1$ | $R^2$ |
|---|---|---|
| 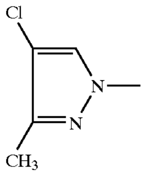 | F | $-O-CH_2-CH_2-O-CH_2-CH_2-OCH_3$ |
| 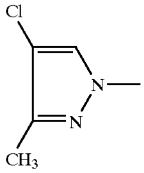 | F | $-O-CH_2-CH_2-O-CH_2-CH_2-OC_2H_5$ |
| 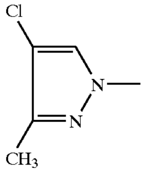 | F | 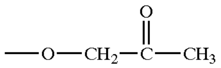 |
| 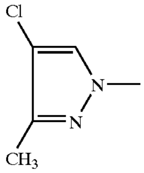 | F | 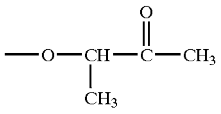 |
| 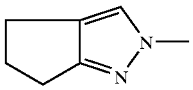 | F | $-SCH_3$ |
| 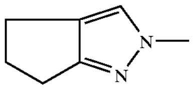 | F | $-SC_2H_5$ |
| 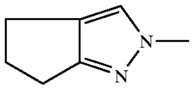 | F | $-S-CH(CH_3)_2$ |
| 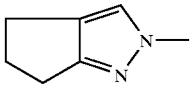 | F | $-S-CH_2-CH=CH_2$ |
| 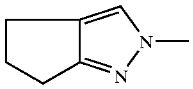 | F | $-S-CH_2-CH=CH-Cl$ |
| 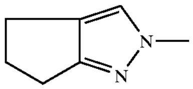 | F | $-S-CH_2-CH=CH-CH_3$ |

-continued
(I)
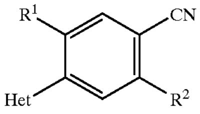
| Het | $R^1$ | $R^2$ |
|---|---|---|
| 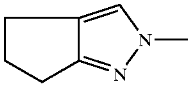 | F | 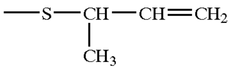 |
| 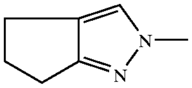 | F | $-S-CH_2-C{\equiv}CH$ |
| 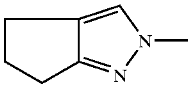 | F | 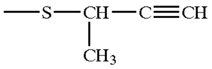 |
| 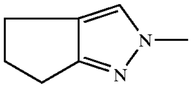 | F | 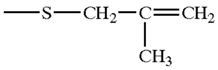 |
| 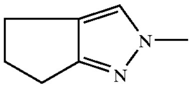 | F | $-S-CH_2-CH_2-OC_2H_5$ |
| 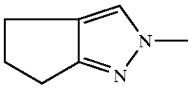 | F | 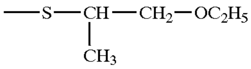 |
| 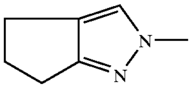 | F | 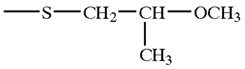 |
| 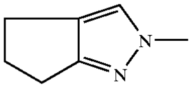 | F | 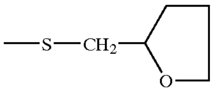 |
| 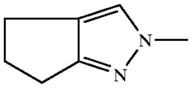 | F | 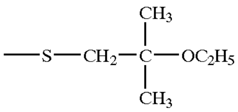 |
| 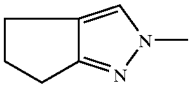 | F | $-S-CH_2-CH_2-O-CH_2-CH_2-OCH_3$ |
| 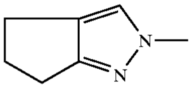 | F | $-S-CH_2-CH_2-O-CH_2-CH_2-OC_2H_5$ |
| 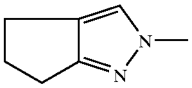 | F | 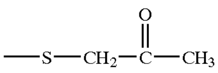 |
| 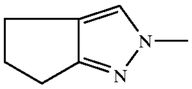 | F | 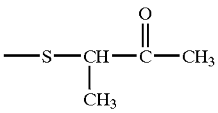 |

The following substituted triazolinones of the general formula (Ia) may be mentioned individually in addition to the compounds given in the Preparation Examples:

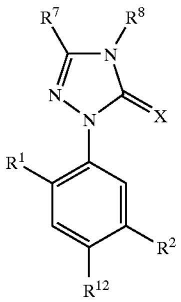

| $R^7$ | $R^8$ | $R^1$ | $R^{12}$ | $R^2$ | X |
|---|---|---|---|---|---|
| $CF_3$ | $CH_3$ | F | CN | OH | O |
| $CF_3$ | $CH_3$ | Cl | CN | OH | O |
| $CF_3$ | $CH_3$ | F | $NO_2$ | OH | O |
| $CF_3$ | $CH_3$ | Cl | $NO_2$ | OH | O |
| $CF_3$ | $CH_3$ | Cl | CN | $CH_3O$ | O |
| $CF_3$ | $CH_3$ | Cl | $NO_2$ | $CH_3O$ | O |
| $CF_3$ | $CH_3$ | F | $NO_2$ | $CH_3O$ | O |
| $CF_3$ | $CH_3$ | F | CN | $-O-CH_2-C\equiv CH$ | O |
| $CF_3$ | $CH_3$ | Cl | CN | $-O-CH_2-C\equiv CH$ | O |
| $CF_3$ | $CH_3$ | F | $NO_2$ | $-O-CH_2-C\equiv CH$ | O |
| $CF_3$ | $CH_3$ | Cl | $NO_2$ | $-O-CH_2-C\equiv CH$ | O |
| $CF_3$ | $CH_3$ | F | CN | 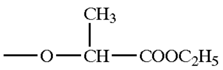 | O |
| $CF_3$ | $CH_3$ | Cl | CN | 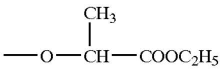 | O |
| $CF_3$ | $CH_3$ | F | $NO_2$ | 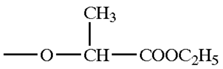 | O |
| $CF_3$ | $CH_3$ | Cl | $NO_2$ | 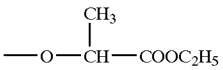 | O |
| $CF_3$ | $CH_3$ | F | CN | 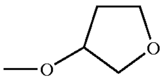 | O |
| $CF_3$ | $CH_3$ | Cl | CN | 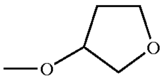 | O |
| $CF_3$ | $CH_3$ | F | $NO_2$ | 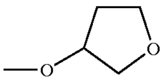 | O |
| $CF_3$ | $CH_3$ | Cl | $NO_2$ | 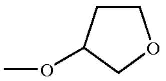 | O |
| $CF_3$ | $CH_3$ | F | CN | $-O-CH_2-CN$ | O |
| $CF_3$ | $CH_3$ | Cl | CN | $-O-CH_2-CN$ | O |
| $CF_3$ | $CH_3$ | F | $NO_2$ | $-O-CH_2-CN$ | O |
| $CF_3$ | $CH_3$ | Cl | $NO_2$ | $-O-CH_2-CN$ | O |
| $CF_3$ | $CH_3$ | F | CN | 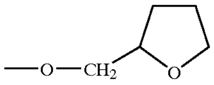 | O |

-continued

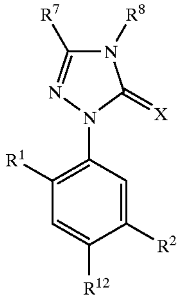

| $R^7$ | $R^8$ | $R^1$ | $R^{12}$ | $R^2$ | X |
|---|---|---|---|---|---|
| $CF_3$ | $CH_3$ | Cl | CN | 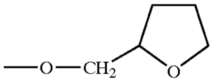 | O |
| $CF_3$ | $CH_3$ | F | $NO_2$ | 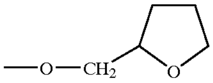 | O |
| $CF_3$ | $CH_3$ | Cl | $NO_2$ | 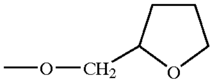 | O |
| $CF_3$ | $CH_3$ | F | CN | 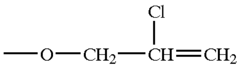 | O |
| $CF_3$ | $CH_3$ | Cl | CN | 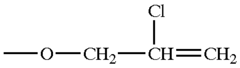 | O |
| $CF_3$ | $CH_3$ | Cl | $NO_2$ | 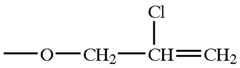 | O |
| $CF_3$ | $CH_3$ | F | $NO_2$ | 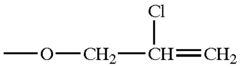 | O |
| $CF_3$ | $CH_3$ | F | CN | $—O—SO_2—CH_3$ | O |
| $CF_3$ | $CH_3$ | Cl | CN | $—O—SO_2—CH_3$ | O |
| $CF_3$ | $CH_3$ | F | $NO_2$ | $—O—SO_2—CH_3$ | O |
| $CF_3$ | $CH_3$ | Cl | $NO_2$ | $—O—SO_2—CH_3$ | O |
| $CF_3$ | $CH_3$ | F | CN | $—O—CH_2—COOCH_3$ | O |
| $CF_3$ | $CH_3$ | Cl | CN | $—O—CH_2—COOCH_3$ | O |
| $CF_3$ | $CH_3$ | F | $NO_2$ | $—O—CH_2—COOCH_3$ | O |
| $CF_3$ | $CH_3$ | Cl | $NO_2$ | $—O—CH_2—COOCH_3$ | O |
| $CF_3$ | $CH_3$ | F | $NO_2$ | F | O |
| $CF_3$ | $CH_3$ | Cl | $NO_2$ | F | O |
| $CF_3$ | $CH_3$ | F | $NO_2$ | Cl | O |
| $CF_3$ | $CH_3$ | Cl | $NO_2$ | Cl | O |
| $CF_3$ | $CH_3$ | F | CN | $—O—CHF_2$ | O |
| $CF_3$ | $CH_3$ | Cl | CN | $—O—CHF_2$ | O |
| $CF_3$ | $CH_3$ | F | $NO_2$ | $—O—CHF_2$ | O |
| $CF_3$ | $CH_3$ | Cl | $NO_2$ | $—O—CHF_2$ | O |
| $CF_3$ | $CH_3$ | F | CN | $—S—CH_3$ | O |
| $CF_3$ | $CH_3$ | Cl | CN | $—S—CH_3$ | O |
| $CF_3$ | $CH_3$ | F | $NO_2$ | $—S—CH_3$ | O |
| $CF_3$ | $CH_3$ | Cl | $NO_2$ | $—S—CH_3$ | O |
| $CF_3$ | $CH_3$ | F | CN | $—S—C_2H_5$ | O |
| $CF_3$ | $CH_3$ | Cl | CN | $—S—C_2H_5$ | O |
| $CF_3$ | $CH_3$ | F | $NO_2$ | $—S—C_2H_5$ | O |
| $CF_3$ | $CH_3$ | Cl | $NO_2$ | $—S—C_2H_5$ | O |
| $CF_3$ | $CH_3$ | F | CN | 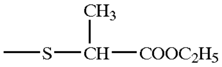 | O |

-continued

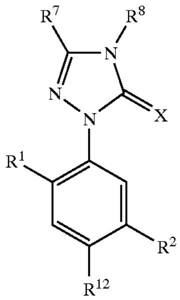

| $R^7$ | $R^8$ | $R^1$ | $R^{12}$ | $R^2$ | X |
|---|---|---|---|---|---|
| $CF_3$ | $CH_3$ | Cl | CN | 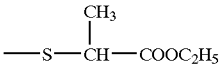 | O |
| $CF_3$ | $CH_3$ | F | $NO_2$ | 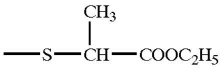 | O |
| $CF_3$ | $CH_3$ | Cl | $NO_2$ | 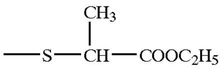 | O |
| $CF_3$ | $CH_3$ | F | CN | 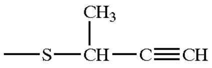 | O |
| $CF_3$ | $CH_3$ | Cl | CN | 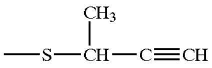 | O |
| $CF_3$ | $CH_3$ | F | $NO_2$ | 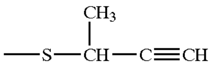 | O |
| $CF_3$ | $CH_3$ | Cl | $NO_2$ | 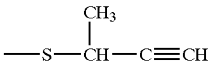 | O |
| $CF_3$ | $CH_3$ | Cl | CN | $-S-CH_2-COOCH_3$ | O |
| $CF_3$ | $CH_3$ | F | CN | $-S-CH_2-COOCH_3$ | O |
| $CF_3$ | $CH_3$ | Cl | $NO_2$ | $-S-CH_2-COOCH_3$ | O |
| $CF_3$ | $CH_3$ | F | $NO_2$ | $-S-CH_2-COOCH_3$ | O |
| $CF_3$ | $CH_3$ | F | CN | $CH_3$ | O |
| $CF_3$ | $CH_3$ | F | CN | $-S(O)-CH_3$ | O |
| $CF_3$ | $CH_3$ | F | CN | $-SO_2-CH_3$ | O |
| $CF_3$ | $CH_3$ | F | CN | $-SO_2-O-CH_3$ | O |
| $CF_3$ | $CH_3$ | F | CN | $-SO_2-NH-CH_3$ | O |
| $CF_3$ | $CH_3$ | F | CN | $-NH-CH_3$ | O |
| $CF_3$ | $CH_3$ | F | CN | $-N(CH_3)_2$ | O |
| $CF_3$ | $CH_3$ | F | CN | $-COOCH_3$ | O |
| $CF_3$ | $CH_3$ | F | CN | $-COOC_2H_5$ | O |
| $CF_3$ | $CH_3$ | Cl | $NO_2$ | $-COOCH_3$ | O |
| $CF_3$ | $CH_3$ | Cl | $NO_2$ | $-COOC_2H_5$ | O |
| $CF_3$ | $CH_3$ | F | CN | $-CO-NH-CH_3$ | O |
| $CF_3$ | $CH_3$ | F | CN | $-CO-N(CH_3)-CH_3$ | O |
| $CF_3$ | $CH_3$ | F | CN | 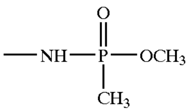 | O |
| $CF_3$ | $CH_3$ | F | CN | 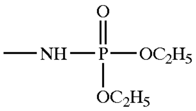 | O |
| $CF_3$ | $C_2H_5$ | F | CN | OH | O |
| $CF_3$ | $C_2H_5$ | F | CN | $OCH_3$ | O |

-continued

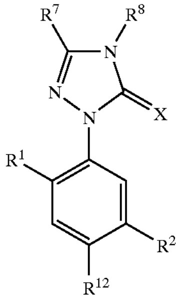

| $R^7$ | $R^8$ | $R^1$ | $R^{12}$ | $R^2$ | X |
|---|---|---|---|---|---|
| $CF_3$ | $C_2H_5$ | F | CN | $—O—CH_2—CH{=}CH_2$ | O |
| $CF_3$ | $C_2H_5$ | F | CN | $—O—CH_2—C{\equiv}CH$ | O |
| $CF_3$ | $C_2H_5$ | F | CN | 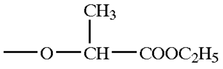 | O |
| $CF_3$ | $C_2H_5$ | F | CN | $—O—CH_2—COOCH_3$ | O |
| $CF_3$ | $C_2H_5$ | F | CN | $—S—CH_3$ | O |
| $CF_3$ | $C_2H_5$ | F | CN | $—S—C_2H_5$ | O |
| $CF_3$ | $C_2H_5$ | F | CN | 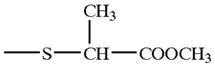 | O |
| $CF_3$ | $C_2H_5$ | F | CN | F | O |
| $CF_3$ | $C_2H_5$ | F | CN | 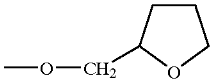 | O |
| $CF_3$ | $C_2H_5$ | F | CN | 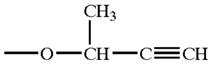 | O |
| $CF_3$ | $C_2H_5$ | Cl | CN | $OCH_3$ | O |
| $CF_3$ | $C_2H_5$ | Cl | CN | $—S—C_2H_5$ | O |
| $CF_3$ | $C_2H_5$ | F | $NO_2$ | $OCH_3$ | O |
| $CF_3$ | $C_2H_5$ | Cl | $NO_2$ | $—O—CH_2—C{\equiv}CH$ | O |
| $CF_3$ | $C_2H_5$ | Cl | CN | 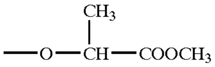 | O |
| $CF_3$ | $C_2H_5$ | F | $NO_2$ | 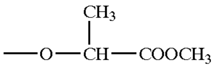 | O |
| $CF_3$ | $C_2H_5$ | Cl | $NO_2$ | 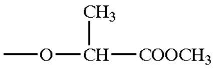 | O |
| $CF_3$ | $C_2H_5$ | F | CN | 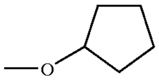 | O |
| $CF_3$ | $C_2H_5$ | F | CN | $—O—CH_2—C_6H_5$ | O |
| $CF_3$ | $—CH_2—CH{=}CH_2$ | F | CN | OH | O |
| $CF_3$ | $—CH_2—CH{=}CH_2$ | F | CN | $OCH_3$ | O |
| $CF_3$ | $—CH_2—CH{=}CH_2$ | F | CN | $—O—CH_2—CH{=}CH_2$ | O |
| $CF_3$ | $—CH_2—CH{=}CH_2$ | F | CN | $—O—CH_2—C{\equiv}CH$ | O |
| $CF_3$ | $—CH_2—CH{=}CH_2$ | F | CN | 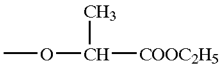 | O |
| $CF_3$ | $—CH_2—CH{=}CH_2$ | F | CN | $—O—CH_2—COOCH_3$ | O |
| $CF_3$ | $—CH_2—CH{=}CH_2$ | F | CN | $—S—CH_3$ | O |

-continued

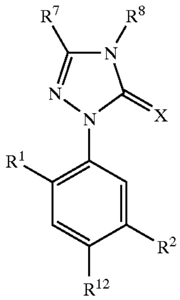

| $R^7$ | $R^8$ | $R^1$ | $R^{12}$ | $R^2$ | X |
|---|---|---|---|---|---|
| $CF_3$ | $-CH_2-CH=CH_2$ | F | CN | $-S-C_2H_5$ | O |
| $CF_3$ | $-CH_2-CH=CH_2$ | F | CN | 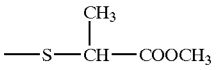 | O |
| $CF_3$ | $-CH_2-CH=CH_2$ | F | CN | F | O |
| $CF_3$ | $-CH_2-CH=CH_2$ | F | CN | 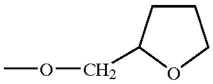 | O |
| $CF_3$ | $-CH_2-CH=CH_2$ | F | CN | 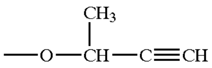 | O |
| $CF_3$ | $-CH_2-CH=CH_2$ | Cl | CN | $OCH_3$ | O |
| $CF_3$ | $-CH_2-CH=CH_2$ | Cl | CN | $-S-C_2H_5$ | O |
| $CF_3$ | $-CH_2-CH=CH_2$ | F | $NO_2$ | $OCH_3$ | O |
| $CF_3$ | $-CH_2-CH=CH_2$ | Cl | $NO_2$ | $-O-CH_2-C\equiv CH$ | O |
| $CF_3$ | $-CH_2-CH=CH_2$ | Cl | CN | 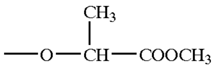 | O |
| $CF_3$ | $-CH_2-CH=CH_2$ | F | $NO_2$ | 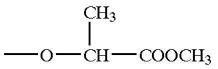 | O |
| $CF_3$ | $-CH_2-CH=CH_2$ | Cl | $NO_2$ | 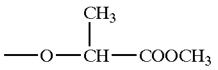 | O |
| $CF_3$ | $-CH_2-CH=CH_2$ | F | CN | 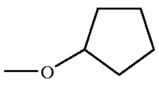 | O |
| $CF_3$ | $-CH_2-CH=CH_2$ | F | CN | $-O-CH_2-C_6H_5$ | O |
| $CF_3$ | $-CHF_2$ | F | CN | OH | O |
| $CF_3$ | $-CHF_2$ | F | CN | $OCH_3$ | O |
| $CF_3$ | $-CHF_2$ | F | CN | $-O-CH_2-CH=CH_2$ | O |
| $CF_3$ | $-CHF_2$ | F | CN | $-O-CH_2-C\equiv CH$ | O |
| $CF_3$ | $-CHF_2$ | F | CN | 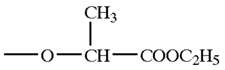 | O |
| $CF_3$ | $-CHF_2$ | F | CN | $-O-CH_2-COOCH_3$ | O |
| $CF_3$ | $-CHF_2$ | F | CN | $-S-CH_3$ | O |
| $CF_3$ | $-CHF_2$ | F | CN | $-S-C_2H_5$ | O |
| $CF_3$ | $-CHF_2$ | F | CN | 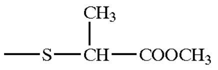 | O |
| $CF_3$ | $-CHF_2$ | F | CN | F | O |

-continued

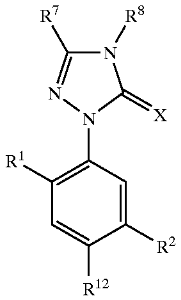

| $R^7$ | $R^8$ | $R^1$ | $R^{12}$ | $R^2$ | X |
|---|---|---|---|---|---|
| $CF_3$ | $—CHF_2$ | F | CN | 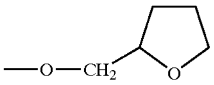 | O |
| $CF_3$ | $—CHF_2$ | F | CN | 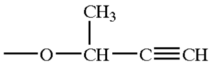 | O |
| $CF_3$ | $—CHF_2$ | Cl | CN | $OCH_3$ | O |
| $CF_3$ | $—CHF_2$ | Cl | CN | $—S—C_2H_5$ | O |
| $CF_3$ | $—CHF_2$ | F | $NO_2$ | $OCH_3$ | O |
| $CF_3$ | $—CHF_2$ | Cl | $NO_2$ | $—O—CH_2—C{\equiv}CH$ | O |
| $CF_3$ | $—CHF_2$ | Cl | CN | 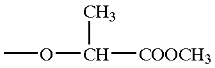 | O |
| $CF_3$ | $—CHF_2$ | F | $NO_2$ | 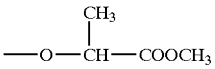 | O |
| $CF_3$ | $—CHF_2$ | Cl | $NO_2$ | 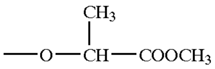 | O |
| $CF_3$ | $—CHF_2$ | F | CN | 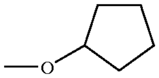 | O |
| $CF_3$ | $—CHF_2$ | F | CN | $—O—CH_2—C_6H_5$ | O |
| $CF_3$ | 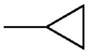 | F | CN | OH | O |
| $CF_3$ | 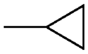 | F | CN | $OCH_3$ | O |
| $CF_3$ | 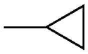 | F | CN | $—O—CH_2—CH{=}CH_2$ | O |
| $CF_3$ | 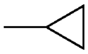 | F | CN | $—O—CH_2—C{\equiv}CH$ | O |
| $CF_3$ | 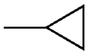 | F | CN | 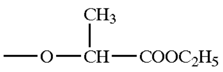 | O |
| $CF_3$ | 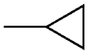 | F | CN | $—O—CH_2—COOCH_3$ | O |
| $CF_3$ | 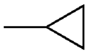 | F | CN | $—S—CH_3$ | O |
| $CF_3$ | 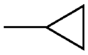 | F | CN | $—S—C_2H_5$ | O |

-continued
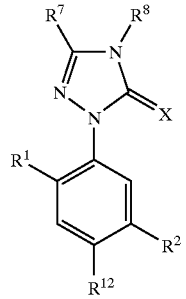
| $R^7$ | $R^8$ | $R^1$ | $R^{12}$ | $R^2$ | X |
|---|---|---|---|---|---|
| $CF_3$ | 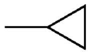 | F | CN | 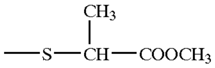 | O |
| $CF_3$ | 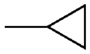 | F | CN | F | O |
| $CF_3$ | 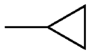 | F | CN | 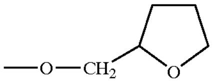 | O |
| $CF_3$ | 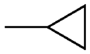 | F | CN | 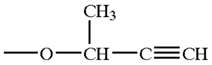 | O |
| $CF_3$ | 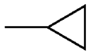 | Cl | CN | $OCH_3$ | O |
| $CF_3$ | 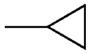 | Cl | CN | $—S—C_2H_5$ | O |
| $CF_3$ | 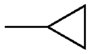 | F | $NO_2$ | $OCH_3$ | O |
| $CF_3$ | 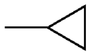 | Cl | $NO_2$ | $—O—CH_2—C≡CH$ | O |
| $CF_3$ | 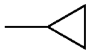 | Cl | CN | 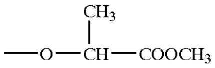 | O |
| $CF_3$ | 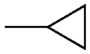 | F | $NO_2$ | 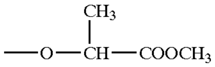 | O |
| $CF_3$ | 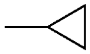 | Cl | $NO_2$ | 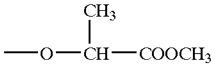 | O |
| $CF_3$ | 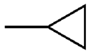 | F | CN | 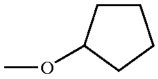 | O |
| $CF_3$ | 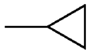 | F | CN | $—O—CH_2—C_6H_5$ | O |
| $—CHF_2$ | $CH_3$ | F | CN | OH | O |
| $—CHF_2$ | $CH_3$ | F | CN | $OCH_3$ | O |
| $—CHF_2$ | $CH_3$ | F | CN | $—O—CH_2—CH═CH_2$ | O |
| $—CHF_2$ | $CH_3$ | F | CN | $—O—CH_2—C≡CH$ | O |
| $—CHF_2$ | $CH_3$ | F | CN | 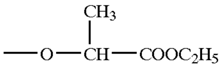 | O |
| $—CHF_2$ | $CH_3$ | F | CN | $—O—CH_2—COOCH_3$ | O |

-continued

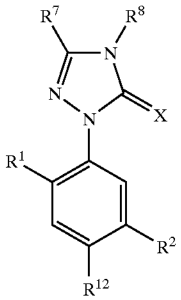

| $R^7$ | $R^8$ | $R^1$ | $R^{12}$ | $R^2$ | X |
|---|---|---|---|---|---|
| $—CHF_2$ | $CH_3$ | F | CN | $—S—CH_3$ | O |
| $—CHF_2$ | $CH_3$ | F | CN | $—S—C_2H_5$ | O |
| $—CHF_2$ | $CH_3$ | F | CN | 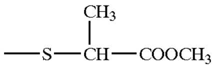 | O |
| $—CHF_2$ | $CH_3$ | F | CN | F | O |
| $—CHF_2$ | $CH_3$ | F | CN | 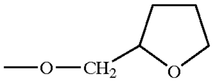 | O |
| $—CHF_2$ | $CH_3$ | F | CN | 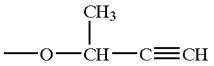 | O |
| $—CHF_2$ | $CH_3$ | Cl | CN | $OCH_3$ | O |
| $—CHF_2$ | $CH_3$ | Cl | CN | $—S—C_2H_5$ | O |
| $—CHF_2$ | $CH_3$ | F | $NO_2$ | $OCH_3$ | O |
| $—CHF_2$ | $CH_3$ | Cl | $NO_2$ | $—O—CH_2—C{\equiv}CH$ | O |
| $—CHF_2$ | $CH_3$ | Cl | CN | 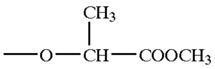 | O |
| $—CHF_2$ | $CH_3$ | F | $NO_2$ | 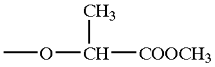 | O |
| $—CHF_2$ | $CH_3$ | Cl | $NO_2$ | 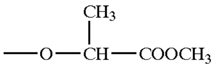 | O |
| $—CHF_2$ | $CH_3$ | F | CN | 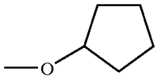 | O |
| $—CHF_2$ | $CH_3$ | F | CN | $—O—CH_2—C_6H_5$ | O |
| $—CF_2Cl$ | $CH_3$ | F | CN | OH | O |
| $—CF_2Cl$ | $CH_3$ | F | CN | $OCH_3$ | O |
| $—CF_2Cl$ | $CH_3$ | F | CN | $—O—CH_2—CH{=}CH_2$ | O |
| $—CF_2Cl$ | $CH_3$ | F | CN | $—O—CH_2—C{\equiv}CH$ | O |
| $—CF_2Cl$ | $CH_3$ | F | CN | 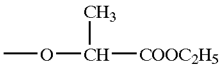 | O |
| $—CF_2Cl$ | $CH_3$ | F | CN | $—O—CH_2—COOCH_3$ | O |
| $—CF_2Cl$ | $CH_3$ | F | CN | $—S—CH_3$ | O |
| $—CF_2Cl$ | $CH_3$ | F | CN | $—S—C_2H_5$ | O |
| $—CF_2Cl$ | $CH_3$ | F | CN | 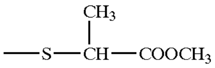 | O |
| $—CF_2Cl$ | $CH_3$ | F | CN | F | O |

-continued

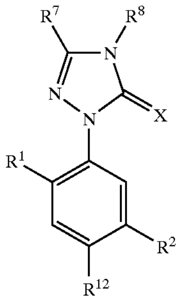

| $R^7$ | $R^8$ | $R^1$ | $R^{12}$ | $R^2$ | X |
|---|---|---|---|---|---|
| $—CF_2Cl$ | $CH_3$ | F | CN | 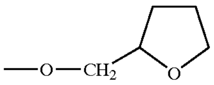 | O |
| $—CF_2Cl$ | $CH_3$ | F | CN | 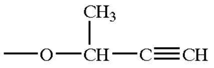 | O |
| $—CF_2Cl$ | $CH_3$ | Cl | CN | $OCH_3$ | O |
| $—CF_2Cl$ | $CH_3$ | Cl | CN | $—S—C_2H_5$ | O |
| $—CF_2Cl$ | $CH_3$ | F | $NO_2$ | $OCH_3$ | O |
| $—CF_2Cl$ | $CH_3$ | Cl | $NO_2$ | $—O—CH_2—C≡CH$ | O |
| $—CF_2Cl$ | $CH_3$ | Cl | CN | 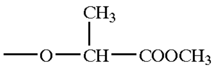 | O |
| $—CF_2Cl$ | $CH_3$ | F | $NO_2$ | 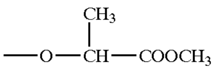 | O |
| $—CF_2Cl$ | $CH_3$ | Cl | $NO_2$ | 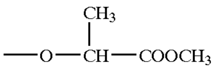 | O |
| $—CF_2Cl$ | $CH_3$ | F | CN | 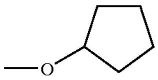 | O |
| $—CF_2Cl$ | $CH_3$ | F | CN | $—O—CH_2—C_6H_5$ | O |
| $—CCl_3$ | $CH_3$ | F | CN | OH | O |
| $—CCl_3$ | $CH_3$ | F | CN | $OCH_3$ | O |
| $—CCl_3$ | $CH_3$ | F | CN | $—O—CH_2—CH=CH_2$ | O |
| $—CCl_3$ | $CH_3$ | F | CN | $—O—CH_2—C≡CH$ | O |
| $—CCl_3$ | $CH_3$ | F | CN | 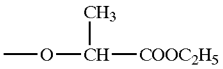 | O |
| $—CCl_3$ | $CH_3$ | F | CN | $—O—CH_2—COOCH_3$ | O |
| $—CCl_3$ | $CH_3$ | F | CN | $—S—CH_3$ | O |
| $—CCl_3$ | $CH_3$ | F | CN | $—S—C_2H_5$ | O |
| $—CCl_3$ | $CH_3$ | F | CN | 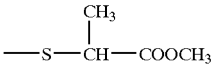 | O |
| $—CCl_3$ | $CH_3$ | F | CN | F | O |
| $—CCl_3$ | $CH_3$ | F | CN | 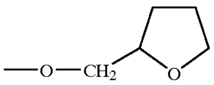 | O |
| $—CCl_3$ | $CH_3$ | F | CN | 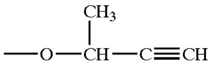 | O |
| $—CCl_3$ | $CH_3$ | Cl | CN | $OCH_3$ | O |

-continued

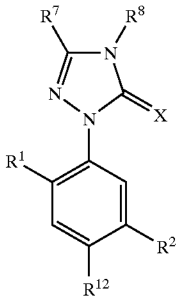

| $R^7$ | $R^8$ | $R^1$ | $R^{12}$ | $R^2$ | X |
|---|---|---|---|---|---|
| $—CCl_3$ | $CH_3$ | Cl | CN | $—S—C_2H_5$ | O |
| $—CCl_3$ | $CH_3$ | F | $NO_2$ | $OCH_3$ | O |
| $—CCl_3$ | $CH_3$ | Cl | $NO_2$ | $—O—CH_2—C{\equiv}CH$ | O |
| $—CCl_3$ | $CH_3$ | Cl | CN | 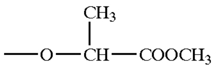 | O |
| $—CCl_3$ | $CH_3$ | F | $NO_2$ | 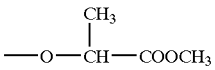 | O |
| $—CCl_3$ | $CH_3$ | Cl | $NO_2$ | 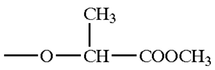 | O |
| $—CCl_3$ | $CH_3$ | F | CN | 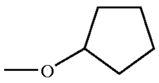 | O |
| $—CCl_3$ | $CH_3$ | F | CN | $—O—CH_2—C_6H_5$ | O |
| $CF_3$ | $CH_3$ | F | CN | OH | S |
| $CF_3$ | $CH_3$ | F | CN | $—O\text{-}i\text{-}C_3H_7$ | S |
| $CF_3$ | $CH_3$ | F | CN | $—O—CH_2—CH{=}CH_2$ | S |
| $CF_3$ | $CH_3$ | F | CN | $—O—CH_2—C{\equiv}CH$ | S |
| $CF_3$ | $CH_3$ | F | CN | 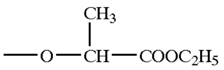 | S |
| $CF_3$ | $CH_3$ | F | CN | $—O—CH_2—COOCH_3$ | S |
| $CF_3$ | $CH_3$ | F | CN | $—S—CH_3$ | S |
| $CF_3$ | $CH_3$ | F | CN | $—S—C_2H_5$ | S |
| $CF_3$ | $CH_3$ | F | CN | 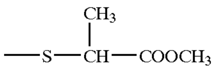 | S |
| $CF_3$ | $CH_3$ | F | CN | F | S |
| $CF_3$ | $CH_3$ | F | CN | 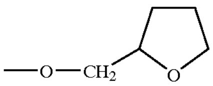 | S |
| $CF_3$ | $CH_3$ | F | CN | 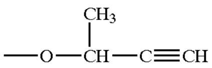 | S |
| $CF_3$ | $CH_3$ | Cl | CN | $OCH_3$ | S |
| $CF_3$ | $CH_3$ | Cl | CN | $—S—C_2H_5$ | S |
| $CF_3$ | $CH_3$ | F | $NO_2$ | $OCH_3$ | S |
| $CF_3$ | $CH_3$ | Cl | $NO_2$ | $—O—CH_2—C{\equiv}CH$ | S |
| $CF_3$ | $CH_3$ | Cl | CN | 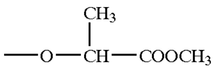 | S |

-continued

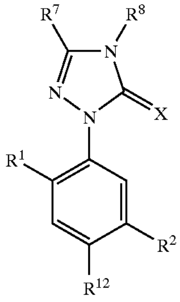

| $R^7$ | $R^8$ | $R^1$ | $R^{12}$ | $R^2$ | X |
|---|---|---|---|---|---|
| $CF_3$ | $CH_3$ | F | $NO_2$ | 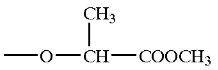 | S |
| $CF_3$ | $CH_3$ | Cl | $NO_2$ | 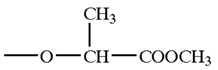 | S |
| $CF_3$ | $CH_3$ | F | CN | 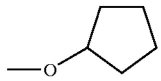 | S |
| $CF_3$ | $CH_3$ | F | CN | $—O—CH_2—C_6H_5$ | S |
| $CF_3$ | $—CHF_2$ | F | CN | OH | S |
| $CF_3$ | $—CHF_2$ | F | CN | $OCH_3$ | S |
| $CF_3$ | $—CHF_2$ | F | CN | $—O—CH_2—CH{=}CH_2$ | S |
| $CF_3$ | $—CHF_2$ | F | CN | $—O—CH_2—C{\equiv}CH$ | S |
| $CF_3$ | $—CHF_2$ | F | CN | 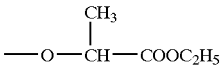 | S |
| $CF_3$ | $—CHF_2$ | F | CN | $—O—CH_2—COOCH_3$ | S |
| $CF_3$ | $—CHF_2$ | F | CN | $—S—CH_3$ | S |
| $CF_3$ | $—CHF_2$ | F | CN | $—S—C_2H_5$ | S |
| $CF_3$ | $—CHF_2$ | F | CN | 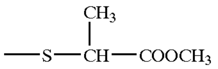 | S |
| $CF_3$ | $—CHF_2$ | F | CN | F | S |
| $CF_3$ | $—CHF_2$ | F | CN | 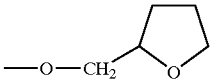 | S |
| $CF_3$ | $—CHF_2$ | F | CN | 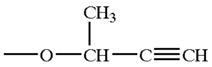 | S |
| $CF_3$ | $—CHF_2$ | Cl | CN | $OCH_3$ | S |

-continued

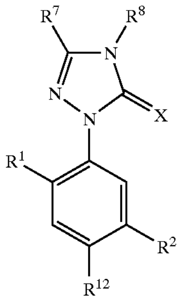

| $R^7$ | $R^8$ | $R^1$ | $R^{12}$ | $R^2$ | X |
|---|---|---|---|---|---|
| $CF_3$ | —$CHF_2$ | Cl | CN | —S—$C_2H_5$ | S |
| $CF_3$ | —$CHF_2$ | F | $NO_2$ | $OCH_3$ | S |
| $CF_3$ | —$CHF_2$ | Cl | $NO_2$ | —O—$CH_2$—C≡CH | S |
| $CF_3$ | —$CHF_2$ | Cl | CN | 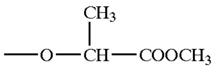 | S |
| $CF_3$ | —$CHF_2$ | F | $NO_2$ | 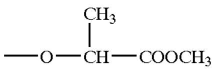 | S |
| $CF_3$ | —$CHF_2$ | Cl | $NO_2$ | 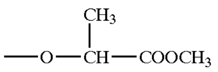 | S |
| $CF_3$ | —$CHF_2$ | F | CN | 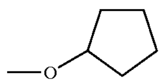 | S |
| $CF_3$ | —$CHF_2$ | F | CN | —O—$CH_2$—$C_6H_5$ | S |

If, for example, 4-cyano-2,5-difluoroph nylhydrazine and acetylacetone are used as the starting substances, the course of the reaction of process (a) according to the invention may be represented by the following equation:

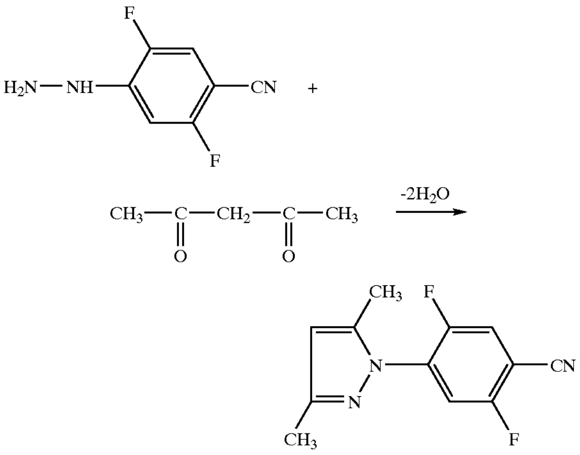

If, for example, 4-(3,5-dimethylpyrazol-1-yl)-2,5-difluorobenzonitrile is used as the starting compound and sulphuryl chloride as the halogenating agent, the course of the reaction of process (b) according to the invention may be represented by the following equation:

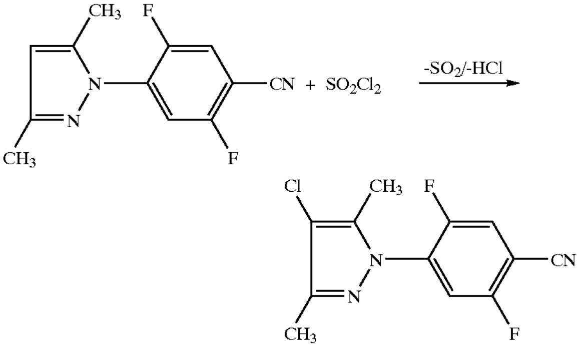

If, for example, 1-(2,5-difluoro-4-cyanophenyl)-4H-pyrazolin-5-one is used as the starting compound and phosphorus oxychloride in the presence of triphenylphosphine is used as the halogenating agent, the course of the reaction of process (c) according to the invention may be represented by the following equation:

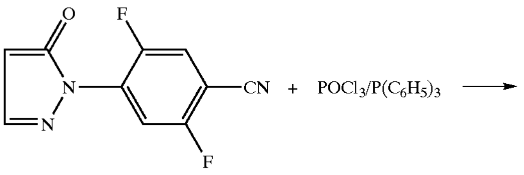

-continued

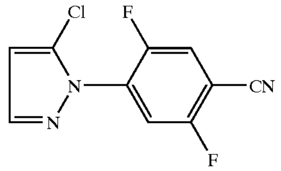

If, for example, 4-cyano-2-fluoro-5-isopropoxyphenyl-hydrazine and ethyl N-ethoxycarbonyl-2,2-dimethylpropane-imidate are used as the starting substances, the course of the reaction of process (d) according to the invention may be represented by the following equation:

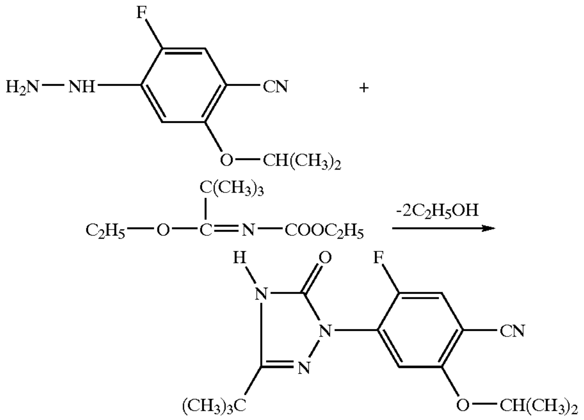

If, for example, 1-(4-cyano-2-fluoro-5-allyloxyphenyl)-3-t-butyl-4H-1,2,4-triazolin-5-one and propargyl bromide are used as the starting substances, the course of the reaction of process (e) according to the invention may be represented-by the following equation:

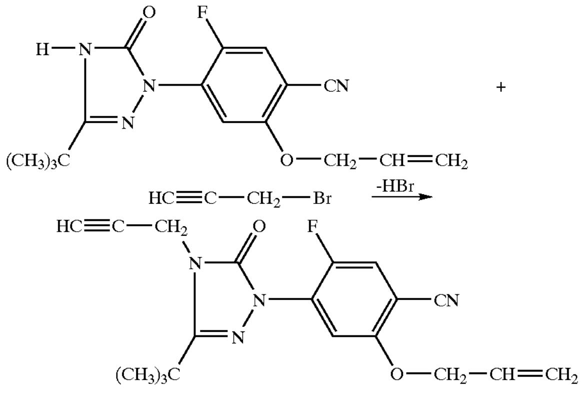

If, for example, piperidin-2-one-(2,5-difluoro-4-cyanophenylhydrazone is used as the starting compound, the course of the reaction of process (f) according to the invention may be represented by the following equation:

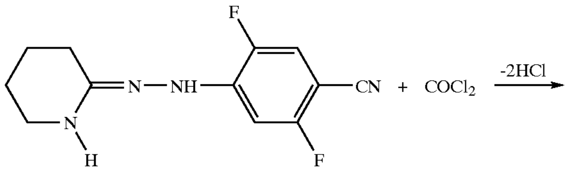

-continued

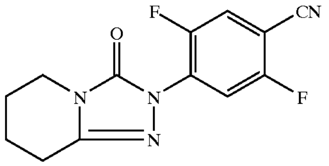

If, for example, N-pivaloyl-N'-(4-cyano-2-fluoro-5-methoxyphenyl)-hydrazine is used as the starting compound, the course of the reaction of process (g) according to the invention may be represented by the following equation:

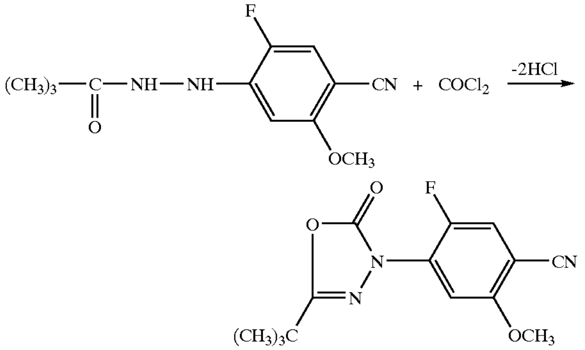

If, for example, 4-(3,4,5-trimethylpyrazol-1-yl)-2-fluorobenzonitrile and t-butylmercaptan are used as the starting substances, the course of the reaction of process (h-α) according to the invention may be represented by the following equation:

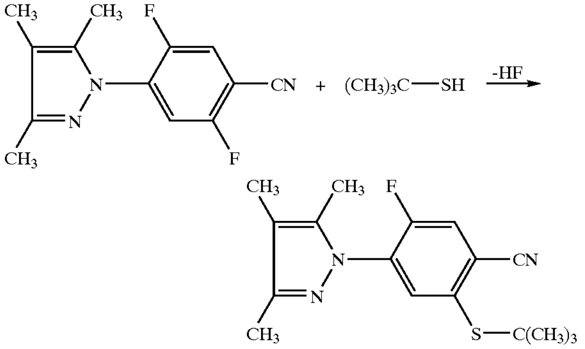

If, for example, 4-(1-pyrazolyl)-2-hydroxybenzonitrile and allyl bromide are used as the starting substances, the course of the reaction of process (h-β) according to the invention may be represented by the following equation:

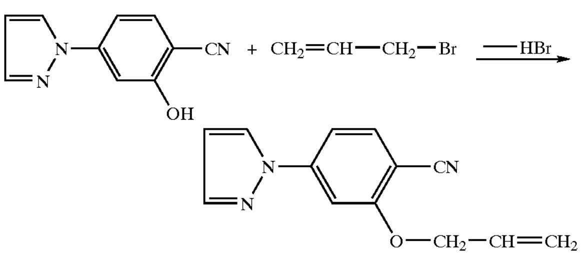

If, for example, 4-(3,5-dimethyl-4-ethoxycarbonylpyrazol-1-yl)-2,5-difluorobenzonitrile is used as the starting compound, the course of the reaction of process (i) according to the invention may be represented by the following equation:

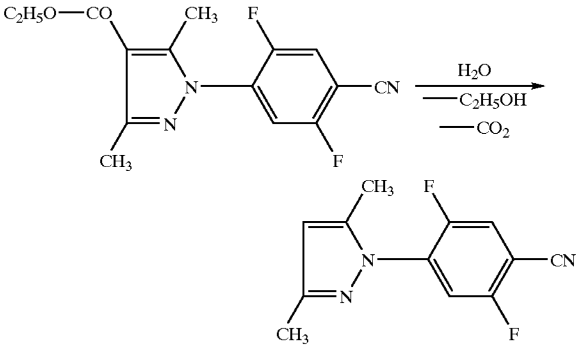

Formula (II) provides a general definition of the 4-cyanophenylhydrazines required as starting substances for carrying out processes (a) and (d) according to the invention. In this formula (II), $R^1$ and $R^2$ preferably represent those radicals which have already been mentioned in connection with the description of the substances of the formula (I) according to the invention as being preferred for these substituents.

The 4-cyanophenylhydrazines of the formula (II) were hitherto unknown and are also a subject of the invention.

They are obtained when 4-fluorobenzonitriles of the formula (XIII)

(XIII)

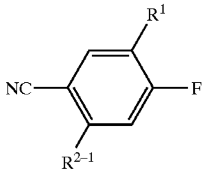

in which $R^{2-1}$ represents halogen and $R^2$ has the abovementioned meaning, are reacted with hydrazine hydrate, if appropriate in the presence of a diluent, such as, for example, ethanol, at temperatures between 20° C. and 130° C., and the resulting 4-cyano-phenylhydrazines of the formula (IIa')

(IIa')

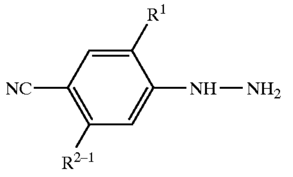

in which $R^1$ and $R^{2-1}$ have the abovementioned meaning, are, if required, reacted in a following 2nd step with alcohols or thiols of the formula (IX)

$R^9$—XH (IX)

in which $R^9$ represents in each case optionally substituted alkyl, alkenyl, alkinyl or cycloalkyl and X represents oxygen or sulphur, if appropriate in the presence of a diluent, such as, for example, acetonitrile, and if appropriate in the presence of a reaction auxiliary, such as, for example, sodium hydride or potassium hydroxide, at temperatures between 0° C. and 80° C.

Alternatively, 4-cyanophenylhydrazines of the formula (IIb')

(IIb')

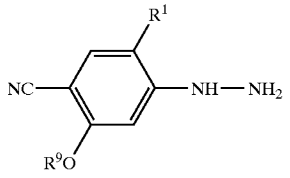

in which $R^1$ has the abovementioned meaning and $R^9$ represents in each case optionally substituted alkyl, alkenyl, alkinyl or cycloalkyl, are also obtained when 4-aminobenzonitriles of the formula (XIV)

(XIV)

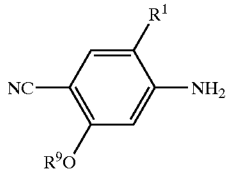

in which $R^1$ and $R^9$ have the abovementioned meaning, are first diazotized in a customary manner, using sodium nitrite in the presence of an acid such as, for example, hydrochloric acid, and the product is subsequently reduced using a reducing agent, such as, for example, tin(II) chloride, likewise in a generally customary manner.

4-Fluorobenzonitriles of the formula (XIII) are known or can be obtained in analogy to known processes (cf., for example, European Patent 191,185; U.S. Pat. No. 3,978,127; DE 2,104,312; J. Heterocycl. Chem. 15, 1373–1378 [1978]; DE 2,711,332; PCT Int. Appl. WO87/7602; Japanese Patent 56/79,660; Zh. org. Khim. 3, 1257–1259 [1967]; J. Chem. Res., Synop. 1984, 382–383; Collect. Czech. Chem. Commun. 49, 992–1000 [1984]; Collect. Czech. Chem. Commun. 42, 2001–2017 [1977]).

4-Aminobenzonitriles of the formula (XIV) are likewise known or can be obtained in analogy to known processes (cf., for example, Japanese Patent 46/3368; European Patent 100,172 or European Patent 224,001).

Formula (III) provides a general definition of the 1,3-diketones furthermore required as starting substances for carrying out process (a) according to the invention. In this formula (III), $R^3$ preferably represents those radicals which have already been mentioned in connection with the description of the substances of the formula (I) according to the invention as being preferred for these substituents.

$R^{4-1}$ preferably represents hydrogen, represents straight-chain or branched alkyl having 1 to 6 carbon atoms or represents straight-chain or branched halogenoalkyl having 1 to 4 carbon atoms and 1 to 9 identical or different halogen atoms, in particular represents hydrogen, methyl, ethyl, n- or i-propyl, n-, i-, s- or t-butyl, represents fluoromethyl, difluoromethyl, trifluoromethyl, chloromethyl, dichloromethyl, trichloromethyl, difluorochloromethyl or dichlorofluoromethyl.

$R^{5-1}$ preferably represents hydrogen, represents straight-chain or branched alkyl having 1 to 6 carbon atoms or represents straight-chain or branched halogenoalkyl having 1 to 4 carbon atoms and 1 to 9 identical or different halogen atoms, in particular represents hydrogen, methyl, ethyl, n- or i-propyl, n-, i-, s- or t-butyl, represents fluoromethyl, difluoromethyl, trifluoromethyl, chloromethyl, dichloromethyl, trichloromethyl, difluorochloromethyl or diehlorofluoromethyl.

1,3-Diketones of the formula (III) and derivatives of these diketones, such as, for example, enol ethers, enol esters, ketals, enol ether ketals, enamines or β-halogenovinyl ketones are generally known compounds of organic chemistry.

Formula (Ij') provides a general definition of the N-aryl-substituted nitrogen-containing heterocycles required as starting substances for carrying out process (b) according to the invention. In this formula (Ij'), $R^1$, $R^2$ and $R^3$ preferably represent those radicals which have already been mentioned in connection with the description of the substances of the formula (I) according to the invention as being preferred for these substituents.

$R^{5-1}$ preferably represents hydrogen, represents straight-chain or branched alkyl having 1 to 6 carbon atoms or represents straight-chain or branched halogenoalkyl having 1 to 4 carbon atoms and 1 to 9 identical or different halogen atoms, in particular represents hydrogen, methyl, ethyl, n- or i-propyl, n-, i-, s- or t-butyl, represents fluoromethyl, difluoromethyl, trifluoromethyl, chloromethyl, dichloromethyl, trichloromethyl, difluorochloromethyl or dichlorofluoromethyl.

The N-aryl-substituted nitrogen-containing heterocycles of the formula (Ij') are compounds according to the invention and can be obtained by means of processes (a), (h-α), (h-β) and (i) according to the invention.

Formula (IV) provides a general definition of the N-arylpyrazolinones required as starting substances for carrying out process (c) according to the invention. In this formula (IV), $R^1$, $R^2$, $R^3$ and $R^4$ preferably represent those radicals which have already been mentioned in connection with the description of the substances of the formula (I) according to the invention as being preferred for these substituents.

The N-arylpyrazolinones of the formula (IV) were hitherto unknown and are likewise a subject of the invention. They: are obtained when β-keto esters of the formula (XV)

(XV)

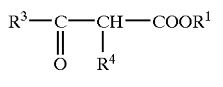

in which $R^{13}$ represents alkyl, in particular represents methyl or ethyl, and $R^3$ and $R^4$ have the abovementioned meaning, are reacted with 4-cyanophenylhydrazines of the formula (II)

(II)

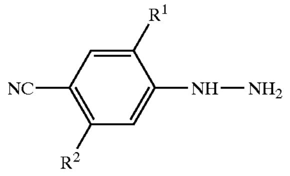

in which $R^1$ and $R^2$ have the abovementioned meaning, if appropriate in the presence of a diluent, such as, for example, ethanol, and, if appropriate, in the presence of a reaction auxiliary, such as, for example, sulphuric acid, at temperatures between 20° C. and 120° C.

β-Keto esters of the formula (XV) are generally known compounds of organic chemistry.

Formula (V) provides a general definition of the iminocarboxylic acid esters required as starting substances for carrying out process (d) according to the invention. In this formula (V), $R^7$ preferably represents those radicals which have already been mentioned in connection with the description of the substances of the formula (I) according to the invention as being preferred for this substituent.

$R^{10}$ and $R^{11}$ each preferably represent independently of one another straight-chain or branched alkyl having 1 to 4 carbon atoms, in particular represent methyl or ethyl.

The iminocarboxylic acid esters of the formula (V) are known or can be obtained in analogy to known processes (cf., for example. Chem. Ber. 119, 2444–2457 [1986]; Bull. chem. Soc. Jpn. 55, 3943–3944 [1982]; Chem. Lett. 1982, 1015–1016; Chem. Lett. 1978, 1403–1404; J. Amer. chem. Soc. 95, 3957–3963 [1973]; J. org. Chem. 36, 3251–3252 [1971]).

Formula (Id) provides a general definition of the N-aryl-substituted nitrogen-containing heterocycles required as starting substances for carrying out process (e) according to the invention. In this formula (Id'), $R^1$, $R^2$ and $R^7$ preferably represent those radicals which have already been mentioned in connection with the description of the substances of the formula (1) according to the invention as being preferred for these substituents.

The N-aryl-substituted nitrogen-containing heterocycles of the formula (Id) are compounds according to the invention and can be obtained by means of process (d) according to the invention.

Formula (VI) provides a general definition of the alkylating agents furthermore required as starting substances for carrying out process (e) according to the invention. In this formula (VI), $R^{8-1}$ preferably represents in each case straight-chain or branched alkyl having 1 to 6 carbon atoms, alkenyl having 3 to 6 carbon atoms, alkinyl having 3 to 6 carbon atoms, halogenoalkyl having 1 to 4 carbon atoms and 1 to 9 identical or different halogen atoms, halogenoalkenyl having 3 to 6 carbon atoms and 1 to 5 identical' or different halogen atoms or halogenoalkinyl having 3 to 6 carbon atoms and 1 to 5 identical or different halogen atoms.

$R^{8-1}$ in particular represents methyl, ethyl, n- or i-propyl, n-, i-, s- or t-butyl, represents methyl, ethyl or t-butyl, each of which is monosubstituted, disubstituted or trisubstituted by fluorine and/or chlorine, represents allyl, represents n- or i-butenyl, represents chloroallyl, represents dichloroallyl, represents propargyl or represents chloropropargyl.

E1 preferably represents halogen, in particular represents chlorine, bromine or iodine, or represents in each case optionally substituted alkylsulphonyloxy, alkoxysulphonyloxy or arylsulphonyloxy, such as, for example, methanesulphonyloxy, trifluoromethanesulphonyloxy, methoxysulphonyloxy, ethoxysulphonyloxy or p-toluenesulphonyloxy.

The alkylating agents of the formula (VI) are generally known compounds of organic chemistry.

Formula (VII) provides a general definition of the amidrazones required as starting substances for carrying out process (f) according to the invention. In this formula (VII), $R^1$ and $R^2$ preferably represent those radicals which have already been mentioned in connection with the description of the substances of the formula (I) according to the invention as being preferred for these substituents.

Preferably, $R^{7-1}$ and $R^{8-2}$ together represent a double-linked alkanediyl radical having 2 to 6 carbon atoms, in particular represent a 1,3-propanediyl radical, a 1,4-butanediyl radical or a 1,5-pentanediyl radical.

The amidrazones of the formula (VII) were hitherto unknown. They are obtained in analogy to known processes (cf., for example, U.S. Pat. No. 4,080,192 or DE-OS (German Published Specification) 1,957,783), when lactams of the formula (XVI)

(XVI)

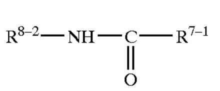

in which $R^{7-1}$ and $R^{8-2}$ have the abovementioned meaning, are initially reacted in a 1st step with a halogenating agent, such as, for example, phosphorus oxychloride, thionyl chloride or phosgene, if appropriate in the presence of a diluent, such as, for example, ethanol or dioxane, and, if appropriate, in the presence of a reaction auxiliary, such as, for example, triethylamine or pyridine, at temperatures between 0° C. and 50° C., and the resulting imide chlorides of the formula (XVII)

(XVII)

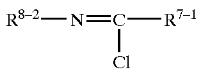

in which $R^{7-1}$ and $R^{8-2}$ have the abovementioned meaning, are subsequently reacted with 4-cyanophenylhydrazines of the formula (II)

(II)

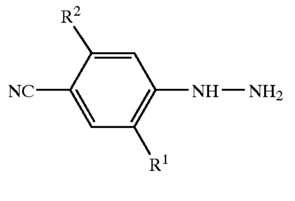

in which $R^1$ and $R^2$ have the abovementioned meaning, if appropriate in the presence of a diluent, such as, for example, ethanol, and, if appropriate, in the presence of a reaction auxiliary, such as, for example, triethylamine or pyridine, at temperatures between 0° C. and 80° C.

Lactams of the formula (XVI) are generally known compounds of organic chemistry.

Formula (VIII) provides a general definition of the phenyl hydrazides required as starting substances for carrying out process (g). In this formula (VIII), $R^1$, $R^2$ and $R^6$ preferably represent those radicals which have already been mentioned in connection with the description of the substances of the formula (I) according to the invention as being preferred for these substituents.

The phenyl hydrazides of the formula (VIII) were hitherto unknown.

They are obtained when 4-cyanophenylhydrazines of the formula (II)

(II)

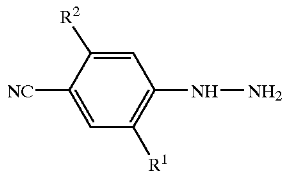

in which $R^1$ and $R^2$ have the abovementioned meaning, are reacted with acylating agents of the formula (XVIII)

(XVIII)

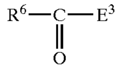

in which $R^6$ has the abovementioned meaning and $E^3$ represents an electron-withdrawing leaving group, preferably represents halogen or represents a radical

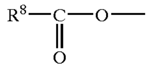

where $R^6$ has the abovementioned meaning and in particular represents chlorine, if appropriate in the presence of a diluent, such as, for example, dichloromethane, and, if appropriate, in the presence of a reaction auxiliary, such as, for example, triethylamine, at temperatures between −20° C. and +60° C.

Acylating agents of the formula (XVIII) are generally known compounds of organic chemistry.

Formula (Ik') provides a general definition of the N-aryl-substituted nitrogen-containing heterocycles required as starting substances for carrying out process (h-α) according to the invention. In this formula (Ik'), $R^1$, $R^3$, $R^4$ and $R^5$ preferably represent those radicals which have already been mentioned in connection with the description of the substances of the formula (I) according to the invention as being preferred for these substituents.

$R^2$ preferably represents fluorine, chlorine or bromine, in particular represents fluorine.

The N-aryl-substituted nitrogen-containing heterocycles of the formula (Ik') are compounds according to the invention and can be obtained by means of processes (a), (b), (c) or (i) according to the invention.

Formula (IX)) represents a general definition of the alcohols or thiols furthermore required as starting substances for carrying out process (h-α) according to the invention. In this formula (IX), $R^9$ and X preferably represent those radicals which have already been mentioned in connection with the description of the substances of the formula (I) according to the invention as being preferred for these substituents.

The alcohols and thiols of the formula (IX) are generally known compounds of organic chemistry.

Formula (X) provides a general definition of the (thio) phenol derivatives required as starting substances for carrying out process (h-β) according to the invention. In this formula (X), $R^1$, $R^3$, $R^4$, $R^5$ and X preferably represent those radicals which have already been mentioned in connection with the description of the substances of the formula (I) according to the invention as being preferred for these substituents.

The (thio)phenol derivatives of the formula (X) were hitherto unknown and are likewise a subject of the invention.

They are obtained either when N-aryl-substituted nitrogen-containing heterocycles of the formula (Ik')

(Ik')

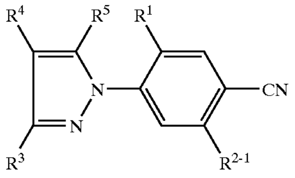

in which $R^{2-1}$ represents halogen, in particular represents fluorine, and $R^1$, $R^3$, $R^4$ and $R^5$ have the abovementioned meaning, are reacted with sodium hydrogen sulfide, if appropriate in the presence of a diluent, such as, for example, methanol, ethanol or their mixtures with water, and, if appropriate, in the presence of a reaction auxiliary, such as, for example, sodium hydroxide or potassium carbonate, if appropriate in the presence of a nitrogen or argon protective gas atmosphere, at temperatures between 0° C. and 50° C., or when N-aryl-substituted nitrogen-containing heterocycles of the formula (Il')

(Il')

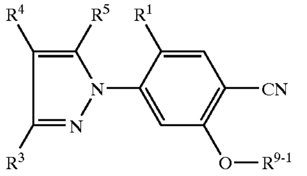

in which $R^1$, $R^3$, $R^4$ and $R^5$ have the abovementioned meaning and $R^{9-1}$ represents allyl or represents benzyl, are reacted with customary reducing agents, such as, for example, molecular hydrogen in the presence of a customary hydrogenation catalyst, such as trimethylsilyl iodide or such as tris-triphenylphosphim-rhodium chloride, if appropriate in the presence of a diluent, such as, for example, ethanol or dichloromethane, and, if appropriate, in the presence of a reaction auxiliary, such as, for example, diazabicyclooctane (DABCO), at temperatures between 20° C. and 120° C.

N-Aryl-substituted nitrogen-containing heterocycles of the formula (Ik') are compounds according to the invention and can be obtained by means of processes (a), (b), (c) or (i) according to the invention.

N-Aryl-substituted nitrogen-containing heterocycles of the formula (Il') are likewise compounds according to the invention and can be obtained by means of processes (a), (b), (c) and (i) according to the invention.

Formula (XI) provides a general definition of the alkylating agents furthermore required as starting substances for carrying out process (h-β) according to the invention. In this formula (XI), $R^9$ preferably represents those radicals which have already been mentioned in connection with the description of the substances of the formula (I) according to the invention as being preferred for this substituent.

$E^2$ preferably represents halogen, in particular represents chlorine, bromine or iodine, or represents in each case optionally substituted alkylsulphonyloxy, alkoxysulphonyloxy or arylsulphonyloxy, such as, for example, methanesulphonyloxy, trifluoromethanesulphonyloxy, methoxysulphonyloxy, ethoxysulphonyloxy or p-toluenesulphonyloxy.

The alkylating agents of the formula (XI) are generally known compounds of organic chemistry.

Formula (XII) provides a general definition of the N-arylpyrazolyl-4-carboxylic acid esters required as starting substances for carrying out process (i) according to the invention. In this formula (XII), $R^1$, $R^2$, $R^3$ and $R^5$ preferably represent those radicals which have already been mentioned in connection with the description of the substances of the formula (I) according to the invention as being preferred for these substituents.

$R^{15}$ preferably represents straight-chain or branched alkyl having 1 to 4 carbon atoms, in particular represents methyl or ethyl.

The N-arylpyrazolyl-4-carboxylic acid esters of the formula (XII) were hitherto unknown.

They are obtained when acrylic ester derivatives of the formula (XIX)

(XIX)

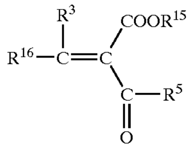

in which $R^3$, $R^5$ and $R^{15}$ have the abovementioned meaning and $R^{16}$ represents an alkoxy radical or represents a dialkylamino radical having in each case 1 to 4 carbon atoms in the individual straight-chain or branched alkyl moieties, in particular having in each case 1 to 2 carbon atoms in the individual alkyl moi ties, are reacted with 4-cyanophenylhydrazines or formula (II)

(II)

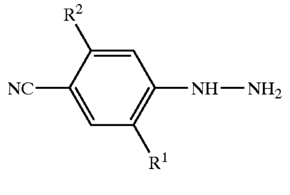

in which $R^1$ and $R^2$ have the abovementioned meaning, if appropriate in the presence of a diluent, such as, for example, ethanol or ethylene glycol monoethyl ether, and, if appropriate, in the presence of a reaction auxiliary, such as, for example, hydrochloric acid or sulphuric acid, at temperatures between 20° C. and 150° C.

Acrylic ester derivatives of the formula (XIX) are known or can be obtained in analogy to known processes (cf., for example, European Patent 257,882; Japanese Patent 62/148,482; PCT Int. Appl. WO 86/1202; European Patent 188,094; U.S. Pat. No. 4,555,517; European Patent 104,432; J. org. Chem. 49, 140–152 [1984]; Austral. J. Chem. 34, 2401–2421 [1981]; BE 888,389; U.S. Pat. No. 4,277,418;

Farmaco. Ed. Sci. 4, 898–906 [1979]; J. chem. Soc. Perkin Trans. 1, 1979; 464–471; J. chem. Soc. Perkin Trans. 1, 1978, 1041–1046).

Suitable diluents for carrying out process (a) according to the invention are inert organic solvents. In particular, these include aliphatic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, nitrites, such as acetonitrile or propionitrile, amides, such as dimethylformamide, dimethylacetamide, N-methylformanilide, N-methylpyrrolidone or hexamethylphosphoric triamide, esters, such as ethyl acetate, sulphoxides, such as dimethyl sulphoxide, alcohols, such as methanol, ethanol or propanol, or acids, such as acetic acid.

If appropriate, process (a) according to the invention is carried out in the presence of a suitable reaction auxiliary. In particular, possible reaction auxiliaries are inorganic mineral acids, such as, for example, hydrochloric acid or sulphuric acid. It is also possible to employ the 4-cyanophenylhydrazines of the formula (II), which are possible as starting substances, in the form of corresponding acid addition salts, such as, for example, hydrochlorides.

When carrying out process (a) according to the invention, the reaction temperatures can be varied within a relatively wide range. In general, the process is carried out at temperatures between −20° C. and 180° C., preferably at temperatures between 20° C. and 120° C.

For carrying out process (a) according to the invention, 0.5 to 10.0 moles, of 1,3-diketone of the formula (III) or, of a corresponding derivative and if appropriate 0.01 to 1.0 mole of reaction auxiliary are generally employed per mole of 4-cyanophenylhydrazine of the formula (II) or of a corresponding acid addition salt. The reaction is carried out and the N-aryl-substituted nitrogen-containing heterocycles of the formula (Ia) are worked up and isolated by generally customary methods (cf. also the Preparation Examples).

When 1,3-diketones of the formula (III) are used in which the substituent $R^{5-1}$ is other than the substituent $R^3$, mixtures of isomers of compounds of the formula (Ial)

(Ia1)

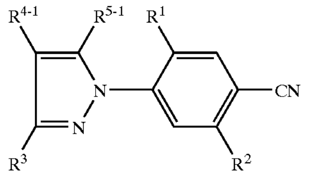

and compounds of the formula (Ia2)

(Ia2)

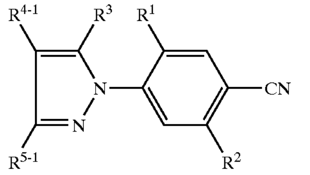

where $R^1$, $R^2$, $R^3$, $R^{4-1}$ and $R^{5-1}$ in each case have the above-mentioned meaning, are usually obtained.

The desired reaction products of the formula (Ia) may be isolated from these mixtures of isomers using customary separation methods (distillation, crystallization, chromatography).

Possible halogenating agents for carrying out process (b) according to the invention are customary halogenating agents. Sulphuryl chloride, elemental chlorine or elemental bromine are particularly preferably used as halogenating agents.

Possible diluents for carrying out process (b) according to the invention are inert organic solvents. In particular, these include aliphatic, alicyclic or aromatic, optionally halogenated hydrocarbons, such as, for example, benzine, benzene, toluene, xylene, chlorobenzene, O-dichlorobenzene, petroleum ether, hexane, cyclohexane, dichloromethane, chloroform or carbon tetrachloride.

When carrying out process (b) according to the invention, the reaction temperatures can be varied within a relatively wide range. In general, the process is carried out at temperatures between 0° C. and 150° C., preferably at temperatures between 35° C. and 70° C.

For carrying out process (b) according to the invention, 1.0 to 5.0 moles, preferably 1.0 to 2.0 moles, of halogenating agent are generally employed per mole of N-aryl-substituted nitrogen-containing heterocycle of the formula (Ij). The reaction is carried out and the reaction products are worked up and isolated by generally customary methods (cf. also the Preparation Examples).

Possible halogenating agents for carrying out process (c) according to the invention are likewise customary halogenating agents. Inorganic acid halides, such as, for example, phosphorus oxychloride, thionyl chloride, phosgene, phosphorus tribromide or diphosgene ($Cl_3C$—O—CO—Cl), are particularly preferably used.

Possible diluents for carrying out process (c) according to the invention are inert organic solvents. In particular, these include aliphatic, alicyclic or aromatic, optionally halogenated hydrocarbons, such as, for example, benzine, benzene, toluene, xylene, chlorobenzene, O-dichlorobenzene, petroleum ether, hexane, cyclohexane, dichloromethane, chloroform or carbon tetrachloride, or basic diluents, such as, for example, pyridine. It is also possible to employ an appropriate excess of halogenating agent simultaneously as the diluent.

Process (c) according to the invention is preferably carried out in the presence of a suitable reaction auxiliary. Possible reaction auxiliaries are, in particular, customary auxiliary nucleophilic substances, such as, for example, triphenylphosphine, dimethylaniline or dimethylformamide.

When carrying out process (c) according to the invention, the reaction temperatures can be varied within a relatively wide range. In general, the process is carried out at temperatures between 0° C. and 200° C., preferably at temperatures between 30° C. and 150° C.

For carrying out process (c) according to the invention, 1.0 to 10.0 moles, preferably 1.0 to 5.0 moles, of halogenating agent and, if appropriate, 0.01 to 1.0 mole, preferably 0.05 to 0.1 mole, of reaction auxiliary are generally employed per mole of N-arylpyrazolinone of the formula (IV). The reaction is carried out and the reaction products are worked up and isolated by generally customary methods (cf. also the Preparation Examples).

Possible diluents for carrying out process (d) according to the invention are inert organic solvents. In particular, these include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, sulphoxides, such as dimethyl sulphoxide, or alcohols, such as methanol, ethanol or propanol.

When carrying out process (d) according to the invention, the reaction temperatures can be varied within a relatively wide range. In general, the process is carried out at temperatures between 0° C. and 180° C., preferably at temperatures between 50° C. and 150° C.

For carrying out process (d) according to the invention, 1.0 to 3.0 moles, preferably 1.0 to 2.0 moles, of iminocarboxylic acid ester of the formula (V) are generally employed per mole of 4-cyanophenylhydrazine of the formula (II). The reaction is carried out and the reaction products are worked up and isolated by generally customary methods (cf. also the Preparation Examples).

Possible diluents for carrying out process (e) according to the invention are inert organic solvents. Aliphatic, cyclic or aromatic, optionally halogenated hydrocarbons, such as, for example, benzine, benzene, toluene, xylene, pentane, hexane, heptane, cyclohexane, petroleum ether, ligroin, methylene chloride, chloroform, carbon tetrachloride, chlorobenzene or dichlorobenzene, ethers, such as diethyl ether, diisopropyl ether, dioxane, tetrahydrofuran or ethylene glycol diethyl ether or ethylene glycol dimethyl ether, ketones, such as acetone, butanone, methyl isopropyl ketone or methyl isobutyl ketone, esters, such as ethyl acetate, nitriles, such as acetonitrile or propionitrile, or amides, such as dimethylformamide, dimethylacetamide, N-methylpyrrolidone or hexamethylphosphoric triamide are preferably used. If alkylating agents of the formula. (VI) are used in liquid form, it is also possible to employ these simultaneously as the diluent, in appropriate excess.

Possible reaction auxiliaries for carrying out process (e) according to the invention are all inorganic and organic bases which can customarily be employed. The hydrides, hydroxides, amides, carbonates or hydrogen carbonates of alkali metals, such as, for example, sodium hydride, sodium amide, sodium hydroxide, sodium carbonate, potassium carbonate or sodium hydrogen carbonate, or else tertiary amines, such as, for example, triethylamine, N,N-dimethylaniline, pyridine, 4-(N,N-dimethylamino)-pyridine, diazabicyclooctane (DABCO), diazabicycloundecene (DBN) or diazabicycloundecene (DBU), are preferably used.

When carrying out preparation process (e), the reaction temperatures can be varied within a relatively wide range. In general, the process is carried out between −20° C. and +150° C., preferably between 0° C. and +100° C.

For carrying out process (e) according to the invention, 1.0 to 15.0 moles, preferably 1.0 to 5.0 moles, of alkylating agent of the formula (VI) and, if appropriate, 1.0 to 3.0 moles, preferably 1.0 to 2.0 moles, of reaction auxiliary are generally employed per mole of N-aryl-substituted nitrogen-containing heterocycle of the formula (Id). The reaction is carried out and the reaction products are worked up and isolated by generally customary methods (cf. also the Preparation Examples).

Possible diluents for carrying out processes (f) and (g) according to the invention are inert organic solvents. In particular, these include aliphatic, alicyclic or aromatic, optionally halogenated hydrocarbons, such as, for example, benzine, benzene, toluene, xylene, chlorobenzene, O-dichlorobenzene, petroleum ether, hexane, cyclohexane, dichloromethane, chloroform or carbon tetrachloride.

Processes (f) and (g) according to the invention are preferably carried out in the presence of a suitable reaction auxiliary. Possible reaction auxiliaries are all customary bases. Tertiary amines, such as triethylamine, N,N-dimethylaniline, pyridine, N,N-dimethylaminopyridine, diazabicyclooctane (DABCO), diazabicyclononene (DBN) or diazabicycloundecene (DBU) are particularly preferably used.

When carrying out processes (f) and (g) according to the invention, the reaction temperatures can be varied within a relatively wide range. In general, the process is carried out at temperatures between −20° C. and 180° C., preferably at temperatures between 0° C. and 150° C.

For carrying out process (f) according to the invention, 1.0 to 5.0 moles, preferably 1.0 to 1.5 moles, of phosgene and, if appropriate, 1.0 to 5.0 moles, preferably 1.0 to 3.0 moles, of reaction auxiliary are generally employed per mole of amidrazone of the formula (VII). The reaction is carried out and the reaction products are worked up and isolated by generally customary methods. For carrying out process (g) according to the invention, 1.0 to 5.0 moles, preferably 1.0 to 1.5 moles, of phosgene and, if appropriate, 1.0 to 5.0 moles, preferably 1.0 to 3.0 moles, of reaction auxiliary are generally employed per mole of phenyl hydrazide of the formula (VIII). The reaction is carried out and the reaction products are worked up and isolated by generally customary methods (cf. also the Preparation Examples).

Possible diluents for carrying out process (h-α) according to the invention are inert organic solvents. In particular, these include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide. It is also possible for the alcohols or thiols of the formula (IX), which are possible as reactants, to be employed simultaneously as the diluent, in appropriate excess.

Process (h-α) according to the invention is preferably carried out in the presence of a suitable reaction auxiliary. Possible reaction auxiliaries are all inorganic and organic bases which can customarily be employed. The hydrides, hydroxides, amides, alkoxides or carbonates of alkali metals, such as, for example, sodium hydride, sodium amide, sodium hydroxide, potassium hydroxide, sodium methoxide, sodium ethoxide, potassium t-butoxide or potassium carbonate, or else tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU) are preferably employed.

When carrying out process (h-α) according to the invention, the reaction temperatures can be varied within a relatively wide range. In general, the process is carried out at temperatures between 0° C. and 150° C., preferably at temperatures between 20° C. and 120° C.

For carrying out process (h-α) according to the invention, 1.0 to 3.0 moles, preferably 1.0 to 1.5 moles, of alcohol or thiol of the formula (IX) and 1.0 to 3.0 moles, preferably 1.0 to 2.0 moles, of reaction auxiliary are generally employed per mole of N-aryl-substituted nitrogen-containing heterocycle of the formula (Ik). The reaction is carried out and the reaction products are worked up and isolated by generally customary methods (cf. also the Preparation Examples).

Possible diluents for carrying out process (h-β) according to the invention are inert organic solvents. Aliphatic, alicyclic or aromatic, optionally halogenated hydrocarbons, such as, for example, benzine, benzene, toluene, xylene, pentane, hexane, heptane, cyclohexane, petroleum ether, ligroin, methylene chloride, chloroform, carbon tetrachloride, chlorobenzene or dichlorobenzene, ethers, such as diethyl ether, diisopropyl ether, dioxane, tetrahydrofuran or ethylene glycol diethyl ether or ethylene glycol dimethyl ether, ketones, such as acetone, butanone, methyl isopropyl ketone or methyl isobutyl ketone, esters, such as ethyl acetate, acids, such as acetic acid, nitrites, such as acetonitrile or propionitrile, amides, such as dimethylformamide, dimethylacetamide, N-methylpyrrolidone or hexamethylphosphoric triamide, are preferably used. If alkylating agents of the formulae (VI), (VII) or (XI) are used in the liquid form, it is also possible for these to be employed simultaneously as diluents, in appropriate excess.

Possible reaction auxiliaries for carrying out process (h-β) according to the invention are all inorganic and organic bases which can customarily be used. The hydrides, hydroxides, amides, carbonates or hydrogen carbonates of alkali metals, such as, for example, sodium hydride, sodium amide, sodium hydroxide, sodium carbonate or sodium hydrogen carbonate, or tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU) are preferably used.

When carrying out process (h-β) according to the invention, the reaction temperatures can be varied within a relatively wide range. In general, the process is carried out between −20° C. and +150° C., preferably between 0° C. and +100° C.

For carrying out process (h-β) according to the invention, 1.0 to 2.0.0 moles, preferably in each case 1.0 to 15.0 moles, of alkylating or acylating agent of the formula (XI) and, if appropriate, 1.0 to 3.0 moles, preferably 1.0 to 2.0 moles, of reaction auxiliary are generally employed per mole of (thio) phenol derivative of the formula (X). The reaction is carried out and the reaction products of the formula (Ih) are worked up and isolated by customary methods.

Possible diluents for carrying out process (i) according to the invention are inorganic or organic solvents. Polar solvents, in particular alcohols, such as, for example, methanol, ethanol or propanol, or their mixtures with water, are preferably used.

Possible reaction auxiliaries for carrying out process (i) according to the invention are all catalysts which can customarily be used for ester hydrolyses and decarboxylations of this type. Bases, such as, for example, sodium hydroxide, sodium alkoxide or sodium carbonate, or acids, such as, for example, hydrochloric acid, hydrobromic acid or sulphuric acid, are preferably used.

When carrying out process (i) according to the invention, the reaction temperatures can be varied within a relatively wide range. In general, the process is carried out at temperatures between 20° C. and 250° C., preferably at temperatures between 50° C. and 150° C.

For carrying out process (i) according to the invention, 1.0 to 15.0 moles, preferably 1.0 to 2.0 moles, of acid or basic reaction auxiliary are generally employed per mole of 1-arylpyrazolyl-4-carboxylic acid ester of the formula (XII) and the mixture is heated for several hours at the reaction temperature required. The reaction products are worked up and isolated by generally customary methods.

Depending on the reaction temperature and the duration of the reaction, it is also possible to isolate the 1-arylpyrazolyl-4-carboxylic acids, which occur as intermediates, and to decarboxylate them in a separate reaction step.

Likewise 4-methyl-3-trifluoromethyl-1,2,4-triazolin-5-one and 2,4,5-trifluorobenzonitrile are used as starting materials, to make the compounds of formula (Ia) the course of the reaction of process (a") according to the on can be represented by the following equation:

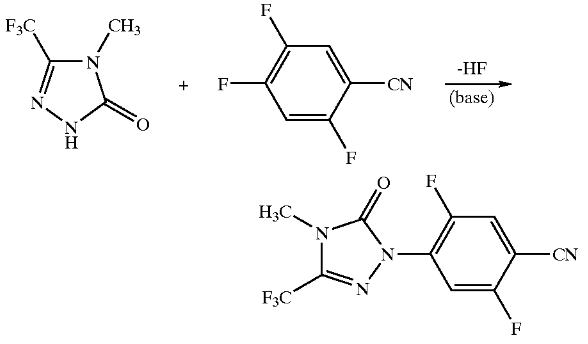

If, for example, 1-(4-cyano-2,5-difluorophenyl)-4-methyl 3-trifluoromethyl-1,2,4-triazolin-5-one and 3-butin-2-ol are used as starting materials, the course of the reaction of process (b") according to the invention can be represented by the following equation:

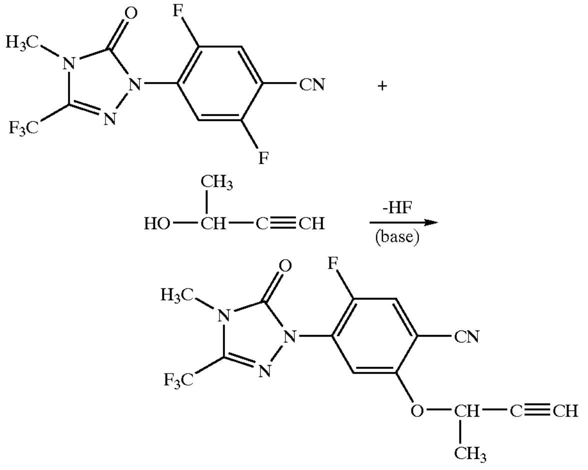

If, for example, 1-(4-cyano-2,5-difluorophenyl)-4-amino-3-trifluoromethyl-1,2,4-triazolin-5-one and sodium nitrite are used as starting materials, the course of the reaction of process (c") according to the invention can be represented by the following equation:

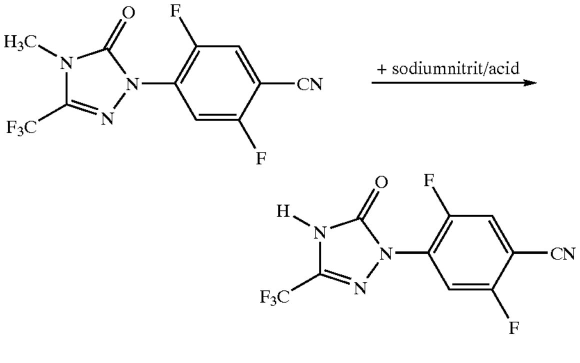

If, for example, 1-(4-cyano-2,5-difluorophenyl)-3-trifluoromethyl-(4H)-1,2,4-triazolin-5-one and chlorodifluoromethane are used as starting materials, the course of the reaction of process (d") according to the invention can be represented by the following equation:

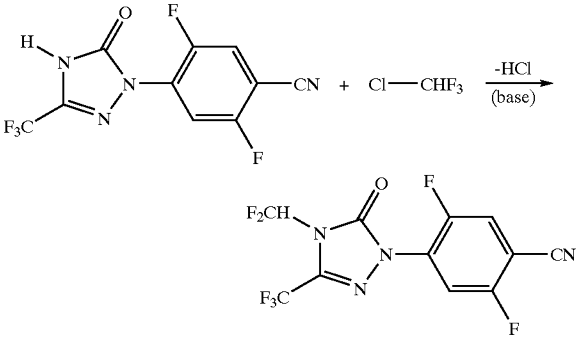

Formula (XX) provides a general definition of the 1H-triazolinones required as starting materials for carrying out process (a") according to the invention. In this formula (XX), $R^7$, $R^8$, and X preferably and particularly preferably represent those radicals which have already been mentioned in connection with the description of the compounds of the formula (a) according to the invention as being preferred and particularly preferred for these substituents.

The 1H-triazolinones of the formula (XX) are known or can be obtained analogously to known processes (compare, for example, EP 399,294; U.S. Pat. No. 4,477,459; DE 2,716,707; U.S. Pat. No. 3,780,052; J. Med. Chem. 14, 335–338 [1971]; DE 2,029,375). The compound 4-amino-3-trifluoromethyl-1H-1,2,4-triazolin-5-one was hitherto unknown and is also a subject of the invention. It is obtained when hydrazine hydrate is reacted first with diphenyl carbonate and subsequently with trifluoroacetic acid at temperatures between −20° C. and +200° C. (compare in this context also the preparation examples).

Formula (XXI) provides a general definition of the halogenobenzene derivatives furthermore required as starting materials for carrying out process (a") according to the invention. In this formula (XXI), $R^1$, $R^{12}$, and $R^2$ preferably represent those radicals which have already been mentioned in connection with the description of the compounds of the formula (Ia) according to the invention as being preferred and particularly preferred for these substituents. Hal preferably represents fluorine, chlorine or bromine, in particular fluorine or chlorine.

The halogenobenzene derivatives of the formula (XXI) have been disclosed or can be obtained in analogy to known processes (compare, for example, EP 191,181; EP 441,004; EP 431,373). The compound 5-chloro-2,4-difluorobenzonitrile was hitherto unknown and is also a subject of the invention. It is obtained when the known compound 2,4,5-trichlorobenzonitrile (compare, for example, EP 441,004) is reacted with potassium fluoride, if appropriate in the presence of a diluent such as, for example, tetramethylene sulphone, at temperatures between 100° C. and 200° C. (compare in this context also the Preparation Examples).

Formula (Ia") provides a general definition of the substituted triazolinones required as educts for carrying out process (b") according to the invention. In this formula (Ia"), $R^1$, $R^7$, $R^8$, $R^{12}$ and X preferably and particularly preferably represent those radicals which have already been mentioned in connection with the description of the substances of the formula (Ia) according to the invention as being preferred and particularly preferred for these substituents. $R^{2\text{-}11"}$ preferably represents fluorine, chlorine or bromine, in particular fluorine or chlorine.

The substituted triazolinones of the formula (Ia") are compounds according to the invention and can be obtained with the aid of processes (a"), (c") and/or (d") according to the invention.

Formula (XXII) provides a general definition of the nucleophiles furthermore required as educts for carrying out process (b") according to the invention. In this formula (XXII), Z preferably represents oxygen or sulphur. $R^{6\text{-}1"}$ preferably and particularly preferably represents those radicals which have already been mentioned in connection with the description of the substances of the formula (I) according to the invention as being preferred and particularly preferred for the substituent $R^6$ with the exception of the hydrogen radical. In the event that Z represents oxygen, $R^{6\text{-}1"}$ furthermore also preferably represents heterocyclyl, with a five- to seven-membered, optionally benzo-fused, saturated or unsaturated heterocycle having 1 to 3 identical or different hetero atoms, in particular nitrogen, oxygen and/or sulphur, preferably being mentioned as heterocyclyl radical.

The nucleophiles of the formula (XXII) are generally known compounds of organic chemistry.

Formula (Ib") provides a general definition of the substituted triazolinones required as educts for carrying out process (c") according to the invention. In this formula (Ib"), $R^1$, $R^2$, $R^7$, $R^{12}$, and X preferably and particularly preferably represent those radicals which have already been mentioned in connection with the description of the substances of the formula (Ia) according to the invention as being preferred and particularly preferred for these substituents. $R^{2\text{-}1}$ preferably represents amino.

The substituted triazolinones of the formula (Ib") are compounds according to the invention and can be obtained with the aid of processes (a"), (b") and/or (d") according to the invention.

Formula (Ic") provides a general definition of the substituted triazolinones required as educts for carrying out process (d') according to the invention. In this formula (Ic"), $R^1$, $R^2$, $R^7$, $R^{12}$, and X preferably and particularly preferably represent those radicals which have already been mentioned in connection with the description of the substances of the formula (Ia) according to the invention as being preferred and particularly preferred for these substituents. $R^{8\text{-}2}$ preferably represents hydrogen.

The substituted triazolinones of the formula (Ic") are compounds according to the invention and can be obtained with the aid of processes (a"), (b") and/or (c") according to the invention.

Formula (XXIII) provides a general definition of the alkylating agents futhermore required as educts for carrying out process (d") according to the invention. In this formula (XXIII), $R^{2-3"}$ referably and particularly preferably represents those radicals which have already been mentioned in connection with the description of the substances of the formula (Ia) according to the invention as being preferred and particularly preferred for the substituent $R^8$, with the exception of the radicals hydrogen, amino, cyano and alkylideneimino. E preferably represents a leaving radical which is customary in alkylating agents such as, for example, halogen, in particular chlorine, bromine or iodine, or in each case optionally substituted alkylsulphonyloxy, alkoxysulphonyloxy or arylsulphonyloxy such as, in particular, methanesulphonyloxy, trifluoromethanesulphonyloxy, methoxysulphonyloxy, ethoxysulphonyloxy or p-toluenesulphonyloxy.

The alkylating agents of the formula (XXIII) are generally known compounds of organic chemistry.

Suitable diluents for carrying out process (a") according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform br carbon tetrachloride; ethers such as diethyl ether, diisopropyl ether, dioxane, tetrahydrofuran or ethylene glycol dimethyl ether or ethylene glycol diethyl ether; ketones such as acetone, butanone or methyl-isobutylketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide, or esters such as methyl acetate or ethyl acetate.

Process (a") according to the invention is preferably carried out in the presence of a suitable reaction auxiliary. Possible reaction auxiliaries are all customary inorganic or organic bases. These preferably include alkaline earth metal hydroxides or alkali metal hydroxides such as sodium hydroxide, calcium hydroxide, potassium hydroxide or else ammonium hydroxide, alkali metal carbonates such as sodium carbonate, potassium carbonate, potassium hydrogencarbonate, sodium hydrogencarbonate or ammonium carbonate, alkali metal acetates or alkaline earth metal acetates such as sodium acetate, potassium acetate, calcium acetate or ammonium acetate, and also tertiary amines such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

When carrying out process (a") according to the invention, the reaction temperatures can be varied within a substantial range. In general, the process is carried out at temperatures between 0° C. and +180° C., preferably at temperatures between +20 C. and +120° C.

Process (a") according to the invention is conventionally carried out under atmospheric pressure. However, it is also possible to carry but the process under elevated or reduced pressure.

To carry out process (a") according to the invention, 1.0 to 3.0 mol, preferably 1.0 to 1.5 mol, of halogenobenzene derivative of the formula (XXI) and, if appropriate, 1.0 to 3.0 mol, preferably 1.0 to 1.5 mol, of base as reaction auxiliary are generally employed per mole of 1H-triazolinone of the formula (XX). The reaction is carried out and the reaction products are worked up and isolated by known methods (compare in this context also the preparation examples).

Possible diluents for carrying out process (b") according to the invention are inert organic solvents. Preferably used solvents are those which have been listed in the description of process (a") according to the invention.

Process (b") according to the invention is preferably carried out in the presence of a suitable reaction auxiliary. Possible reaction auxiliaries are all customary inorganic or organic bases. These include, for example, the hydrides, hydroxides, amides, alcoholates, acetates, carbonates or hydrogencarbonates of alkaline earth metals or alkali metals such as, for example, sodium hydride, sodium amide, sodium methylate, sodium ethylate, potassium tert.-butylate, sodium hydroxide, potassium hydroxide, ammonium hydroxide, sodium acetate, potassium acetate, calcium acetate, ammonium acetate, sodium carbonate, potassium carbonate, potassium hydrogencarbonate, sodium hydrogencarbonate or ammonium carbonate, and also tertiary amines such as trimethylamine, triethylamine, tributylamine, N,N-dimethylaniline, pyridine, N-methylpiperidine, N,N-dimethylaminopyridine, diazabicyclooctane (DABCO), diazabicyclononene (DNB) or diazabicycloundecene (DBU).

When carrying out process (b") according to the invention, the reaction temperatures can be varied within a substantial range. In general, the process is carried out at temperatures between −20° C. and +150° C., preferably at temperatures between 0° C. and +120° C.

Process (b") according to the invention is conventionally carried out under atmospheric pressure. However, it is also possible to carry out the process under elevated or reduced pressure.

To carry out process (b") according to the invention, 1.0 to 3.0 mol, preferably 1.0 to 1.5 mol, of nucleophile of the formula and, if appropriate, 0.1 to 3.0 mol, preferably 1.0 to 1.5 mol, of base as reaction auxiliary are generally employed per mole of substituted triazolinone of the formula (Ia).

The reaction is carried out and the reaction products are worked up and isolated by known methods (compare in this context also the preparation examples).

Process (c") according to the invention is conventionally carried out in the presence of a suitable acid. Possible acids are, in particular, aqueous mineral acids. Dilute hydrochloric acid is particularly preferably used.

Suitable diluents for carrying out process (c") according to the invention are all diluents which are customary for such diazotisation reactions. It is particularly preferred to use a suitable excess of the aqueous mineral acids which have been employed as reagents, such as, for example, hydrochloric acid, simultaneously as the diluent.

When carrying out process (c") according to the invention, the reaction temperatures can be varied within a substantial range. In general, the process is carried out at temperatures between −20° C. and +100° C., preferably at temperatures between −10° C. and +80° C.

Process (c") according to the invention is conventionally carried out under atmospheric pressure. However, it is also possible to carry out the process under elevated or reduced pressure.

To carry out process (c") according to the invention, 1.0 to 3.0 mol, preferably 1.0 to 2.0 mol, of sodium nitrite and 1.0 to 10.0 mol. preferably 1.0 to 5.0 mol, of acid are generally employed per mole of substituted triazolinone of the formula (Ib").

The reaction is carried out and the reaction products are worked up and isolated by known methods (compare in this context also the preparation examples).

Possible diluents for carrying out process (d") according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran or ethylene glycol dimethyl ether or ethylene glycol diethyl ether; ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethyl-phosphoric triamide; esters such as methyl acetate or ethyl acetate, or sulphoxides such as dimethyl sulphoxide.

If appropriate, process (d") according to the invention can also be carried out in a two-phase system such as, for example, water/toluene or water/dichloromethane, if appropriate in the presence of a suitable phase transfer catalyst. Examples of such catalysts which may be mentioned are: tetrabutylammonium iodide, tetrabutylammonium bromide, tetrabutylammonium chloride, tributyl-methyl-phosphonium bromide, trimethyl-$C_{13}/C_{15}$-alkylammonium chloride, trimethyl-$C_{13}/C_{15}$-alkylammonium bromide, dibenzyl-dimethyl-ammoniummethylsulphate, dimethyl-$C_{12}/C_{14}$-alkyl-benzylammonium chloride, dimethyl-$C_{12}/C_{14}$-alkyl-benzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)-ethyl]-amine.

Process (d") according to the invention is preferably carried out in the presence of a suitable reaction auxiliary. Suitable reaction auxiliaries are all customary inorganic or organic bases. These include, for example, the hydrides, hydroxides, amides, alcoholates, acetates, carbonates or hydrogencarbonates of alkaline earth metals or alkali metals such as, for example, sodium hydride, sodium amide, sodium methylate, sodium ethylate, potassium tert.-butylate, sodium hydroxide, potassium hydroxide, ammonium hydroxide, sodium acetate, potassium acetate, calcium acetate, ammonium acetate, sodium carbonate, potassium carbonate, potassium hydrogencarbonate, sodium hydrogencarbonate or ammonium carbonate, and also tertiary amines such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

When carrying out process (d") according to the invention, the reaction temperatures can be varied within a substantial range. In general, the process is carried out at temperatures between −20° C. and +150° C., preferably at temperatures between 0° C. and +120° C.

Process (d") according to the invention is conventionally carried out under atmospheric pressure. However, it is also possible to carry out the process under elevated or reduced pressure.

To carry out process (d") according to the invention, 1.0 to 3.0 mol, preferably 1.0 to 2.0 mol, of alkylating agent of the formula (V) and, if appropriate, 1.0 to 3.0 mol, preferably 1.0 to 2.0 mol, of base as reaction auxiliary are generally employed per mole of substituted triazolinone of the formula (Ic").

The reaction is carried out and the reaction products are worked up and isolated by known methods (compare in this context also the preparation examples).

The end products of the formula (Ia) are purified with the aid of conventional methods, for example by column chromatography or by recrystallisation.

They are characterised with the aid of the melting point or, in the case of compounds which do not crystallise, with the aid of proton nuclear resonance spectroscopy ($^1H$ NMR).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver* and *Centaurea.*

Dicotyledon cultures of the genera: *Gossypium, Glycine, Beta, Daucus, Phaseolus, Pisum, Solanum, Linum, Ipomoea, Vicia, Nicotiana, Lycopersicon, Arachis, Brassica, Lactuca, Cucumis* and *Cucurbita.*

Monocotyledon weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.*

Monocotyledon cultures of the genera: *Oryza, Zea, Triticum, Hordeum, Avena, Secale, Sorghum, Panicum, Saccharum, Ananas, Asparagus* and *Allium.*

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

Here, the active compounds of the formula (I) and (Ia) according to the invention can be employed with particularly good success for combating dicotyledon weeds in monocotyledon and dicotyledon crops, such as, for example, soya or wheat. The intermediates of the formula (X) also possess a good herbicidal activity.

The active compounds according to the invention furthermore engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amount of active compound applied to the plants or their environment and the way in which the compounds are employed. In each case, growth regulators are intended to influence the crop plants in the particular manner desired.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds of formula (IA) are furthermore suitable for combating animal pests, perferably arthropods and nematodes, in particular insects and arachnids, encountered in agriculture, in forestry, in the protection of stored products and of materials, and in the hygiene field. They are active against normally sensitive and resistant species and against all or some stages of development.

The abovementioned pests include:

From the order of the Isopoda, for example, *Oniscus asellus, Armadillidium vulgare* and *Porcellio scaber;* from the order of the Diplopoda, for example, *Blaniulus guttulatus;* from the order of the Chilopoda, for example, *Geophilus carpophagus* and *Scutigera* spec.;

from the order of the Symphyla, for example, *Scutigerella immaculata;* from the order of the Thysanura, for example, *Lepisma saccharina;* from the order of the Collembola, for example, *Onychiurus armatus;* from the order of the Orthoptera, for example, *Blatta orientalis, Periplaneta americana, Leucophaea, maderae, Blattella germanica, Acheta domesticus, Gryllotalpa* spp., *Locusta migratoria migratorioides, Melanoplus differentialis* and *Schistocerca gregaria;* from the order of the Dermaptera, for example, *Forficula auricularia;* from the order of the Isoptera, for example, *Reticulitermes* spp.;

from the order of the Anoplura, for example, *Phylloxera vastatrix, Pemphigus* spp., *Pediculus humanus corporis, Haematopinus* spp. and *Linognathus* spp.;

from the order of the Mallophaga, for example, *Trichodectes* spp. and *Damalinea* spp.;

from the order of the Thysanoptera, for example, *Hercinothrips femoralis* and *Thrips tabaci;* from the order of the Heteroptera, for example, *Eurigaster* spp., *Dysdercus intermedius, Piesma quadrata, Cimex lectularius, Rhodnius prolixus* and *Triatoma* spp.;

from the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the Hymenoptera, for example, *Diprion* spp., *Hoplocampa* spp., *Lasius* spp., *Monomorium pharaonis* and *Vespa* spp.;

from the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the Siphonaptera, for example, *Xenopsylla cheopis* and *Ceratophyllus* spp.;

from the order of the Arachnida, for example, *Scorpio maurus* and *Latrodectus mactans;* from the order of the Acarina, for example, *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.

The active compounds according to the invention are distinguished by a powerful insecticidal and acaricidal activity. They can be used particularly successfully for combating the greenhouse red spider mite (*Tetranychus urticae*). Besides, the active compounds have, in particular, leaf-acting insecticidal properties.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances. When appropriate the active compounds can be used in coating compositions for seed, furthermore in formulations used with burning equipment, such as fumigating catridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral-oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dye-stuffs, and trace nutrients such as salts of iron, manganese, boron, copper, cobalt, molybdenum and zinc.

The formulations in general contain between 0.1 and 95 percent by weight of active compound, preferably between 0.5 and 90%.

When used as herbicides, the active compounds according to the invention, as such or in the form of their formulations, can also be used as mixtures with known herbicides, when used as herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba or picloram; aryloxyalkanoic acids such as, for example, 2,4-D, 2,4-DB, 2,4-DP, fluroxypur, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuronmethyl triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

When used as herbicides, the active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

When used as herbicides, the active compounds according to the invention can be applied either before or after emergence of the plants.

They can also be incorporated into the soil before sowing.

When used as herbicides, the amount of active compound used can vary within a substantial range. It depends essentially on the nature of the desired effect. In general, the amounts used are between 0.01 and 10 kg of active compound per hectare of soil surface, preferably between 0.05 and 5 kg per hectare.

When used as insecticides and acaricides, the active compounds according to the invention can also be present in their commercially available formulations and in the use forms, prepared from these formulations, as a mixture with other active compounds, such as insecticides, attractants, sterilising agents, acaricides, nematicides, fungicides, growth-regulating substances or herbicides. The insecticides include, for example, phosphates, carbamates, carboxylates, chlorinated hydrocarbons, phenylureas and substances produced by microorganisms.

When used as insecticides and acaricides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95 percent by weight of active compound, preferably between 0.0001 and 1 percent by weight.

When used as insecticides and acaricides, the compounds are employed in a customary manner appropriate for the use forms.

When used as growth regulators, the active compounds according to the invention can be present in the formulations also as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the compounds are used as plant growth regulators, the amounts applied can also be varied within a substantial range. In general, 0.01 to 50 kg, preferably 0.05-to 10 kg, of active compound are used per hectare of soil surface.

As far as the time of application is concerned, the application of the growth regulators is carried out in a preferred period, the exact limits of which depend on the climatic and vegetative conditions.

The preparation and the use of the active compounds according to the invention can be seen from the Examples which follow.

PREPARATION EXAMPLES

Example 1

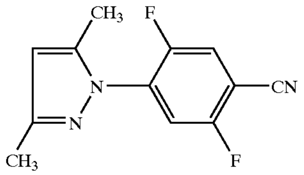

(Process a)

21.1 g (0.125 mol) of 4-cyano-2,5-difluorophenylhydrazine and 12.5 g (0.125 mol) of 2,4-pentanedione are stirred for 2 hours at room temperature in 250 ml of ethanol, and the mixture is subsequently heated at 70° C. for 15 hours and then evaporated in vacuo. The residue is stirred with petroleum ether and filtered off with suction.

28 g (96% of theory) of 4-(3,5-dimethyl-1-pyrazolyl)-2,5-difluorobenzonitrile of melting point 122° C. are obtained.

Example 2

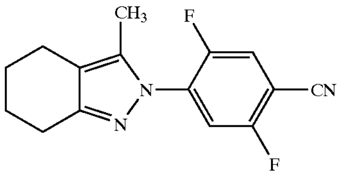

(Process a)

5.2 ml (0.04 mol) of 2-acetylcyclohexanone (cf., for example, J. org. Chem. 34, 1425–1429 [1969]) are added to 6.76 g (0.04 mol) of 4-cyano-2,5-difluorophenylhydrazine in 40 ml of glacial acetic acid, the reaction mixture is stirred at room temperature for 2 hours and then stirred into 250 ml of ice-water, the mixture is extracted with dichloromethane, dried over sodium sulphate and evaporated in vacuo, and the residue is recrystallized from dichloromethane/n-hexane.

3.21 g (23.5% of theory) of 4-(5-methyl-3,4-tetramethylene-1-pyrazolyl)-2,5-difluorobenzonitrile of melting point 120° C. are obtained.

Example 3

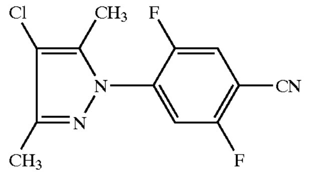

(Process b)

1.68 g (=1 ml; 0.012 mol) of sulphuryl chloride are added to 2.3 g (0.01 mol) of 4-(3,5-dimethyl-1-pyrazolyl)-2,5-difluorobenzonitrile in 50 ml of dichloromethane, the mixture is stirred at 35° C. for 15 hours, allowed to come to room temperature, dried over sodium sulphate and evaporated in vacuo, and the residue is purified by stirring with petroleum ether.

2.0 g (75% of theory) of 4-(3,5-dimethyl-4-chloro-1-pyrazolyl)-2,5-difluorobenzonitrile of melting point 153° C. are obtained.

Example 4

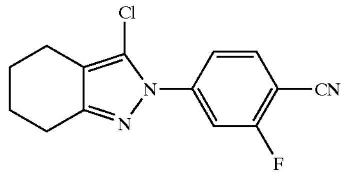

(Process c)

1.78 g (0.0068 mol) of triphenylphospine are added to 15 g (0.068 mol) of 1-(4-cyano-3-fluorophenyl)-3,4-tetramethylene-(1H,4H)-pyrazolin-5-one in 28.8 ml (0.2 mol) of phosphorus oxychloride, and the mixture is heated at reflux temperature for 15 hours. For working up, the cooled reaction mixture is poured into 300 ml of ice-water, the mixture is stirred for 1 hour, and precipitated product is filtered off with suction, washed with water and dried.

15.2 g (81% of theory) of 1-(4-cyano-3-fluorophenyl)-5-chloro-3,4-tetramethylenepyrazole of melting point 84–86° C. are obtained.

Example 5

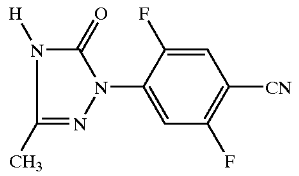

(Process d)

8.45 g (0.05 mol) of 4-cyano-2,5-difluorophenylhydrazine and 12.08 g (0.078 mol) of ethyl N-ethoxycarbonylethaneimidate (cf., for example, Chem. Ber. 119, 2444–2457 [1986]) are heated at reflux temperature for 8 hours in 50 ml of xylene, the mixture is then cooled to room temperature, and solids are filtered off with suction and recrystallized from dichloromethane/petroleum ether.

5.91 g (50% of theory) of 1-(4-cyano-2,5-difluorophenyl)-3-methyl-4,5-dihydro-1,2,4-triazolin-5-one of melting point 174° C. are obtained.

Example 6

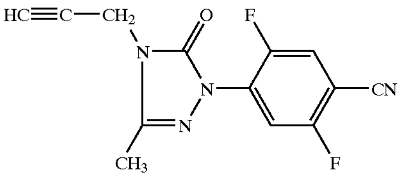

(Process e)

2.36 g (0.01 mol) of 1-(4-cyano-2,5-difluorophenyl)-2-methyl-4,5-dihydro-1,2,4-triazolin-5-one and 1.52 g (0.011 mol) of potassium carbonate in 20 ml of acetonitrile are heated at reflux temperature for 2 hours, the mixture is subsequently cooled to 25° C., an 80 percent strength solution of 1.31 g (0.011 mol) of propargyl bromide in toluene is added, and the mixture is heated at reflux temperature for 4 more hours. For working up, the mixture is evaporated in vacuo, and the residue is taken up in dichloromethane, washed with saturated aqueous sodium hydrogen carbonate solution and water, dried over sodium sulphate, evaporated in vacuo and recrystallized from dichloromethane/petroleum ether.

2.16 g (79% of theory) of 1-(4-cyano-2,5-difluorophenyl-3-methyl-4-propargyl-4,5-dihydro-1,2,4-triazolin-5-one of melting point 127° C. are obtained.

Example 7

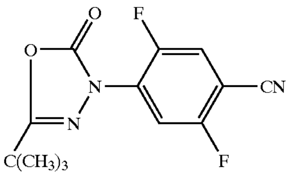

(Process g)

11.9 g (0.12 mol) of phosgene are passed into a solution of 20.24 g (0.08 mol) of 1-(4-cyano-2,5-difluorophenyl)-2-pivaloylhydrazine in 200 ml of toluene, 24.24 g (0.24 mol) of triethylamine in 20 ml of toluene are then added dropwise with stirring, and the mixture is heated at 100° C. for one hour. For working up, excess phosgene is removed, any triethylamine hydrochloride which has precipitated is filtered off, the mixture is concentrated in vacuo, and the residue is recrystallized from dichloromethane/petroleum ether.

14.33 g (64% of theory) of 3-(4-cyano-2,5-difluorophenyl)-5-t-butyl-1,3,4-oxadiazolin-2-one of melting point 137° C. are obtained.

Example 8

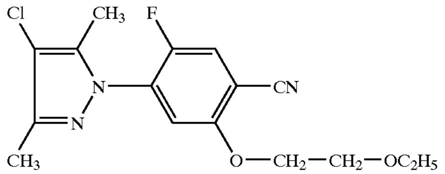

(Process h-α)

0.8 g (0.025 mol) of 80 percent pure sodium hydride (in paraffin oil) is added to 2.7 (0.01 mol) of 4-(3,5-dimethyl-4-chloro-1-pyrazolyl)-2,5-difluorobenzonitrile in 50 ml of ethylene glycol monomethyl ether at 0° C., and the mixture is stirred for 4 hours at 0° C. and subsequently for 15 hours at room temperature. For working up, 200 ml of water are slowly added with cooling, the mixture is stirred at room temperature for one hour, and any solids which have precipitated are filtered off, washed with water and dried.

3.2 g (95% of theory) of 4-(3,5-dimethyl-4-chloro-1-pyrazolyl)-2-(2-ethoxyethoxy)-5-fluorobenzonitrile of melting point 86° C. are obtained.

Example 9

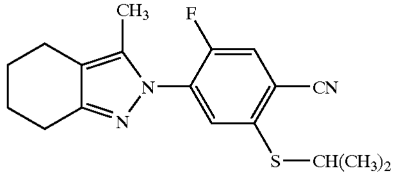

(Process h-α)

1.02 ml (0.011 mol) of isopropylmercaptan and 0.84 g (0.015 mol) of powdered potassium hydroxide are added in succession to 3 g (0.011 mol) of 4-(5-methyl-3,4-tetramethylene-1-pyrazolyl)-2,5-difluorobenzonitrile in 30 ml of absolute acetonitrile. The mixture is subsequently stirred at 40° C. until starting material is no longer detectable in the thin-layer chromatogram, dichloromethane is then added, and the mixture is filtered. The filtrate is evaporated in vacuo, the residue is chromatographed on silica gel (eluent: cyclohexane/ethyl acetate 3:1) and recrystallized from n-hexane.

1.7 g (47% of theory) of 4-(5-methyl-3,4-tetramethylene-1-pyrazolyl)-5-fluoro-2-isopropylthiobenzonitrile of melting point 105° C. are obtained.

Example 10

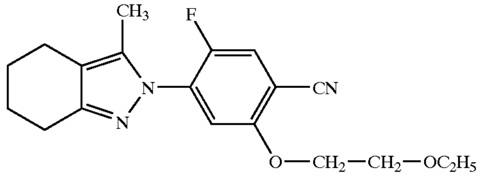

(Process h-α)

1.7 ml (0.017 mol) of 2-ethoxyethanol is added dropwise with stirring at room temperature to 0.51 g (0.017 mol) of sodium hydride in 30 ml of N-methylpyrrolidone, the mixture is stirred at room temperature for 15 more minutes, 4.1 g (0.015 mol) of 4-(5-methyl-3,4-tetramethylene-1-pyrazolyl)-2,5-difluorobenzonitrile are then added, and stirring is continued at 80° C. until starting material is no longer detectable in the thin-layer chromatogram. For working up, the cooled reaction mixture is stirred into 200 ml of ice-water, the mixture is extracted with toluene, and the extract is dried over sodium sulphate, concentrated in vacuo, chromatographed on silica gel (eluent: cyclohexane/ethyl acetate 2:1) and recrystallized from diethyl ether/n-hexane.

3.51 g (68% of theory) of 4-(5-methyl-3,4-tetramethylene-1-pyrazolyl-2-(2-ethoxyethoxy)-5-fluorobenzonitrile of melting point 84° C. are obtained.

The following N-aryl-substituted nitrogen-containing heterocycles of the general formula (I) are obtained in a corresponding manner and in accordance with the general preparation instructions:

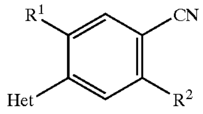

(I)

TABLE 1

| Example No | $R^1$ | $R^2$ | Het | Melting point/° C. |
|---|---|---|---|---|
| 11 | F | $—O—CH_2—CH_2—OC_2H_5$ | 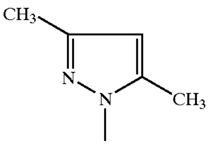 | 103 |
| 12 | H | $—S—CH_2—COOC_2H_5$ | 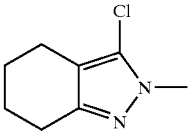 | 112–114 |
| 13 | H | $—O—CH_2—CH_2—OCH_3$ | 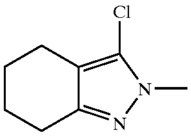 | 69–72 |
| 14 | H | $—O—CH_2—CH_2—OC_2H_5$ | 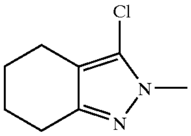 | 62–64 |
| 15 | H | 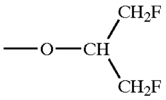 | 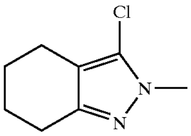 | |
| 16 | F | F | 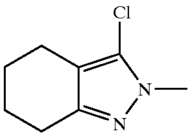 | 112–113 |
| 17 | F | $—S—CH_2—COOC_2H_5$ | 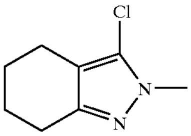 | 106–108 |
| 18 | F | $—O—CH_2—CH_2—OC_2H_5$ | 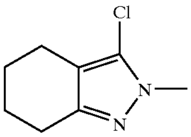 | 107–109 |

TABLE 1-continued
| Example No | $R^1$ | $R^2$ | Het | Melting point/° C. |
|---|---|---|---|---|
| 19 | F | F | 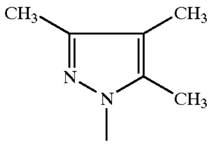 | 146–149 |
| 20 | F | $OCH_3$ | 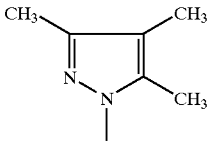 | 179–181 |
| 21 | F | $—S—CH_2—COOC_2H_5$ | 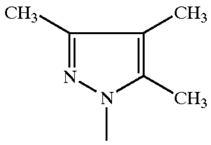 | 136–137 |
| 22 | F | $—O—CH_2—CH_2—OCH_3$ | 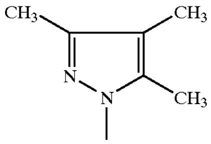 | 127–128 |
| 23 | F | 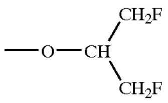 | 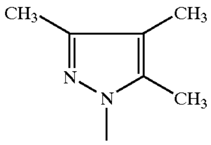 | 94–96 |
| 24 | H | $—O—CH_2—CH{=}CH_2$ | 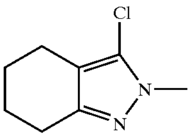 | 123–125 |
| 25 | H | F | 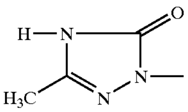 | 246–250 |
| 26 | H | F | 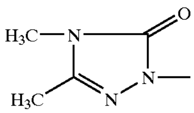 | 181–186 |
| 27 | F | $—O—CH_2—CH_2—O—CH_3$ | 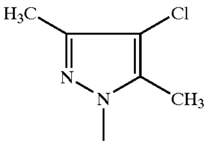 | 94 |
| 28 | F | $—O—CH_2—C{\equiv}CH$ | 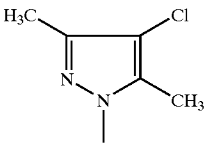 | 136 |

TABLE 1-continued
| Example No | $R^1$ | $R^2$ | Het | Melting point/° C. |
|---|---|---|---|---|
| 29 | F | $—O—CH_2—CH=CH_2$ | 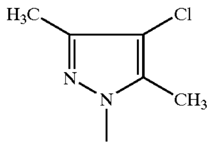 | 118 |
| 30 | F | $—O—CH(CH_3)_2$ | 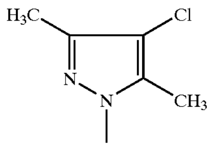 | 88 |
| 31 | F | $—S—CH_2—COOC_2H_5$ | 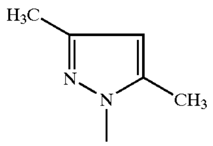 | 110 |
| 32 | F | $—O—CH(CH_2F)_2$ | 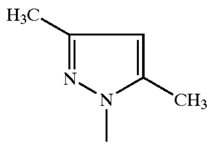 | 110 |
| 33 | F | 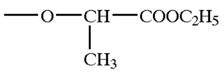 | 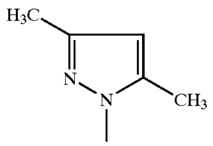 | 86 |
| 34 | F | $—O—CH(CH_2F)_2$ | 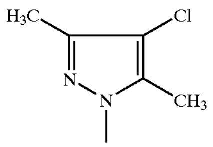 | 116 |
| 35 | F | $—O—CH_2CH_2—O—C_2H_5$ | 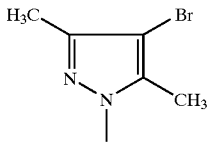 | 97 |
| 36 | F | $—S—CH_2—COOC_2H_5$ | 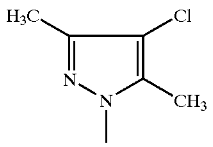 | 94 |
| 37 | F | $—O—CH_2CH_2—O—CH_3$ | 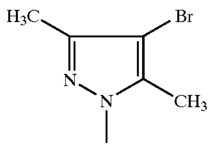 | 104 |
| 38 | F | $—O—CH_2—CH=CH_2$ | 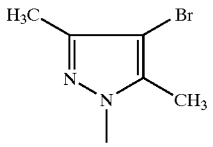 | 126 |

TABLE 1-continued
| Example No | $R^1$ | $R^2$ | Het | Melting point/° C. |
|---|---|---|---|---|
| 39 | F | $—O—CH(CH_2F)_2$ | 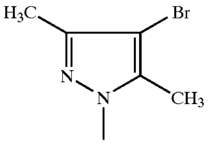 | 122 |
| 40 | F | $—S—CH_2—COOC_2H_5$ | 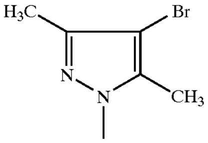 | 107 |
| 41 | F | $—O—CH_2—C{\equiv}CH$ | 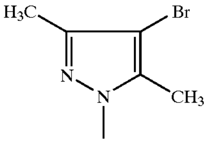 | 104 |
| 42 | F | $—O—CH(CH_3)_2$ | 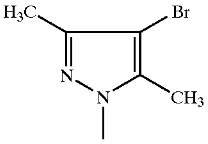 | 108 |
| 43 | F | $—S—CH_2—COOCH_3$ | 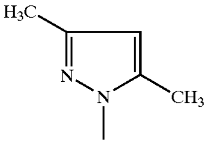 | 103 |
| 44 | F | $—S—CH_2—COOCH_3$ | 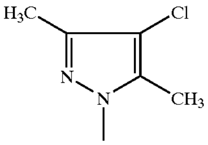 | 108 |
| 45 | F | $—S—CH_2—COOCH(CH_3)_2$ | 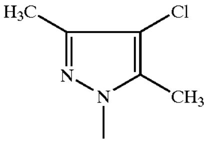 | 135 |
| 46 | F | 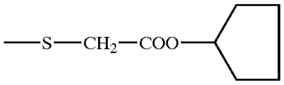 | 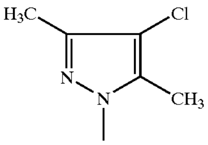 | 120 |
| 47 | F | $—O—CH_2CH_2OCH_3$ | 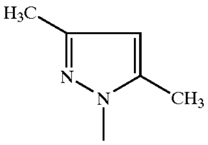 | 112 |

TABLE 1-continued

| Example No | $R^1$ | $R^2$ | Het | Melting point/° C. |
|---|---|---|---|---|
| 48 | F | $—O—CH_2—C{\equiv}CH$ | 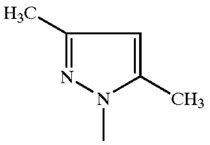 | 141 |
| 49 | F | $—O—CH_2CH{=}CH_2$ | 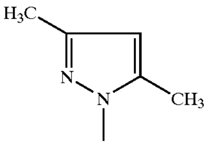 | 120 |
| 50 | F | $—O—C_3H_7$-iso | 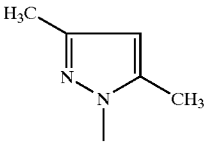 | 99 |

Preparation of the Starting Compounds

Example II-1

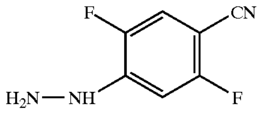

11 g (0.22 mol) of hydrazine hydrate are added to 30 g (0.19 mol) of 2,4,5-trifluorobenzonitrile (cf., for example, EP-A 191,181) in 120 ml of ethanol, the mixture is heated at reflux temperature for 2 hours, cooled to room temperature and concentrated in vacuo, the residue is stirred with 50 ml of water, and any product which has precipitated is filtered off with suction and dried.

24 g (75% of theory) of 4-cyano-2,5-difluorophenylhydrazine of melting point 158° C. are obtained.

Example II-2

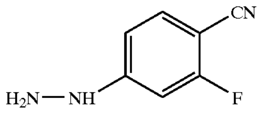

45 g (0.9 mol) of hydrazine hydrate are added dropwise with stirring to 90 g (0.65 mol) of 2,4-difluorobenzonitrile (cf., for example, EP-A 122,693) in 300 ml of methanol, the mixture is heated at reflux temperature for 3 hours and then concentrated in vacuo, and the residue is stirred with 300 ml of water, filtered off with suction and dried.

73 g (74% of theory) of 4-cyano-3-fluorophenylhydrazine of melting point 136° C. are obtained.

Example II-3

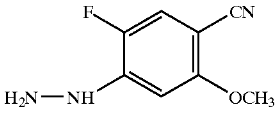

5 g (0.125 mol) of powdered sodium hydroxide are added to 13 g (0.076 mol) of 4-cyano-2,5-difluorophenylhydrazine in 100 ml of methanol, the mixture is then heated at reflux temperature for 6 hours and subsequently evaporated in vacuo, the residue is transferred to 50 ml of water, the mixture is rendered neutral by the dropwise addition of acetic acid, and any solids which have precipitated are filtered off with suction and recrystallized from toluene.

9 g (65% of theory) of 4-cyano-2-fluoro-5-methoxyphenylhydrazine of melting point 155–156° C. are obtained.

Example IV-1

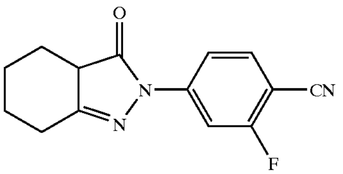

11.3 ml (0.096 mol) of 2-ethoxycarbonylcyclohexanone (cf., for example, J. chem. Soc. D 1970, 326–327) are added to 11 g (0.08 mol) of 4-cyano-3-fluorophenylhydrazine in 80 ml of ethanol, the mixture is heated at reflex temperature for 8 hours and then cooled to 60° C., 0.5 ml of sulphuric acid are added, the mixture is then stirred at 60° C. for 15 hours, 500 ml of water are then added, and any product which has precipitated is filtered off with suction, washed with water and dried.

17.7 g (99% of theory) of 1-(4-cyano-3-fluorophenyl)-3,4-tetramethylene-(1H,4H)-pyrazolin-5-one of melting point 218–220° C. are obtained.

Example VIII-1

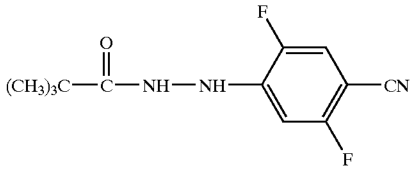

12.05 g (0.1 mol) of pivaloyl chloride are added dropwise at 0° C. with stirring and ice-cooling to 16.9 g (0.1 mol) of 4-cyano-2,5-difluorophenylhydrazine and 12.4 g (0.105 mol) of triethylamine in 50 ml of dichloromethane; when the addition is complete, the mixture is stirred at 20° C. for 10 hours and then evaporated in vacuo, the residue is distributed between dichloromethane and water, the organic phase is dried over sodium sulphate, and the solvent is removed in vacuo.

24.85 g (98% of theory) of 1-(4-cyano-2,5-difluorophenyl)-2-pivaloylhydrazine of melting point 167° C. are obtained.

Example X-1

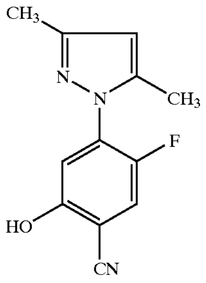

Melting point: 116° C.

Example X-2

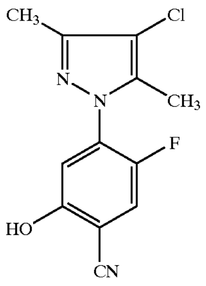

Melting point: >260° C.

USE EXAMPLES

In the following Use Examples, the compound shown below was employed as comparison substance:

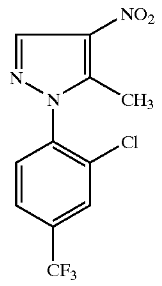

(A)

1-(2-Chloro-4-trifluoromethylphenyl)-5-methyl-4-nitropyrazole (disclosed in EP-A 200,872/Example 19)

Example A

Pre-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100% total destruction

In this test, for example the compounds of Preparation Examples 10, 14, 16, 17, 18 and 23 are clearly superior to the prior art, with respect to both effectiveness and crop plant selectivity.

Example B

Post-emergence Test

Solvents 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)

100%=total destruction

A clearly superior effectiveness as well as crop plant selectivity, compared with the prior art, is shown in this test for example by the compounds of the following Preparation Examples: 9, 10, 12, 14, 16, 17, 18, 23 and 44.

Example C

Defoliation and Desiccation of the Leaves of Cotton

Solvent: 30 parts by weight of dimethylformamide

Emulsifiers 1 part by weight of polyoxyethylene sorbitan monolaurate

To produce a suitable preparation of active compound, 1 part by weight of active compound is mixed with the stated amounts of solvent and emulsifier and the mixture is made up to the desired concentration with water.

Cotton plants are grown in a greenhouse until the 5th true leaf has unfolded completely. In this stage, the plants are sprayed with the preparations of active compound until dripping wet. After 1 week, the shedding of leaves and the desiccation of the leaves are rated, in comparison with the control plants.

The figures of merit have the following meanings:

0 denotes no desiccation of leaves, no shedding of leaves

+denotes slight desiccation of the leaves, slight shedding of leaves

++denotes severe desiccation of the leaves, severe shedding of leaves

+++denotes very severe desiccation of the leaves, very severe shedding of leaves.

A clear superiority compared with the untreated control is shown in this test for example by the compounds of the following Preparation Examples: 13 and 16.

PREPARATION EXAMPLES

Example 51

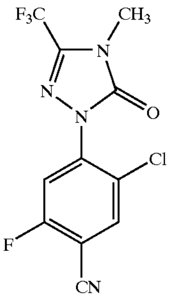

(Process a")

5.3 g (0.038 mol) of potassium carbonate is added at room temperature to 5.3 g (0.032 mol) of 4-methyl-3-trifluoromethyl-1,2,4-triazolin-5-one (compare, for example, U.S. Pat. No. 3,780,052) and 5.5 g (0.032 mol) of 5-chloro-2,4-difluorobenzonitrile in 100 ml of dimethyl sulphoxide, and the mixture is subsequently heated for 36 hours at 100° C. For work-up, the cooled reaction mixture is poured into water, the pH is brought to 2 using dilute hydrochloric acid, and the mixture is extracted several times using dichloromethane. The combined organic phases are dried over sodium sulphate and concentrated in vacuo. The residue is chromatographed over silica gel (eluent:dichloromethane).

1.8 g (18% of theory) of 1-(2-chloro-4-cyano-5-fluorophenyl)-4-methyl-3-trifluoromethyl-1,2,4-triazolin-5-one of melting point 105° C. are obtained.

Example 52

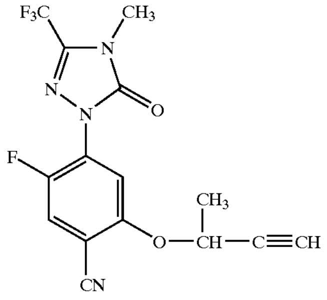

Process (b")

0.6 g (0.014 mol) of sodium hydride (60% in mineral oil) is added with stirring at room temperature to 1.0 g (0.014 mol) of 3-butin-2-ol in 50 ml of acetonitrile, the mixture is stirred for 15 minutes at room temperature, 2.9 g (0.01 mol) of 1-(2,5-difluoro-4-cyano-phenyl)-4-methyl-3-trifluoromethyl-1,2,4-triazolin-5-one are then added, and the mixture is subsequently stirred for a further 2 hours at room temperature. For work-up, the reaction mixture is concentrated in vacuo, the residue is partitioned between dichloromethane and water, and the organic phase is dried over sodium sulphate and freed from solvent in vacuo.

1.8 g (54% of theory) of 1-(2-fluoro-4-cyano-5-but-1-in-3-yl-oxy-phenyl)-4-methyl-3-trifluoromethyl-1,2,4-triazolin-5-one of melting point 41° C. are obtained.

Example 53

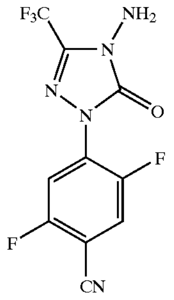

Process (a")

1.7 g (0.012 mol) of potassium carbonate are added at room temperature to 1.7 g (0.01 mol) of 4-amino-3-trifluoromethyl-1,2,4-triazolin-5-one and 1.6 g (0.01 mol) of 2,4,5-trifluorobenzonitrile (compare, for example, EP 191, 181) in 30 ml of dimethyl sulphoxide, and the mixture is subsequently stirred for a further 14 hours at room temperature. For work-up, the reaction mixture is transferred into water, the pH is brought to 2 using dilute hydrochloric acid, and the mixture is extracted several times using dichloromethane. The combined organic phases are dried over sodium sulphate and concentrated in vacuo, and the residue is stirred with water, filtered off with suction and dried.

2.6 g (87% of theory) of 1-(2,5-difluoro-4-cyanophenyl)-4-amino-3-trifluoromethyl-1,2,4-triazolin-5-one of melting point 141° C. are obtained.

Example 54

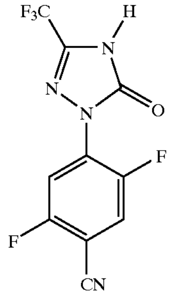

Process (c")

A saturated aqueous solution of 1.4 g (0.02 mol) of sodium nitrite is added at –5° C. to 0° C. in the course of 15 minutes with stirring to 3.0 g (0.01 mol) of 1-(2,5-difluoro-4-cyano-phenyl)-4-amino-3-trifluoromethyl-1,2,4-triazolin-5-one in 40 ml of 10% strength hydrochloric acid, the cold bath is subsequently removed, the mixture is stirred for 1 hour at room temperature and is then again cooled to –5° C. to 0 C. and filtered, and the residue is washed with water and dried.

1.8 g (62% of theory) of 1-(2,5-difluoro-4-cyanophenyl)-3-trifluoromethyl-1,2,4-triazolin-5-one of melting point 51° C. are obtained.

Example 55

Process (d')

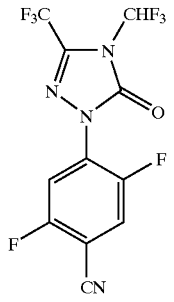

15 g (0.17 mol) of chlorodifluoromethane are passed at 0° C. to 10° C. in the course of 5 hours into a suspension of 2.5 g (0.009 mol) of 1-(2,5-difluoro-4-cyanophenyl)-3-trifluoromethyl-4H-1,2,4-triazolin-5-one, 1.0 g (0.017 mol) of potassium hydroxide and 0.25 g of tetrabutylammonium bromide in 50 ml of tetrahydrofuran, and, during this time, the consumption of base is compensated for after 1, 2 and 3 hours in each case by adding further 1.0 g portions (0.017 mol) of potassium hydroxide. For work-up, the reaction mixture is poured into water and extracted several times using ethyl acetate, the combined organic phases are dried over sodium sulphate, and the solvent is subsequently removed in vacuo. The residue is chromatographed over silica gel (eluent: dichloromethane).

2.2 g (75% of theory) of 1-(2,5-difluoro-4-cyanophenyl)-3-trifluoromethyl-4-difluoromethyl-1,2,4-triazolin-5-one of melting point 68° C. are obtained.

PREPARATION OF THE STARTING COMPOUNDS

Example XX-1

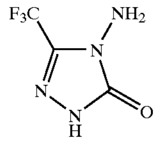

2782 g (13 mol) of diphenyl carbonate are added: in portions in the course of 2 hours with stirring and ice-cooling to 1300 g (26 mol) of hydrazine hydrate in such a way that the temperature of the reaction mixture-does not rise above 30° C., the mixture is subsequently stirred for 2 hours at 80° C. and then cooled again, and 3164 g (26 mol) of trifluoroacetic acid are added, also in portions. The mixture is then stirred for another 2 hours at 80° C., and water is subsequently distilled off until the residue has reached a temperature of 180° C. When cooled, 1100 g (16.2 mol) of aqueous ammonia (25% strength) are added, and the mixture is heated for 3 hours at reflux temperature. For work-up, all volatile components are distilled off under gradually reduced pressure (down to 20 mbar) until the residue has reached a temperature of 180° C., and the residue is recrystallised from 2000 ml of water, filtered off with suction and dried.

702 g (32% of theory) of 3-trifluoromethyl-4-amino-1H-1,2,4-triazolin-5-one of melting point 163° C. are obtained.

Example XXI-1

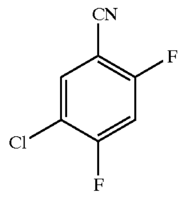

220 g (1.06 mol) of 2,4,5-trichlorobenzonitrile (compare, for example, EP 441,004) are added with stirring at room temperature to 250 g (4.31 mol) of potassium fluoride in 400 ml of distilled tetramethylene sulphone, and the mixture is subsequently stirred for 10 hours at 195° C. to 200° C. For work-up, the mixture is cooled, 500 ml of water are added, and the mixture is subjected to steam distillation. The organic portion is taken up in dichloromethane and the mixture is dried over sodium sulphate, concentrated in vacuo and distilled.

108 g (58% of theory) of 2,4-difluoro-5-chlorobenzonitrile of boiling point 105–107° C. at 30 mbar and of melting point 48–50° C. are obtained.

The following substituted triazolinones of the general formula (Ia) are obtained in a corresponding manner and following the general information on the preparation:

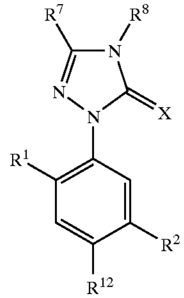
(I)
| Ex. No. | 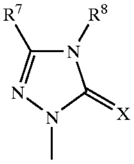 | $R^1$ | $R^{12}$ | $R^2$ | Physical Properties |
|---|---|---|---|---|---|
| 56 | 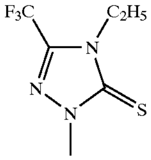 | F | CN | F | $^1$H NMR*): 1.45–1.55; 4.22–4.3; 7.58–7.62 |
| 57 | 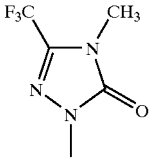 | F | CN | H | m.p. 99° C. |
| 58 | 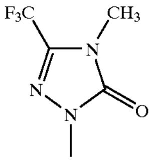 | Cl | $NO_2$ | H | m.p. 110° C. |
| 59 | 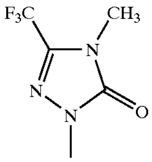 | Cl | CN | H | m.p. 108° C. |
| 60 | 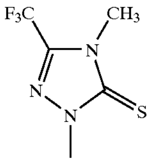 | F | CN | H | m.p. 96° C. |
| 61 | 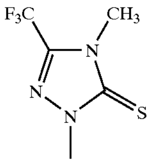 | F | CN | F | m.p. 103° C. |

-continued
(I)
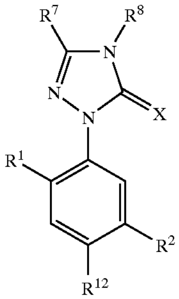
| | | | | | |
|---|---|---|---|---|---|
| 62 | 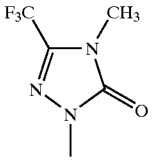 | F | CN | $CH_3$—O— | m.p. 56° C. |
| 63 | 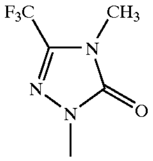 | H | CN | F | m.p. 82° C. |
| 64 | 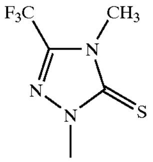 | H | CN | F | m.p. 125° C. |
| 65 | 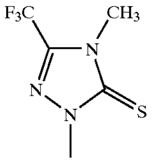 | F | CN | $CH_3$—O— | m.p. 131° C. |
| 66 | 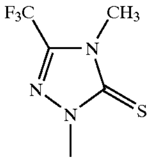 | H | CN | 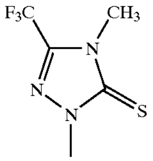 | m.p. 190° C. |
| 67 | 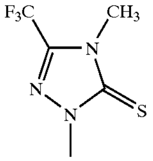 | H | CN | $CH_3$—O— | m.p. 215° C. |
| 68 | 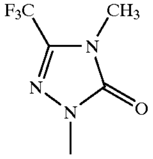 | H | CN | $CH_3$—O— | m.p. 187° C. |

-continued
(I)
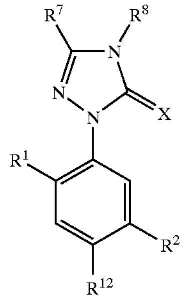
| | | | | | |
|---|---|---|---|---|---|
| 69 | 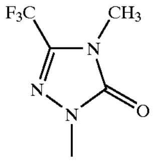 | F | CN | $C_2H_5$—O— | m.p. 126° C. |
| 70 | 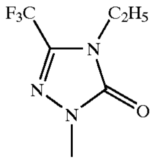 | H | CN | F | m.p. 130° C. |
| 71 | 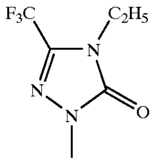 | H | CN | 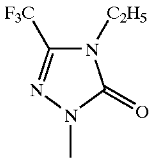 | m.p. 138° C. |
| 72 | 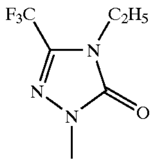 | F | CN | F | m.p. 68° C. |
| 73 | 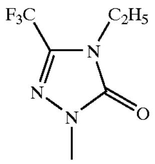 | Cl | CN | H | m.p. 145° C. |
| 74 | 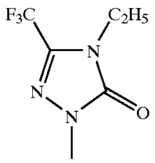 | F | CN | H | m.p. 204° C. |
| 75 | 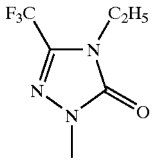 | F | CN | 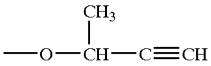 | $^1$H NMR*): 1.75–1.78; 2.6; 3.9–4.0 |

-continued
(I)
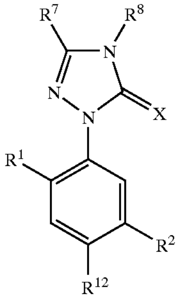
| | | | | | |
|---|---|---|---|---|---|
| 76 | 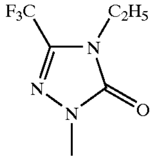 | F | CN | $CH_3$—O— | m.p. 133–135° C. |
| 77 | 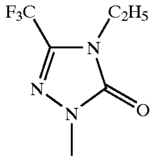 | F | CN | —NH—$CH_3$ | m.p. 143° C. |
| 78 | 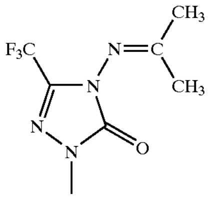 | F | CN | F | m.p. 148° C. |
| 79 | 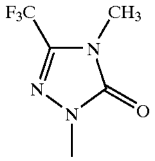 | F | CN | F | m.p. 74° C. |
| 80 | 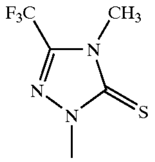 | F | CN | 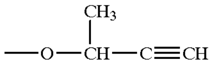 | m.p. 116° C. |
| 81 | 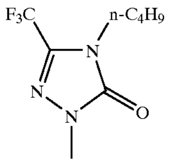 | F | CN | F | $^1$H NMR*): 1.38–1.5; 1.73–1.83; 3.82–3.88 |
| 82 | 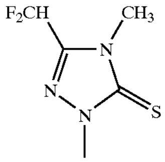 | F | CN | F | m.p. 177° C. |

-continued
(I)
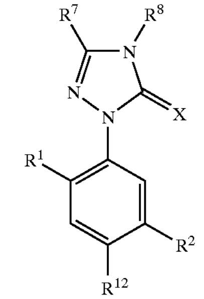
| | | | | | |
|---|---|---|---|---|---|
| 83 | 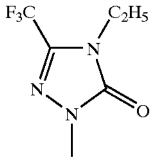 | F | $NO_2$ | 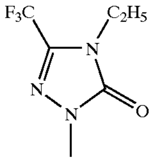 | m.p. 177° C. |
| 84 | 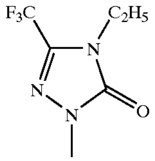 | F | CN | $—(O—CH_2—CH_2)_2—OCH_3$ | $^1$H NMR*): 3.48; 3.55–3.6; 3.9–3.97 |
| 85 | 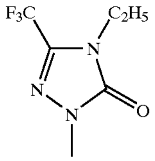 | F | CN | $—O—C_2H_5$ | $^1$H NMR*): 1.4–1.46; 1.5–1.55; 3.9–3.98; 4.14–4.2 |
| 86 | 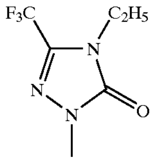 | F | CN | $—O-i-C_3H_7$ | $^1$H NMR*): 3.9–3.98; 4.6–4.68; 7.2–7.23; 7.42–7.45 |
| 87 | 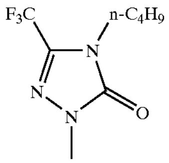 | F | CN | 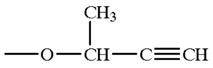 | $^1$H NMR*): 1.72–1.8; 3.8–3.87; 7.45–7.5 |
| 88 | 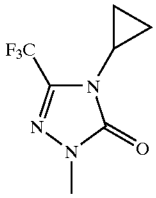 | F | CN | F | m.p. 90° C. |
| 89 | 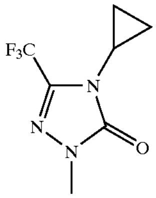 | F | $NO_2$ | F | m.p. 99° C. |

-continued
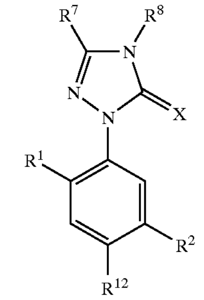
(I)
| | | | | | |
|---|---|---|---|---|---|
| 90 | 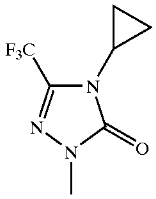 | F | CN | 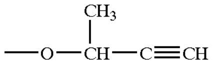 | m.p. 95° C. |
| 91 | 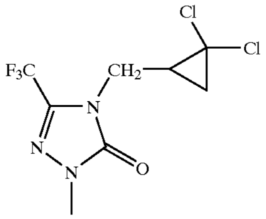 | F | CN | F | $^1$H NMR*): 1.75–1.8; 2.08–2.18; 3.85–3.92; 7.03–7.18 |
| 92 | 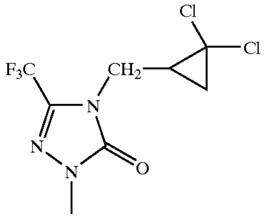 | F | CN | 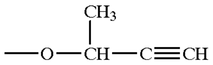 | $^1$H NMR*): 1.75–1.8; 4.33–4.42; 4.9–4.98; 7.45–7.5 |
| 93 | 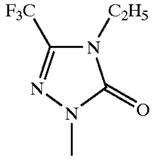 | F | CN | $—O—CH_2—Si(CH_3)_3$ | m.p. 101° C. |
| 94 | 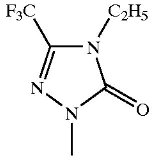 | F | CN | $—O—CH_2—CH{=}CH_2$ | m.p. 76° C. |
| 95 | 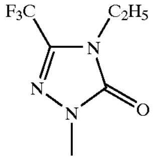 | F | CN | $—O—(CH_2)_2—O\text{-i-}C_3H_7$ | $^1$H NMR*): 1.18–1.22; 1.4–1.45; 3.8–3:85; 4.22–4.25 |

-continued
(I)
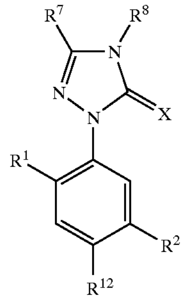
| | | | | | |
|---|---|---|---|---|---|
| 96 | 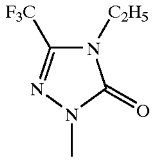 | F | CN | —O—$(CH_2)_2$—$CH(CH_3)$=$CH_2$ | ¹H NMR*): 1.85; 3.9–3.98; 4.15–4.2; 7.2–7.23 |
| 97 | 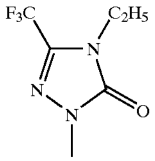 | F | CN | —O—$CH(CH_3)$—$CH_2$—$OCH_3$ | ¹H NMR*): 3.4; 3.9–3.98; 7.1–7.13; 7.38–7.42 |
| 98 | 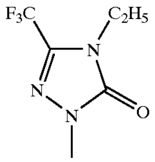 | Cl | CN | F | m.p. 121° C. |
| 99 | 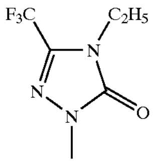 | F | CN | 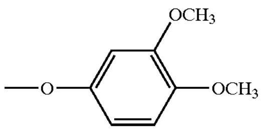 | m.p. 154° C. |
| 100 | 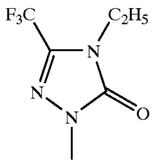 | F | CN | —$N(CH_3)_2$ | ¹H NMR*): 3.17; 3.9–3.98; 7.1–7.13; 7.38–7.42 |
| 101 | 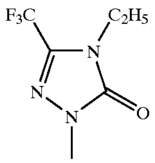 | Cl | CN | 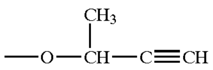 | ¹H NMR*): 1.75–1.8; 3.9–3.98; 4.9–5.0; 7.35; 7.75 |
| 102 | 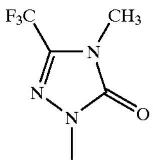 | Cl | CN | —O—$CH_3$ | m.p. 133° C. |

-continued
(I)
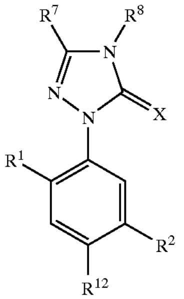
| | | | | | |
|---|---|---|---|---|---|
| 103 | 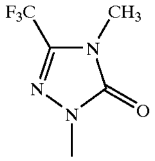 | F | CN | $—O\text{-}n\text{-}C_3H_7$ | m.p. 71° C. |
| 104 | 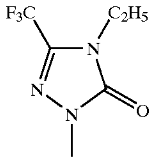 | F | CN | $—O—CH_2—C{\equiv}CH$ | $^1H$ NMR*): 2.53; 3.9–3.98; 4.85; 7.4–7.42 |
| 105 | 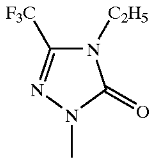 | F | CN | $—O—(CH_2)_2—S—C_2H_5$ | $^1H$ NMR*): 2.67–2.78; 3.9–3.98; 4.22–4.3; 7.23–7.25 |
| 106 | 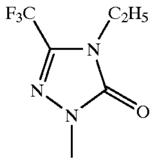 | Cl | CN | Cl | m.p. 97° C. |
| 107 | 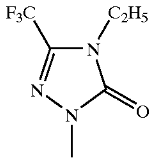 | F | CN | 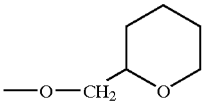 | $^1H$ NMR*): 1.45–1.65; 3.9–3.98; 3.95–4.05; 7.25–7.28 |
| 108 | 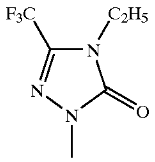 | F | CN | 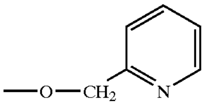 | m.p. 94° C. |
| 109 | 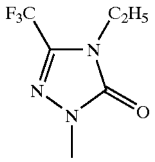 | F | CN | $—S—C_2H_5$ | $^1H$ NMR*): 3.05–3.1; 3.9–3.98; 7.5–7.55; 7.67–7.7 |

-continued
(I)
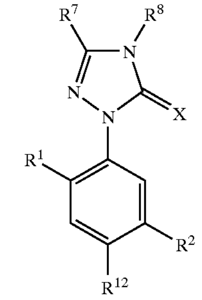
| Ex. No. | | $R^1$ | $R^{12}$ | $R^2$ | Physical Properties |
|---|---|---|---|---|---|
| 110 | 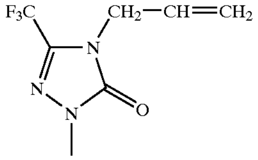 | F | CN | F | $^1$H NMR*): 4.48–4.5; 5.35–5.4; 5.87–5.97; 7.5–7.56 |
| | 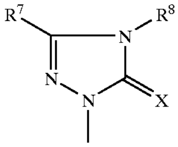 | | | | |
| 111 | 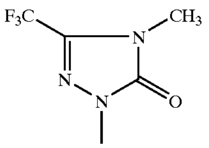 | F | CN | —O-n-$C_3H_7$ | mp. 33° C. |
| 112 | 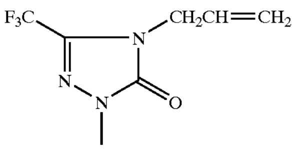 | F | CN | 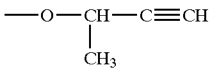 | $^1$H-NMR: 1.75–1.78; 4.45–4.48; 7.45–7.50. |
| 113 | 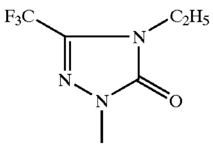 | F | CN | —NH—$CH_2CH{=}CH_2$ | $^1$H-NMR: 1.40–1.45; 3.85–3.90; 6.83–6.86. |
| 114 | 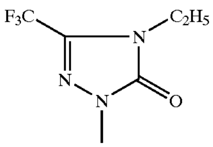 | F | CN | 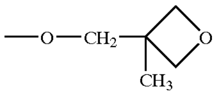 | mp. 101° C. |
| 115 | 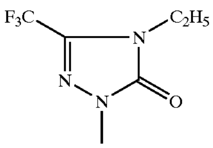 | F | CN | 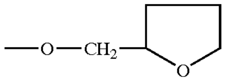 | $^1$H-NMR: 1.40–1.45; 4.08–4.15; 7.45–7.48. |
| 116 | 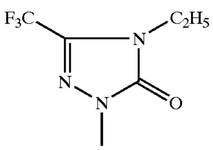 | F | CN | 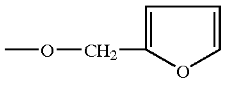 | mp. 91° C. |

-continued
(I)
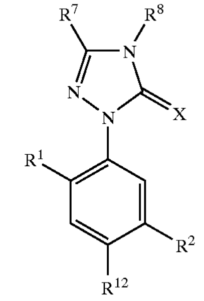
| | | | | | |
|---|---|---|---|---|---|
| 117 | 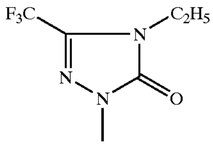 | F | CN | —O—CH($CH_2OC_2H_5$)$_2$ | $^1$H-NMR: 3.52–3.60; 3.90–3.98; 4.55–4.60. |
| 118 | 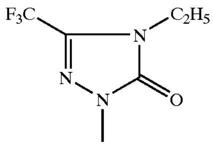 | F | CN | 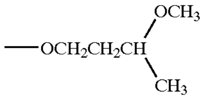 | mp. 81° C. |
| 119 | 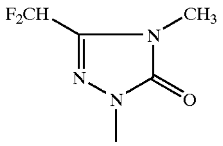 | F | CN | 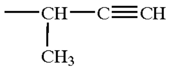 | $^1$H-NMR: 2.60; 4.90–4.98; 7.45–7.50. |
| 120 | 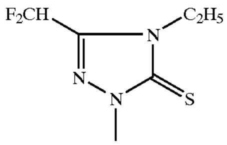 | F | CN | F | mp. 161° C. |
| 121 | 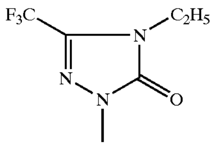 | F | CN | 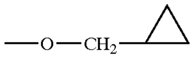 | mp. 96° C. |
| 122 | 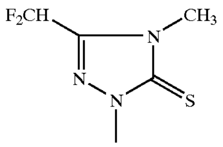 | F | CN | 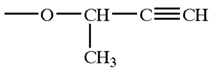 | mp. 176° C. |
| 123 | 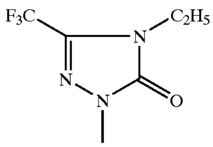 | F | CN | —O—($CH_2CH_2O$)$_5$$CH_3$ | $^1$H-NMR: 3.52–3.56; 3.60–3.70; 4.75–4.78. |
| 124 | 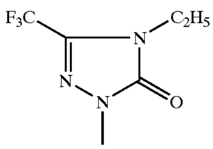 | F | CN | —O—($CH_2CH_2O$)$_2$$CH_2CH{=}CH_2$ | $^1$H-NMR: 3.60–3.65; 3.88–3.96; 5.85–6.00. |

-continued
(I)
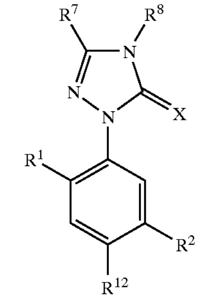
| | | | | | |
|---|---|---|---|---|---|
| 125 | 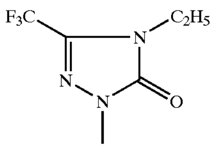 | F | CN | —O—$CH_2CH{=}CHCH_3$ | mp. 117° C. |
| 126 | 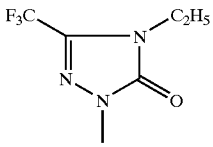 | F | CN | 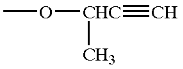 | mp. 47° C. |
| 127 | 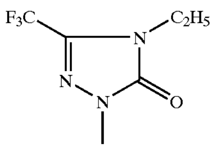 | F | CN | 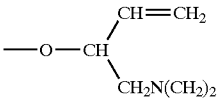 | $^1$H-NMR: 2.37; 3.90–3.98; 5.82–5.95. |
| 128 | 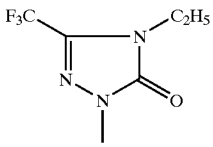 | F | CN | 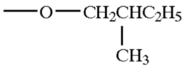 | mp. 74° C. |
| 129 | 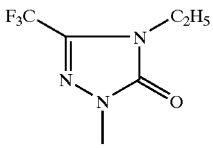 | F | CN | —O—$CH_2CH(CH_3)_2$ | mp. 87° C. |
| 130 | 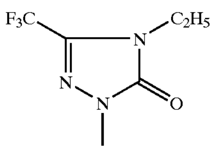 | F | CN | 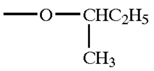 | $^1$H-NMR: 3.90–3.98; 4.38–4.45; 7.43–7.46. |
| 131 | 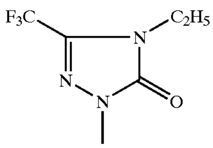 | F | CN | —O—$CH_2CH_2CH(CH_3)_2$ | mp. 75° C. |
| 132 | 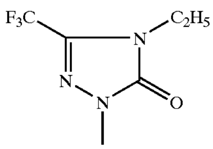 | F | CN | —O—$CH_2C(CH_3)_3$ | mp. 117° C. |

-continued
(I)
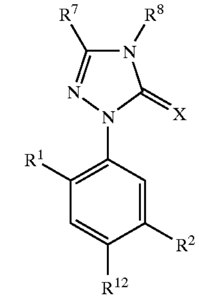
| | | | | | |
|---|---|---|---|---|---|
| 133 | 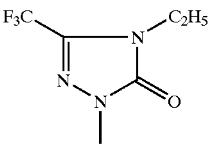 | F | CN | 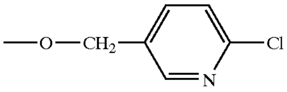 | mp. 141° C. |
| 134 | 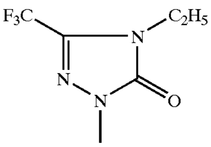 | F | CN | 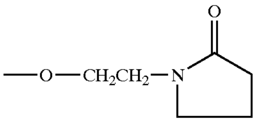 | mp. 143° C. |
| 135 | 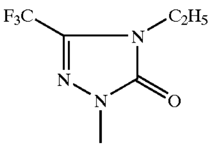 | F | CN | 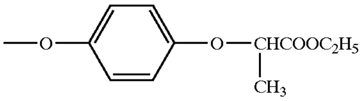 | $^1$H-NMR: 3.85–3.92; 4.16–4.26; 4.70–4.76. |
| 136 | 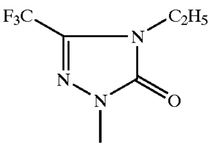 | F | CN | 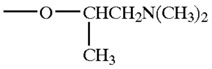 | $^1$H-NMR: 2.32; 3.90–3.98; 4.53–4.60. |
| 137 | 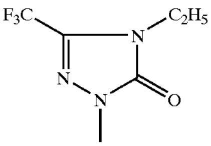 | F | CN | $—OCH_2CH_2OCH_2CH_2N(CH_3)_2$ | mp. 65° C. |
| 138 | 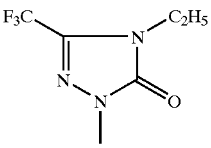 | F | CN | 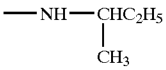 | mp. 91° C. |
| 139 | 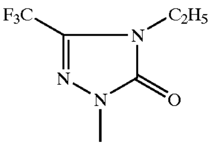 | F | CN | $—NH—CH(CH_3)_2$ | mp. 100° C. |
| 140 | 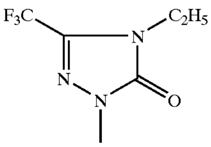 | F | CN | $—NH—C_6H_{13}n$ | mp. 86° C. |

-continued
(I)
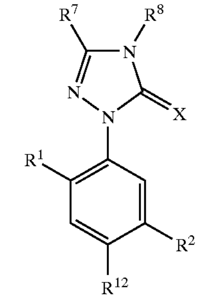
| | | | | | |
|---|---|---|---|---|---|
| 141 | 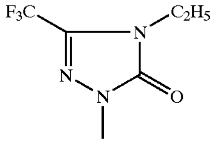 | F | CN | 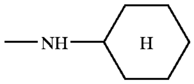 | mp. 126° C. |
| 142 | 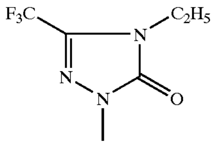 | F | $NO_2$ | F | mp. 81° C. |
| 143 | 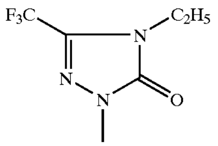 | F | CN | $—NHCH_2CH_2OCH_3$ | mp. 57° C. |
| 144 | 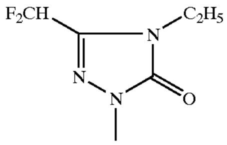 | F | CN | F | mp. 117° C. |
| 145 | 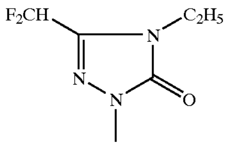 | F | CN | 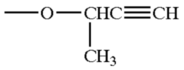 | mp. 96° C. |
| 146 | 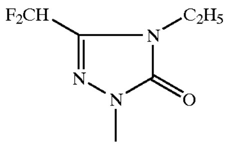 | F | CN | $—O—CH_2C≡CH$ | $^1$H-NMR: 2.62–2.64; 3.95–4.02; 4.85. |
| 147 | 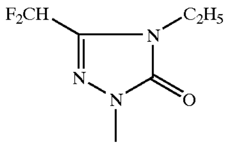 | F | CN | 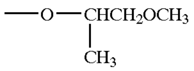 | mp. 78° C. |
| 148 | 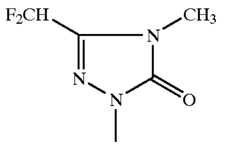 | F | CN | 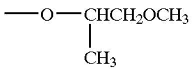 | $^1$H-NMR: 1.28–1.30; 3.40; 3.50; 4.55–4.65. |

-continued
(I)
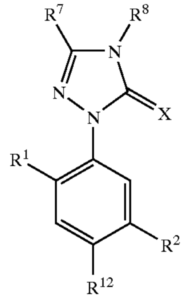
| | | | | | |
|---|---|---|---|---|---|
| 149 | 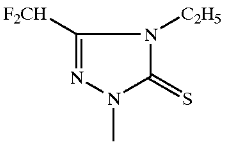 | F | CN | 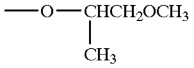 | mp. 90° C. |
| 150 | 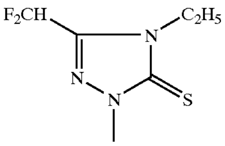 | F | CN | 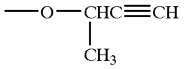 | mp. 134° C. |
| 151 | 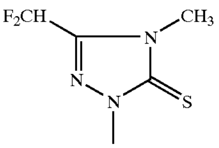 | F | CN | $—O—CH(CH_3)_2$ | mp. 135° C. |
| 152 | 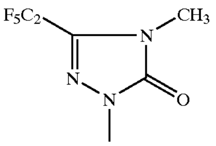 | F | CN | F | mp. 96° C. |
| 153 | 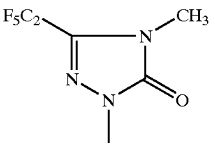 | F | CN | 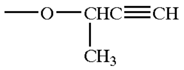 | mp. 115° C. |
| 154 | 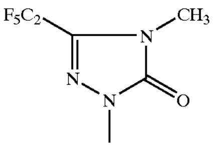 | F | CN | $—O—CH_2C{\equiv}CH$ | (Sirup) |
| 155 | 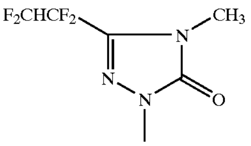 | F | CN | F | mp. 110° C. |
| 156 | 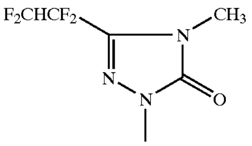 | F | CN | 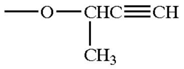 | mp. 88° C. |

-continued
(I)
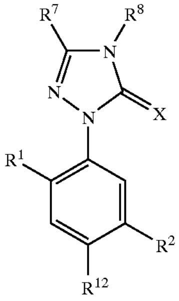
| | | | | | |
|---|---|---|---|---|---|
| 157 | 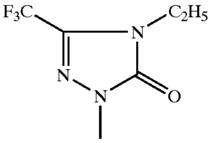 | F | CN | $NH_2$ | mp. 193° C. |
| 158 | 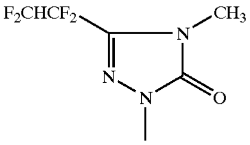 | F | CN | $—O—CH_2C{\equiv}CH$ | mp. 83° C. |
| 159 | 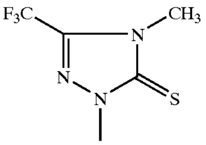 | Cl | CN | 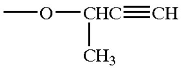 | mp. 104° C. |
| 160 | 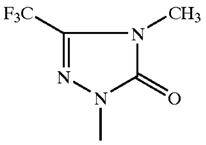 | F | $NO_2$ | F | mp. 72° C. |
| 161 | 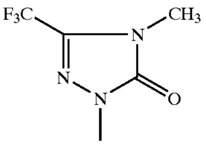 | F | $NO_2$ | 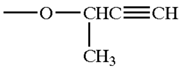 | mp. 72° C. |
| 162 | 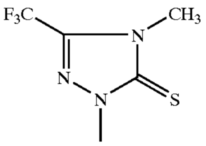 | F | CN | 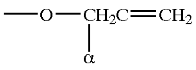 | mp. 82° C. |
| 163 | 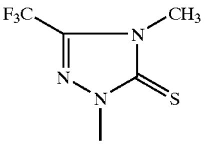 | F | CN | 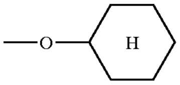 | |
| 164 | 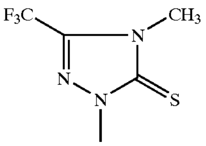 | F | CN | $—O—CH_2C{\equiv}CCH_3$ | mp. 138° C. |

-continued
(I)
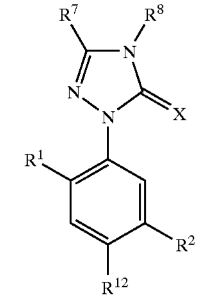
| | | | | | |
|---|---|---|---|---|---|
| 165 | 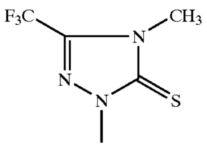 | F | CN | 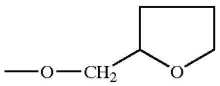 | mp. 72° C. |
| 166 | 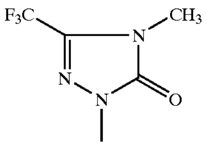 | F | CN | 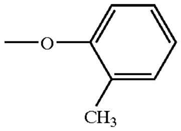 | wax |
| 167 | 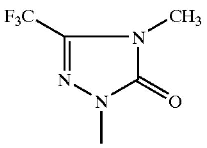 | F | CN | 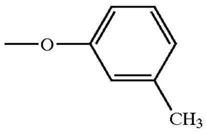 | $n_D^{20}$ = 1.5373 |
| 168 | 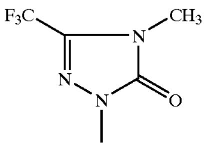 | F | CN | 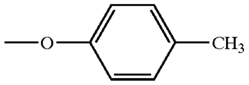 | mp. 121° C. |
| 169 | 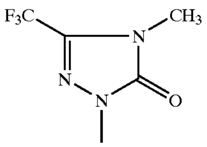 | F | CN | 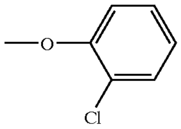 | mp. 112° C. |
| 170 | 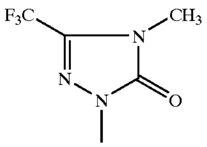 | F | CN | 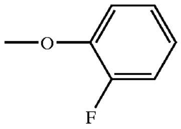 | mp. 132° C. |
| 171 | 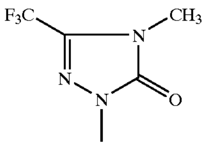 | F | CN | 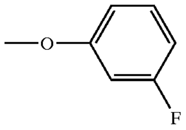 | mp. 74° C. |
| 172 | 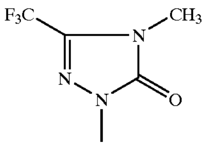 | F | CN | 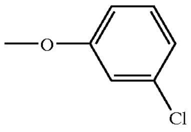 | mp. 45° C. |

-continued
(I)
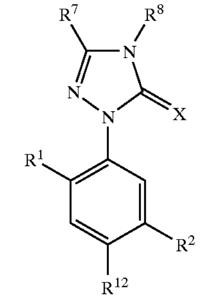
| | | | | | |
|---|---|---|---|---|---|
| 173 | 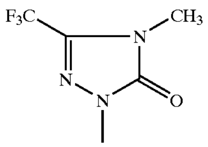 | F | CN | 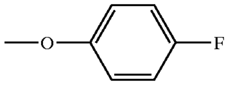 | mp. 150° C. |
| 174 | 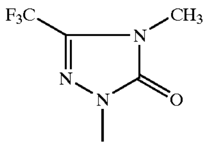 | F | CN | $—NHC_3H_7n$ | mp. 124° C. |
| 175 | 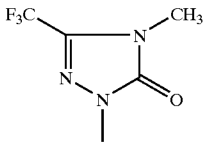 | F | CN | $—NHC_2H_5$ | mp. 134° C. |
| 176 | 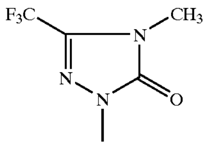 | F | CN | $NH_2$ | mp. 126° C. |
| 177 | 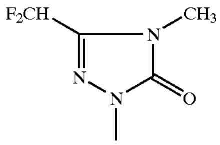 | F | CN | F | mp. 116° C. |
| 178 | 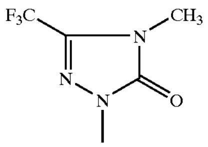 | F | CN | 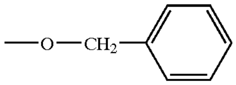 | mp. 98° C. |
| 179 | 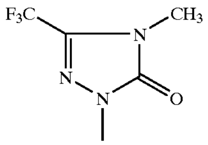 | F | CN | $—O—CH_2CH(CH_3)_2$ | mp. 53° C. |
| 180 | 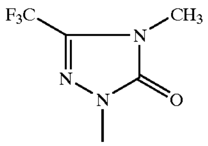 | F | CN | $O—C_4H_9n$ | mp. 50° C. |

-continued
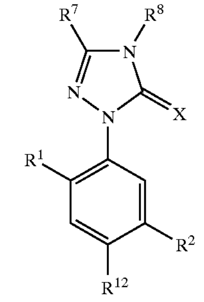
(I)
| | | | | | |
|---|---|---|---|---|---|
| 181 | 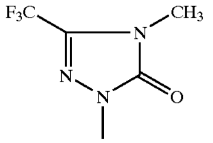 | F | CN | $—O—CH_2COOC_2H_5$ | mp. 214° C. |
| 182 | 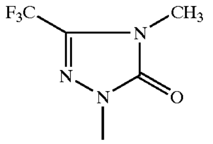 | F | CN | 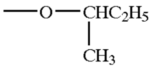 | |
| 183 | 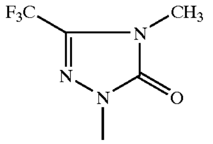 | F | CN | 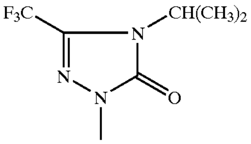 | mp. 58° C. |
| 184 | 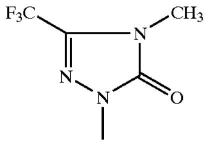 | F | CN | 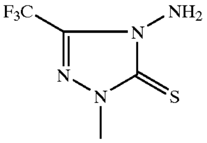 | mp. 66° C. |
| 185 | 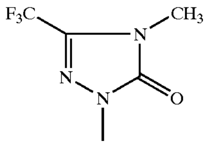 | F | CN | 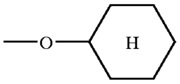 | |
| 186 | 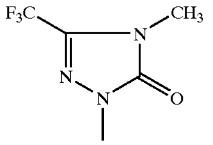 | F | CN | 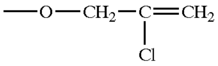 | mp. 53° C. |
| 187 | 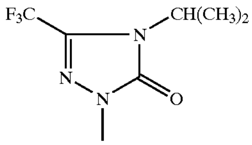 | F | CN | F | $n_D^{20}$ = 1.5012 |
| 188 | 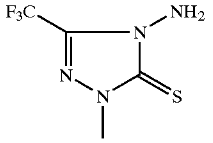 | F | CN | F | mp. 69° C. |

-continued
(I)
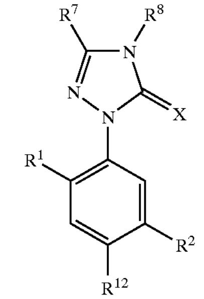
| | | | | | |
|---|---|---|---|---|---|
| 189 | 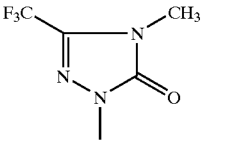 | F | CN | $-O-CH_2CH{=}CH_2$ | mp. 45° C. |
| 190 | 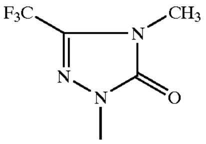 | F | CN | $-OCH_2C{\equiv}CH$ | mp. 99° C. |
| 191 | 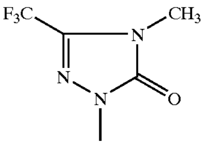 | F | CN | $-OCH_2CH_2SC_2H_5$ | |
| 192 | 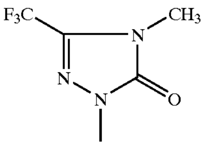 | F | CN | $-O-CH_2Si(CH_3)_3$ | mp. 89° C. |
| 193 | 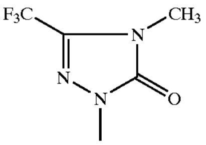 | F | CN | $-O-\underset{CH_3}{\underset{\mid}{CH}}CH_2OCH_3$ | |
| 194 | 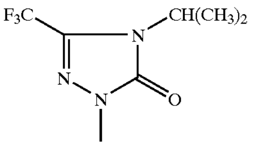 | F | CN | —OCH | mp. 133° C. |
| 195 | 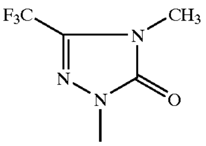 | H | CN | CN | mp. 148° C. |
| 196 | 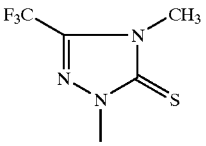 | H | CN | CN | mp. 78° C. |

-continued
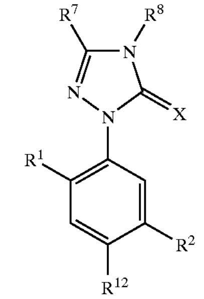
(I)
| | | | | | |
|---|---|---|---|---|---|
| 197 | 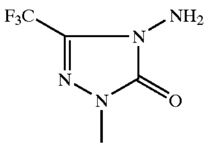 | H | CN | F | mp. 168° C. |
| 198 | 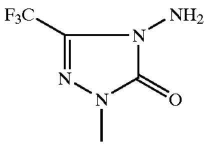 | H | CN | CN | mp. 85° C. |
| 199 | 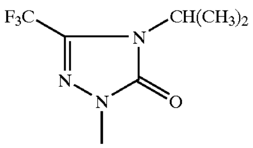 | H | CN | CN | mp. 128° C. |
| 200 | 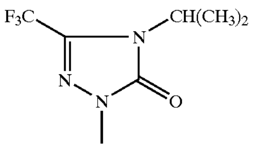 | H | CN | F | mp. 76° C. |
| 201 | 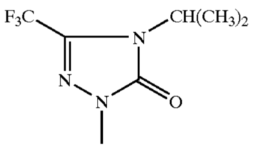 | F | CN | 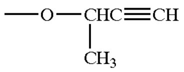 | |
| 202 | 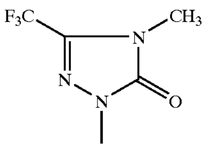 | F | CN | $—O—CH_2CF_2CF_3$ | |
| 203 | 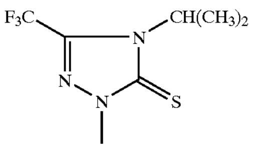 | F | CN | F | mp. 44° C. |
| 204 | 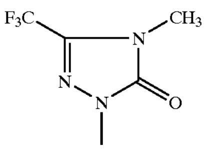 | F | CN | 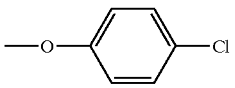 | mp. 111° C. |

-continued
(I)
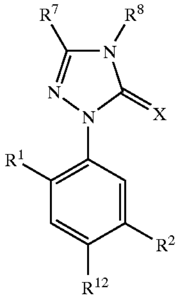
| | | | | | |
|---|---|---|---|---|---|
| 205 | 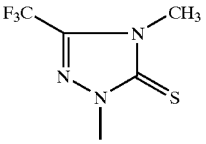 | Cl | CN | F | mp. 110° C. |
| 206 | 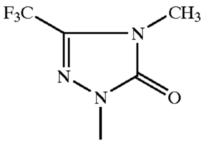 | F | CN | —$OCH_2C{\equiv}CCH_3$ | mp. 70° C. |
| 207 | 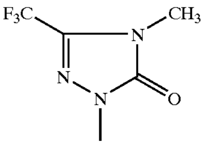 | F | CN | —$OCH_2CH{=}CHCH_3$ | mp. 57° C. |
| 208 | 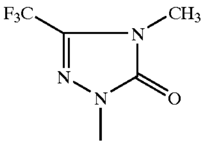 | F | CN | 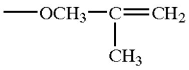 | $n_D^{20}$ = 1.5200 |
| 209 | 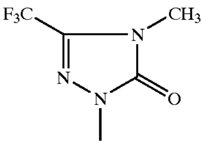 | F | CN | 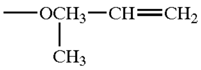 | $n_D^{20}$ = 1.5149 |
| 210 | 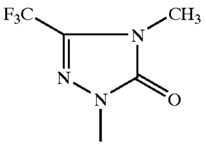 | F | CN | 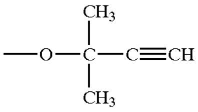 | mp. 84° C. |
| 211 | 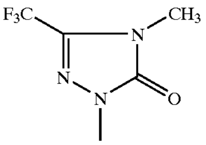 | F | CN | 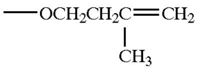 | mp. 80° C. |
| 212 | 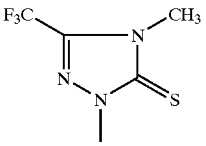 | F | CN | —$OC_3H_7n$ | mp. 92° C. |

-continued
(I)
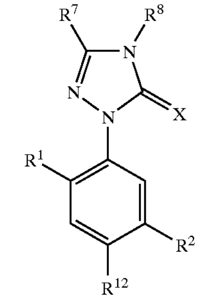
| | | | | | |
|---|---|---|---|---|---|
| 213 | 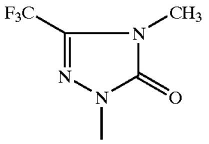 | Cl | CN | 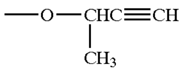 | |
| 214 | 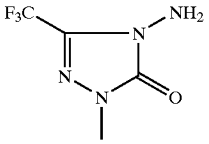 | H | CN | 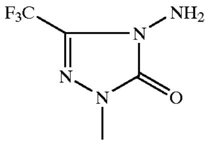 | mp. 202° C. |
| 214 | 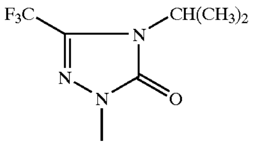 | H | CN | 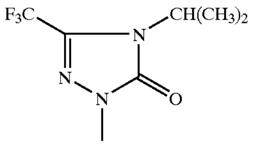 | mp. 142° C. |
| 215 | 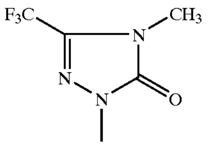 | F | CN | 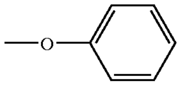 | mp. 54° C. |
| 216 | 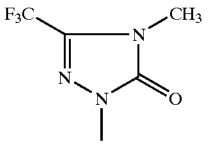 | H | CN | 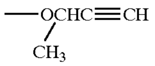 | mp. 140° C. |
| 217 | 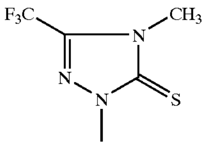 | F | CN | —$OCH(CH_3)2$ | mp. 61° C. |
| 218 | 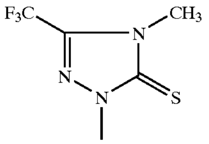 | F | CN | —$OCH_2C{\equiv}CH$ | mp. 142° C. |
| 219 | 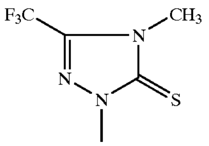 | F | CN | 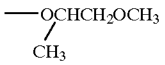 | |

-continued
(I)
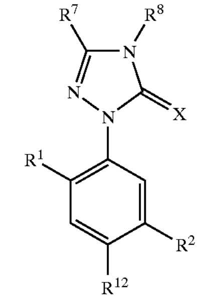
| | | | | | |
|---|---|---|---|---|---|
| 220 | 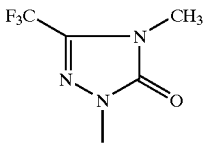 | F | CN | 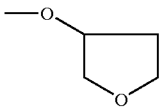 | mp. 86° C. |
| 221 | 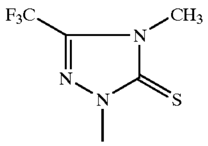 | F | CN | $—OC_2H_5$ | mp. 150° C. |
| 222 | 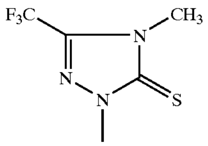 | F | CN | $—OC_4H_9n$ | mp. 37° C. |
| 223 | 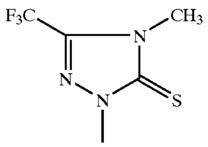 | F | CN | 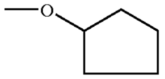 | mp. 104° C. |
| 224 | 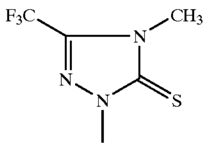 | F | CN | 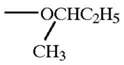 | mp. 33° C. |
| 225 | 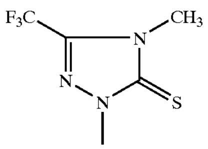 | F | CN | $—OCH_2CH(CH_3)_2$ | mp. 79° C. |
| 226 | 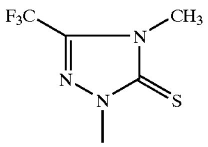 | F | CN | $—OCH_2CH{=}CH_2$ | mp. 100° C. |
| 227 | 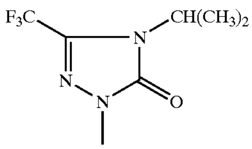 | H | CN | 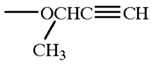 | mp. 108° C. |

-continued
(I)
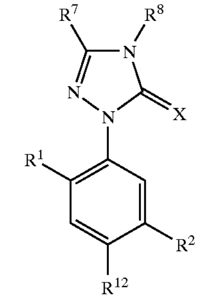
| | | | | | |
|---|---|---|---|---|---|
| 228 | 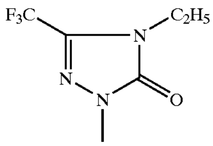 | F | CN | Cl | mp. 53° C. |
| 229 | 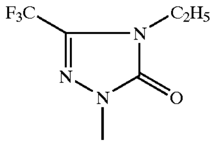 | F | CN | 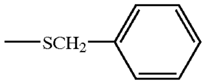 | $^{1}$H-NMR: 3.90–3.96; 4.20; 7.65–7.68. |
| 230 | 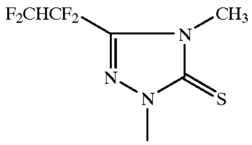 | F | CN | F | mp. 85° C. |
| 231 | 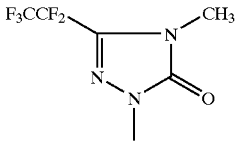 | F | CN | 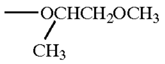 | $^{1}$H-NMR: 1.38–1.40; 3.40; 4.57–4.62, 7.40–7.45. |
| 232 | 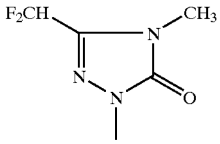 | F | CN | $NH_2$ | mp. 208° C. |
| 233 | 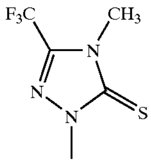 | F | CN | $NH_2$ | mp. 182° C. |
| 234 | 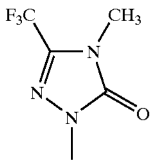 | F | CN | 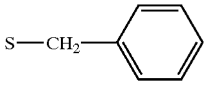 | mp. 77° C. |
| 235 | 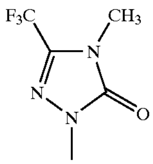 | F | CN | 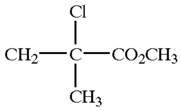 | Oil |

-continued
(I)
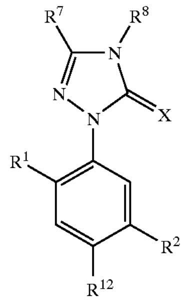
| | | | | | |
|---|---|---|---|---|---|
| 236 | 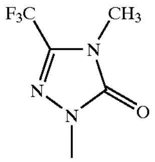 | F | $NO_2$ | $OCH_2C{\equiv}CH$ | Oil |
| 237 | 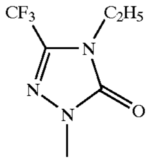 | F | CN | $N(CH_2C{\equiv}CH)_2$ | Oil |
| 238 | 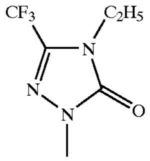 | F | CN | $CH_2CCl_3$ | mp. 114° C. |
| 239 | 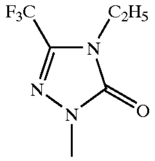 | F | CN | 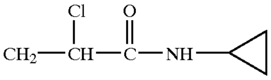 | Oil |
| 240 | 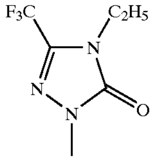 | F | CN | OH | mp. 193° C. |
| 241 | 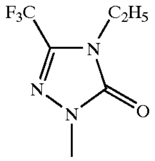 | F | CN | 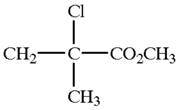 | Oil |
| 242 | 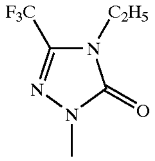 | F | CN | 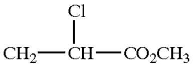 | mp. 88° C. |

-continued
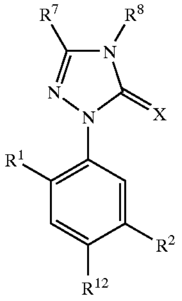
(I)
| | | | | | |
|---|---|---|---|---|---|
| 243 | 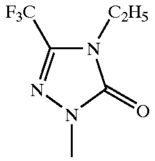 | F | CN | 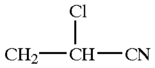 | mp. 140° C. |
| 244 | 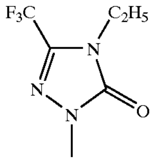 | F | CN | 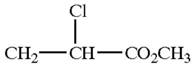 | Oil |
| 245 | 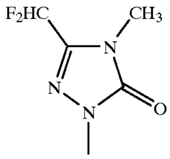 | F | CN | 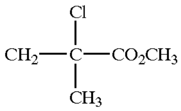 | mp. 113° C. |
| 246 | 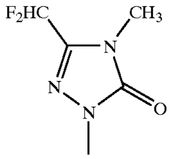 | F | CN | 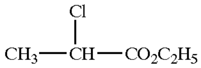 | Oil |
| 247 | 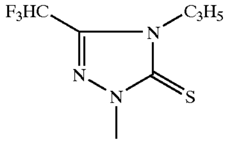 | F | CN | 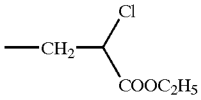 | $^1$H-NMR: δ = 1.25–1.35 3.92–4.00 4.55–4.60 |
| 248 | 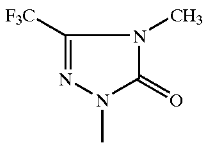 | Cl | CN | 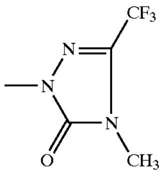 | m.p. 121° C. |
| 249 | 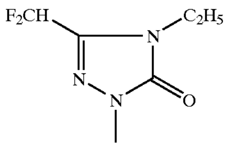 | F | CN | $—OCH_3$ | m.p. 120° C. |

-continued
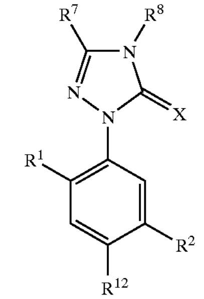
(I)
| | | | | | |
|---|---|---|---|---|---|
| 250 | 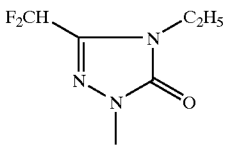 | F | CN | —OiC$_3$H$_7$ | m.p. 115–116° C. |
| 251 | 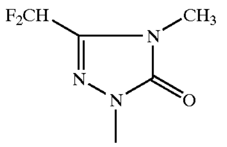 | F | CN | 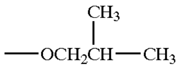 | $^1$H-NMR: δ = 1.05–1.08 3.50; 3.70–3.73; 7.20–7.22 |
| 252 | 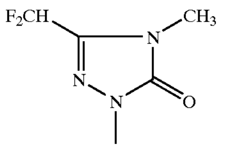 | F | CN | —OC$_4$H$_9$n | m.p. 98° C. |
| 253 | 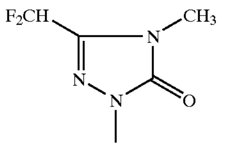 | F | CN | —OC$_3$H$_7$n | m.p. 95° C. |
| 254 | 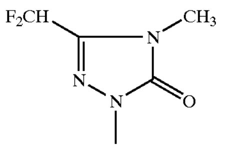 | F | CN | —OC$_3$H$_7$i | $^1$H-NMR: δ = 1.40–1.45; 3.52; 4.55–4.65 |
| 255 | 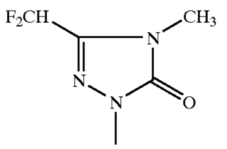 | F | CN | —OC$_2$H$_5$ | m.p. 131° C. |
| 256 | 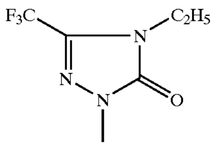 | F | CN | —NH—CH$_2$—C≡CH | m.p. 188–190° C. |
| 257 | 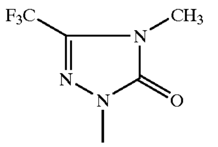 | F | CN | —OH | m.p. 200° C. |

-continued
(I)
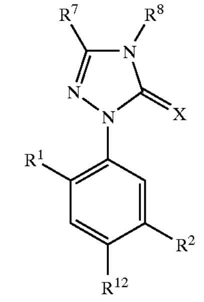
| | | | | | |
|---|---|---|---|---|---|
| 258 | 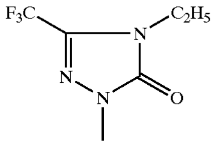 | F | CN | $—SO_2—N(CH_3)_2$ | m.p. 222–224° C. |
| 259 | 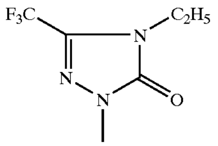 | F | CN | 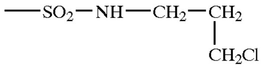 | m.p. 142–143° C. |
| 260 | 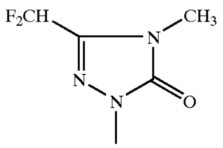 | F | CN | —OH | m.p. 157° C. |
| 261 | 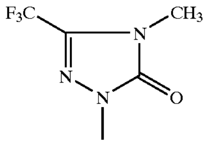 | F | CN | $—SO_2—N(CH_3)_2$ | m.p. 173–174° C. |
| 262 | 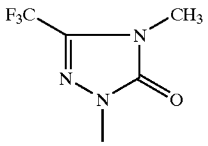 | F | CN | 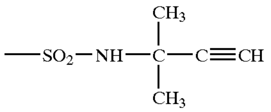 | m.p. 199–201° C. |
| 263 | 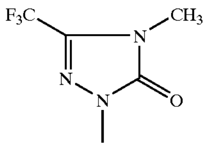 | F | CN | $—SO_2NH_2$ | 100° C. destr. |
| 264 | 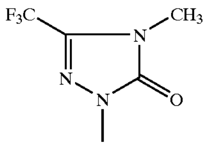 | F | CN | $—SO_2—NH—CH_2—CH{=}CH_2$ | m.p. 172–173° C. |
| 265 | 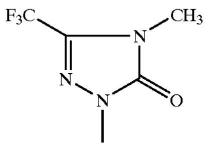 | F | CN | 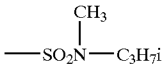 | m.p. 152–153° C. |

-continued
(I)
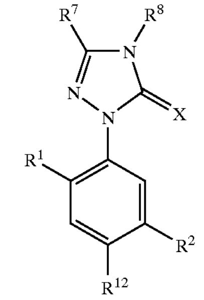
| | | | | | |
|---|---|---|---|---|---|
| 266 | 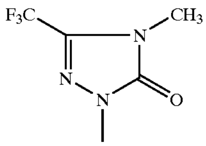 | F | CN | 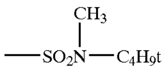 | m.p. 90–91° C. |
| 267 | 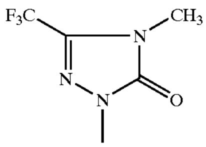 | F | CN | 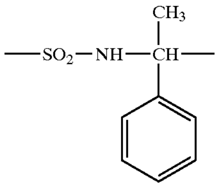 | 96° C. destr. |
| 268 | 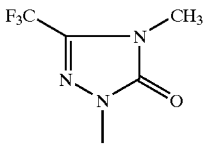 | F | CN | 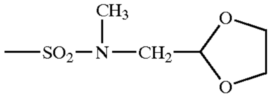 | m.p. 112–113° C. |
| 269 | 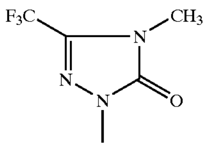 | F | CN | 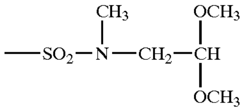 | m.p. 148–149° C. |
| 270 | 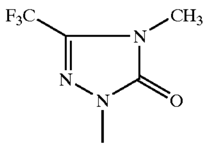 | F | CN | 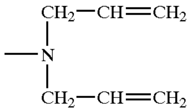 | m.p. 93–94° C. |
| 271 | 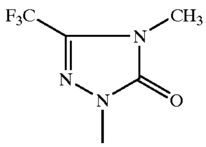 | F | CN | 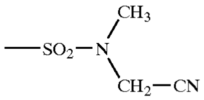 | m.p. 162–164° C. |
| 272 | 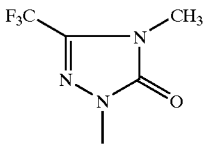 | F | CN | 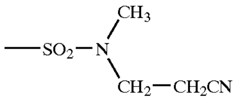 | m.p. 205–207° C. |

-continued
(I)
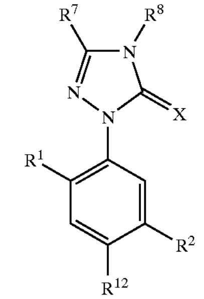
| | | | | | |
|---|---|---|---|---|---|
| 273 | 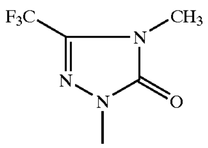 | F | CN | 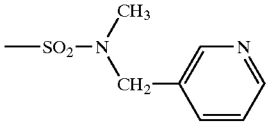 | m.p. 147–148° C. |
| 274 | 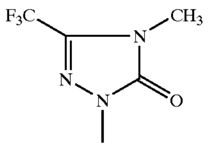 | F | CN | $—SO_2—NH—C_3H_7i$ | m.p. 196–197° C. |
| 275 | 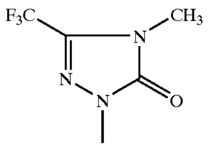 | F | CN | 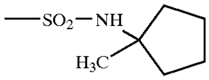 | m.p. 150–152° C. |
| 276 | 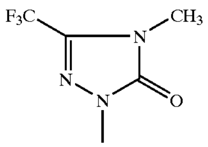 | F | CN | $—SO_2—NH—C_4H_9t$ | m.p. 183–184° C. |
| 277 | 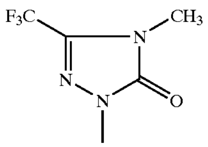 | F | CN | 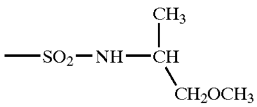 | m.p. 126–127° C. |
| 278 | 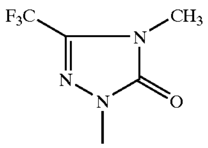 | F | CN | $—SO_2OC_2H_5$ | m.p. 117–118° C. |
| 279 | 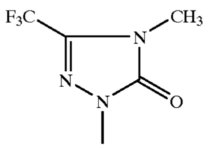 | F | CN | 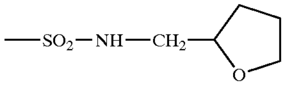 | m.p. 122–123° C. |
| 280 | 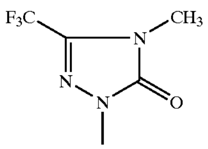 | F | CN | 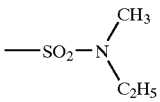 | m.p. 168–170° C. |

-continued
(I)
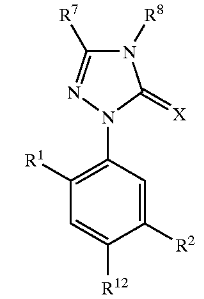
| | | | | | |
|---|---|---|---|---|---|
| 281 | 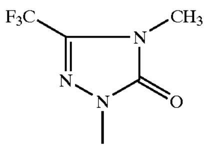 | F | CN | 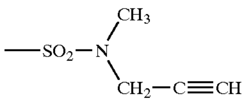 | m.p. 139–141° C. |
| 282 | 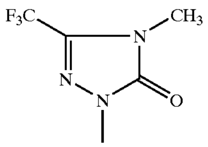 | F | CN | $—SO_2OH$ | m.p. 84–86° C. |
| 283 | 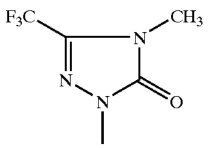 | F | CN | 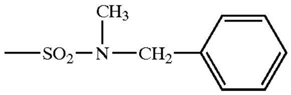 | m.p. 155–156° C. |
| 284 | 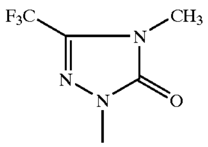 | F | CN | 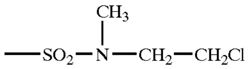 | m.p. 146–148° C. |
| 285 | 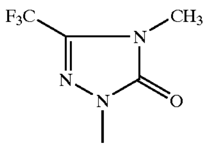 | F | CN | $—OCH_2—CH_2—CH{=}CH_2$ | m.p. 82° C. |
| 286 | 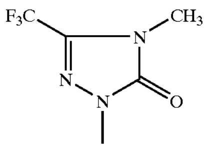 | F | CN | 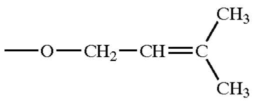 | m.p. 76° C. |
| 287 | 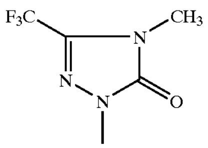 | F | CN | $—O—CH_2—CH_2—OC_4H_9n$ | $^1$H-NMR: δ = 0.85; 1.2–1.6; 3.5; 3.7; 3.75; 4.3; 7.7; 8.2 |
| 288 | 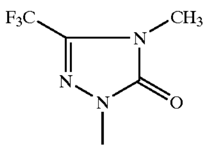 | F | CN | 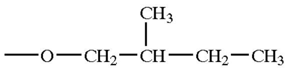 | $^1$H-NMR: δ = 0.8–2.0 3.7; 4.0; 7.65; 8.2 |

-continued
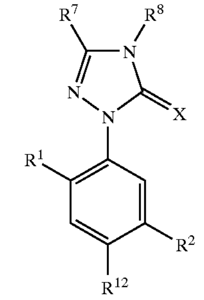
(I)
| | | | | | |
|---|---|---|---|---|---|
| 289 | 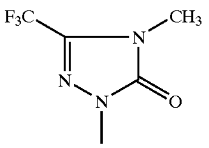 | F | CN | 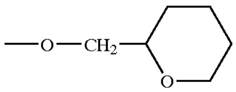 | m.p. 76° C. |
| 290 | 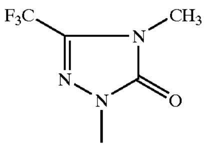 | F | CN | —OH | m.p. 200° C. |
| 291 | 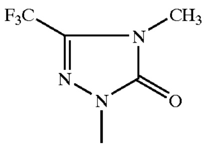 | F | CN | 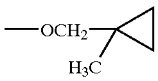 | $^1$H-NMR: δ = 0.3–0.7; 1.2; 3.4; 3.95; 7.45; 8.1 |
| 292 | 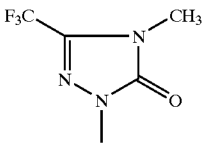 | F | CN | 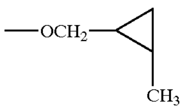 | $^1$H-NMR: δ = 0.3–1.2; 3.4; 4.05; 7.45; 8.05 |
| 293 | 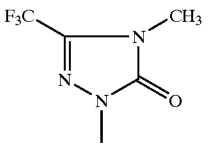 | F | CN | 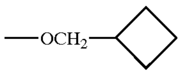 | $^1$H-NMR: δ = 1.8–2.2; 2.75; 3.4; 4.1; 7.45; 8.1 |
| 294 | 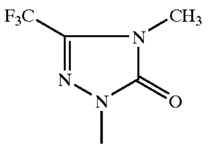 | F | CN | $—O—(CH_2)_3—C{\equiv}CH$ | m.p. 73° C. |
| 295 | 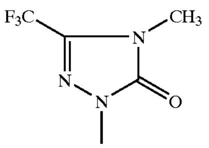 | F | CN | $—O—(CH_2)_2—C{\equiv}C—CH_3$ | m.p. 84° C. |
| 296 | 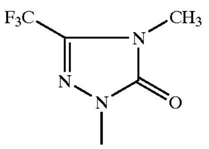 | F | CN | $—OCH_2—C{\equiv}C—C_2H_5$ | $^1$H-NMR: δ = 1.05; 2.2; 3.4; 5.0; 7.55; 8.1 |

-continued
(I)
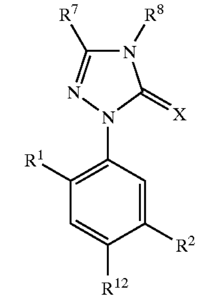
| | | | | | |
|---|---|---|---|---|---|
| 297 | 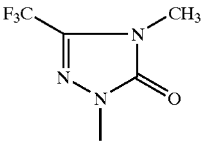 | F | CN | 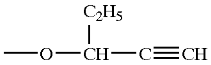 | ¹H-NMR: δ = 1.1; 1.95, 3.4; 3.75; 5.15; 7.6; 8.1 |
| 298 | 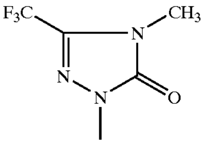 | F | CN | 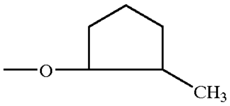 | ¹H-NMR: δ = 0.8–2.2; 3.4; 4.5; 7.45; 8.0 |
| 299 | 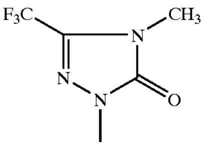 | F | CN | 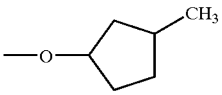 | ¹H-NMR: δ = 0.9–2.4; 3.4; 4.95; 7.45; 8.05 |
| 300 | 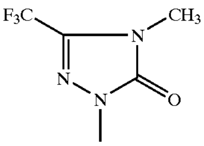 | F | CN | 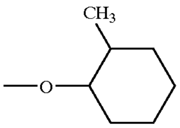 | ¹H-NMR: δ = 0.7–2.1; 3.4; 4.0; 7.55; 8.1 |
| 301 | 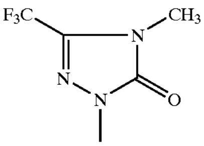 | F | CN | 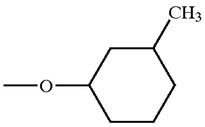 | ¹H-NMR: δ = 0.8–2.2; 3.4; 4.45; 7.55; 8.05 |
| 302 | 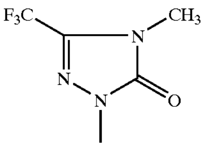 | F | CN | 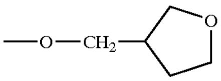 | ¹H-NMR: δ = 1.8; 2.15; 2.85; 3.5; 3.7–4.1; 7.2; 7.5 |
| 303 | 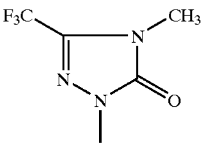 | F | CN | —SH | ¹H-NMR: δ = 3.35; 8.05; 8.3 |
| 304 | 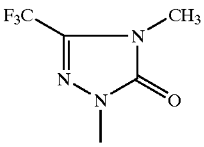 | F | CN | O—$CH_2$—CN | ¹H-NMR: δ = 3.4; 5.4; 7.65; 8.2 |

-continued
(I)
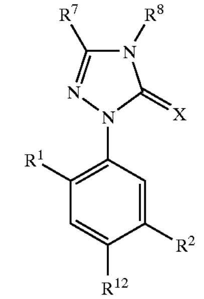
| | | | | | |
|---|---|---|---|---|---|
| 305 | 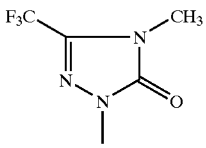 | F | CN | 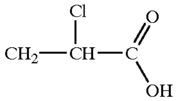 | $^1$H-NMR: δ = 3.2–3.65; 4.5; 7.85; 8.15 |
| 306 | 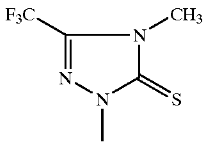 | F | CN | 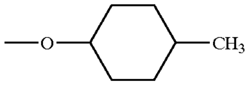 | $^1$H-NMR: δ = 0.8–2.1; 3.7; 4.4; 7.7; 8.15 |
| 307 | 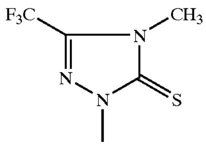 | F | CN | $-O-CH_2-CH_2-SCH_3$ | m.p. 69° C. |
| 308 | 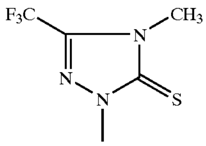 | F | CN | $-O-CH_2-C{\equiv}C-C_2H_5$ | m.p. 134° C. |
| 309 | 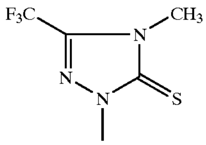 | F | CN | 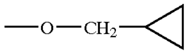 | m.p. 62° C. |
| 310 | 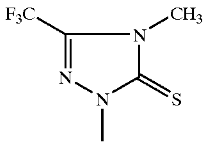 | F | CN | 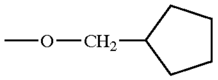 | $^1$H-NMR: δ = 1.2–2.5; 3.75; 3.95; 7.25; 7.5 |
| 311 | 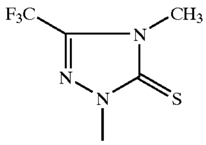 | F | CN | 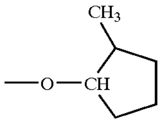 | $^1$H-NMR: δ = 1.0–2.3; 3.7; 4.45; 7.6; 8.15 |
| 312 | 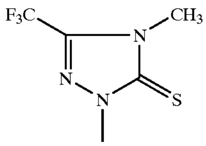 | F | CN | 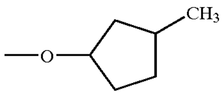 | $^1$H-NMR: δ = 1.0–2.4; 3.75; 4.8; 7.25; 7.45 |

-continued
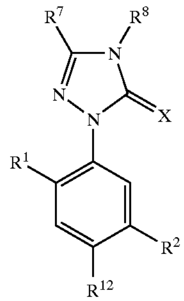
(I)
| | | | | | |
|---|---|---|---|---|---|
| 313 | 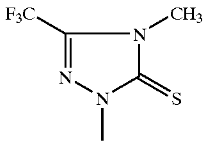 | F | CN | 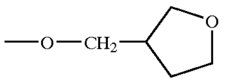 | $^1$H-NMR: δ = 1.7; 2.05; 2.7; 3.5–4.2; 7.65; 8.15 |
| 314 | 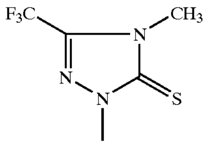 | F | CN | 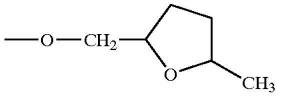 | $^1$H-NMR: δ = 1.1–2.2; 3.7; 3.9–4.4; 7.65; 8.15 |
| 315 | 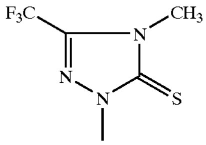 | F | CN | 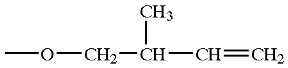 | $^1$H-NMR: δ = 1.2; 2.8; 3.75; 3.9; 5.1; 5.8; 7.3; 7.5 |
| 316 | 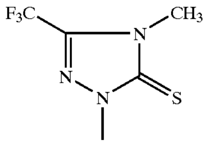 | F | CN | 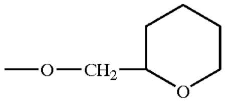 | m.p. 57° C. |
| 317 | 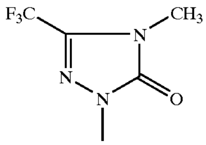 | H | $NO_2$ | $—CH_3$ | m.p. 158° C. |
| 318 | 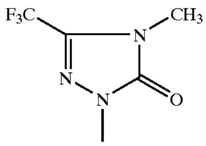 | F | CN | 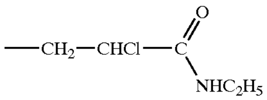 | $^1$H-NMR: δ = 1.0; 3.1; 3.3–3.6; 4.65; 7.75; 8.2; 8.4 |
| 319 | 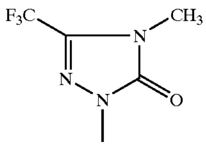 | F | CN | 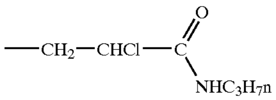 | $^1$H-NMR: δ = 0.8; 1.35; 3.0; 3.3–3.6; 4.7; 7.7; 8.2; 8.35 |

-continued
(I)
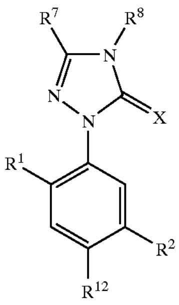
| | | | | | |
|---|---|---|---|---|---|
| 320 | 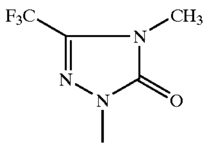 | F | CN | 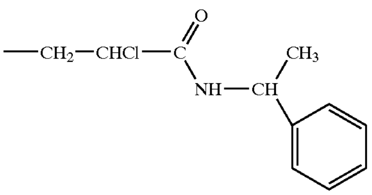 | m.p. 93° C. |
| 321 | 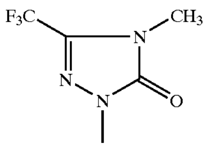 | F | CN | 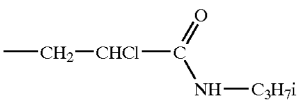 | m.p. 44° C. |
| 322 | 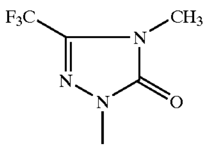 | F | CN | 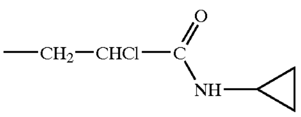 | m.p. 124° C. |
| 323 | 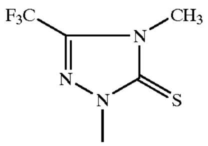 | F | CN | 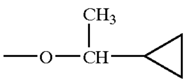 | $^1$H-NMR: δ = 0.2–0.7; 1.1–1.5; 3.75; 3.9; 7.3; 7.5 |
| 324 | 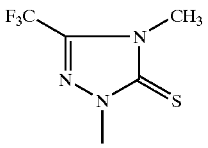 | F | CN | 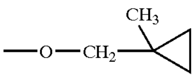 | m.p. 103° C. |
| 325 | 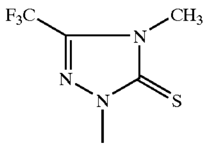 | F | CN | 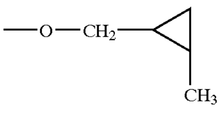 | $^1$H-NMR: δ = 0.3–0.6; 0.8; 0.9–1.1; 3.7; 4.0; 7.6; 8.15 |
| 326 | 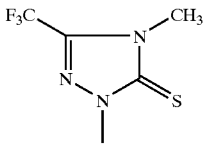 | F | CN | 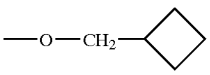 | $^1$H-NMR: δ = 1.8–2.2; 2.75; 3.7; 4.1; 7.6; 8.15 |

-continued
(I)
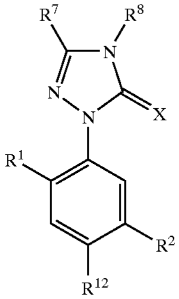
| | | | | | |
|---|---|---|---|---|---|
| 327 | 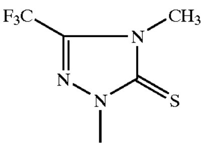 | F | CN | 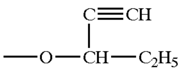 | m.p. 69° C. |
| 328 | 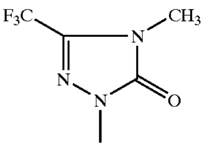 | H | CN | $—CF_3$ | m.p. 160° C. |
| 329 | 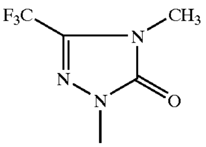 | F | CN | $—O—CH_2—CH_2—CF{=}CF_2$ | m.p. 65° C. |
| 330 | 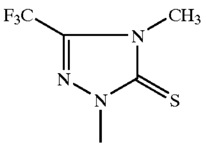 | F | CN | $—O—CH_2—CH_2—CF{=}CF_2$ | m.p. 50° C. |
| 331 | 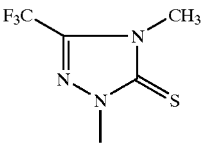 | F | CN | $—N(CH_3)_2$ | m.p. 117° C. |
| 332 | 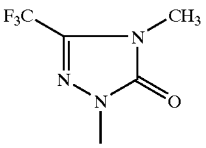 | F | CN | $—N(CH_3)_2$ | m.p. 64° C. |
| 333 | 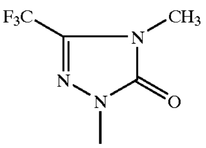 | F | CN | $—OSO_2CF_3$ | $^1$H-NMR: δ = 3.4; 8.2; 8.55 |
| 334 | 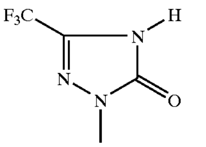 | F | CN | F | m.p. 87° C. |

-continued (I)

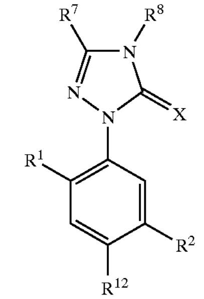

| | | | | | |
|---|---|---|---|---|---|
| 335 | 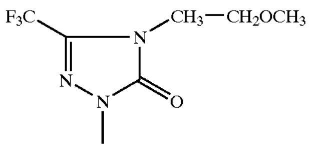 | F | CN | F | m.p. 66–68° C. |
| 336 | 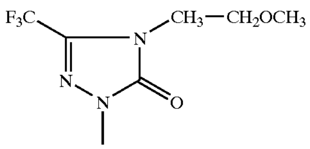 | F | CN | $-OCH_2-C\equiv CH$ | $^1H$-NMR: δ = 2.65; 3.40; 4.05–4.10 |
| 337 | 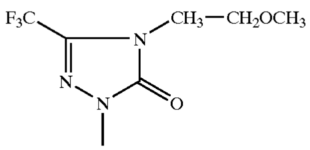 | F | CN | 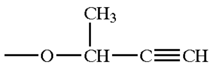 | $^1H$-NMR: δ = 2.60; 3.40; 4.90–5.00 |
| 338 | 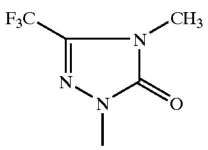 | F | CN | Cl | m.p. 86° C. |

*)The $^3H$ NMR spectra were recorded in deuterochloroform ($CDCl_3$) with tetramethylsilane (TMS) as the internal standard. The data given represent the chemical shift as δ value in ppm.]

USE EXAMPLES

In the examples which follow, the compounds listed ed as comparison substances:

(A)

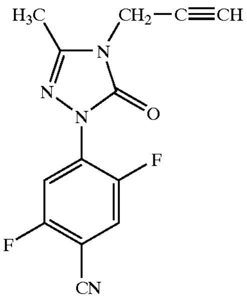

3-Methyl-4-propargyl-1-(2,5-difluoro-4-cyano-phenyl)-1,2,4-triazolin-5-one (B)

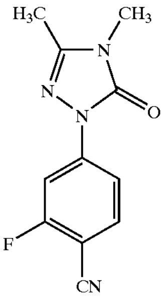

3,4-Dimethyl-1-(3-fluoro-4-cyano-phenyl)-1,2,4-triazolin-5-one (both disclosed in DE 3,839,480)

Example A

Pre-emergence Test

Solvent: 5 parts by weight of acetone

Emulsifier: 1 part by weight of alkylaryl polyglycol ether

To produce a suitable preparation of active compound, one part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control.

The figures denote:

0%=no action (like untreated control)

100%=total destruction

While Comparison Example (A) exhibits no herbicidal activity against weeds such as *Setaria, Amaranthus, Chenopodium, Galinsoga, Matricaria, solanum* and *Viola*, at an application rate of 250 g/ha, activities between 40 and 100% are shown, in this test, for example, by the compounds of Preparation Examples 57, 59, 67 and 79 and activities between 95 and 100% by the compounds of Preparation Examples 60, 61, 62, 65 and 69.

Example B

*Tetranychus* Test (OP Resistant)

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentrations.

Bean plants (*Phaseolus vulgaris*) which are severely infested with all developmental stages of the two-spotted spider mite (*Tetranychus urticae*) are dipped into a preparation of active compound at the desired concentration.

After the specified period of time, the mortality in percent is determined 100% means that all the spider mites have been killed; 0% means that no spider mite has been killed.

In this test, a clearly superior acaricidal activity compared with Example (B), which is known from the prior art, is shown, for example, by compound 13 of the preparation examples.

Example C

Phaedon-test

Solvent: 31 parts by weight of acetone

Emulsifier: 1 part by weight of alkylaryl polyglycol ether

To produce a suitable preparation of active compound, one part by weight of active compound is mixed with the stated amount of solvent, the stated amount of emulsifier is added and the concentrate is diluted with water to the desired concentration.

Cabbage leaves are treated with that suitable preparation of active compound. A such treated leave is put into a plastic box together with two Phaedon cochleariae in development stage. After 3 days an untreated leave is added. After the specified period of time, the mortality in percent is determined. 100% means that all the Phaedon cochleariae have been killed; 0% means that no Phaedon cochleariae has been killed.

In this test a clearly superior acaricidal activity compared with the prior art is shown, for example, by compounds 70 and 112.

Example D

Myzus-test

Solvent: 31 parts by weight of acetone

Emulsifier: 1 part by weight of alkylaryl polyglycol ether

To produce a suitable preparation of active compound, one part by weight of active compound is mixed with the stated amount of solvent, the stated amount of emulsifier is added and the concentrate is diluted with water to the desired concentration.

Shoots of *Vicia faba*, which are stricken by *Myzus persicae*, are treated with such preparation of active compound in suitable concentration and put into a plastic box.

After the specified period of time the mortality in percent is determined. 100% means that all *Myzus persicae* have been killed; 0% means that no *Myzus persicae* has been killed.

In this test a clearly superior acaricidal activity in comparison to the prior art is shown for examples 97 and 102.

It will be understood that the specification and examples are illustrative but not limitative of the present invention and that other embodiments within the spirit and scope of the invention will suggest themselves to those skilled in the art.

We claim:

1. A substituted triazolinone of the formula (Ia):

(Ia)

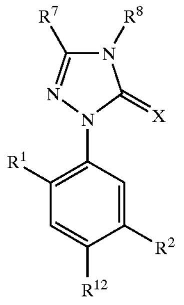

wherein $R^1$ represents hydrogen, fluorine, chlorine, bromine or iodine;

$R^2$ represents nitro, cyano, fluorine, chlorine, bromine, iodine, $R^{13}$, —O—$R^{13}$, —S—$R^{13}$, —S(O)—$R^{13}$, —$SO_2$—$R^{13}$, —O—$SO_2$—$R^{13}$, —C(O)—O—$R^{13}$, —$NR^{13}R^{14}$, —$SO_2$—$NR^{13}R^{14}$, —C(O)—$NR^{13}R^{14}$, —NH—P(O)($OR^{13}$)($R^{14}$), —NH—P(O)($OR^{13}$)($OR^{14}$), or a radical of the formula:

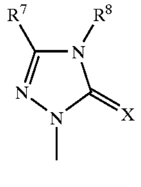

$R^7$ represents straight-chain or branched halogenoalkyl having 1 to 6 carbon atoms and 1 to 13 identical or different halogen atoms;

$R^8$ represents hydrogen, amino, cyano, straight-chain or branched alkyl having 1 to 8 carbon atoms, in each case straight-chain or branched alkenyl or alkinyl having 2 to 6 carbon atoms, straight-chain or branched halogenoalkyl having 1 to 6 carbon atoms and 1 to 13 identical or different halogen atoms, in each case straight-chain or branched halogenoalkenyl or halogenoalkinyl having 2 to 6 carbon atoms and 1 to 11 different halogen atoms, straight-chain or branched alkoxyalkyl having 1 to 4 carbon atoms in the alkoxy moiety and 1 to 4 carbon atoms in the alkyl moiety, straight-chain or branched alkylideneimino having 1 to 8 carbon atoms, or cycloalkyl or cycloalkylalkyl each of which has 3 to 8 carbon atoms in the cycloalkyl moiety and, in the case of cycloalkylalkyl, has 1 to 4 carbon atoms in the alkyl moiety, and each of which is optionally monosubstituted or polysubstituted in the cycloalkyl moiety by identical or different halogen substituents;

$R^{12}$ represents cyano or nitro;

X represent oxygen or sulfur, $R^{13}$ and $R^{14}$ independently represent hydrogen or straight-chain or branched alkyl which has 1 to 8 carbon atoms and which is optionally monosubstituted or polysubstituted by identical or different substituents selected from the group consisting of:

halogen, cyano, carboxyl, carbamoyl, in each case straight-chain or branched alkoxy, alkoxyalkoxy, alkylthio, alkylsulphinyl, alkylsulphonyl alkoxycarbonyl, alkoxycarbonylalkyl, N-alkylaminocarbonyl, cycloalkylaminocarbonyl, N,N-dialkylaminocarbonyl, trialkylsilyl or alkylsulphonylaminocarbonyl, each of which has 1 to 8 carbon atoms in the individual alkyl moieties;

$R^{13}$ and $R^{14}$ furthermore present alkenyl or alkinyl, each of which has 2 to 8 carbon atoms and each of which is optionally monosubstituted or polysubstituted by identical or different halogen substituents;

$R^{13}$ and $R^{14}$ furthermore represent cycloalkyl which has 3 to 7 carbon atoms and which is optionally monosubstituted or polysubstituted by identical or different halogen substituents or by straight-chain or branched alkyl having 1 to 4 carbon atoms, or represent $C_3$–$C_7$-cycloalkyl-$C_1$–$C_3$-alkyl;

$R^{13}$ and $R^{14}$ furthermore represent alkyl or aryl, each of which has 6 to 10 carbon atoms in the aryl moiety and, when present, 1 to 4 carbon atoms in the straight-chain or branched alkyl moiety, and each of which is optionally monosubstituted or polysubstituted in the aryl moiety by identical or different substituents selected from the group consisting of:

halogen, cyano, nitro, in each case straight-chain or branched alkyl, alkoxy, alkylthio, alkylsulphinyl or alkylsulphonyl, each of which has 1 to 6 carbon atoms, in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched alkoxycarbonyl or alkoximinoalkyl, each of which has 1 to 6 carbon atoms in the individual alkyl moieties, and phenyl which is optionally monosubstituted or polysubstituted by identical or different halogen substituents and/or by straight-chain or branched alkyl or alkoxy, each of which has 1 to 6 carbon atoms, and/or by straight-chain or branched halogenoalkyl or halogenoalkoxy, each of which has 1 to 6 carbon atoms and 1 to 13 identical or different halogen atoms.

2. The substituted triazolinone according to claim 1, wherein $R^1$ represents hydrogen, fluorine, chlorine or bromine;

$R^2$ represents nitro, cyano, fluorine, chlorine, bromine, $R^{13}$, —O—$R^{13}$, —S—$R^{13}$, —S(O)—$R^{13}$, —$SO_2$—$R^{13}$, —O—$SO_2$—$R^{13}$, —$SO_2$—O—$R^{13}$, —C(O)—O—$R^{13}$, —$NR^{13}R^{14}$, —$SO_2$—$NR^{13}R^{14}$, —C(O)—$NR^{13}R^{14}$, —NH—P(O)($OR^{13}$)($R^{14}$), —NH—P(O)($OR^{13}$($OR^{14}$), or a radical of the formula:

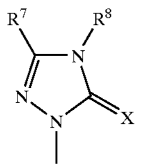

$R^7$ represents straight-chain or branched halogenoalkyl having 1 to 4 carbon atoms and 1 to 9 identical or different halogen atoms;

$R^8$ represents hydrogen, amino, cyano, straight-chain or branched alkyl having 1 to 6 carbon atoms, in each case straight-chain or branched alkenyl or alkinyl having 2 to 4 carbon atoms, straight-chain or branched halogenoalkyl having 1 to 4 carbon atoms and 1 to 9 identical or different halogen atoms, in each case straight-chain or branched halogenoalkenyl or halogenoalkinyl having 2 to 4 carbon atoms and 1 to 7 different halogen atoms, straight-chain or branched alkoxyalkyl having 1 to 3 carbon atoms in the alkoxy moiety and 1 to 3 carbon atoms in the alkyl moiety, straight-chain or branched alkylideneimino having 1 to 6 carbon atoms, or cycloalkyl or cycloalkylalkyl each of which has 3 to 7 carbon atoms in the cycloalkyl moiety and, in the case of cycloalkylalkyl, has 1 to 3 carbon atoms in the alkyl moiety, and each of which is optionally monosubstituted to tetrasubstituted in the cycloalkyl moiety by identical or different halogen substituents;

$R^{12}$ represents cyano or nitro;

X represents oxygen or sulfur;

$R^{13}$ and $R^{14}$ independently represent hydrogen or straight-chain or branched alkyl which has 1 to 6 carbon atoms and which is optionally monosubstituted by a substituent selected from the group consisting of:

cyano, carboxyl, carbamoyl, in each case straight-chain or branched alkoxy, alkoxyalkoxy, alkylthio, alkylsulphinyl, alkysulphonyl, alkoxycarbonyl, alkoxycarbonylalkyl, N-alkylaminocarbonyl, N,N-dialkylaminocarbonyl, trialkylsilyl or alkylsulphonylaminocarbonyl, each of which has 1 to 6 carbon atoms in the individual alkyl moieties;

$R^{13}$ and $R^{14}$ furthermore represent straight-chain or branched halogenoalkyl having 1 to 4 carbon atoms and 1 to 9 identical or different halogen atoms, which is optionally substituted by $C_{1-2}$-alkoxycarbonyl, $C_{1-6}$-cycloalkylaminocarbonyl or cyano;

$R^{13}$ and $R^{14}$ furthermore represent alkenyl or alkinyl, each of which has 2 to 6 carbon atoms and each of which is optionally monosubstituted or trisubstituted by identical or different halogen substituents;

$R^{13}$ and $R^{14}$ furthermore represent cycloalkyl which has 3 to 6 carbon atoms and which is optionally monosubstituted to tetrasubstituted by identical or different halogen substituents or by straight-chain or branched alkyl having 1 to 3 carbon atoms, or represent $C_3$–$C_6$-cycloalkyl-$C_1$–$C_2$-alkyl;

$R^{13}$ and $R^{14}$ furthermore represent phenylalkyl or phenyl, the phenylalkyl having 1 to 3 carbon atoms in the straight-chain or branched alkyl moiety, and each of which is optionally monosubstituted to trisubstituted in the phenyl moiety by identical or different substituents selected from the group consisting of:

halogen, cyano, nitro, in each case straight-chain or branched alkyl, alkoxy, alkylthio, alkylsulphinyl or alkylsulphonyl, each of which has 1 to 4 carbon atoms, in each case straight-chain or branched halogenoalkyl, halogenoalkoxy, halogenoalkylthio, halogenoalkylsulphinyl or halogenoalkylsulphonyl, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different halogen substituents and/or by straight-chain or branched alkyl or alkoxy, each of which has 1 to 4 carbon atoms, and/or by straight-chain or branched halogenoalkyl or halogenoalkoxy, each of which has 1 to 4 carbon atoms and 1 to 9 identical or different halogen atoms.

3. The substituted triazolinone according to claim 1, which is 1-(4-cyano-2-fluorophenyl)-4-methyl-3-trifluoromethyl-1,2,4-triazolin-5-one of the formula:

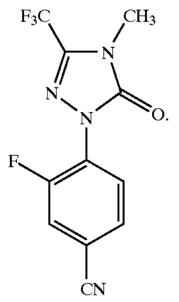

4. The substituted triazolinone according to claim 1, which is 1-(2-chloro-4-cyanophenyl)-4-methyl-3-trifluoromethyl-1,2,4-triazolin-5-one of the formula:

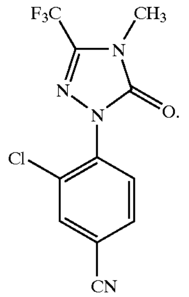

5. The substituted triazolinone according to claim 1, which is 1-(2-fluoro-4-cyanophenyl)-4-methyl-3-trifluoromethyl-1,2,4-triazolin-5-thione of the formula:

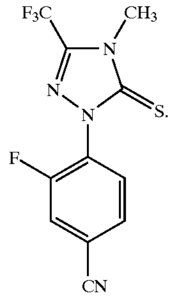

6. The substituted triazolinone according to claim 1, which is 1-(2,5-difluoro-4-cyanophenyl)-4-methyl-3-trifluoromethyl-1,2,4-triazolin-5-thione of the formula:

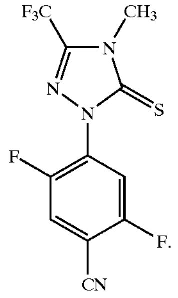

7. The substituted triazolinone according to claim 1, which is 1-(2-fluoro-4-cyano-5-methoxyphenyl)-4-methyl-3-trifluoromethyl-1,2,4-triazolin-5-one of the formula:

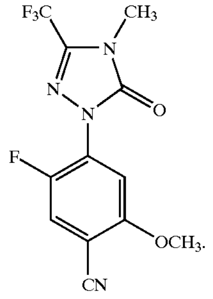

8. The substituted triazolinone according to claim 1, which is 1-(4-cyano-3-fluorophenyl)-4-ethyl-3-trifluoromethyl-1,2,4-triazolin-5-one of the formula:

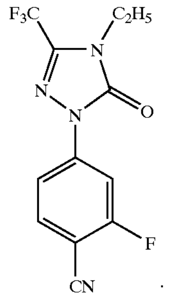

9. The substituted triazolinone according to claim 1, which is 1-(5-allylamino-4-cyano-2-fluorophenyl)-4-ethyl-3-trifluoromethyl-1,2,4-triazolin-5-one of the formula:

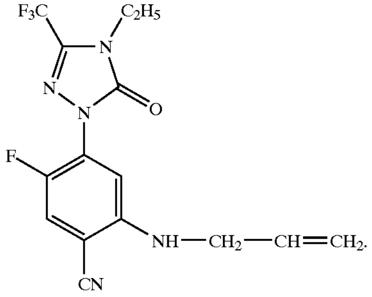

10. The substituted triazolinone according to claim 1, which is 1-(2,5-difluoro-4-cyanophenyl)-4-methyl-3-trifluoromethyl-1,2,4-triazolin-5-one of the formula:

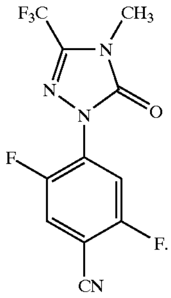

11. A herbicidal or plant growth-regulating composition comprising an effective amount therefor of a substituted triazolinone according to claim 1 and a diluent.

12. The herbicidal or plant growth-regulating composition according to claim 11, wherein the substituted triazolinone is selected from the group consisting of:

a) 1(4-cyano-2-fluorophenyl)-4-methyl-3-trifluoromethyl-1,2,4-triazolin-5-one;

b) 1-(2-chloro-4-cyanophenyl)4-methyl-3-trifluoromethyl-1,2,4-triazolin-5-one;

c) 1-(2-fluoro-4-cyanophenyl)-4-methyl-3-trifluoromethyl-1,2,4-triazolin-5-thione;

d) 1-(2,5-difluoro-4-cyanophenyl)4-methyl-3-trifluoromethyl-1,2,4-triazolin-5-thione;

e) 1-(2-fluoro-4-cyano-5-methoxyphenyl)-4-methyl-3-trifluoromethyl-1,2,4-triazolin-5-one;

f) 1-(4-cyano-3-fluorophenyl)-4-ethyl-3-trifluoromethyl-1,2,4-triazolin-5-one;

g) 1-(5-allylamino-4-cyano-2-fluorophenyl)-4-ethyl-3-trifluoromethyl-1,2,4-triazolin-5-one; and h) 1-(2,5-difluoro-4-cyanophenyl)-4-methyl-3-trifluoromethyl-1,2,4-triazolin-5-one.

13. A method of combating unwanted vegetation which comprises applying to such vegetation or to a locus from which it is desired to exclude such vegetation a herbicidally effective amount of a triazolinone according to claim 1.

14. The method according to claim 13, wherein the triazolinone is selected from the group consisting of:

a) 1-(cyano-2-fluorophenyl)-4-methyl-3-trifluoromethyl-1,2,4-triazolin-5-one;

b) 1-(2-chloro 4-cyanophenyl)-4-methyl-3-trifluoromethyl-1,2,4-triazolin-5-one;

c) 1-(2-fluoro-4-cyanophenyl)-4-methyl-3-trifluoromethyl-1,2,4-triazolin-5-thione;

d) 1-(2,5-difluoro-4-cyanophenyl)-4-methyl-3-trifluoromethyl-1,2,4-triazolin-5-thione;

e) 1-(2-fluoro-4-cyano-5-methoxyphenyl)-4-methyl-3-trifluoromethyl-1,2,4-triazolin-5-one;

f) 1-(4-cyano-3-fluorophenyl)-4-ethyl-3-trifluoromethyl-1,2,4-triazolin-5-one;

g) 1-(5-allylamino-4-cyano-2-fluorophenyl)-4-ethyl-3-trifluoromethyl-1,2,4-triazolin-5-one; and h) 1-(2,5-difluoro-4-cyanophenyl)-4-methyl-3-trifluoromethyl-1,2,4-triazolin-5-one.

15. A method for regulating the growth of plants which comprises applying to such plants or to a locus in which such plants are grown or are to be grown a plant growth regulating effective amount of a substituted triazolinone according to claim 1.

16. The method according to claim 15, wherein the triazolinone is selected from the group consisting of:

a) 1-(4-cyano-2-fluorophenyl)-4-methyl-3-trifluoromethyl-1,2,4-triazolin-5-one;

b) 1-(2-chloro-4-cyanophenyl)-4-methyl-3-trifluoromethyl-1,2,4-triazolin-5-one;

c) 1-(2-fluoro-4-cyanophenyl)-4-methyl-3-trifluoromethyl-1,2,4-triazolin-5-thione;

d) 1-(2,5-difluoro-4-cyanophenyl)-4-methyl-3-trifluoromethyl-1,2,4-triazolin-5-thione;

e) 1-(2-fluoro-4-cyano-5-methoxyphenyl)-4-methyl-3-trifluoromethyl-1,2,4-triazolin-5-one;

f) 1-(4-cyano-3-fluorophenyl)-4-ethyl-3-trifluoromethyl-1,2,4-triazolin-5-one;

g) 1-(5-allylamino-4-cyano-2-fluorophenyl)-4-ethyl-3-trifluoromethyl-1,2,4-triazolin-5-one; and h) 1-(2,5-difluoro-4-cyanophenyl)-4-methyl-3-trifluoromethyl-1,2,4-triazolin-5-one.

17. A substituted triazolinone of the formula (Ia"):

(Ia")

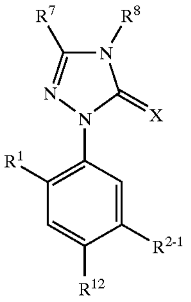

wherein $R^1$ represents hydrogen, fluorine, chlorine, bromine or iodine;

$R^{2-1}$ represents fluorine, chlorine, bromine or iodine;

$R^7$ represents straight-chain or branched halogenoalkyl having 1 to 6 carbon atoms and 1 to 13 identical or different halogen atoms;

$R^8$ represents hydrogen, amino, cyano, straight-chain or branched alkyl having 1 to 8 carbon atoms, in each case straight-chain or branched alkenyl or alkinyl having 2 to 6 carbon atoms, straight-chain or branched halogenoalkyl having 1 to 6 carbon atoms and 1 to 13 identical or different halogen atoms, in each case straight-chain or branched halogenoalkenyl or halogenoalkinyl having 2 to 6 carbon atoms and 1 to 11 different halogen atoms, straight-chain or branched alkoxyalkyl having 1 to 4 carbon atoms in the alkoxy moiety and 1 to 4 carbon atoms in the alkyl moiety, straight-chain or branched alkylideneimino having 1 to 8 carbon atoms, or cycloalkyl or cycloalkylalkyl each of which has 3 to 8 carbon atoms in the cycloalkyl moiety and, in the case of cycloalkylalkyl, has 1 to 4 carbon atoms in the alkyl moiety, and each of which is optionally monosubstituted or polysubstituted in the cycloalkyl moiety by identical or different halogen substituents;

$R^{12}$ represents cyano or nitro; and

X represents oxygen or sulfur.

18. A substituted triazolinone of the formula (Ib"):

(Ib")

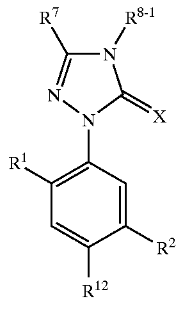

wherein $R^1$ represents hydrogen, fluorine, chlorine, bromine or iodine;

$R^2$ represents nitro, cyano, fluorine, chlorine, bromine, iodine, $R^{13}$, —O—$R^{13}$, —S—$R^{13}$, —S(O)—$R^{13}$, —$SO_2$—$R^{13}$, —O—$SO_2$—$R^{13}$, —$SO_2$—O—$R^{13}$, —C(O)—O—$R^{13}$, —$NR^{13}R^{14}$, —$SO_2$—$NR^{13}R^{14}$, —C(O)—$NR^{13}R^{14}$, —NH—P(O)($OR^{13}$)($R^{14}$), —NH—P(O)($OR^{13}$)($OR^{14}$), or a radical of the formula:

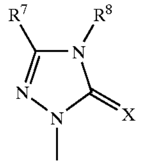

$R^7$ represents straight-chain or branched halogenoalkyl having 1 to 6 carbon atoms and 1 to 13 identical or different halogen atoms;

$R^{8-1}$ represents amino;

$R^{12}$ represents cyano or nitro;

X represents oxygen or sulfur;

$R^{13}$ and $R^{14}$ independently represent hydrogen or straight-chain or branched alkyl which has 1 to 8 carbon atoms and which is optionally monosubstituted or polysubstituted by identical or different substituents selected from the group consisting of:

halogen, cyano, carboxyl, carbamoyl, in each case straight-chain or branched alkoxy, alkoxyalkoxy, alkylthio, alkylsulphinyl, alkylsulphonyl, alkoxycarbonyl, alkoxycarbonylalkyl, N-alkylaminocarbonyl, cycloalkylaminocarbonyl, N,N-dialkylaminocarbonyl, trialkylsilyl or alkylsulphonylaminocarbonyl, each of which has 1 to 8 carbon atoms in the individual alkyl moieties;

$R^{13}$ and $R^{14}$ furthermore represent alkenyl or alkinyl, each of which has 2 to 8 carbon atoms and each of which is optionally monosubstituted or polysubstituted by identical or different halogen substituents;

$R^{13}$ and $R^{14}$ furthermore represent cycloalkyl which has 3 to 7 carbon atoms and which is optionally monosubstituted or polysubstituted by identical or different halogen substituents or by straight-chain or branched alkyl having 1 to 4 carbon atoms;

$R^{13}$ and $R^{14}$ furthermore represent aryl, which has 6 to 10 carbon atoms in the aryl moiety and is optionally monosubstituted or polysubstituted in the aryl moiety by identical or different substituents selected from the group consisting of:

halogen, cyano, nitro, in each case straight-chain or branched alkyl, alkoxy, alkylthio, alkylsulphinyl or alkylsulphonyl, each of which has 1 to 6 carbon atoms, in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched alkoxycarbonyl or alkoximinoalkyl, each of which has 1 to 6 carbon atoms in the individual alkyl moieties, and phenyl which is optionally monosubstituted or polysubstituted by identical or different halogen substituents and/or by straight-chain or branched alkyl or alkoxy, each of which has 1 to 6 carbon atoms, and/or by straight-chain or branched halogenoalkyl or halogenoalkoxy, each of which has 1 to 6 carbon atoms and 1 to 13 identical or different halogen atoms.

19. A substituted triazolinone of the formula (Ic"):

(Ic")

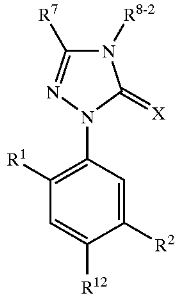

wherein $R^1$ represents hydrogen, fluorine, chlorine, bromine or iodine;

$R^2$ represents nitro, cyano, fluorine, chlorine, bromine, iodine, $R^3$, —O—$R^{13}$, —S—$R^{13}$, —S(O)—$R^{13}$, —$SO_2$—$R^{13}$, —O—$SO_2$—$R^{13}$, —$SO_2$—O—$R^{13}$, —C(O)—O—$R^{13}$, —$NR^{13}R^{14}$, —$SO_2$—$NR^{13}R^{14}$, —C(O)—$NR^{13}R^{14}$, —NH—P(O)($OR^{13}$)($R^{14}$), —NH—P(O)($OR^{13}$)($OR^{14}$), or a radical of the formula:

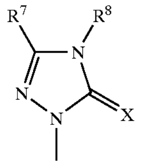

$R^7$ represents straight-chain or branched halogenoalkyl having 1 to 6 carbon atoms and 1 to 13 identical or different halogen atoms;

$R^{8-2}$ represents hydrogen;

$R^{12}$ represents cyano or nitro;

X represents oxygen or sulfur;

$R^{13}$ and $R^{14}$ independently represent hydrogen or straight-chain or branched alkyl which has 1 to 8 carbon atoms and which is optionally monosubstituted or polysubstituted by identical or different substituents selected from the group consisting of:

halogen, cyano, carboxyl, carbamoyl, in each case straight-chain or branched alkoxy, alkoxyalkoxy, alkylthio, alkylsulphinyl, alkylsulphonyl, alkoxycarbonyl, alkoxycarbonylalkyl, N-alkylaminocarbonyl, cycloalkylaminocarbonyl, N,N-dialkylaminocarbonyl, trialkylsilyl or alkylsulphonylaminocarbonyl, each of which has 1 to 8 carbon atoms in the individual alkyl moieties;

$R^{13}$ and $R^{14}$ furthermore represent alkenyl or alkinyl, each of which has 2 to 8 carbon atoms and each of which is optionally monosubstituted or polysubstituted by identical or different halogen substituents;

$R^{13}$ and $R^{14}$ furthermore represent cycloalkyl which has 3 to 7 carbon atoms and which is optionally monosubstituted or polysubstituted by identical or different halogen substituents or by straight-chain or branched alkyl having 1 to 4 carbon atoms;

$R^{13}$ and $R^{14}$ furthermore represent aryl, which has 6 to 10 carbon atoms in the aryl moiety and is optionally monosubstituted or polysubstituted in the aryl moiety by identical or different substituents selected from the group consisting of:

halogen, cyano, nitro, in each case straight-chain or branched alkyl, alkoxy, alkylthio, alkylsulphinyl or alkylsulphonyl, each of which has 1 to 6 carbon atoms, in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched alkoxycarbonyl or alkoximinoalkyl, each of which has 1 to 6 carbon atoms in the individual alkyl moieties, and phenyl which is optionally monosubstituted or polysubstituted by identical or different halogen substituents and/or by straight-chain or branched alkyl or alkoxy, each of which has 1 to 6 carbon atoms, and/or by straight-chain or branched halogenoalkyl or halogenoalkoxy, each of which has 1 to 6 carbon atoms and 1 to 13 identical or different halogen atoms.

* * * * *